US010322995B2

(12) United States Patent
Frackenpohl et al.

(10) Patent No.: US 10,322,995 B2
(45) Date of Patent: Jun. 18, 2019

(54) SUBSTITUTED CYANO CYCLOALKYL PENTA-2,4-DIENES, CYANO CYCLOALKYL PENT-2-EN-4-YNES, CYANO HETEROCYCLYL PENTA-2,4-DIENES AND CYANO HETEROCYCLYL PENT-2-EN-4-YNES AS ACTIVE SUBSTANCES AGAINST ABIOTIC PLANT STRESS

(71) Applicant: BAYER CROPSCIENCE AKTIENGESELLSCHAFT, Monheim am Rhein (DE)

(72) Inventors: Jens Frackenpohl, Frankfurt (DE); Lothar Willms, Hofheim (DE); Jan Dittgen, Frankfurt (DE); Dirk Schmutzler, Hattersheim (DE); Martin Jeffrey Hills, Idstein (DE); Juan Pedro Ruiz-Santaella Moreno, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/327,714

(22) PCT Filed: Jul. 17, 2015

(86) PCT No.: PCT/EP2015/066402

§ 371 (c)(1),
(2) Date: Jan. 20, 2017

(87) PCT Pub. No.: WO2016/012362

PCT Pub. Date: Jan. 28, 2016

(65) Prior Publication Data

US 2017/0210701 A1 Jul. 27, 2017

(30) Foreign Application Priority Data

Jul. 22, 2014 (EP) .................................... 14177917

(51) Int. Cl.

| | |
|---|---|
| ***C07F 5/02*** | (2006.01) |
| ***C07F 7/00*** | (2006.01) |

(Continued)

(52) U.S. Cl.

CPC ............ *C07C 255/46* (2013.01); *A01N 37/34* (2013.01); *A01N 41/12* (2013.01); *A01N 43/04* (2013.01); *A01N 43/20* (2013.01); *A01N 43/36* (2013.01); *A01N 43/40* (2013.01); *A01N 43/54* (2013.01); *A01N 43/84* (2013.01); *A01N 53/00* (2013.01); *A01N 55/04* (2013.01); *C07C 381/10* (2013.01); *C07D 207/16* (2013.01); *C07D 211/60* (2013.01); *C07D 213/40* (2013.01);

(Continued)

(58) Field of Classification Search

CPC ... C07C 255/46; C07D 207/16; C07D 211/60; C07D 213/40; C07D 239/26; C07D 265/30; C07D 279/12; C07D 305/08; C07F 5/025; C07F 7/1804; C07F 7/2208; C07F 7/30; A01N 37/34; A01N 43/04; A01N 43/36; A01N 43/40; A01N 53/00

See application file for complete search history.

(56) References Cited

U.S. PATENT DOCUMENTS 4,581,057 A 4/1986 Nooden et al.
5,059,615 A 10/1991 Fugmann et al.

(Continued)

FOREIGN PATENT DOCUMENTS

DE 3839170 A1 5/1990
EP 240257 A2 10/1987

(Continued)

OTHER PUBLICATIONS

Machine translation of claims and description sections of EP 2511255 (Oct. 2012).*

(Continued)

*Primary Examiner* — John Pak
(74) *Attorney, Agent, or Firm* — McBee Moore Woodward & Vanik IP, LLC

(57) ABSTRACT

Substituted cyano cycloalkyl penta-2,4-dienes, cyano cycloalkyl pent-2-en-4-ynes, cyano heterocyclyl penta-2,4-dienes and cyano heterocyclyl pent-2-en-4-ynes as active substances against abiotic plant stress Cyanocycloalkylpenta-2,4-dienes, cyanocycloalkylpent-2-en-4-ynes, cyanoheterocyclylpenta-2,4-dienes and cyanoheterocyclylpent-2-en-4-ynes of the general formula (I) or salts thereof (I)

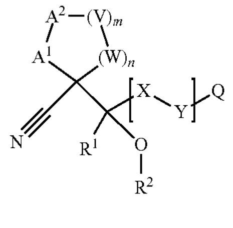

where [X-Y], Q, $R^1$, $R^2$, $A^1$, $A^2$, V, W, m and n are each as defined in the description, to processes for preparation thereof and to the use thereof for enhancing stress tolerance in plants with respect to abiotic stress, and/or for increasing plant yield.

16 Claims, No Drawings

(51) Int. Cl.

| | |
|---|---|
| ***C07F 7/18*** | (2006.01) |
| ***C07F 7/22*** | (2006.01) |
| ***C07F 7/30*** | (2006.01) |
| ***A01N 37/34*** | (2006.01) |
| ***A01N 41/12*** | (2006.01) |
| ***A01N 43/04*** | (2006.01) |
| ***A01N 43/20*** | (2006.01) |
| ***A01N 43/36*** | (2006.01) |
| ***A01N 43/40*** | (2006.01) |
| ***A01N 43/54*** | (2006.01) |
| ***A01N 43/84*** | (2006.01) |
| ***A01N 53/00*** | (2006.01) |
| ***A01N 55/04*** | (2006.01) |
| ***C07C 255/46*** | (2006.01) |
| ***C07C 381/10*** | (2006.01) |
| ***C07D 207/16*** | (2006.01) |
| ***C07D 211/60*** | (2006.01) |
| ***C07D 213/40*** | (2006.01) |
| ***C07D 305/08*** | (2006.01) |
| ***C07D 239/26*** | (2006.01) |
| ***C07D 265/30*** | (2006.01) |
| ***C07D 279/12*** | (2006.01) |

(52) U.S. Cl.

CPC ......... *C07D 239/26* (2013.01); *C07D 265/30* (2013.01); *C07D 279/12* (2013.01); *C07D 305/08* (2013.01); *C07F 5/025* (2013.01); *C07F 7/00* (2013.01); *C07F 7/1804* (2013.01); *C07F 7/2208* (2013.01); *C07F 7/30* (2013.01); *C07C 2601/02* (2017.05); *C07C 2601/04* (2017.05); *C07C 2601/08* (2017.05); *C07C 2601/14* (2017.05); *C07C 2603/74* (2017.05)

(56) References Cited

U.S. PATENT DOCUMENTS

| | | | |
|---|---|---|---|
| 5,518,995 A | 5/1996 | Abrams et al. | |
| 2010/0160166 A1 | 6/2010 | Abrams et al. | |
| 2014/0051577 A1 | 2/2014 | Frackenpohl et al. | |
| 2017/0197910 A1 * | 7/2017 | Frackenpohl .......... | A01N 53/00 |

FOREIGN PATENT DOCUMENTS

| | | | |
|---|---|---|---|
| EP | 0371882 A2 | | 6/1990 |
| EP | 2511255 | * | 10/2012 |
| EP | 2740356 A1 | | 6/2014 |
| EP | 2740720 A1 | | 6/2014 |
| JP | H-02286668 A | | 11/1990 |
| NL | 6811769 A | | 2/1969 |
| WO | 9415467 A1 | | 7/1994 |
| WO | 9723441 A1 | | 7/1997 |
| WO | 2005108345 A1 | | 11/2005 |
| WO | 2012139892 A1 | | 10/2012 |
| WO | WO 2016-008862 | * | 1/2016 |

OTHER PUBLICATIONS

Derwent abstract 2012-N19151, abstracting EP 2511255 (Oct. 2012).*

Tamura et al. "Syntheses and Biological Activities of 5-(Hydroxy-2,6,6-Trimethyl-2-Cyclohexen-1-yl)-3-Methyl-CIS,Trans-2,4-Pentadienoic Ester and Some Other Abscisic Acid Analogs", Arg. Bio. Chem.(1969) vol. 33, pp. 1357-1360.

Tamura et al. "Syntheses and Biological Activities of New Plant Growth Inhibitors Structurally Related to Abscisic Acid", Agr. Biol. Chem. (1970) vol. 34, pp. 1393-1401.

Kim et al. "Synthesis and Biological Activities of New Fluorinated Abscisic Acid", Bioorg. Med. Chem. Lett (1995), vol. 5, pp. 275-278.

Nakano et al. "Synthesis and biological Activity of 7'-8'-, and 9'-Alkyl Analogues of Abscisic Acid", Biosci. Biotech. Biochem., (1995) vol. 59 No. 9. pp. 1699-1706.

Todoroki et al. "8'-and 9'-Methoxyabscisic Acids as Antimetabolic Analogs of Abscisic Acid", Biosci. Biotech. Biochem., (1994) vol. 58 No. 4, pp. 707-715.

Todoroki et al. "Development of Specific Inhibitors of CYP707A, a Key Enzyme in the Catabolism of Abscisic Acid", Current Med. Chem. (2010) vol. 17. pp. 3230-3244.

Popandova et al. "Interaction of Aliphatic and Alycyclic Nitriles With Benzylideneacetophenone in the Presence of Lithium Amide in Liquid Ammonia", Dokl. Bolgarsk. Akad. Nauk (1971) vol. 24, pp. 621-624.

Cuvigny et al. "Recherches Sur Les Alcoylamidures De Lithium. Synthese De B Hydroxy Nitriles", Journal of Organometallic Chemistry, (1973) vol. 57, pp. 36-C38.

Todoroki et al. "8',8'-Difluoro- and 8',8',8'-Trifluoroabscisic Acids as Highly Potent, Long-Lasting Analogues of Abscisic Acid", Phytochem (1995), vol. 38 pp. 561-568.

Kim et al. "Synthesis and Biological Activities of New Flurinated Abscisic Acid", Bioorganic & Medicinal Chem. Ltrs., (1995) vol. 5, No. 3, pp. 275-278.

Todoroki et al. "Development of Specific Inhibitors of CYP707A, A Key Enzyme in the Catabolism of Abscisic Acid", Current Medicinal Chemistry (2010) No. 17, pp. 3230-3244.

Popandova et al. "Interaction of Aliphatic and Alicyclic Nitriles With Benzylideneacetophenone in the Presence of Lithium Amide in Liquid Ammonia", Dokl. Bolgarsk. Akad. Nauk (1971) vol. 24, pp. 621-624.

Cuvigny et al. Recherches Sur Les Alcoylamidures De Lithium. Synthese De β Hydroxy Nitriles, Journal of Organ. Chem., vol. 57 (1973) pp. C36-C38.

Todoroki et al. "8',8'-Difluoro- and 8',8',8'-Trifluoroabscisic Acids As Highly Potent, Long-Lasting Analogues of Abscisic Acid", (1995) Phytochemistry. vol. 38, No. 3, pp. 561-568.

* cited by examiner

SUBSTITUTED CYANO CYCLOALKYL PENTA-2,4-DIENES, CYANO CYCLOALKYL PENT-2-EN-4-YNES, CYANO HETEROCYCLYL PENTA-2,4-DIENES AND CYANO HETEROCYCLYL PENT-2-EN-4-YNES AS ACTIVE SUBSTANCES AGAINST ABIOTIC PLANT STRESS

The invention relates to substituted cyanocycloalkyl-penta-2,4-dienes, cyanocycloalkylpent-2-en-4-ynes, cyano-heterocyclylpenta-2,4-dienes and cyanoheterocyclylpent-2-en-4-ynes, to processes for preparation thereof and to the use thereof for enhancing stress tolerance in plants with respect to abiotic stress, and/or for increasing plant yield.

CROSS-REFERENCE TO RELATED APPLICATIONS

This application is a National Stage entry of International Application No. PCT/EP2015/066402 filed 17 Jul. 2015 which claims priority to European Patent Applications No. 141779147.3, filed 22 Jul. 2014.

BACKGROUND OF THE INVENTION

Field of the Invention

Description of Related Art

It is known that particular 5-(1,2-epoxy-2,6,6-trimethyl-cyclohexyl)-3-methylpenta-2,4-dienoic acids and derivatives thereof have properties which influence plant growth (cf. NL6811769). The growth-moderating effect of particular 1,2-epoxy analogues of abscisic acid on rice seedlings is also described in Agr. Biol. Chem. 1969, 33, 1357 and Agr. Biol. Chem. 1970, 34, 1393. The use of substituted 5-cyclohex-2-en-1-ylpenta-2,4-dienyl- and 5-cyclohex-2-en-1-ylpent-2-en-4-ynylols, 5-cyclohex-2-en-1-ylpenta-2,4-dienyl and 5-cyclohex-2-en-1-ylpent-2-en-4-ynyl thioethers and 5-cyclohex-2-en-1-ylpenta-2,4-dienyl- and 5-cyclohex-2-en-1-ylpent-2-en-4-ynylamines as inhibitors of epoxy-carotenoid dioxygenase and as germination inhibitors is described in US2010/0160166. The preparation of particular abscisic acid derivatives with a 3-methyl substituent in the 2,4-pentadienoic acid unit and the use thereof for influencing germination and plant growth is described in U.S. Pat. No. 5,518,995 and EP0371882. It is also known that particular abscisic acid derivatives with a 3-methyl substituent can be used to increase tolerance of plants to low temperatures (cf. WO94/15467). The increase in the yield of soybean seeds through use of a mixture of abscisic acid and a suitable fertilizer is described in U.S. Pat. No. 4,581,057.

It is likewise known that 5-(cyclohex-2-en-1-yl)-3-methylpenta-2,4-dienoic acid derivatives having unsaturated substituents at position C6 of the 5-cyclohex-2-en-1-yl unit can influence the water balance and the germination of plants (cf. WO97/23441). There have additionally been descriptions of trifluoromethyl, alkyl and methoxymethyl substituents at position C6 of the 5-cyclohex-2-en-1-yl unit in 5-(cyclohex-2-en-1-yl)-3-methylpenta-2,4-dienoic acids (cf. Biosci. Biotech. Biochem. 1994, 58, 707; Biosci. Biotech. Biochem. 1995, 59, 699; Phytochem. 1995, 38, 561; Bioorg. Med. Chem. Lett. 1995, 5, 275). Bicyclic tetralone-based 3-methylpenta-2,4-dienoic acid derivatives are described in WO2005/108345. It is additionally known that (2Z,4E)-5-[(1S,6S)-1-hydroxy-2,2,6-trimethylcyclohexyl]penta-2,4-dienoic acid and (2Z,4E)-5-[(1R,6R)-1-hydroxy-2,2,6-trimethylcyclohexyl]penta-2,4-dienoic acid interact with cytochrome P707A (cf. Current Med. Chem. 2010, 17, 3230).

It is also known that abscisic acid and derivatives thereof can be used as active pharmaceutical ingredients for regulation of calcium transport (cf. EP240257).

It is likewise known that particular cyanocyclopropyl-substituted azolylmethylcarbinols (cf. DE3839170) and cyanocyclopropyl-substituted aryltriazolylethanols (cf. JP02286668) can be used as active agrochemical ingredients for controlling pathogenic fungi. Moreover, only few cyanocycloalkyl-substituted alkenols have been described before, for example 1-[(2E)-1-hydroxy-1,3-diphenylprop-2-en-1-yl]cyclopentanecarbonitrile (in Dokl. Bolgarsk. Akad. Nauk 1971, 24, 621) and 1-[(2E)-1-hydroxy-3-phenylprop-2-en-1-yl]cyclohexanecarbonitrile (in J. Organomt. Chem. 1973, 57, C36-C38).

However, there has been no description of the use of the inventive cyanocycloalkylpenta-2,4-dienes and cyanocycloalkylpent-2-en-4-ynes for increasing stress tolerance in plants with respect to abiotic stress, for enhancing plant growth and/or for increasing the plant yield.

It is known that plants can react with specific or unspecific defence mechanisms to natural stress conditions, for example cold, heat, drought stress (stress caused by aridity and/or lack of water), injury, pathogenic attack (viruses, bacteria, fungi, insects) etc., but also to herbicides [Pflanzenbiochemie [Plant Biochemistry], p. 393-462, Spektrum Akademischer Verlag, Heidelberg, Berlin, Oxford, Hans W. Heldt, 1996; Biochemistry and Molecular Biology of Plants, P. 1102-1203, American Society of Plant Physiologists, Rockville, Md., eds. Buchanan, Gruissem, Jones, 2000].

In plants, there is knowledge of numerous proteins, and the genes which code for them, which are involved in defence reactions to abiotic stress (for example cold, heat, drought stress, salt, flooding). Some of these form part of signal transduction chains (e.g. transcription factors, kinases, phosphatases) or cause a physiological response of the plant cell (e.g. ion transport, deactivation of reactive oxygen species). The signaling chain genes of the abiotic stress reaction include transcription factors of the DREB and CBF classes (Jaglo-Ottosen et al., 1998, Science 280: 104-106). Phosphatases of the ATPK and MP2C type are involved in the reaction to salt stress. In addition, in the event of salt stress, the biosynthesis of osmolytes such as proline or sucrose is frequently activated. This involves, for example, sucrose synthase and proline transporters (Hasegawa et al., 2000, Annu Rev Plant Physiol Plant Mol Biol 51: 463-499). The stress defence of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which deactivate the reactive oxygen species (ROS) which form in the event of oxidative stress (Kirch et al., 2005, Plant Mol Biol 57: 315-332). Heat shock factors (HSF) and heat shock proteins (HSP) are activated in the event of heat stress and play a similar role here as chaperones to that of dehydrins in the event of cold and drought stress (Yu et al., 2005, Mol Cells 19: 328-333).

A number of signaling substances which are endogenous to plants and are involved in stress tolerance or pathogenic defence are already known. Examples here include salicylic acid, benzoic acid, jasmonic acid or ethylene [Biochemistry and Molecular Biology of Plants, p. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defence reactions which cause elevated stress tolerance or pathogen tolerance of the plant [Sembdner, and Parthier, 1993, Ann. Rev. Plant Physiol. Plant Mol. Biol. 44: 569-589].

It is additionally known that chemical substances can increase the tolerance of plants to abiotic stress. Such substances are applied either by seed dressing, by leaf spraying or by soil treatment. For instance, an increase in abiotic stress tolerance of crop plants by treatment with elicitors of systemic acquired resistance (SAR) or abscisic acid derivatives is described (Schading and Wei, WO2000/28055, Churchill et al., 1998, Plant Growth Regul 25: 35-45). In addition, effects of growth regulators on the stress tolerance of crop plants have been described (Morrison and Andrews, 1992, J Plant Growth Regul 11: 113-117, RD-259027). In this context, it is likewise known that a growth-regulating naphthylsulphonamide (4-bromo-N-(pyridin-2-ylmethyl)naphthalene-1-sulphonamide) influences the germination of plant seeds in the same way as abscisic acid (Park et al. Science 2009, 324, 1068-1071). It is also known that a further naphthylsulphonamide, N-(6-aminohexyl)-5-chloronaphthalene-1-sulphonamide, influences the calcium level in plants which have been exposed to cold shock (Cholewa et al. Can. J. Botany 1997, 75, 375-382).

Similar effects are also observed on application of fungicides, especially from the group of the strobilurins or of the succinate dehydrogenase inhibitors, and are frequently also accompanied by an increase in yield (Draber et al., DE3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In the event of osmotic stress, a protective effect has been observed as a result of application of osmolytes, for example glycine betaine or the biochemical precursors thereof, e.g. choline derivatives (Chen et al., 2000, Plant Cell Environ 23: 609-618, Bergmann et al., DE4103253). The effect of antioxidants, for example naphthols and xanthines, of increasing abiotic stress tolerance in plants has also already been described (Bergmann et al., DD277832, Bergmann et al., DD277835). However, the molecular causes of the antistress action of these substances are largely unknown.

It is also known that the tolerance of plants to abiotic stress can be increased by a modification of the activity of endogenous poly-ADP-ribose polymerases (PARP) or poly-(ADP-ribose) glycohydrolases (PARG) (de Block et al., The Plant Journal, 2004, 41, 95; Levine et al., FEBS Lett. 1998, 440, 1; WO2000/04173; WO2004/090140).

It is thus known that plants possess several endogenous reaction mechanisms which can bring about an effective defence against a wide variety of different harmful organisms and/or natural abiotic stress.

Since the ecologic and economic demands on modern plant treatment compositions are increasing constantly, for example with respect to toxicity, selectivity, application rate, formation of residues and favourable manufacture, there is a constant need to develop novel plant treatment compositions which have advantages over those known, at least in some areas.

SUMMARY

It was therefore an object of the present invention to provide further compounds which increase tolerance to abiotic stress in plants, more particularly bring about enhancement of plant growth and/or contribute to an increase in plant yield.

The present invention accordingly provides cyanocycloalkylpenta-2,4-dienes, cyanocycloalkylpent-2-en-4-ynes, cyanoheterocyclylpenta-2,4-dienes and cyanoheterocyclylpent-2-en-4-ynes of the general formula (I) or salts thereof (I)

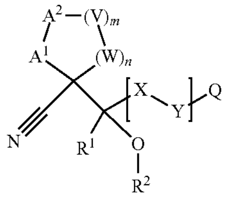

where

[X-Y] represents the moieties $[X\text{-}Y]^1$

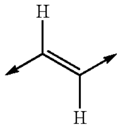

and $[X\text{-}Y]^2$

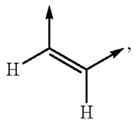

$[X\text{-}Y]^3$

Q represents the moieties

Q-1

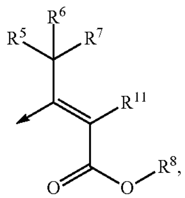

-continued

Q-2

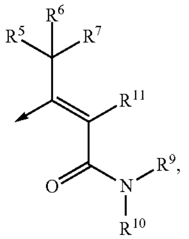

Q-3

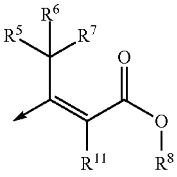

and

Q-4

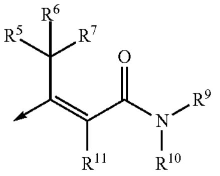

where $R^5$, $R^6$, $R^7$, $R^8$, $R^9$, $R^{10}$ and $R^{11}$ are each as defined below and where the arrow represents a bond to the respective [X-Y] moiety, $R^1$ is hydrogen, alkyl, aryl, heteroaryl, heterocyclyl, cycloalkyl, alkenyl, alkynyl, alkynylalkyl, alkoxyalkyl, hydroxyalkyl, haloalkyl, haloalkenyl, haloalkoxyalkyl, alkylthioalkyl, arylalkyl, heterocyclylalkyl, halocycloalkyl, cycloalkenyl, alkoxyalkoxyalkyl, cycloalkylalkyl, cycloalkenylalkyl, haloalkynyl, alkylsulphinylalkyl, alkylsulphonylalkyl, halocycloalkylalkyl cycloalkylsulphinylalkyl, cycloalkylsulphonylalkyl, arylsulphinylalkyl, arylsulphonylalkyl, arylthioalkyl, cycloalkylthioalkyl, alkoxyhaloalkyl, haloalkoxyhaloalkyl, $R^2$ is hydrogen, alkyl, alkoxyalkyl, alkoxyalkoxyalkyl, alkenyl, alkynyl, alkylcarbonyl, arylcarbonyl, heteroarylcarbonyl, cycloalkylcarbonyl, alkenylcarbonyl, heterocyclylcarbonyl, alkoxycarbonyl, alkenyloxycarbonyl, aryloxyalkyl, arylalkoxycarbonyl, cycloalkoxycarbonyl, cycloalkylalkoxycarbonyl, arylalkoxyalkyl, arylalkyl, alkoxyalkoxyalkyl, alkylthioalkyl, trialkylsilyl, alkyl (bisalkyl)silyl, alkyl(bisaryl)silyl, aryl(bisalkyl)silyl, cycloalkyl(bisalkyl)silyl, halo(bisalkyl)silyl, trialkylsilylalkoxyalkyl, trialkylsilylalkyl, alkynyloxycarbonyl, cycloalkyl, cycloalkylalkyl, aminocarbonyl, alkylaminocarbonyl, bisalkylaminocarbonyl, cycloalkylaminocarbonyl, alkylsulphonyl, haloalkylsulphonyl, arylsulphonyl, heteroarylsulphonyl, cycloalkylsulphonyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, 2, n is 0, 1, 2, $R^3$ and $R^4$ are each independently hydrogen, alkyl, halogen, cycloalkyl, alkoxy, aryl, heterocyclyl, heteroaryl, arylalkyl, alkylthio, haloalkyl, haloalkyloxy, haloalkylthio, alkoxyalkyl, alkylthioalkyl, heteroarylalkyl, heterocyclylalkyl, cycloalkylalkyl, cycloalkenyl, alkynyl, alkenyl, haloalkenyl, haloalkynyl, alkylsulphinyl, alkylsulphonyl, cycloalkylsulphinyl, cycloalkylsulphonyl, arylsulphinyl, arylsulphonyl, alkoxyhaloalkyl, haloalkoxyhaloalkyl, $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, halogen, alkyl, haloalkyl, cycloalkyl, cycloalkylalkyl, $R^7$ is hydrogen, halogen, alkyl, haloalkyl, haloalkoxy, haloalkoxyalkyl, haloalkoxyhaloalkyl, alkoxyhaloalkyl, alkynyloxyhaloalkyl, alkenyloxyhaloalkyl, alkylthio, haloalkylthio, aryl, arylalkyl, heteroaryl, heteroarylalkyl, heterocyclyl, alkoxy, hydroxyl, alkylcarbonyloxy, arylcarbonyloxy, cycloalkylcarbonyloxy, trisalkylsilyloxy, bisalkyl(alkyl)silyloxy, alkyl(bisaryl)silyloxy, aryl (bisalkyl)silyloxy, cycloalkyl(bisalkyl)silyloxy, halo (bisalkyl)silyloxy, trialkylsilylalkoxyalkyloxy, trialkylsilylalkyloxy, alkylsulphinyl, alkylsulphonyl, cycloalkylsulphinyl, cycloalkylsulphonyl, arylsulphinyl, arylsulphonyl, cycloalkyl, cycloalkylalkyl, $R^6$ and $R^7$ together with the atoms to which they are bonded form a fully saturated 3- to 6-membered ring optionally interrupted by heteroatoms and optionally having further substitution, $R^8$ is hydrogen, alkyl, alkoxyalkyl, cycloalkyl, cycloalkylalkyl, aryl, arylalkyl, heteroarylalkyl, bisarylalkyl, trisarylalkyl, alkenyl, cycloalkenylalkyl, alkynylalkyl, trialkylsilylalkoxyalkyl, alkoxyalkoxyalkyl, alkylthioalkyl, haloalkyl, arylsulphonylalkyl, trialkylsilyl, alkyl(bisaryl) silyl, alkyl(bisalkyl)silyl, bisalkylaminoalkyl, heterocyclylalkyl, alkynyl, cyanoalkyl, heterocyclyl, cycloalkenyl, $R^9$ is hydrogen, alkyl, cycloalkyl, halogen, alkynylalkyl, haloalkyl, alkynyl, alkenyl, cyanoalkyl, cycloalkylalkyl, arylalkyl, heteroarylalkyl, alkylcarbonyl, alkoxycarbonyl, alkenyloxycarbonyl, alkenylalkyloxycarbonyl, arylalkyloxycarbonyl, cycloalkoxycarbonyl, cycloalkylalkoxycarbonyl, alkylsulphonyl, arylsulphonyl, cycloalkylsulphonyl, alkylsulphinyl, arylsulphinyl, cycloalkylsulphinyl, alkoxycarbonylalkyl, hydroxycarbonylalkyl, arylalkoxycarbonylalkyl, cycloalkylalkoxycarbonylalkyl, alkoxycarbonylcycloalkyl, hydroxycarbonylcycloalkyl, arylalkoxycarbonylcycloalkyl, alkenyloxycarbonylcycloalkyl, aminocarbonylcycloalkyl, alkylaminocarbonylcycloalkyl, cycloalkylaminocarbonylcycloalkyl, alkoxycarbonylcycloalkenyl, hydroxycarbonylcycloalkenyl, bisalkylaminoalkyl, hydroxycarbonylheterocyclyl, alkoxycarbonylheterocyclyl, alkenyloxycarbonylheterocyclyl, alkenylalkoxycarbonylheterocyclyl, arylalkoxycarbonylheterocyclyl, cycloalkoxycarbonylheterocyclyl, cycloalkylalkoxycarbonylheterocyclyl, aminocarbonylheterocyclyl, alkylaminocarbonylheterocyclyl, bisalkylaminocarbonylheterocyclyl, cycloalkylaminocarbonylheterocyclyl, arylalkylaminocarbonylheterocyclyl, alkenylaminocarbonylheterocyclyl, hydroxycarbonylheterocyclylalkyl, alkoxycarbonylheterocyclylalkyl, hydroxycarbonylcycloalkylalkyl, alkoxycarbonylcycloalkylalkyl, hydroxyl, alkoxy, heterocyclyl, heterocyclylalkyl, aryl, cycloalkenyl, cycloalkenylalkyl, $R^{10}$ is hydrogen, alkyl, cycloalkyl, halogen, haloalkyl, alkynyl, alkenyl, cyanoalkyl, arylalkyl, heteroarylalkyl, alkylcarbonyl, alkoxycarbonyl, alkylsulphonyl, arylsulphonyl, cycloalkylsulphonyl, alkylsulphinyl, arylsulphinyl, cycloalkylsulphinyl, alkoxycarbonylalkyl or $R^9$ and $R^{10}$ with the nitrogen to which they are attached form an optionally halogen-, alkyl-, haloalkyl-, alkoxy-, alkoxycarbonyl-, cycloalkoxycarbonyl-, cycloalkylalkoxycarbonyl-, alkenyloxycarbonyl-, hydroxycarbonyl-, aminocarbonyl-, alkylaminocarbonyl-, cycloalkylaminocarbonyl-, arylalkylaminocarbonyl-substituted three- to eight-membered ring which is optionally interrupted by O, S or N or $R^9$ and $R^{10}$ together form part of an optionally substituted sulphilimine or amidine group or form an iminophosphorane and $R^{11}$ is hydrogen, alkyl, cycloalkyl, haloalkyl, alkoxyalkyl, alkylthioalkyl.

DETAILED DESCRIPTION OF A PREFERRED EMBODIMENT

The compounds of the formula (I) can form salts. Salts can be formed by the action of a base on those compounds of the formula (I) which bear an acidic hydrogen atom, for example in the case that $R^1$ contains a COOH group or a sulphonamide group —$NHSO_2$—. Examples of suitable bases are organic amines such as trialkylamines, morpholine, piperidine or pyridine, and the hydroxides, carbonates and hydrogencarbonates of ammonium, alkali metals or alkaline earth metals, in particular sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, especially sodium salts or potassium salts, or else ammonium salts, salts with organic amines or quaternary ammonium salts, for example with cations of the formula $[NRR'R''R''']^+$ in which R to R''' are each independently an organic radical, especially alkyl, aryl, arylalkyl or alkylaryl. Also useful are alkylsulphonium and alkylsulphoxonium salts, such as $(C_1\text{-}C_4)$-trialkylsulphonium and $(C_1\text{-}C_4)$-trialkylsulphoxonium salts.

The inventive compounds of the general formula (I) and salts thereof, and those used in accordance with the invention, are also referred to for short as "compounds of the general formula (I)".

Preference is given to compounds of the general formula (I) in which

[X-Y] represents the moieties and $[X\text{-}Y]^1$

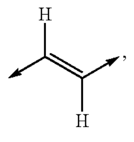

$[X\text{-}Y]^2$

Q represents the moieties

Q-1

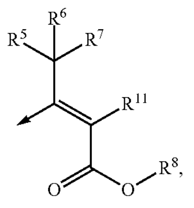

-continued

Q-2

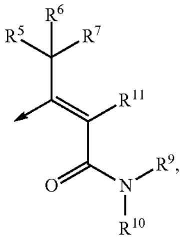

Q-3

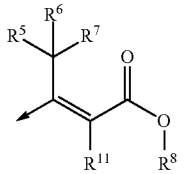 and

Q-4

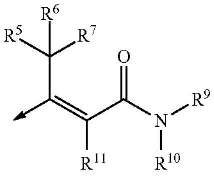

where $R^5$, $R^6$, $R^7$, $R^8$, $R^9$, $R^{10}$ and $R^{11}$ are each as defined below and where the arrow represents a bond to the respective [X-Y] moiety;

$R^1$ is hydrogen, $(C_1\text{-}C_8)$-alkyl, aryl, heteroaryl, heterocyclyl, $(C_3\text{-}C_{10})$-cycloalkyl, $(C_2\text{-}C_8)$-alkenyl, $(C_2\text{-}C_8)$-alkynyl, $(C_2\text{-}C_8)$-alkynyl-$(C_1\text{-}C_8)$-alkyl, $(C_1\text{-}C_8)$-alkoxy-$(C_1\text{-}C_8)$-alkyl, hydroxy-$(C_1\text{-}C_8)$-alkyl, $(C_1\text{-}C_8)$-haloalkyl, $(C_2\text{-}C_8)$-haloalkenyl, $(C_1\text{-}C_8)$-haloalkoxy-$(C_1\text{-}C_8)$-alkyl, $(C_1\text{-}C_8)$-alkylthio-$(C_1\text{-}C_8)$-alkyl, aryl-$(C_1\text{-}C_8)$-alkyl, heterocyclyl-$(C_1\text{-}C_8)$-alkyl, $(C_3\text{-}C_8)$-halocycloalkyl, $(C_4\text{-}C_8)$-cycloalkenyl, $(C_1\text{-}C_8)$-alkoxy-$(C_1\text{-}C_8)$-alkoxy-$(C_1\text{-}C_8)$-alkyl, $(C_3\text{-}C_8)$-cycloalkyl-$(C_1\text{-}C_8)$-alkyl, $(C_3\text{-}C_8)$-cycloalkenyl-$(C_1\text{-}C_8)$-alkyl, $(C_2\text{-}C_8)$-haloalkynyl, $(C_1\text{-}C_8)$-alkylsulphinyl-$(C_1\text{-}C_8)$-alkyl, $(C_1\text{-}C_8)$-alkylsulphonyl-$(C_1\text{-}C_8)$-alkyl, $(C_3\text{-}C_8)$-halocycloalkyl-$(C_1\text{-}C_8)$-alkyl, $(C_3\text{-}C_8)$-cycloalkylsulphinyl-$(C_1\text{-}C_8)$-alkyl, $(C_3\text{-}C_8)$-cycloalkylsulphonyl-$(C_1\text{-}C_8)$-alkyl, arylsulphinyl-$(C_1\text{-}C_8)$-alkyl, arylsulphonyl-$(C_1\text{-}C_8)$-alkyl, arylthio-$(C_1\text{-}C_8)$-alkyl, $(C_3\text{-}C_8)$-cycloalkylthio-$(C_1\text{-}C_8)$-alkyl, $(C_1\text{-}C_8)$-alkoxy-$(C_1\text{-}C_8)$-haloalkyl, $(C_1\text{-}C_8)$-haloalkoxy-$(C_1\text{-}C_8)$-haloalkyl, $R^2$ is hydrogen, $(C_1\text{-}C_8)$-alkyl, $(C_1\text{-}C_8)$-alkoxy-$(C_1\text{-}C_8)$-alkyl, $(C_1\text{-}C_8)$-alkoxy-$(C_1\text{-}C_8)$-alkoxy-$(C_1\text{-}C_8)$-alkyl, $(C_2\text{-}C_8)$-alkenyl, $(C_2\text{-}C_8)$-alkynyl, $(C_1\text{-}C_8)$-alkylcarbonyl, arylcarbonyl, heteroarylcarbonyl, $(C_3\text{-}C_8)$-cycloalkylcarbonyl, $(C_2\text{-}C_8)$-alkenylcarbonyl, heterocyclylcarbonyl, $(C_1\text{-}C_8)$-alkoxycarbonyl, $(C_2\text{-}C_8)$-alkenyloxycarbonyl, aryloxy-$(C_1\text{-}C_8)$-alkyl, aryl-$(C_1\text{-}C_8)$-alkoxycarbonyl, $(C_3\text{-}C_8)$-cycloalkoxycarbonyl, $(C_3\text{-}C_8)$-cycloalkyl-$(C_1\text{-}C_8)$-alkoxycarbonyl, aryl-$(C_1\text{-}C_8)$-alkoxy-$(C_1\text{-}C_8)$-alkyl, aryl-$(C_1\text{-}C_8)$-alkyl, $(C_1\text{-}C_8)$-alkoxy-$(C_1\text{-}C_8)$-alkoxy-$(C_1\text{-}C_8)$-alkyl, $(C_1\text{-}C_8)$-alkylthio-$(C_1\text{-}C_8)$-alkyl, tris[$(C_1\text{-}C_8)$-alkyl]silyl, $(C_1\text{-}C_8)$-alkylbis-[$(C_1\text{-}C_8)$-alkyl]silyl, $(C_1\text{-}C_8)$-alkylbis(aryl)silyl, arylbis[$(C_1\text{-}C_8)$-alkyl]silyl, $(C_3\text{-}C_8)$-cycloalkylbis[$(C_1\text{-}C_8)$-alkyl]silyl, halobis[$(C_1\text{-}C_8)$-alkyl]silyl, tris[$(C_1\text{-}C_8)$-alkyl]silyl-$(C_1\text{-}C_8)$-alkoxy-$(C_1\text{-}C_8)$-alkyl, tris[$(C_1\text{-}C_8)$-alkyl]silyl-$(C_1\text{-}C_8)$-alkyl, $(C_2\text{-}C_8)$-alkynyloxycarbonyl, $(C_3\text{-}C_8)$-cycloalkyl, $(C_3\text{-}C_8)$-cycloalkyl-$(C_1\text{-}C_8)$-alkyl, aminocarbonyl, $(C_1\text{-}C_8)$- alkylaminocarbonyl, bis[($C_1$-$C_8$)-alkyl]aminocarbonyl, ($C_3$-$C_8$)-cycloalkylaminocarbonyl, ($C_1$-$C_8$)-alkylsulphonyl, ($C_1$-$C_8$)-haloalkylsulphonyl, arylsulphonyl, heteroarylsulphonyl, ($C_3$-$C_8$)-cycloalkylsulphonyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, 2, n is 0, 1, 2, $R^3$ and $R^4$ are each independently hydrogen, ($C_1$-$C_8$)-alkyl, halogen, ($C_3$-$C_8$)-cycloalkyl, ($C_1$-$C_8$)-alkoxy, aryl, heterocyclyl, heteroaryl, aryl-($C_1$-$C_8$)-alkyl, ($C_1$-$C_8$)-alkylthio, ($C_1$-$C_8$)-haloalkyl, ($C_1$-$C_8$)-haloalkyloxy, ($C_1$-$C_8$)-haloalkylthio, ($C_1$-$C_8$)-alkoxy-($C_1$-$C_8$)-alkyl, ($C_1$-$C_8$)-alkylthio-($C_1$-$C_8$)-alkyl, heteroaryl-($C_1$-$C_8$)-alkyl, heterocyclyl-($C_1$-$C_8$)-alkyl, ($C_1$-$C_8$)-alkoxy-($C_1$-$C_8$)-haloalkyl, ($C_1$-$C_8$)-haloalkoxy-($C_1$-$C_8$)-haloalkyl, ($C_2$-$C_8$)-alkynyl, ($C_2$-$C_8$)-alkenyl, $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, halogen, ($C_1$-$C_8$)-alkyl, ($C_1$-$C_8$)-haloalkyl, ($C_3$-$C_8$)-cycloalkyl, ($C_3$-$C_8$)-cycloalkyl-($C_1$-$C_8$)-alkyl, $R^7$ is hydrogen, halogen, ($C_1$-$C_8$)-alkyl, ($C_1$-$C_8$)-haloalkyl, ($C_1$-$C_8$)-haloalkoxy, ($C_1$-$C_8$)-haloalkoxy-($C_1$-$C_8$)-alkyl, ($C_1$-$C_8$)-haloalkoxy-($C_1$-$C_8$)-haloalkyl, ($C_1$-$C_8$)-alkoxy-($C_1$-$C_8$)-haloalkyl, ($C_1$-$C_8$)-alkynyloxy-($C_1$-$C_8$)-haloalkyl, ($C_1$-$C_8$)-alkenyloxy-($C_1$-$C_8$)-haloalkyl, ($C_1$-$C_8$)-alkylthio, ($C_1$-$C_8$)-haloalkylthio, optionally substituted phenyl, aryl-($C_1$-$C_8$)-alkyl, heteroaryl, heteroaryl-($C_1$-$C_8$)-alkyl, heterocyclyl, ($C_1$-$C_8$)-alkoxy, hydroxyl, ($C_1$-$C_8$)-alkylcarbonyloxy, arylcarbonyloxy, ($C_3$-$C_8$)-cycloalkylcarbonyloxy, tris[($C_1$-$C_8$)-alkyl]silyloxy, bis[($C_1$-$C_8$)-alkyl]-[($C_1$-$C_8$)-alkyl]silyloxy, ($C_1$-$C_8$)-alkylbisarylsilyloxy, arylbis[($C_1$-$C_8$)-alkyl]silyloxy, ($C_3$-$C_8$)-cycloalkylbis[($C_1$-$C_8$)-alkyl]silyloxy, halobis[($C_1$-$C_8$)-alkyl]silyloxy, tris[($C_1$-$C_8$)-alkyl]silyl-($C_1$-$C_8$)-alkoxy-($C_1$-$C_8$)-alkyloxy, tris[($C_1$-$C_8$)-alkyl]silyl-($C_1$-$C_8$)-alkyloxy, ($C_3$-$C_8$)-cycloalkyl, ($C_3$-$C_8$)-cycloalkyl-($C_1$-$C_8$)-alkyl, $R^6$ and $R^7$ together with the atoms to which they are bonded form a fully saturated 3- to 6-membered ring optionally interrupted by heteroatoms and optionally having further substitution, $R^8$ is hydrogen, ($C_1$-$C_8$)-alkyl, ($C_1$-$C_8$)-alkoxy-($C_1$-$C_8$)-alkyl, ($C_3$-$C_8$)-cycloalkyl, ($C_3$-$C_8$)-cycloalkyl-($C_1$-$C_8$)-alkyl, optionally substituted phenyl, aryl-($C_1$-$C_8$)-alkyl, heteroaryl-($C_1$-$C_8$)-alkyl, bisaryl-($C_1$-$C_8$)-alkyl, trisaryl-($C_1$-$C_8$)-alkyl, ($C_2$-$C_8$)-alkenyl, ($C_4$-$C_8$)-cycloalkenyl-($C_1$-$C_8$)-alkyl, ($C_2$-$C_8$)-alkynyl-($C_1$-$C_8$)-alkyl, tri-($C_1$-$C_8$)-alkylsilyl-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkyl, ($C_1$-$C_8$)-alkylthio-($C_1$-$C_8$)-alkyl, ($C_1$-$C_8$)-haloalkyl, arylsulphonyl-($C_1$-$C_8$)-alkyl, tri-($C_1$-$C_8$)-alkylsilyl, ($C_1$-$C_8$)-alkyl(bisaryl)silyl, ($C_1$-$C_8$)-alkyl(bis-($C_1$-$C_8$)-alkyl)silyl, bis($C_1$-$C_8$)-alkylamino-($C_1$-$C_8$)-alkyl, heterocyclyl-($C_1$-$C_8$)-alkyl, ($C_2$-$C_8$)-alkynyl, cyano-($C_1$-$C_8$)-alkyl, heterocyclyl, optionally further-substituted phenyl, $R^9$ is hydrogen, ($C_1$-$C_8$)-alkyl, ($C_3$-$C_8$)-cycloalkyl, halogen, ($C_2$-$C_8$)-alkynyl-($C_1$-$C_8$)-alkyl, ($C_1$-$C_8$)-haloalkyl, ($C_2$-$C_8$)-alkynyl, ($C_2$-$C_8$)-alkenyl, cyano-($C_1$-$C_8$)-alkyl, ($C_3$-$C_8$)-cycloalkyl-($C_1$-$C_8$)-alkyl, aryl-($C_1$-$C_8$)-alkyl, heteroaryl-($C_1$-$C_8$)-alkyl, ($C_1$-$C_8$)-alkylcarbonyl, ($C_1$-$C_8$)-alkoxycarbonyl, ($C_2$-$C_8$)-alkenyloxycarbonyl, ($C_2$-$C_8$)-alkenyl-($C_1$-$C_8$)-alkyloxycarbonyl, aryl-($C_1$-$C_8$)-alkyloxycarbonyl, ($C_3$-$C_8$)-cycloalkoxycarbonyl, ($C_3$-$C_8$)-cycloalkyl-($C_1$-$C_8$)-alkoxycarbonyl, ($C_1$-$C_8$)-alkylsulphonyl, arylsulphonyl, ($C_3$-$C_8$)-cycloalkylsulphonyl, ($C_1$-$C_8$)-alkylsulphinyl, arylsulphinyl, ($C_3$-$C_8$)-cycloalkylsulphinyl, ($C_1$-$C_8$)-alkoxycarbonyl-($C_1$-$C_8$)-alkyl, hydroxycarbonyl-($C_1$-$C_8$)-alkyl, aryl-($C_1$-$C_8$)-alkoxycarbonyl-($C_1$-$C_8$)-alkyl, ($C_3$-$C_8$)-cycloalkyl-($C_1$-$C_8$)-alkoxycarbonyl-($C_1$-$C_8$)-alkyl, ($C_1$-$C_8$)-alkoxycarbonyl-($C_3$-$C_8$)-cycloalkyl, hydroxycarbonyl-($C_3$-$C_8$)-cycloalkyl, aryl-($C_1$-$C_8$)-alkoxycarbonyl-($C_3$-$C_8$)-cycloalkyl, ($C_2$-$C_8$)-alkenyloxycarbonyl-($C_3$-$C_8$)-cycloalkyl, aminocarbonyl-($C_3$-$C_8$)-cycloalkyl, ($C_1$-$C_8$)-alkylaminocarbonyl-($C_3$-$C_8$)-cycloalkyl, ($C_3$-$C_8$)-cycloalkylaminocarbonyl-($C_3$-$C_8$)-cycloalkyl, ($C_1$-$C_8$)-alkoxycarbonyl-($C_4$-$C_8$)-cycloalkenyl, hydroxycarbonyl-($C_4$-$C_8$)-cycloalkenyl, bis-($C_1$-$C_8$)-alkylamino-($C_1$-$C_8$)-alkyl, hydroxycarbonyl-heterocyclyl, ($C_1$-$C_8$)-alkoxycarbonylheterocyclyl, ($C_2$-$C_8$)-alkenyloxycarbonylheterocyclyl, ($C_2$-$C_8$)-alkenyl-($C_1$-$C_8$)-alkoxycarbonylheterocyclyl, aryl-($C_1$-$C_8$)-alkoxycarbonylheterocyclyl, ($C_3$-$C_8$)-cycloalkoxycarbonylheterocyclyl, ($C_3$-$C_8$)-cycloalkyl-($C_1$-$C_8$)-alkoxycarbonylheterocyclyl, aminocarbonylheterocyclyl, ($C_1$-$C_8$)-alkylaminocarbonylheterocyclyl, bis-($C_1$-$C_8$)-alkylaminocarbonylheterocyclyl, ($C_3$-$C_8$)-cycloalkylaminocarbonylheterocyclyl, aryl-($C_1$-$C_8$)-alkylaminocarbonylheterocyclyl, ($C_2$-$C_8$)-alkenylaminocarbonylheterocyclyl, hydroxycarbonylheterocyclyl-($C_1$-$C_8$)-alkyl, ($C_1$-$C_8$)-alkoxycarbonylheterocyclyl-($C_1$-$C_8$)-alkyl, hydroxycarbonyl-($C_3$-$C_8$)-cycloalkyl-($C_1$-$C_8$)-alkyl, ($C_1$-$C_8$)-alkoxycarbonyl-($C_3$-$C_8$)-cycloalkyl-($C_1$-$C_8$)-alkyl, hydroxyl, ($C_1$-$C_8$)-alkoxy, heterocyclyl, heterocyclyl-($C_1$-$C_8$)-alkyl, optionally substituted phenyl, $R^{10}$ is hydrogen, ($C_1$-$C_8$)-alkyl, ($C_3$-$C_8$)-cycloalkyl, halogen, ($C_1$-$C_8$)-haloalkyl, ($C_2$-$C_8$)-alkynyl, ($C_2$-$C_8$)-alkenyl, cyano-($C_1$-$C_8$)-alkyl, aryl-($C_1$-$C_8$)-alkyl, heteroaryl-($C_1$-$C_8$)-alkyl, ($C_1$-$C_8$)-alkylcarbonyl, ($C_1$-$C_8$)-alkoxycarbonyl, ($C_1$-$C_8$)-alkylsulphonyl, arylsulphonyl, ($C_3$-$C_8$)-cycloalkylsulphonyl, ($C_1$-$C_8$)-alkylsulphinyl, arylsulphinyl, ($C_3$-$C_8$)-cycloalkylsulphinyl, ($C_1$-$C_8$)-alkoxycarbonyl-($C_1$-$C_8$)-alkyl, $R^9$ and $R^{10}$ together with the nitrogen to which they are bonded form an optionally halogen-, ($C_1$-$C_8$)-alkyl-, ($C_1$-$C_8$)-haloalkyl-, ($C_1$-$C_8$)-alkoxy-, ($C_1$-$C_8$)-alkoxycarbonyl-, ($C_3$-$C_8$)-cycloalkoxycarbonyl-, ($C_3$-$C_8$)-cycloalkyl-($C_1$-$C_8$)-alkoxycarbonyl-, ($C_2$-$C_8$)-alkenyloxycarbonyl-, hydroxycarbonyl-, aminocarbonyl-, ($C_1$-$C_8$)-alkylaminocarbonyl-, ($C_3$-$C_8$)-cycloalkylaminocarbonyl-, aryl-($C_1$-$C_8$)-alkylaminocarbonyl-substituted three- to eight-membered ring optionally interrupted by O, S or N, or $R^9$ and $R^{10}$ together form an N-(bis-($C_1$-$C_6$)-alkyl)sulphanylidene, N-(aryl-($C_1$-$C_6$)-alkyl)sulphanylidene, N-(bis-($C_3$-$C_7$)-cycloalkyl)sulphanylidene, N—(($C_1$-$C_6$)-alkyl-($C_3$-$C_7$)-cycloalkyl)sulphanylidene group or an N,N-di-($C_1$-$C_6$)-alkylformylidene group and $R^{11}$ is hydrogen, ($C_1$-$C_8$)-alkyl, ($C_3$-$C_8$)-cycloalkyl, ($C_1$-$C_8$)-haloalkyl, ($C_1$-$C_8$)-alkoxy-($C_1$-$C_8$)-alkyl, ($C_1$-$C_8$)-alkylthio-($C_1$-$C_8$)-alkyl.

Particular preference is given to compounds of the general formula (I) in which

[X-Y] represents the moieties and

[X-Y]$^1$

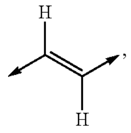

[X-Y]$^2$

Q represents the moieties

Q-1

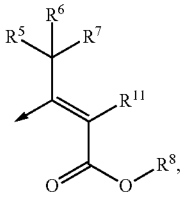

Q-2

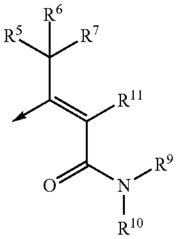

and

Q-3

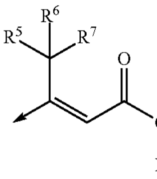

where $R^5$, $R^6$, $R^7$, $R^8$, $R^9$, $R^{10}$ and $R^{11}$ are each as defined below and where the arrow represents a bond to the respective [X-Y] moiety, $R^1$ is hydrogen, ($C_1$-$C_7$)-alkyl, aryl, heteroaryl, heterocyclyl, ($C_3$-$C_{10}$)-cycloalkyl, ($C_2$-$C_7$)-alkenyl, ($C_2$-$C_7$)-alkynyl, ($C_1$-$C_7$)-alkoxy-($C_1$-$C_7$)-alkyl, hydroxy-($C_1$-$C_7$)-alkyl, ($C_1$-$C_7$)-haloalkyl, ($C_2$-$C_7$)-haloalkenyl, ($C_1$-$C_7$)-haloalkoxy-($C_1$-$C_7$)-alkyl, ($C_1$-$C_7$)-alkylthio-($C_1$-$C_7$)-alkyl, aryl-($C_1$-$C_7$)-alkyl, heterocyclyl-($C_1$-$C_7$)-alkyl, ($C_3$-$C_7$)-halocycloalkyl, ($C_4$-$C_7$)-cycloalkenyl, ($C_1$-$C_7$)-alkoxy-($C_1$-$C_7$)-alkoxy-($C_1$-$C_7$)-alkyl, ($C_1$-$C_7$)-alkoxy-($C_1$-$C_7$)-haloalkyl, ($C_1$-$C_7$)-haloalkoxy-($C_1$-$C_7$)-haloalkyl, ($C_3$-$C_8$)-cycloalkyl-($C_1$-$C_7$)-alkyl, $R^2$ is hydrogen, ($C_1$-$C_7$)-alkyl, ($C_1$-$C_7$)-alkoxy-($C_1$-$C_7$)-alkyl, ($C_1$-$C_7$)-alkoxy-($C_1$-$C_7$)-alkoxy-($C_1$-$C_7$)-alkyl, ($C_2$-$C_7$)-alkenyl, ($C_2$-$C_7$)-alkynyl, ($C_1$-$C_7$)-alkylcarbonyl, arylcarbonyl, heteroarylcarbonyl, ($C_3$-$C_7$)-cycloalkylcarbonyl, ($C_2$-$C_7$)-alkenylcarbonyl, heterocyclylcarbonyl, ($C_1$-$C_7$)-alkoxycarbonyl, ($C_2$-$C_7$)-alkenyloxycarbonyl, aryloxy-($C_1$-$C_7$)-alkyl, aryl-($C_1$-$C_7$)-alkoxycarbonyl, ($C_3$-$C_7$)-cycloalkoxycarbonyl, ($C_3$-$C_7$)-cycloalkyl-($C_1$-$C_7$)-alkoxycarbonyl, aryl-($C_1$-$C_7$)-alkoxy-($C_1$-$C_7$)-alkyl, aryl-($C_1$-$C_7$)-alkyl, ($C_1$-$C_7$)-alkoxy-($C_1$-$C_7$)-alkoxy-($C_1$-$C_7$)-alkyl, ($C_1$-$C_7$)-alkylthio-($C_1$-$C_7$)-alkyl, tris[($C_1$-$C_7$)-alkyl]silyl, ($C_1$-$C_7$)-alkylbis-[($C_1$-$C_7$)-alkyl]silyl, ($C_1$-$C_7$)-alkylbis(aryl)silyl, arylbis[($C_1$-$C_7$)-alkyl]silyl, ($C_3$-$C_7$)-cycloalkylbis[($C_1$-$C_7$)-alkyl]silyl, halobis[($C_1$-$C_7$)-alkyl]silyl, tris[($C_1$-$C_7$)-alkyl]silyl-($C_1$-$C_7$)-alkoxy-($C_1$-$C_7$)-alkyl, tris[($C_1$-$C_7$)-alkyl]silyl-($C_1$-$C_7$)-alkyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, 2, n is 0, 1, 2, $R^3$ and $R^4$ are each independently hydrogen, ($C_1$-$C_7$)-alkyl, halogen, ($C_3$-$C_7$)-cycloalkyl, ($C_1$-$C_7$)-alkoxy, aryl, heterocyclyl, heteroaryl, aryl-($C_1$-$C_7$)-alkyl, ($C_1$-$C_7$)-alkylthio, ($C_1$-$C_7$)-haloalkyl, ($C_1$-$C_7$)-haloalkyloxy, ($C_1$-$C_7$)-haloalkylthio, ($C_1$-$C_7$)-alkoxy-($C_1$-$C_7$)-alkyl, ($C_1$-$C_7$)-alkylthio-($C_1$-$C_7$)-alkyl, heteroaryl-($C_1$-$C_7$)-alkyl, heterocyclyl-($C_1$-$C_7$)-alkyl, ($C_1$-$C_7$)-alkoxy-($C_1$-$C_7$)-haloalkyl, ($C_1$-$C_7$)-haloalkoxy-($C_1$-$C_7$)-haloalkyl, ($C_2$-$C_7$)-alkynyl, ($C_2$-$C_7$)-alkenyl, $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, halogen, ($C_1$-$C_7$)-alkyl, ($C_1$-$C_7$)-haloalkyl, ($C_3$-$C_7$)-cycloalkyl, ($C_3$-$C_7$)-cycloalkyl-($C_1$-$C_7$)-alkyl, $R^7$ is hydrogen, halogen, ($C_1$-$C_8$)-alkyl, ($C_1$-$C_8$)-haloalkyl, ($C_1$-$C_7$)-haloalkoxy, ($C_1$-$C_7$)-haloalkoxy-($C_1$-$C_7$)-alkyl, ($C_1$-$C_7$)-haloalkoxy-($C_1$-$C_7$)-haloalkyl, ($C_1$-$C_7$)-alkoxy-($C_1$-$C_7$)-haloalkyl, ($C_1$-$C_7$)-alkynyloxy-($C_1$-$C_7$)-haloalkyl, ($C_1$-$C_7$)-alkenyloxy-($C_1$-$C_7$)-haloalkyl, ($C_1$-$C_7$)-alkylthio, ($C_1$-$C_7$)-haloalkylthio, optionally substituted phenyl, aryl-($C_1$-$C_7$)-alkyl, heteroaryl, heteroaryl-($C_1$-$C_7$)-alkyl, heterocyclyl, ($C_1$-$C_7$)-alkoxy, hydroxyl, ($C_1$-$C_7$)-alkylcarbonyloxy, arylcarbonyloxy, ($C_3$-$C_7$)-cycloalkylcarbonyloxy, tris[($C_1$-$C_7$)-alkyl]silyloxy, bis[($C_1$-$C_7$)-alkyl]-[($C_1$-$C_7$)-alkyl]silyloxy, ($C_1$-$C_7$)-alkylbisarylsilyloxy, arylbis[($C_1$-$C_7$)-alkyl]silyloxy, ($C_3$-$C_7$)-cycloalkylbis[($C_1$-$C_7$)-alkyl]silyloxy, halobis[($C_1$-$C_7$)-alkyl]silyloxy, tris[($C_1$-$C_7$)-alkyl]silyl-($C_1$-$C_7$)-alkoxy-($C_1$-$C_7$)-alkyloxy, tris[($C_1$-$C_7$)-alkyl]silyl-($C_1$-$C_7$)-alkyloxy, ($C_3$-$C_7$)-cycloalkyl, ($C_3$-$C_7$)-cycloalkyl-($C_1$-$C_7$)-alkyl, $R^6$ and $R^7$ together with the atoms to which they are bonded form a fully saturated 3- to 6-membered ring optionally interrupted by heteroatoms and optionally having further substitution, $R^8$ is hydrogen, ($C_1$-$C_7$)-alkyl, ($C_1$-$C_7$)-alkoxy-($C_1$-$C_7$)-alkyl, ($C_3$-$C_7$)-cycloalkyl, ($C_3$-$C_7$)-cycloalkyl-($C_1$-$C_7$)-alkyl, optionally substituted phenyl, aryl-($C_1$-$C_7$)-alkyl, heteroaryl-($C_1$-$C_7$)-alkyl, bisaryl-($C_1$-$C_7$)-alkyl, trisaryl-($C_1$-$C_7$)-alkyl, ($C_2$-$C_7$)-alkenyl, ($C_4$-$C_7$)-cycloalkenyl-($C_1$-$C_7$)-alkyl, ($C_2$-$C_7$)-alkynyl-($C_1$-$C_7$)-alkyl, tri-($C_1$-$C_7$)-alkylsilyl-($C_1$-$C_7$)-alkoxy-($C_1$-$C_7$)-alkyl, ($C_1$-$C_7$)-alkoxy-($C_1$-$C_7$)-alkoxy-($C_1$-$C_7$)-alkyl, ($C_1$-$C_7$)-alkylthio-($C_1$-$C_7$)-alkyl, ($C_1$-$C_7$)-haloalkyl, arylsulphonyl-($C_1$-$C_7$)-alkyl, tri-($C_1$-$C_7$)-alkylsilyl, ($C_1$-$C_7$)-alkyl(bisaryl)silyl, ($C_1$-$C_7$)-alkyl(bis-($C_1$-$C_7$)-alkyl)silyl, bis($C_1$-$C_7$)-alkylamino-($C_1$-$C_7$)-alkyl, heterocyclyl-($C_1$-$C_7$)-alkyl, ($C_2$-$C_7$)-alkynyl, cyano-($C_1$-$C_7$)-alkyl, heterocyclyl, optionally further-substituted phenyl, $R^9$ is hydrogen, ($C_1$-$C_7$)-alkyl, ($C_3$-$C_7$)-cycloalkyl, halogen, ($C_2$-$C_7$)-alkynyl-($C_1$-$C_7$)-alkyl, ($C_1$-$C_7$)-haloalkyl, ($C_2$-$C_7$)-alkynyl, ($C_2$-$C_7$)-alkenyl, cyano-($C_1$-$C_7$)-alkyl, ($C_3$-

$C_7$)-cycloalkyl-($C_1$-$C_7$)-alkyl, aryl-($C_1$-$C_7$)-alkyl, heteroaryl-($C_1$-$C_7$)-alkyl, ($C_1$-$C_7$)-alkylcarbonyl, ($C_1$-$C_7$)-alkoxycarbonyl, ($C_2$-$C_7$)-alkenyloxycarbonyl, ($C_2$-$C_7$)-alkenyl-($C_1$-$C_7$)-alkyloxycarbonyl, aryl-($C_1$-$C_7$)-alkyloxycarbonyl, ($C_3$-$C_7$)-cycloalkoxycarbonyl, ($C_3$-$C_7$)-cycloalkyl-($C_1$-$C_7$)-alkoxycarbonyl, ($C_1$-$C_7$)-alkylsulphonyl, arylsulphonyl, ($C_3$-$C_7$)-cycloalkylsulphonyl, ($C_1$-$C_7$)-alkylsulphinyl, arylsulphinyl, ($C_3$-$C_7$)-cycloalkylsulphinyl, ($C_1$-$C_7$)-alkoxycarbonyl-($C_1$-$C_7$)-alkyl, hydroxycarbonyl-($C_1$-$C_7$)-alkyl, aryl-($C_1$-$C_7$)-alkoxycarbonyl-($C_1$-$C_7$)-alkyl, ($C_3$-$C_7$)-cycloalkyl-($C_1$-$C_7$)-alkoxycarbonyl-($C_1$-$C_7$)-alkyl, ($C_1$-$C_7$)-alkoxycarbonyl-($C_3$-$C_7$)-cycloalkyl, hydroxycarbonyl-($C_3$-$C_7$)-cycloalkyl, aryl-($C_1$-$C_7$)-alkoxycarbonyl-($C_3$-$C_7$)-cycloalkyl, ($C_2$-$C_7$)-alkenyloxycarbonyl-($C_3$-$C_7$)-cycloalkyl, aminocarbonyl-($C_3$-$C_7$)-cycloalkyl, ($C_1$-$C_7$)-alkylaminocarbonyl-($C_3$-$C_7$)-cycloalkyl, ($C_3$-$C_7$)-cycloalkylaminocarbonyl-($C_3$-$C_7$)-cycloalkyl, ($C_1$-$C_7$)-alkoxycarbonyl-($C_4$-$C_7$)-cycloalkenyl, hydroxycarbonyl-($C_4$-$C_7$)-cycloalkenyl, bis-($C_1$-$C_7$)-alkylamino-($C_1$-$C_7$)-alkyl, hydroxycarbonyl-heterocyclyl, ($C_1$-$C_7$)-alkoxycarbonylheterocyclyl, ($C_2$-$C_7$)-alkenyloxycarbonylheterocyclyl, ($C_2$-$C_7$)-alkenyl-($C_1$-$C_7$)-alkoxycarbonylheterocyclyl, aryl-($C_1$-$C_7$)-alkoxycarbonylheterocyclyl, ($C_3$-$C_7$)-cycloalkoxycarbonylheterocyclyl, ($C_3$-$C_7$)-cycloalkyl-($C_1$-$C_7$)-alkoxycarbonylheterocyclyl, aminocarbonylheterocyclyl, ($C_1$-$C_7$)-alkylaminocarbonylheterocyclyl, bis-($C_1$-$C_7$)-alkylaminocarbonylheterocyclyl, ($C_3$-$C_7$)-cycloalkylaminocarbonylheterocyclyl, aryl-($C_1$-$C_7$)-alkylaminocarbonylheterocyclyl, ($C_2$-$C_7$)-alkenylaminocarbonylheterocyclyl, hydroxycarbonylheterocyclyl-($C_1$-$C_7$)-alkyl, ($C_1$-$C_7$)-alkoxycarbonylheterocyclyl-($C_1$-$C_7$)-alkyl, hydroxycarbonyl-($C_3$-$C_7$)-cycloalkyl-($C_1$-$C_7$)-alkyl, ($C_1$-$C_7$)-alkoxycarbonyl-($C_3$-$C_7$)-cycloalkyl-($C_1$-$C_7$)-alkyl, hydroxyl, ($C_1$-$C_7$)-alkoxy, heterocyclyl, heterocyclyl-($C_1$-$C_7$)-alkyl, optionally substituted phenyl, $R^{10}$ is hydrogen, ($C_1$-$C_7$)-alkyl, ($C_3$-$C_7$)-cycloalkyl, halogen, ($C_1$-$C_7$)-haloalkyl, ($C_2$-$C_7$)-alkynyl, ($C_2$-$C_7$)-alkenyl, cyano-($C_1$-$C_7$)-alkyl, aryl-($C_1$-$C_7$)-alkyl, heteroaryl-($C_1$-$C_7$)-alkyl, ($C_1$-$C_7$)-alkylcarbonyl, ($C_1$-$C_7$)-alkoxycarbonyl, ($C_1$-$C_7$)-alkylsulphonyl, arylsulphonyl, ($C_3$-$C_7$)-cycloalkylsulphonyl, ($C_1$-$C_7$)-alkylsulphinyl, arylsulphinyl, ($C_3$-$C_7$)-cycloalkylsulphinyl, ($C_1$-$C_7$)-alkoxycarbonyl-($C_1$-$C_7$)-alkyl, $R^9$ and $R^{10}$ together with the nitrogen to which they are bonded form an optionally halogen-, ($C_1$-$C_7$)-alkyl-, ($C_1$-$C_7$)-haloalkyl-, ($C_1$-$C_7$)-alkoxy-, ($C_1$-$C_7$)-alkoxycarbonyl-, ($C_3$-$C_7$)-cycloalkoxycarbonyl-, ($C_3$-$C_7$)-cycloalkyl-($C_1$-$C_7$)-alkoxycarbonyl-, ($C_2$-$C_7$)-alkenyloxycarbonyl-, hydroxycarbonyl-, aminocarbonyl-, ($C_1$-$C_7$)-alkylaminocarbonyl-, ($C_3$-$C_7$)-cycloalkylaminocarbonyl-, aryl-($C_1$-$C_7$)-alkylaminocarbonyl-substituted three- to eight-membered ring optionally interrupted by O, S or N, or $R^9$ and $R^{10}$ together form an N-(bis-($C_1$-$C_6$)-alkyl)sulphanylidene, N-(aryl-($C_1$-$C_6$)-alkyl)sulphanylidene, N-(bis-($C_3$-$C_7$)-cycloalkyl)sulphanylidene, N—(($C_1$-$C_6$)-alkyl-($C_3$-$C_7$)-cycloalkyl)sulphanylidene group or an N,N-di-($C_1$-$C_6$)-alkylformylidene group and $R^{11}$ is hydrogen, ($C_1$-$C_7$)-alkyl, ($C_3$-$C_7$)-cycloalkyl, ($C_1$-$C_7$)-haloalkyl, ($C_1$-$C_7$)-alkoxy-($C_1$-$C_7$)-alkyl, ($C_1$-$C_7$)-alkylthio-($C_1$-$C_7$)-alkyl.

Very particular preference is given to compounds of the general formula (I) in which

[X-Y] represents the moieties and

[X-Y][1]

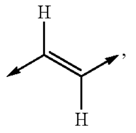

[X-Y][2]

Q represents the moieties

Q-1

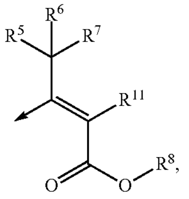

Q-2

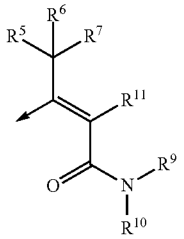

and

Q-3

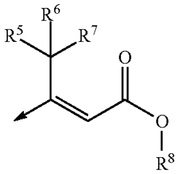

where $R^5$, $R^6$, $R^7$, $R^8$, $R^9$, $R^{10}$ and $R^{11}$ are each as defined below and where the arrow represents a bond to the respective [X-Y] moiety, $R^1$ is hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3- dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 1-methylcyclohexyl, 2-methylcyclohexyl, 3-methylcyclohexyl, 1-methoxycyclohexyl, 2-methoxycyclohexyl, 3-methoxycyclohexyl, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, hydroxymethyl, hydroxyethyl, hydroxypropyl, hydroxybutyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, difluoromethyl, 2,2-difluoroethyl, 2,2,2-trifluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, methylthiomethyl, methylthioethyl, ethylthioethyl, methylthio-n-propyl, ethylthio-n-propyl, aryl-($C_1$-$C_6$)-alkyl, heterocyclyl-($C_1$-$C_6$)-alkyl, ($C_3$-$C_6$)-halocycloalkyl, 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, methoxymethoxymethyl, methoxyethoxymethyl, methoxyethoxyethyl, methoxymethoxyethyl, ethoxy-n-propoxymethyl, ethoxy-n-propoxyethyl, ethoxyethoxymethyl, ethoxyethoxyethyl, $R^2$ is hydrogen, tert-butyldimethylsilyl, trimethylsilyl, triethylsilyl, tri-(isopropyl)silyl, tri-(n-propyl)silyl, dimethyl(phenyl)silyl, tert-butyldiphenylsilyl, diethylisopropylsilyl, Isopropyldimethylsilyl, tert-hexyldimethylsilyl, 2-(trimethylsilyl)ethoxymethyl, 2-(trimethylsilyl)ethyl, methyl, ethyl, n-propyl, isopropyl, n-butyl, isobutyl, n-pentyl, iso-pentyl, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, methoxymethoxymethyl, methoxyethoxymethyl, methoxyethoxyethyl, methoxymethoxyethyl, ethoxy-n-propoxymethyl, ethoxy-n-propoxyethyl, ethoxyethoxymethyl, ethoxyethoxyethyl, allyl, methylcarbonyl, ethylcarbonyl, n-propylcarbonyl, isopropylcarbonyl, n-butylcarbonyl, n-pentylcarbonyl, tert-butylcarbonyl, isobutylcarbonyl, iso-pentylcarbonyl, neo-pentylcarbonyl, n-hexylcarbonyl, arylcarbonyl, heteroarylcarbonyl, cyclopropylcarbonyl, cyclobutylcarbonyl, cyclopentylcarbonyl, cyclohexylcarbonyl, ($C_2$-$C_6$)-alkenylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, phenyloxycarbonyl, p-Cl-phenyloxycarbonyl, benzyloxycarbonyl, p-Cl-benzyloxycarbonyl, p-methoxybenzyloxycarbonyl, p-methylbenzyloxycarbonyl, cyclopropyloxycarbonyl, cyclobutyloxycarbonyl, cyclopentyloxycarbonyl, cyclohexyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, ethylthio-n-propyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, n is 0, 1, $R^3$ and $R^4$ are each independently hydrogen, methyl, ethyl, n-propyl, isopropyl, n-butyl, isobutyl, tert-butyl, n-hexyl, fluorine, chlorine, bromine, iodine, cyclopropyl, cyclobutyl, cyclopentyl, cyclohexyl, cyclopropyl-cyclopropyl, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl, methoxy, ethoxy, n-propoxy, isopropoxy, n-butyloxy, tert-butyloxy, isobutyloxy, n-pentyloxy, aryl, heterocyclyl, heteroaryl, benzyl, p-Cl-benzyl, p-F-benzyl, p-methoxybenzyl, p-methylbenzyl, methylthio, ethylthio, n-propylthio, n-butylthio, n-pentylthio, isopropylthio, isobutylthio, tert-butylthio, n-pentylthio, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluororethyl, 2-chloro-2,2-difluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, vinyl, prop-1-en-1-yl, but-1-en-1-yl, allyl, 1-methylprop-2-en-1-yl, 2-methylprop-2-en-1-yl, but-2-en-1-yl, 1-methyl-but-3-en-1-yl and 1-methyl-but-2-en-1-yl, 2-methylprop-1-en-1-yl, but-3-en-1-yl, pentenyl, 2-methylpentenyl, hexenyl, ethynyl, propargyl, 1-methylprop-2-yn-1-yl, 2-butynyl, 2-pentynyl, 2-hexynyl, but-2-yn-1-yl, but-3-yn-1-yl, 1-methyl-but-3-yn-1-yl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, methylthiomethyl, heteroaryl-($C_1$-$C_6$)-alkyl, heterocyclyl-($C_1$-$C_6$)-alkyl, $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, fluorine, chlorine, bromine, iodine, methyl, ethyl, n-propyl, n-butyl, isobutyl, isopropyl, n-pentyl, n-hexyl, isopentyl, trifluoromethyl, pentafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluoroethyl, 2-chloro-2,2-difluoroethyl, difluoro-tert-butyl, cyclopropyl, cyclobutyl, cyclopentyl, $R^7$ is hydrogen, fluorine, chlorine, bromine, iodine, ($C_1$-$C_8$)-alkyl, ($C_1$-$C_8$)-haloalkyl, ($C_1$-$C_6$)-haloalkoxy, ($C_1$-$C_6$)-haloalkoxy-($C_1$-$C_6$)-alkyl, ($C_1$-$C_6$)-haloalkoxy-($C_1$-$C_6$)-haloalkyl, ($C_1$-$C_6$)-alkoxy-($C_1$-$C_6$)-haloalkyl, ($C_1$-$C_6$)-alkynyloxy-($C_1$-$C_6$)-haloalkyl, ($C_1$-$C_6$)-alkenyloxy-($C_1$-$C_6$)-haloalkyl, ($C_1$-$C_6$)-alkylthio, ($C_1$-$C_6$)-haloalkylthio, optionally substituted phenyl, aryl-($C_1$-$C_6$)-alkyl, heteroaryl, heteroaryl-($C_1$-$C_6$)-alkyl, heterocyclyl, ($C_1$-$C_6$)-alkoxy, hydroxyl, ($C_1$-$C_6$)-alkylcarbonyloxy, arylcarbonyloxy, ($C_3$-$C_6$)-cycloalkylcarbonyloxy, tris[($C_1$-$C_6$)-alkyl]silyloxy, bis[($C_1$-$C_6$)-alkyl]-[($C_1$-$C_6$)-alkyl]silyloxy, ($C_1$-$C_6$)-alkylbisarylsilyloxy, arylbis[($C_1$-$C_6$)-alkyl]silyloxy, ($C_3$-$C_6$)-cycloalkylbis[($C_1$-$C_6$)-alkyl]silyloxy, halobis[($C_1$-$C_6$)-alkyl]silyloxy, tris[($C_1$-$C_6$)-alkyl]silyl-($C_1$-$C_6$)-alkoxy-($C_1$-$C_6$)-alkyloxy, tris[($C_1$-$C_6$)-alkyl]silyl-($C_1$-$C_6$)-alkyloxy, ($C_3$-$C_7$)-cycloalkyl, ($C_3$-$C_7$)-cycloalkyl-($C_1$-$C_6$)-alkyl, $R^6$ and $R^7$ together with the atoms to which they are bonded form a fully saturated 3- to 6-membered ring optionally interrupted by heteroatoms and optionally having further substitution, $R^8$ is hydrogen, ($C_1$-$C_6$)-alkyl, ($C_1$-$C_6$)-alkoxy-($C_1$-$C_6$)-alkyl, ($C_3$-$C_6$)-cycloalkyl, ($C_3$-$C_6$)-cycloalkyl-($C_1$-$C_6$)-alkyl, optionally substituted phenyl, aryl-($C_1$-$C_6$)-alkyl, heteroaryl-($C_1$-$C_6$)-alkyl, bisaryl-($C_1$-$C_6$)-alkyl, trisaryl-($C_1$-$C_6$)-alkyl, ($C_2$-$C_6$)-alkenyl, ($C_4$-$C_6$)-cycloalkenyl-($C_1$-$C_6$)-alkyl, ($C_2$-$C_6$)-alkynyl-($C_1$-$C_6$)-alkyl, tri-($C_1$-$C_6$)-alkylsilyl-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkylthio-($C_1$-$C_6$)-alkyl, ($C_1$-$C_6$)-haloalkyl, arylsulphonyl-($C_1$-$C_6$)-alkyl, tri-($C_1$-$C_6$)-alkylsilyl, ($C_1$-$C_6$)-alkyl(bisaryl)silyl, ($C_1$-$C_6$)-alkyl(bis-($C_1$-$C_6$)-alkyl)silyl, bis($C_1$-$C_6$)-alkylamino-($C_1$-$C_6$)-alkyl, heterocyclyl-($C_1$-$C_6$)-alkyl, ($C_2$-$C_6$)-alkynyl, cyano-($C_1$-$C_6$)-alkyl, heterocyclyl, optionally further-substituted phenyl, $R^9$ is hydrogen, ($C_1$-$C_6$)-alkyl, ($C_3$-$C_6$)-cycloalkyl, halogen, ($C_2$-$C_6$)-alkynyl-($C_1$-$C_6$)-alkyl, ($C_1$-$C_6$)-haloalkyl, ($C_2$-$C_6$)-alkynyl, ($C_2$-$C_6$)-alkenyl, cyano-($C_1$-$C_6$)-alkyl, ($C_3$-$C_6$)-cycloalkyl-($C_1$-$C_6$)-alkyl, aryl-($C_1$-$C_6$)-alkyl, heteroaryl-($C_1$-$C_6$)-alkyl, ($C_1$-$C_6$)-alkylcarbonyl, ($C_1$-$C_6$)-alkoxycarbonyl, ($C_2$-$C_6$)-alkenyloxycarbonyl, ($C_2$-$C_{86}$)-alkenyl-($C_1$-$C_6$)-alkyloxycarbonyl, aryl-($C_1$-$C_6$)-alkyloxycarbonyl, ($C_3$-$C_6$)-cycloalkoxycarbonyl, ($C_3$-$C_6$)-cycloalkyl-($C_1$-$C_6$)-alkoxycarbonyl, ($C_1$-$C_6$)-alkylsulphonyl, arylsulphonyl, ($C_3$-$C_6$)-cycloalkylsulphonyl, ($C_1$-$C_6$)-alkylsulphinyl, arylsulphinyl, ($C_3$-$C_6$)-cycloalkylsulphinyl, ($C_1$-$C_6$)-alkoxycarbonyl-($C_1$-$C_6$)-alkyl, hydroxycarbonyl-($C_1$-$C_6$)-alkyl, aryl-($C_1$-$C_6$)-alkoxycarbonyl-($C_1$-$C_6$)-alkyl, ($C_3$-$C_6$)-cycloalkyl-($C_1$-$C_6$)-alkoxycarbonyl-($C_1$-$C_6$)-alkyl, ($C_1$-$C_6$)-alkoxycarbonyl-($C_3$-$C_6$)-cycloalkyl, hydroxycarbonyl-($C_3$-$C_6$)-cycloalkyl, aryl-($C_1$-$C_6$)-alkoxycarbonyl-($C_3$-$C_6$)-cycloalkyl, ($C_2$-$C_6$)-alkenyloxycarbonyl-($C_3$-$C_6$)-cycloalkyl, aminocarbonyl-($C_3$-$C_6$)-cycloalkyl, ($C_1$-$C_6$)-alkylaminocarbonyl-($C_3$-$C_6$)-cycloalkyl, ($C_3$-$C_6$)-cycloalkylaminocarbonyl-($C_3$-$C_6$)-cycloalkyl, ($C_1$-$C_6$)-alkoxycarbonyl-($C_4$-$C_6$)-cycloalkenyl, hydroxycarbonyl-($C_4$-$C_6$)-cycloalkenyl, bis-($C_1$-$C_6$)-alkylamino-($C_1$-$C_6$)-alkyl, hydroxycarbonyl-heterocyclyl, ($C_1$-$C_6$)-alkoxycarbonylheterocyclyl, ($C_2$-$C_6$)-alkenyloxycarbonylheterocyclyl, ($C_2$-$C_6$)-alkenyl-($C_1$-$C_6$)-alkoxycarbonylheterocyclyl, aryl-($C_1$-$C_6$)-alkoxycarbonylheterocyclyl, ($C_3$-$C_6$)-cycloalkoxycarbonylheterocyclyl, ($C_3$-$C_6$)-cycloalkyl-($C_1$-$C_6$)-alkoxycarbonylheterocyclyl, aminocarbonylheterocyclyl, ($C_1$-$C_6$)-alkylaminocarbonylheterocyclyl, bis-($C_1$-$C_6$)-alkylaminocarbonylheterocyclyl, ($C_3$-$C_6$)-cycloalkylaminocarbonylheterocyclyl, aryl-($C_1$-$C_6$)-alkylaminocarbonylheterocyclyl, ($C_2$-$C_6$)-alkenylaminocarbonylheterocyclyl, hydroxycarbonylheterocyclyl-($C_1$-$C_6$)-alkyl, ($C_1$-$C_6$)-alkoxycarbonylheterocyclyl-($C_1$-$C_6$)-alkyl, hydroxycarbonyl-($C_3$-$C_6$)-cycloalkyl-($C_1$-$C_6$)-alkyl, ($C_1$-$C_6$)-alkoxycarbonyl-($C_3$-$C_6$)-cycloalkyl-($C_1$-$C_6$)-alkyl, hydroxyl, ($C_1$-$C_6$)-alkoxy, heterocyclyl, heterocyclyl-($C_1$-$C_6$)-alkyl, optionally substituted phenyl, $R^{10}$ is hydrogen, ($C_1$-$C_6$)-alkyl, ($C_3$-$C_6$)-cycloalkyl, halogen, ($C_1$-$C_6$)-haloalkyl, ($C_2$-$C_6$)-alkynyl, ($C_2$-$C_6$)-alkenyl, cyano-($C_1$-$C_6$)-alkyl, aryl-($C_1$-$C_6$)-alkyl, heteroaryl-($C_1$-$C_6$)-alkyl, ($C_1$-$C_6$)-alkylcarbonyl, ($C_1$-$C_6$)-alkoxycarbonyl, ($C_1$-$C_6$)-alkylsulphonyl, arylsulphonyl, ($C_3$-$C_6$)-cycloalkylsulphonyl, ($C_1$-$C_6$)-alkylsulphinyl, arylsulphinyl, ($C_3$-$C_6$)-cycloalkylsulphinyl, ($C_1$-$C_6$)-alkoxycarbonyl-($C_1$-$C_6$)-alkyl, $R^9$ and $R^{10}$ together with the nitrogen to which they are bonded form an optionally fluorine-, chlorine-, bromine-, iodine-, ($C_1$-$C_6$)-alkyl-, ($C_1$-$C_6$)-haloalkyl-, ($C_1$-$C_6$)-alkoxy-, ($C_1$-$C_6$)-alkoxycarbonyl-, ($C_3$-$C_7$)-cycloalkoxycarbonyl-, ($C_3$-$C_6$)-cycloalkyl-($C_1$-$C_6$)-alkoxycarbonyl-, ($C_2$-$C_6$)-alkenyloxycarbonyl-, hydroxycarbonyl-, aminocarbonyl-, ($C_1$-$C_6$)-alkylaminocarbonyl-, ($C_3$-$C_7$)-cycloalkylaminocarbonyl-, aryl-($C_1$-$C_6$)-alkylaminocarbonyl-substituted three- to seven-membered ring optionally interrupted by O, S or N, or $R^9$ and $R^{10}$ together are N-(di-n-butylsulphanylidene), N-(diisopropylsulphanylidene), N-(di-n-propylsulphanylidene), N-(di-n-pentylsulphanylidene), N-(diisobutylsulphanylidene), N-(cyclobutylisopropylsulphanylidene), N-(n-propylisopropylsulphanylidene), N-(cyclopropylisopropylsulphanylidene), N-(isobutylisopropylsulphanylidene), N,N-dimethylformylidene, $R^{11}$ is hydrogen, $(C_1-C_6)$-alkyl, $(C_3-C_6)$-cycloalkyl, $(C_1-C_6)$-haloalkyl, $(C_1-C_6)$-alkoxy-$(C_1-C_6)$-alkyl, $(C_1-C_6)$-alkylthio-$(C_1-C_6)$-alkyl.

Specific preference is given to compounds of the formula (I) in which

[X-Y] represents the moieties

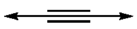 and $[X-Y]^1$

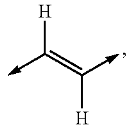, $[X-Y]^2$ $R^1$ is hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-methylcyclohexyl, 2-methylcyclohexyl, 3-methylcyclohexyl, 1-methoxycyclohexyl, 2-methoxycyclohexyl, 3-methoxycyclohexyl, aryl-$(C_1-C_8)$-alkyl, heterocyclyl-$(C_1-C_8)$-alkyl, $R^2$ is hydrogen, tert-butyldimethylsilyl, trimethylsilyl, triethylsilyl, tri(isopropyl)silyl, tri(n-propyl)silyl, dimethyl(phenyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, methyl, ethyl, allyl, methylcarbonyl, ethylcarbonyl, n-propylcarbonyl, isopropylcarbonyl, n-butylcarbonyl, tert-butylcarbonyl, isobutylcarbonyl, isopentylcarbonyl, neopentylcarbonyl, arylcarbonyl, heteroarylcarbonyl, cyclopropylcarbonyl, cyclobutylcarbonyl, cyclopentylcarbonyl, cyclohexylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, ethylthio-n-propyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, n is 0, 1, $R^3$ and $R^4$ are each independently hydrogen, methyl, ethyl, n-propyl, isopropyl, n-butyl, isobutyl, tert-butyl, fluorine, chlorine, bromine, iodine, cyclopropyl, cyclobutyl, cyclopentyl, cyclohexyl, methoxy, ethoxy, n-propoxy, isopropoxy, n-butyloxy, tert-butyloxy, isobutyloxy, n-pentyloxy, optionally substituted phenyl, heterocyclyl, heteroaryl, benzyl, p-Cl-benzyl, p-F-benzyl, p-methoxybenzyl, p-methylbenzyl, methylthio, ethylthio, n-propylthio, n-butylthio, n-pentylthio, isopropylthio, isobutylthio, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluoroethyl, 2-chloro-2,2-difluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, vinyl, prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, ethynyl, propargyl, 1-methylprop-2-yn-1-yl, 2-butynyl, 2-pentynyl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, methylthiomethyl, $R^3$ and $R^4$ together with the atom to which they are bonded form a fully saturated 3- to 6-membered ring optionally interrupted by heteroatoms and optionally having further substitution, and Q is one of the Q-1.1 to Q-3.55 moieties described in the table below.

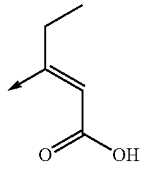

Q-1.1

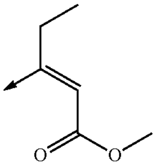

Q-1.2

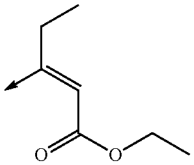

Q-1.3

Q-1.4
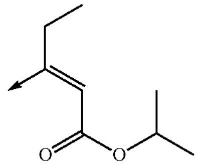
Q-1.5
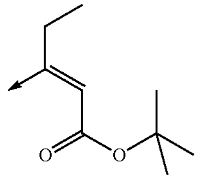
Q-1.6
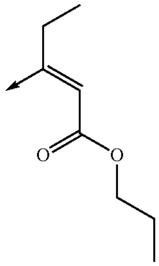
Q-1.7
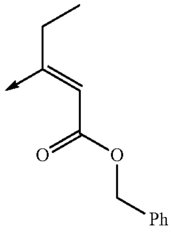
Q-1.8
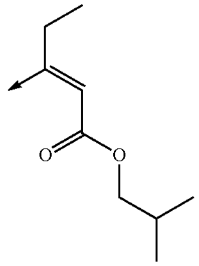
Q-1.9
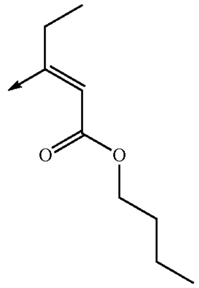
Q-1.10
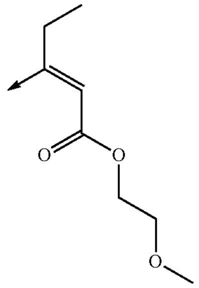
Q-1.11
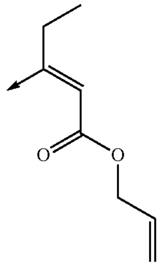
Q-1.12
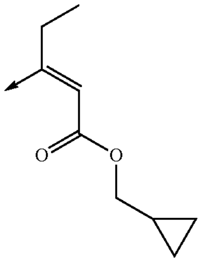
Q-1.13
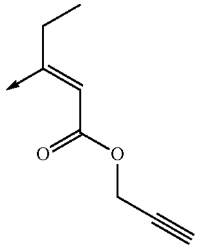
Q-1.14
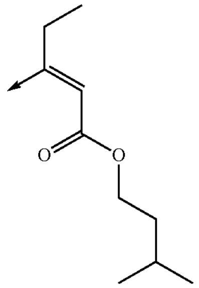
Q-1.15
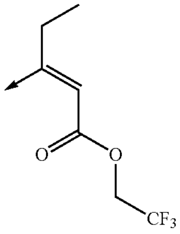

-continued
Q-1.16
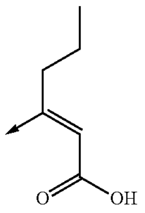
Q-1.17
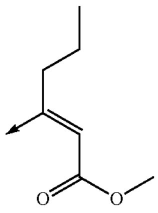
Q-1.18
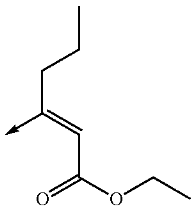
Q-1.19
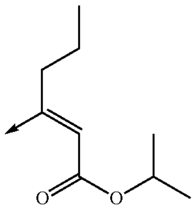
Q-1.20
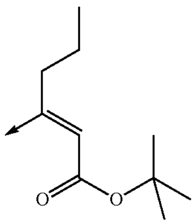
Q-1.21
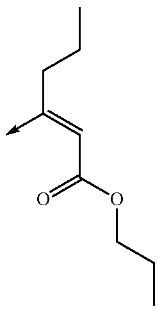
-continued
Q-1.22
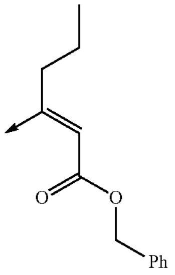
Q-1.23
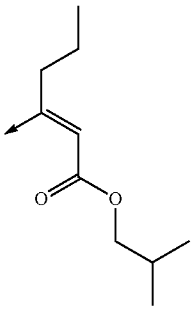
Q-1.24
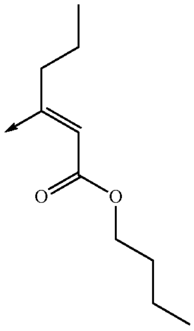
Q-1.25
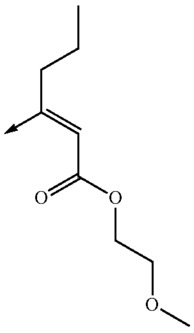
Q-1.26
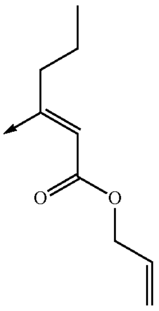

-continued
Q-1.27
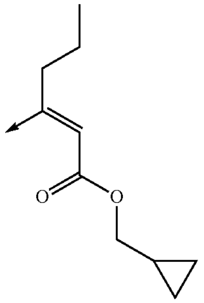
Q-1.28
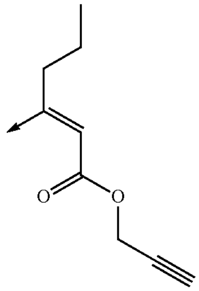
Q-1.29
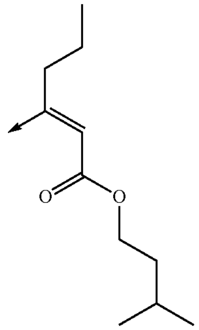
Q-1.30
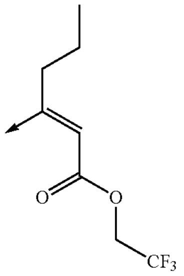
Q-1.31
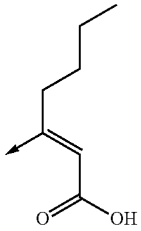
-continued
Q-1.32
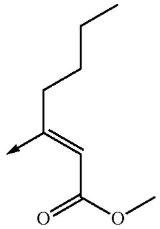
Q-1.33
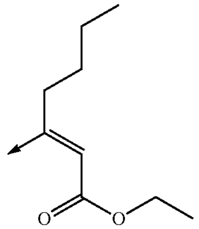
Q-1.34
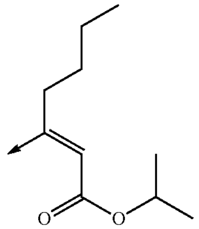
Q-1.35
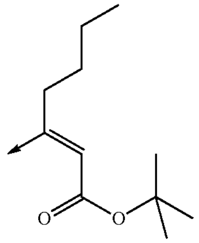
Q-1.36
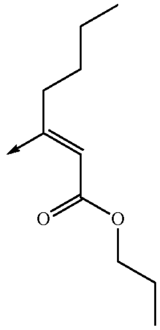
Q-1.37
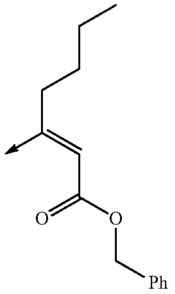

Q-1.38
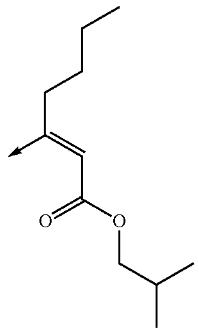
Q-1.39
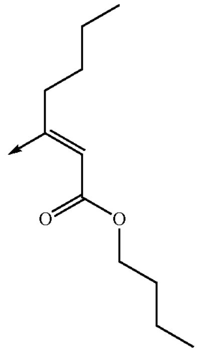
Q-1.40
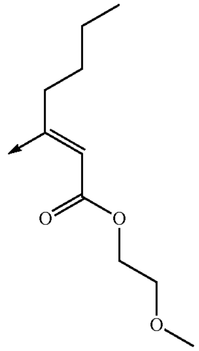
Q-1.41
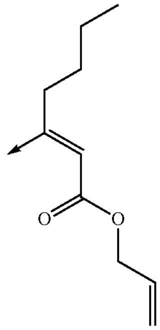
Q-1.42
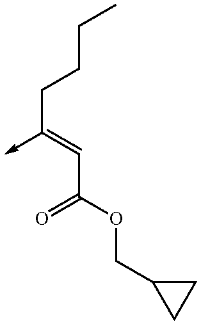
Q-1.43
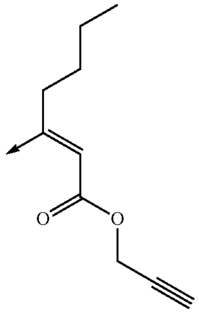
Q-1.44
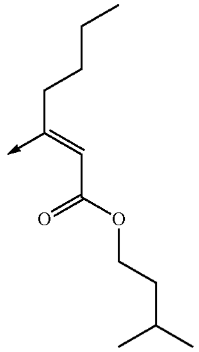
Q-1.45
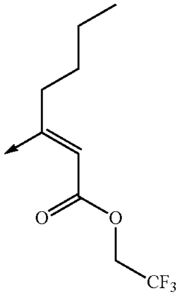
Q-1.46
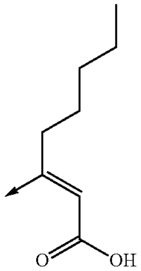

-continued
Q-1.47
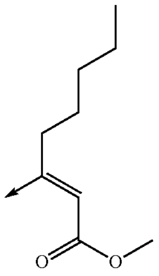
Q-1.48
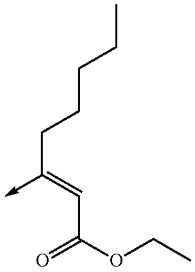
Q-1.49
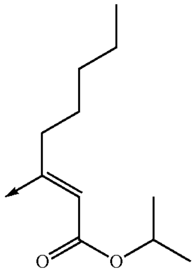
Q-1.50
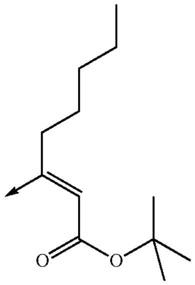
Q-1.51
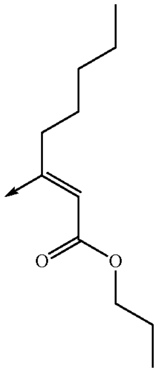
-continued
Q-1.52
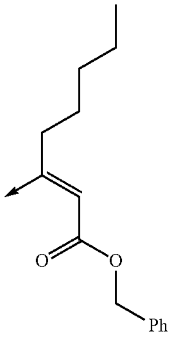
Q-1.53
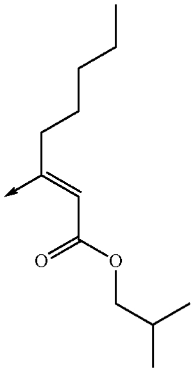
Q-1.54
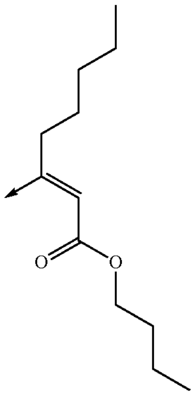
Q-1.55
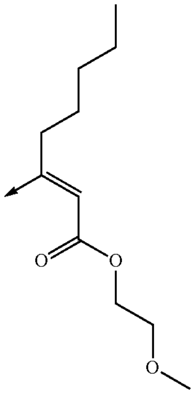

-continued
Q-1.56
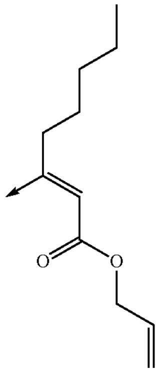
Q-1.57
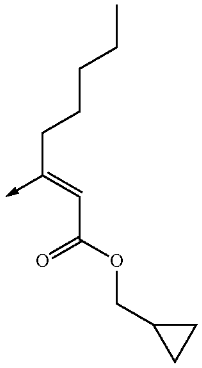
Q-1.58
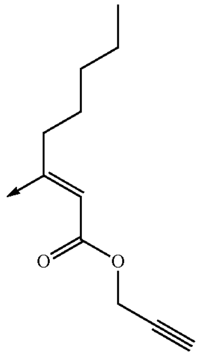
Q-1.59
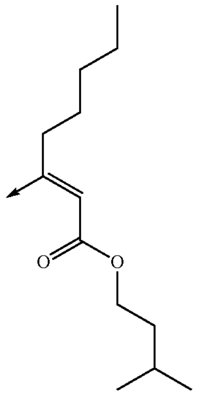
-continued
Q-1.60
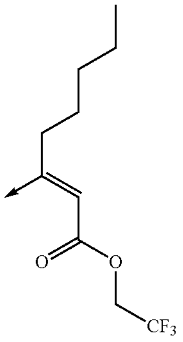
Q-1.61
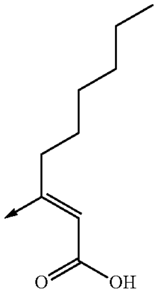
Q-1.62
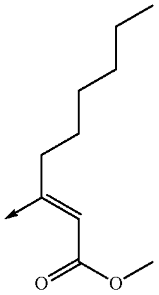
Q-1.63
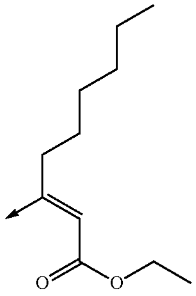
Q-1.64
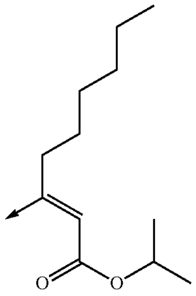

-continued
Q-1.65
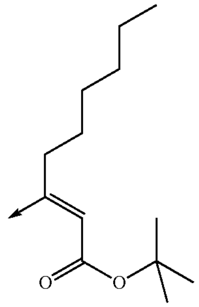
Q-1.66
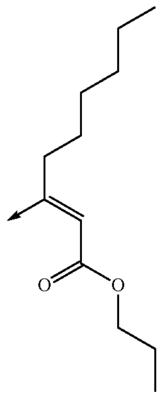
Q-1.67
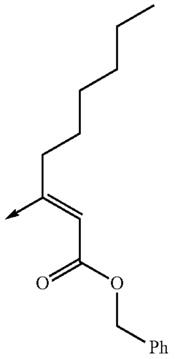
Q-1.68
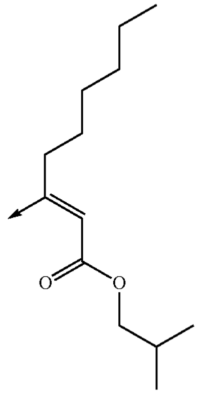
-continued
Q-1.69
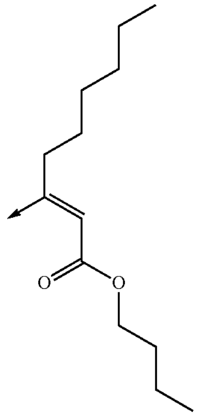
Q-1.70
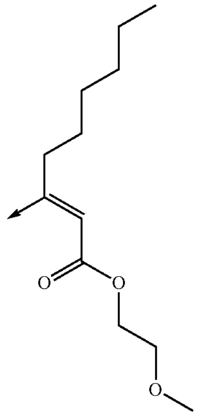
Q-1.71
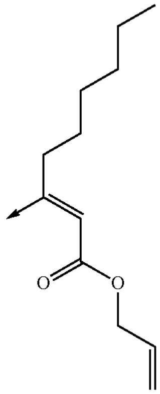
Q-1.72
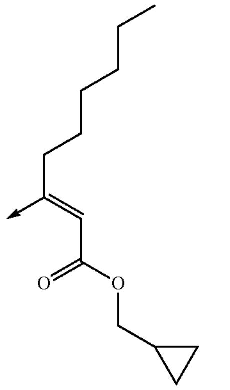

-continued
Q-1.73
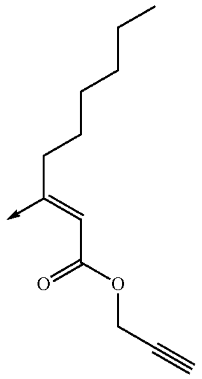
Q-1.74
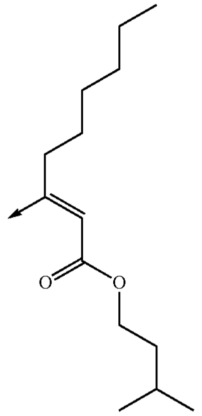
Q-1.75
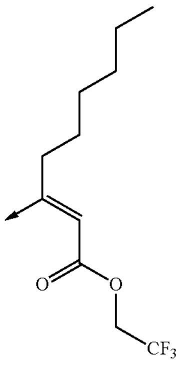
Q-1.76
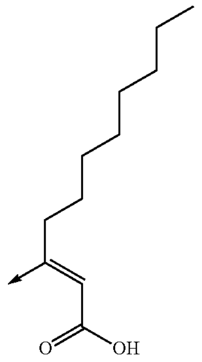
-continued
Q-1.77
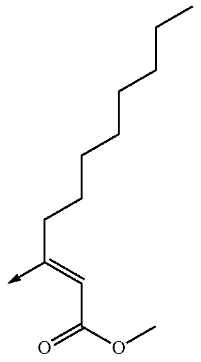
Q-1.78
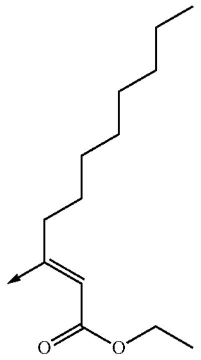
Q-1.79
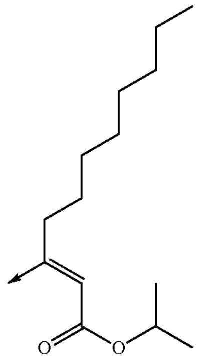
Q-1.80
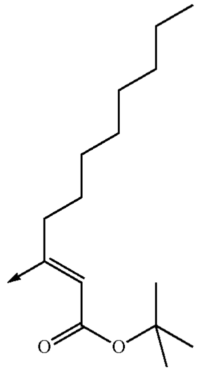

-continued
Q-1.81
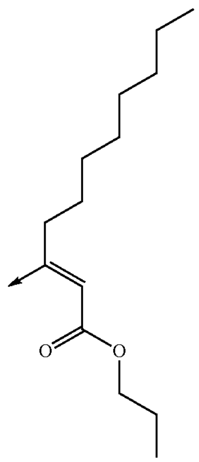
Q-1.82
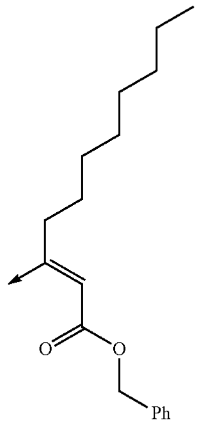
Q-1.83
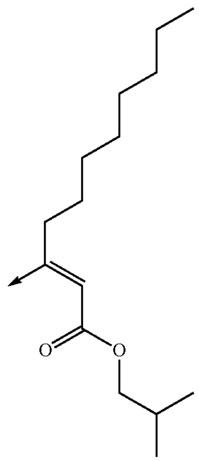
-continued
Q-1.84
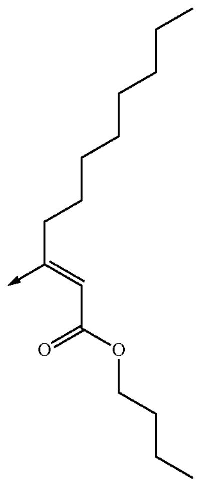
Q-1.85
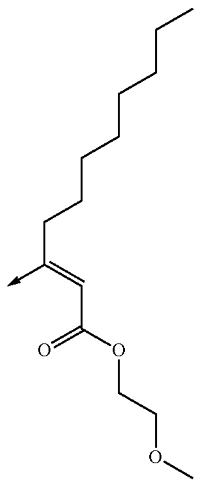
Q-1.86
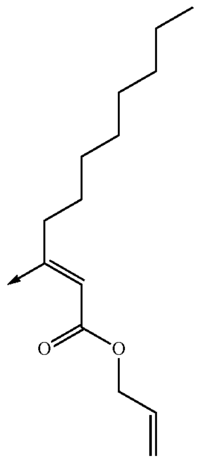

-continued
Q-1.87
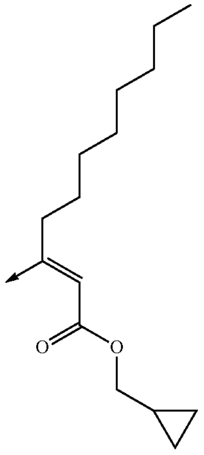
Q-1.88
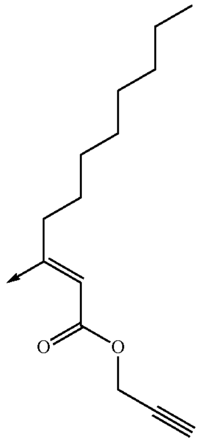
Q-1.89
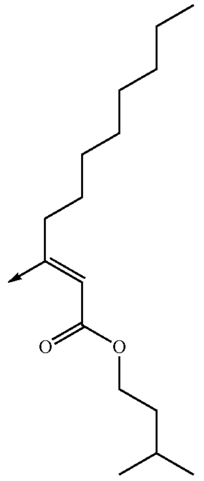
-continued
Q-1.90
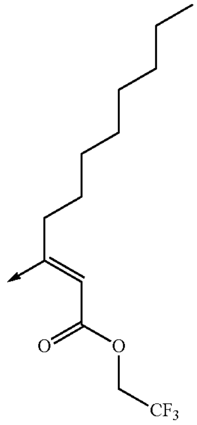
Q-1.91
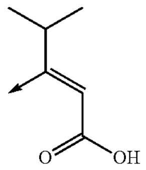
Q-1.92
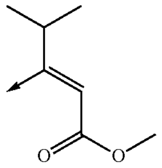
Q-1.93
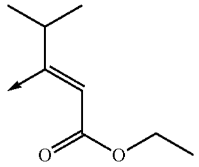
Q-1.94
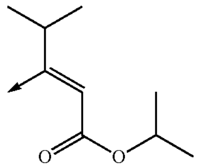
Q-1.95
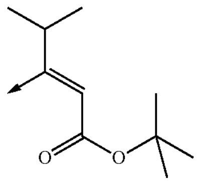
Q-1.96
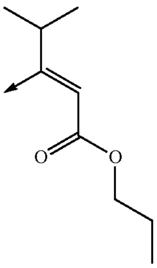

-continued
Q-1.97
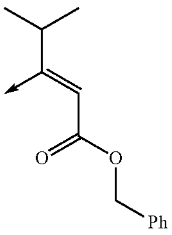
Q-1.98
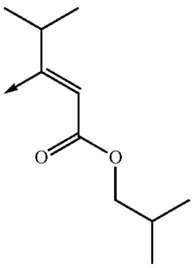
Q-1.99
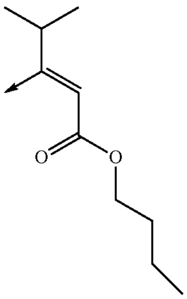
Q-1.100
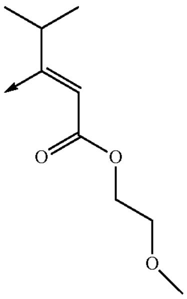
Q-1.101
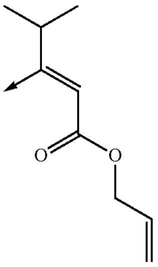
-continued
Q-1.102
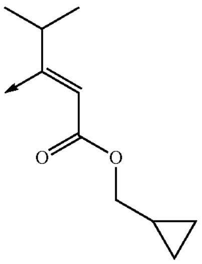
Q-1.103
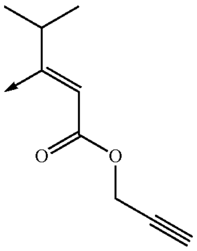
Q-1.104
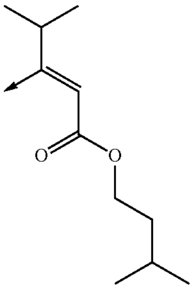
Q-1.105
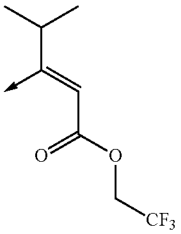
Q-1.106
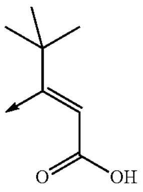
Q-1.107
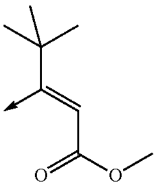

-continued
Q-1.108
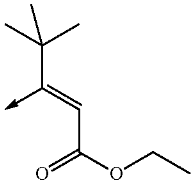
Q-1.109
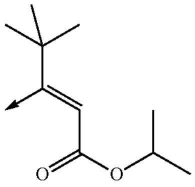
Q-1.110
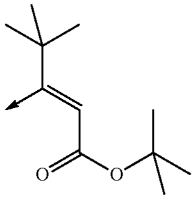
Q-1.111
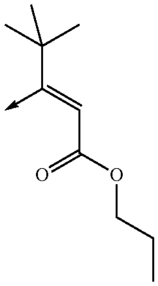
Q-1.112
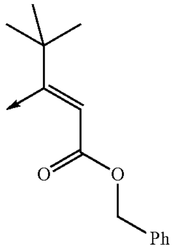
Q-1.113
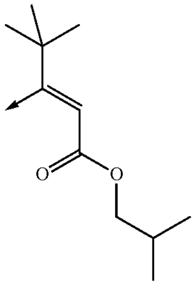
-continued
Q-1.114
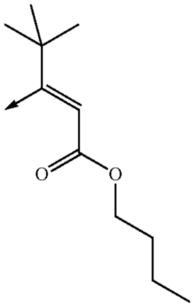
Q-1.115
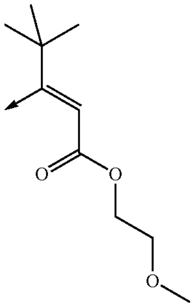
Q-1.116
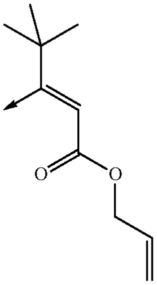
Q-1.117
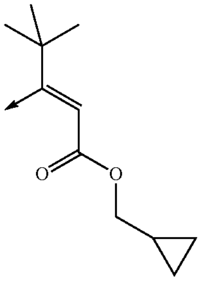
Q-1.118
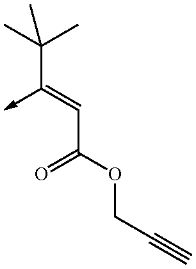

-continued
Q-1.119
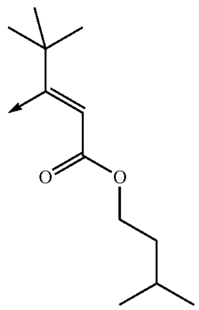
Q-1.120
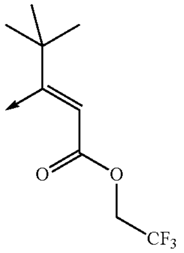
Q-1.121
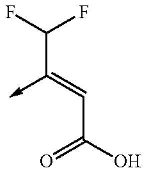
Q-1.122
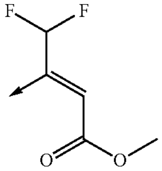
Q-1.123
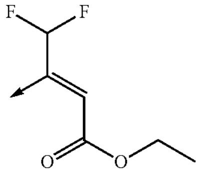
Q-1.124
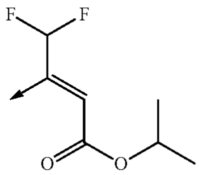
Q-1.125
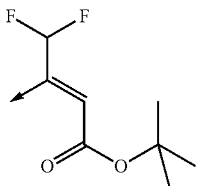
-continued
Q-1.126
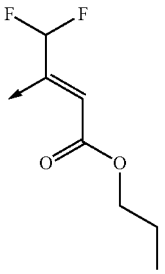
Q-1.127
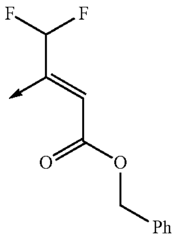
Q-1.128
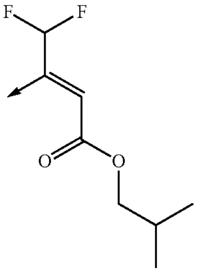
Q-1.129
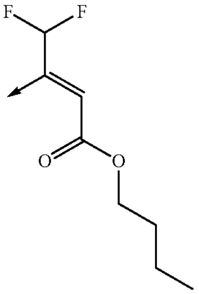
Q-1.130
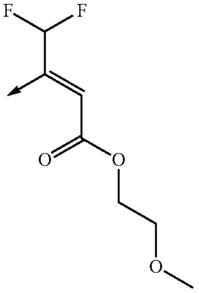

-continued
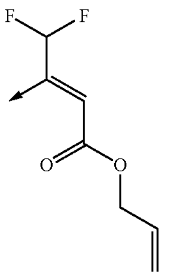
Q-1.131
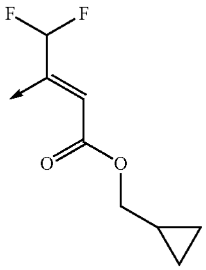
Q-1.132
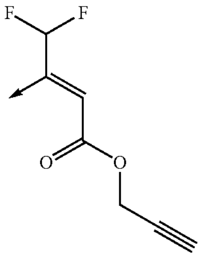
Q-1.133
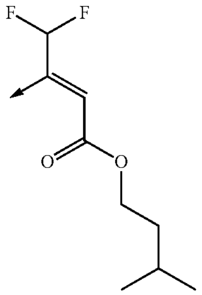
Q-1.134
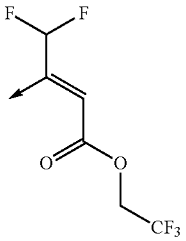
Q-1.135
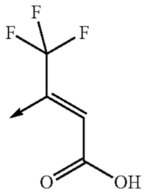
Q-1.136
-continued
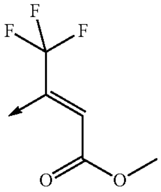
Q-1.137
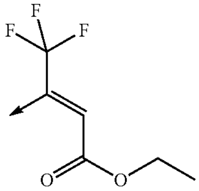
Q-1.138
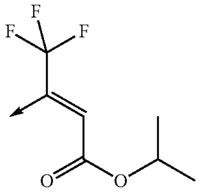
Q-1.139
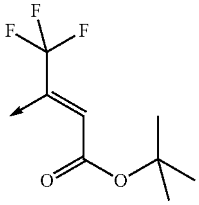
Q-1.140
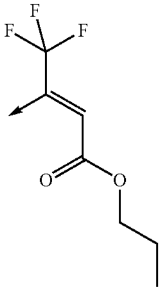
Q-1.141
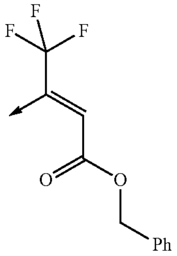
Q-1.142

-continued
Q-1.143
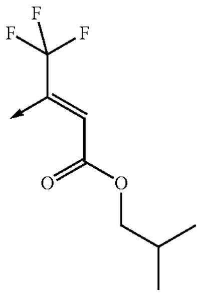
Q-1.144
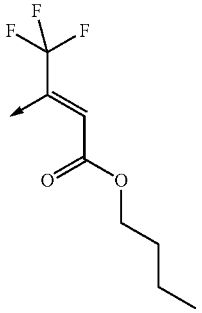
Q-1.145
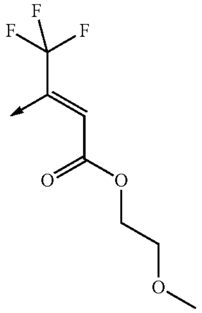
Q-1.146
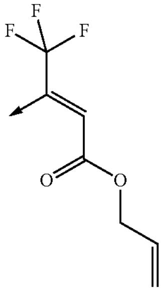
Q-1.147
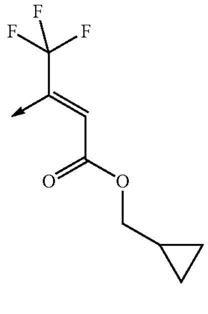
-continued
Q-1.148
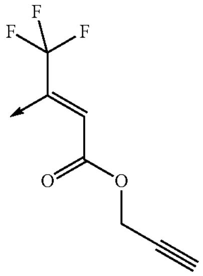
Q-1.149
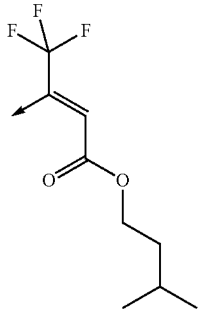
Q-1.150
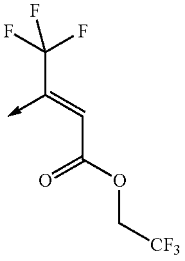
Q-1.151
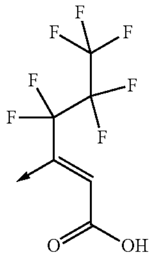
Q-1.152
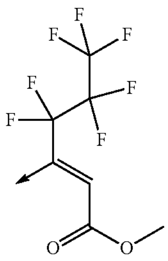

-continued
Q-1.153
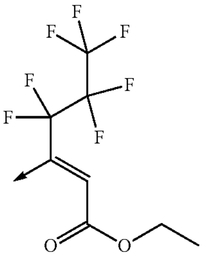
Q-1.154
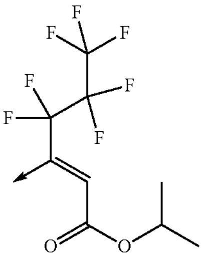
Q-1.155
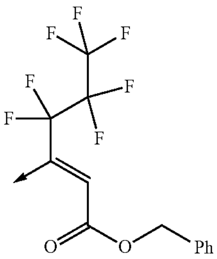
Q-1.156
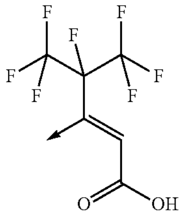
Q-1.157
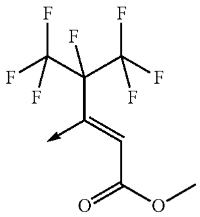
Q-1.158
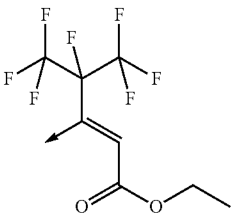
-continued
Q-1.159
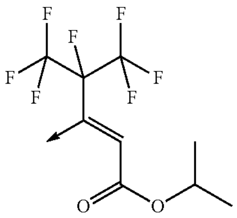
Q-1.160
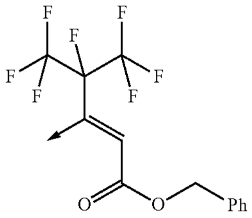
Q-1.161
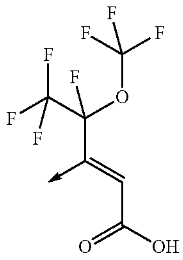
Q-1.162
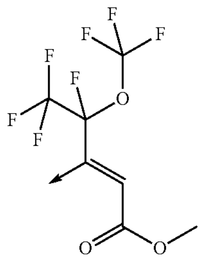
Q-1.163
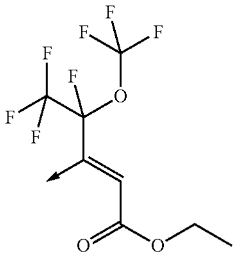
Q-1.164
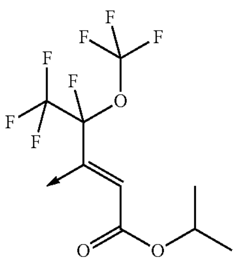

Q-1.165
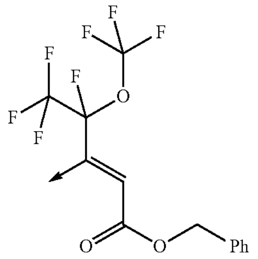
Q-1.166
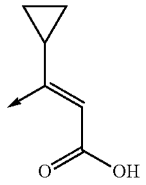
Q-1.167
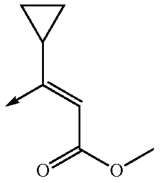
Q-1.168
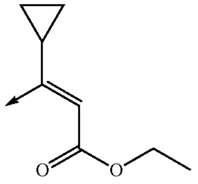
Q-1.169
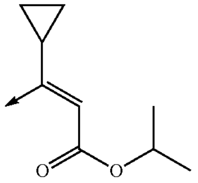
Q-1.170
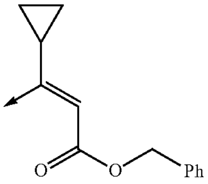
Q-1.171
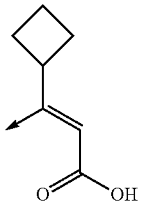
Q-1.172
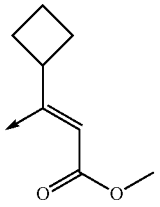
Q-1.173
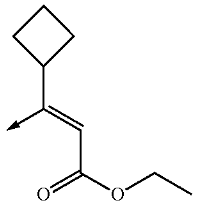
Q-1.174
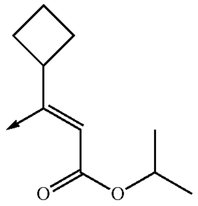
Q-1.175
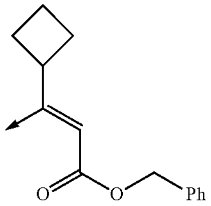
Q-1.176
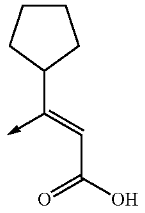
Q-1.177
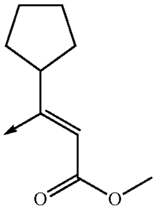
Q-1.178
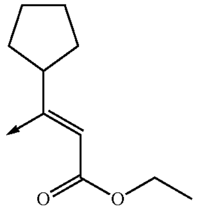
Q-1.179
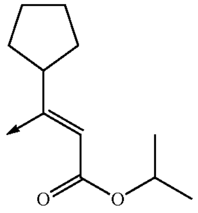

-continued
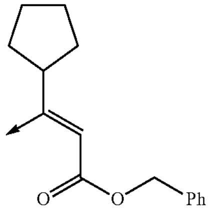
Q-1.180
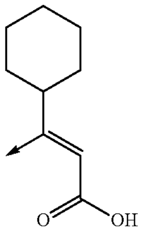
Q-1.181
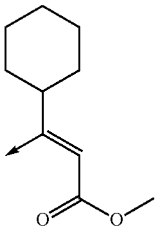
Q-1.182
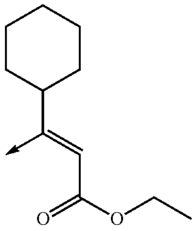
Q-1.183
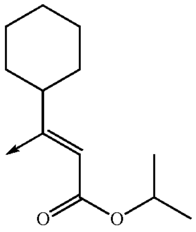
Q-1.184
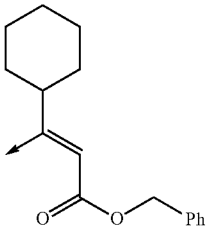
Q-1.185
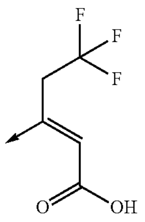
Q-1.186
-continued
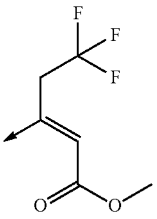
Q-1.187
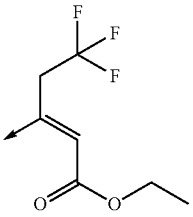
Q-1.188
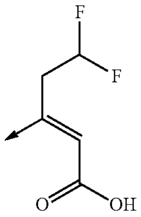
Q-1.189
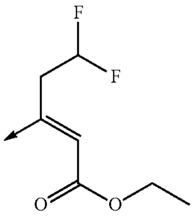
Q-1.190
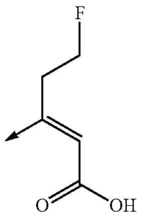
Q-1.191
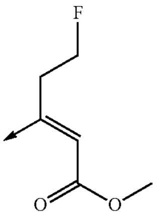
Q-1.192
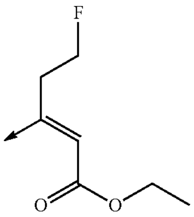
Q-1.193

-continued
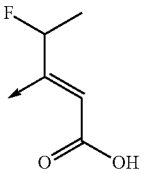
Q-1.194
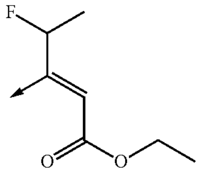
Q-1.195
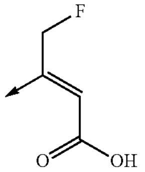
Q-1.196
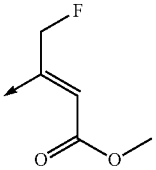
Q-1.197
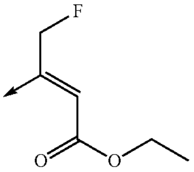
Q-1.198
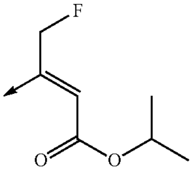
Q-1.199
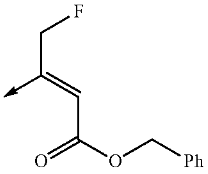
Q-1.200
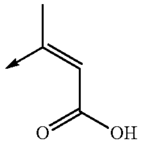
Q-1.201
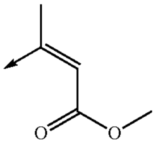
Q-1.202
-continued
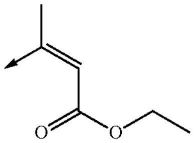
Q-1.203
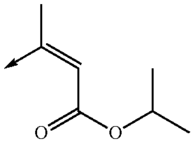
Q-1.204
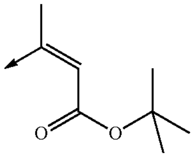
Q-1.205
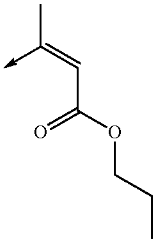
Q-1.206
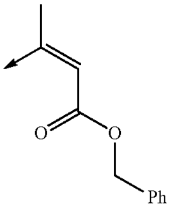
Q-1.207
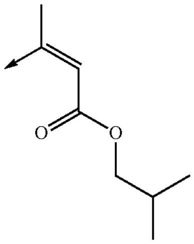
Q-1.208
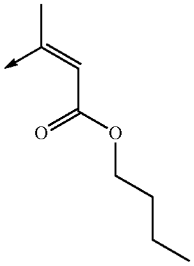
Q-1.209

-continued
Q-1.210
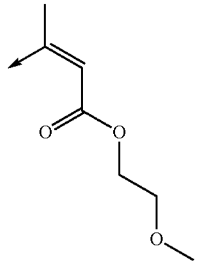
Q-1.211
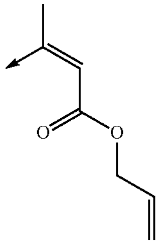
Q-1.212
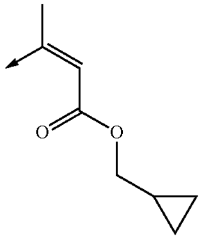
Q-1.213
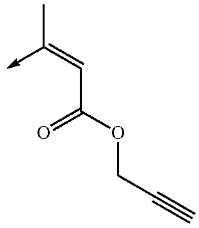
Q-1.214
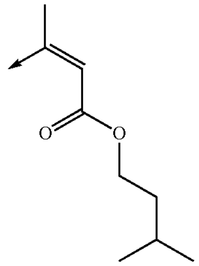
Q-1.215
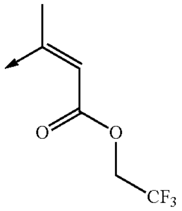
-continued
Q-1.216
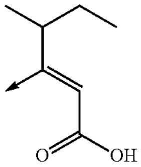
Q-1.217
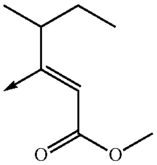
Q-1.218
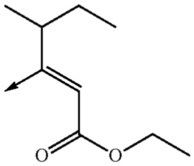
Q-1.219
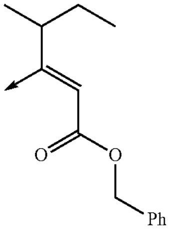
Q-1.220
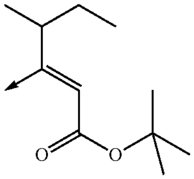
Q-1.221
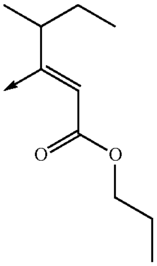
Q-1.222
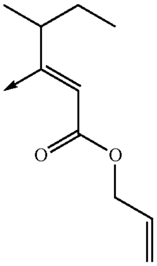

Q-1.223
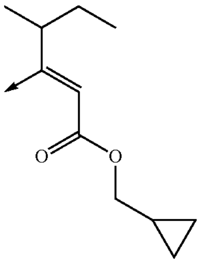
Q-1.224
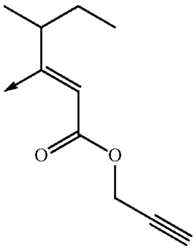
Q-1.225
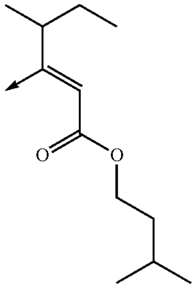
Q-1.226
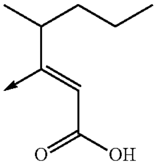
Q-1.227
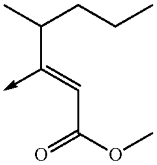
Q-1.228
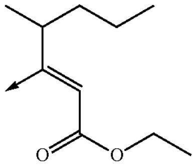
Q-1.229
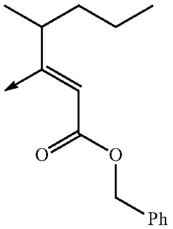
Q-1.230
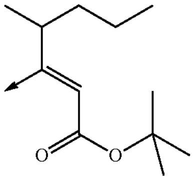
Q-1.231
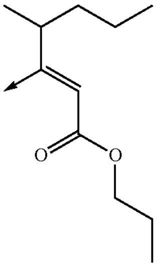
Q-1.232
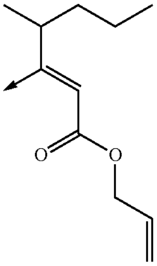
Q-1.233
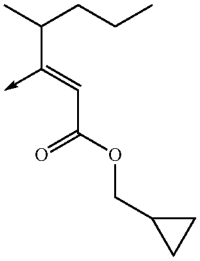
Q-1.234
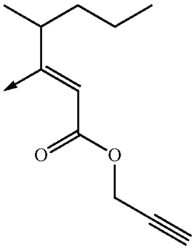
Q-1.235
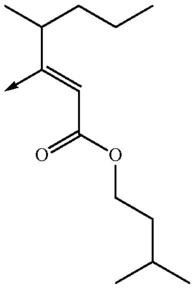

-continued
Q-1.236
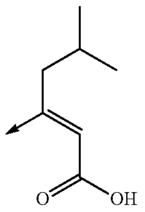
Q-1.237
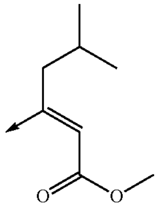
Q-1.238
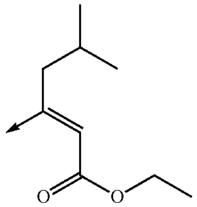
Q-1.239
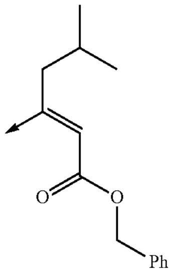
Q-1.240
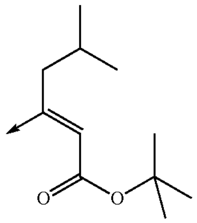
Q-1.241
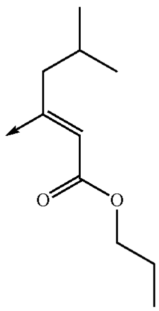
-continued
Q-1.242
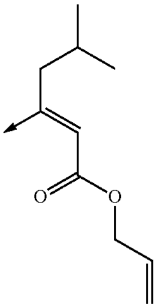
Q-1.243
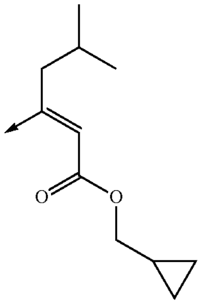
Q-1.244
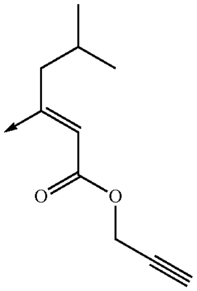
Q-1.245
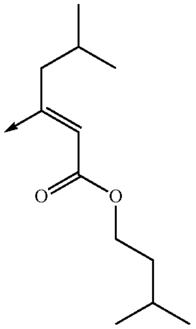
Q-1.246
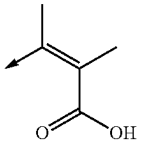
Q-1.247
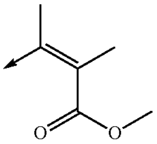

-continued
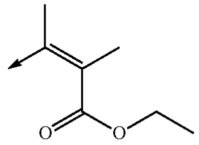
Q-1.248
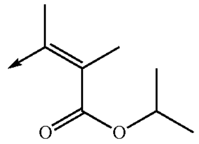
Q-1.249
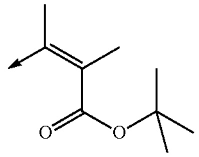
Q-1.250
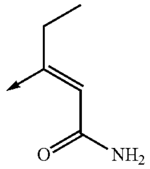
Q-2.1
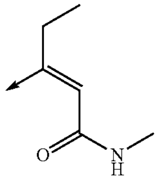
Q-2.2
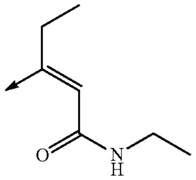
Q-2.3
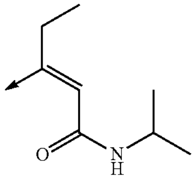
Q-2.4
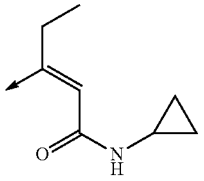
Q-2.5
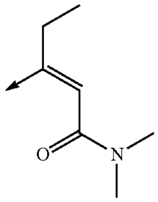
Q-2.6
-continued
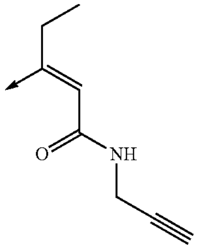
Q-2.7
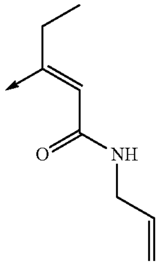
Q-2.8
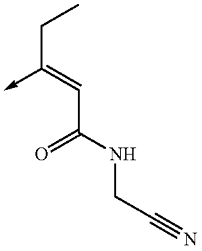
Q-2.9
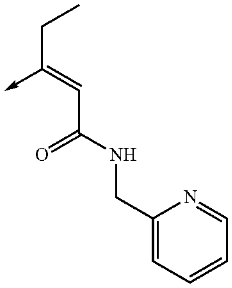
Q-2.10
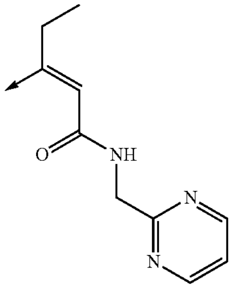
Q-2.11

-continued
Q-2.12
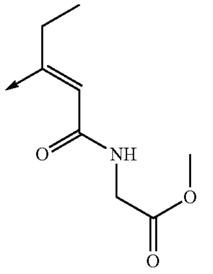
Q-2.13
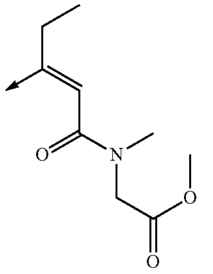
Q-2.14
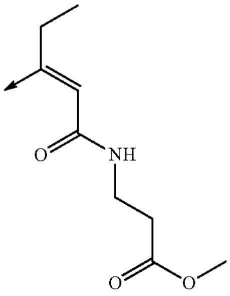
Q-2.15
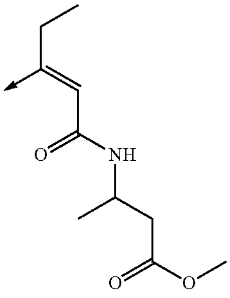
Q-2.16
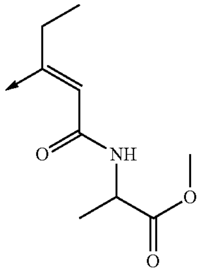
-continued
Q-2.17
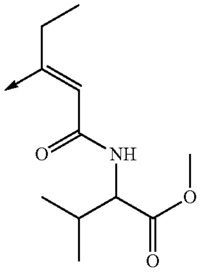
Q-2.18
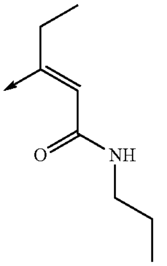
Q-2.19
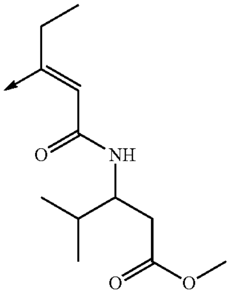
Q-2.20
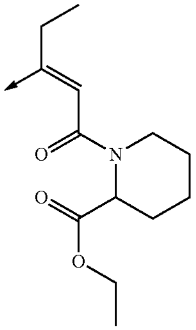
Q-2.21
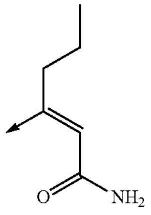
Q-2.22
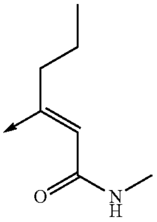

Q-2.23
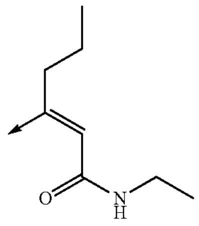
Q-2.24
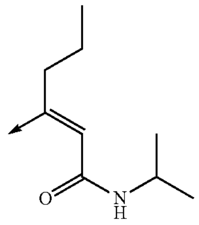
Q-2.25
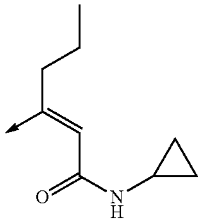
Q-2.26
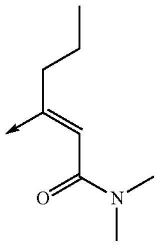
Q-2.27
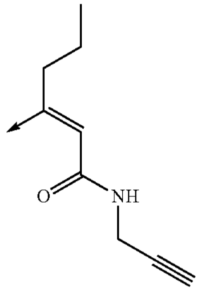
Q-2.28
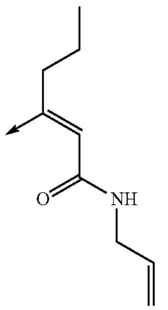
Q-2.29
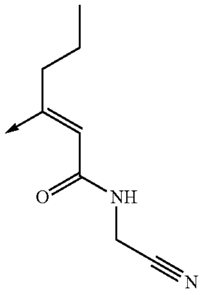
Q-2.30
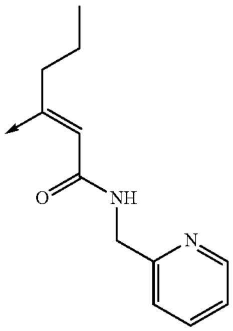
Q-2.31
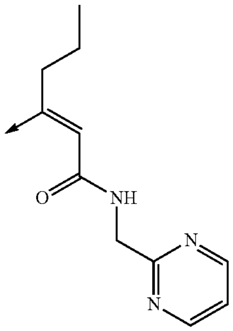
Q-2.32
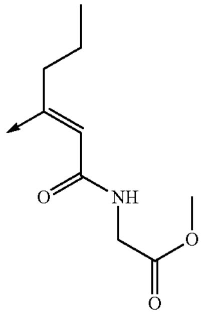
Q-2.33
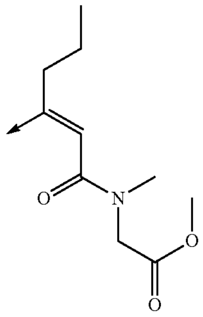

-continued
Q-2.34
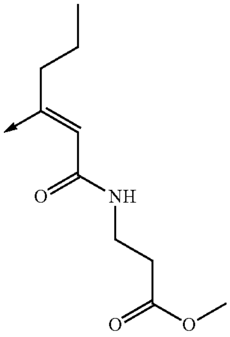
Q-2.35
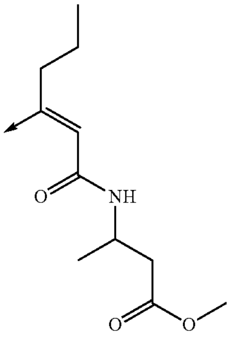
Q-2.36
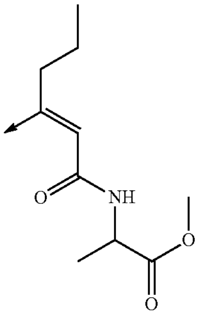
Q-2.37
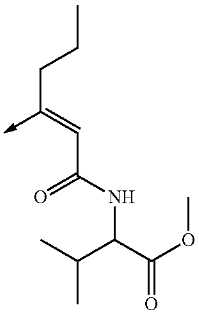
-continued
Q-2.38
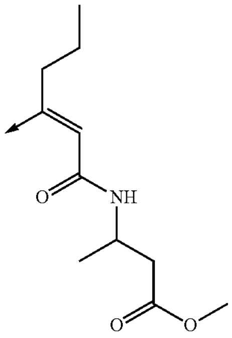
Q-2.39
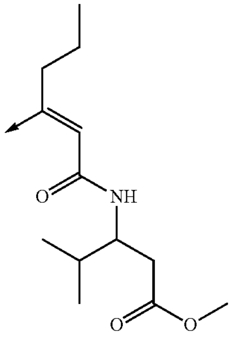
Q-2.40
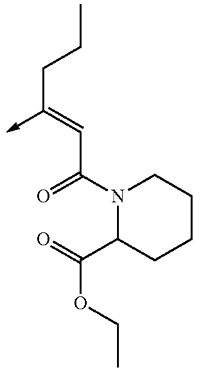
Q-2.41
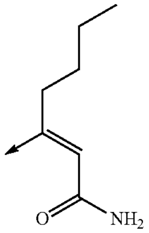
Q-2.42
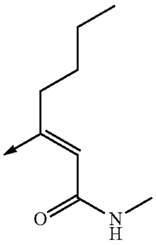

Q-2.43
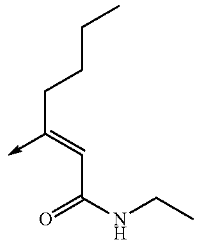
Q-2.44
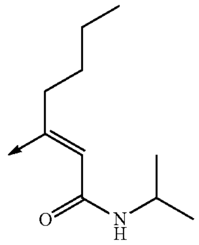
Q-2.45
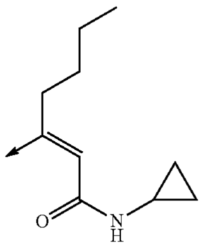
Q-2.46
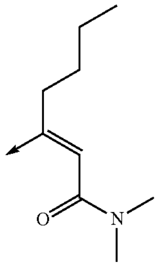
Q-2.47
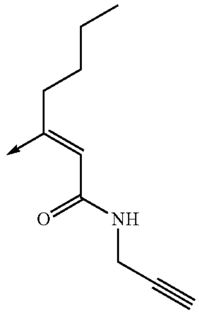
Q-2.48
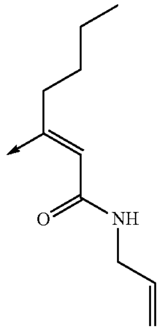
Q-2.49
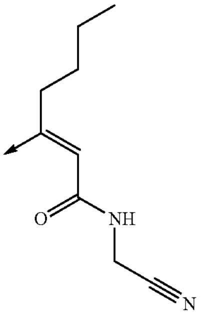
Q-2.50
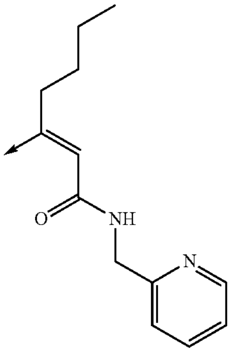
Q-2.51
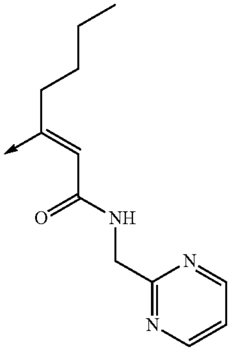

Q-2.52
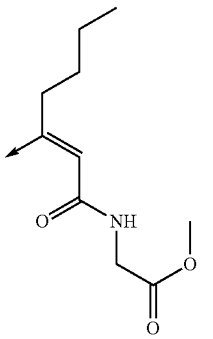
Q-2.53
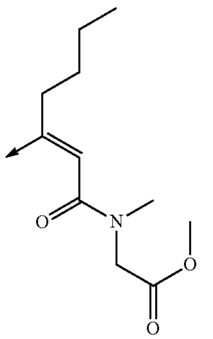
Q-2.54
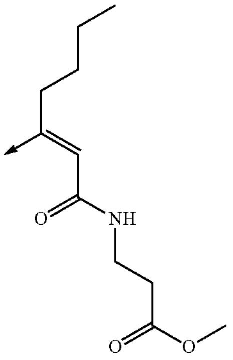
Q-2.55
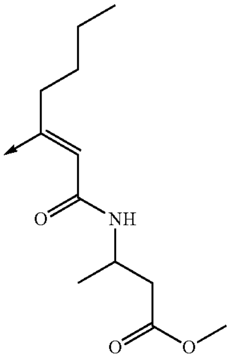
Q-2.56
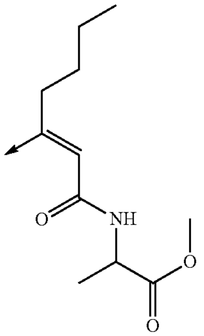
Q-2.57
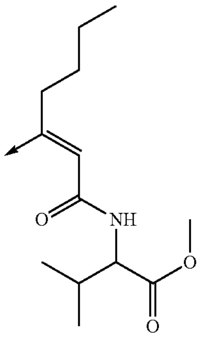
Q-2.58
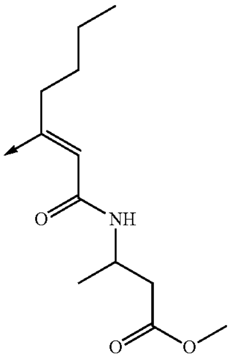
Q-2.59
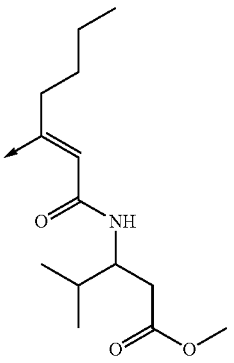

-continued
Q-2.60
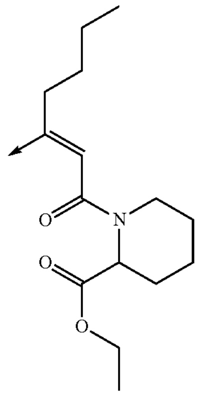
Q-2.61
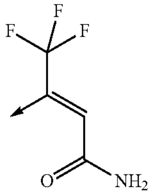
Q-2.62
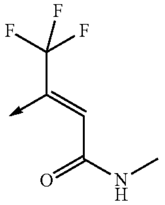
Q-2.63
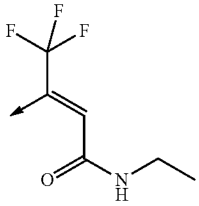
Q-2.64
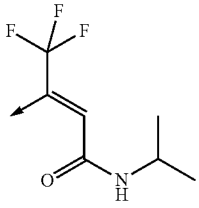
Q-2.65
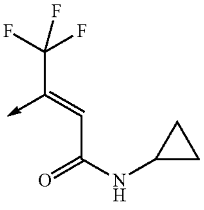
-continued
Q-2.66
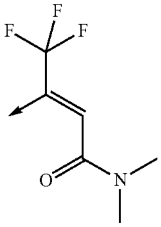
Q-2.67
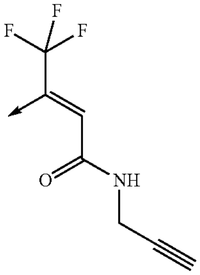
Q-2.68
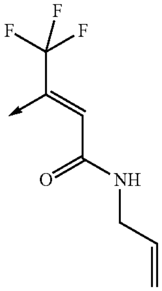
Q-2.69
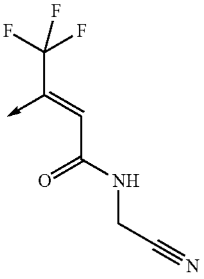
Q-2.70
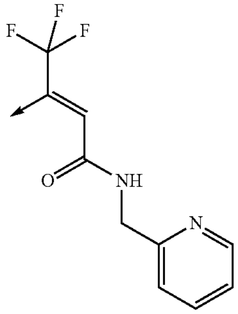

-continued
Q-2.71
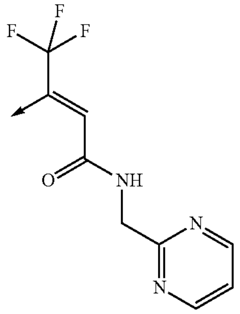
Q-2.72
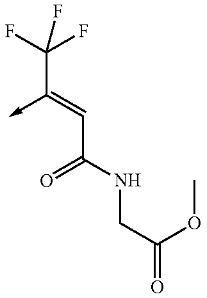
Q-2.73
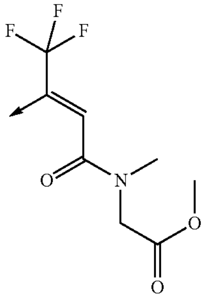
Q-2.74
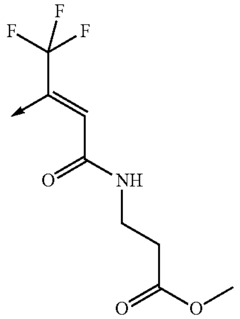
Q-2.75
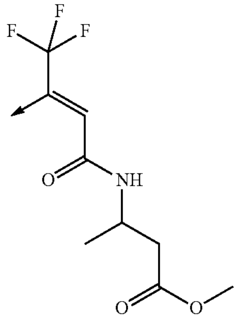
-continued
Q-2.76
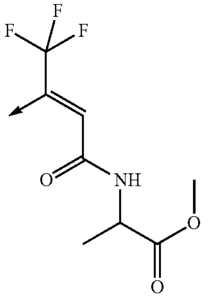
Q-2.77
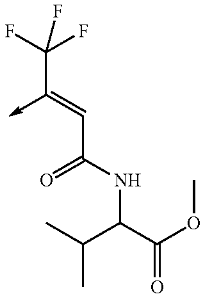
Q-2.78
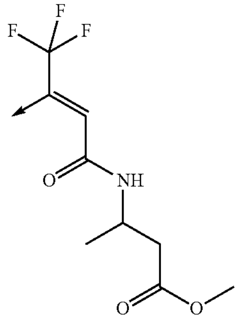
Q-2.79
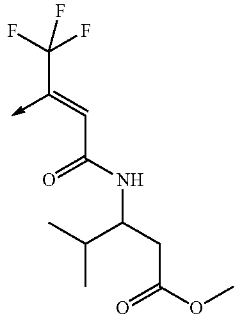
Q-2.80
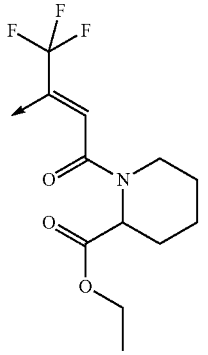

-continued
Q-2.81
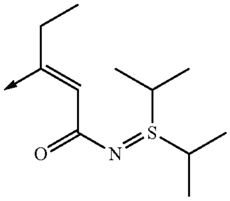
Q-2.82
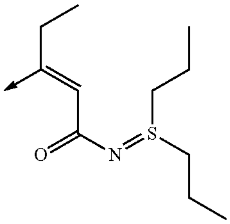
Q-2.83
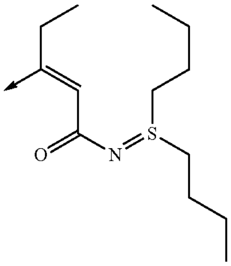
Q-2.84
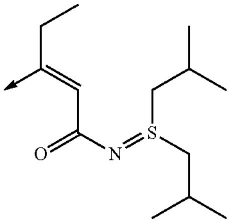
Q-2.85
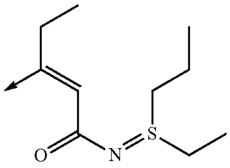
Q-2.86
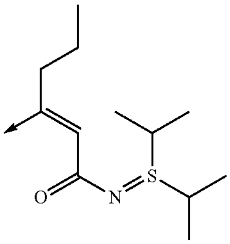
-continued
Q-2.87
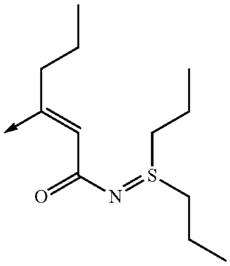
Q-2.88
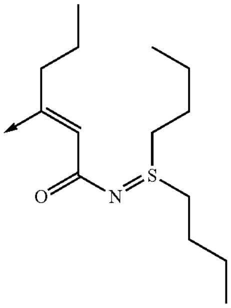
Q-2.89
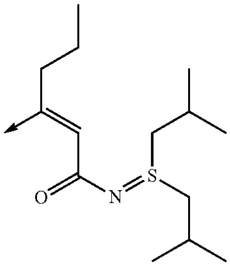
Q-2.90
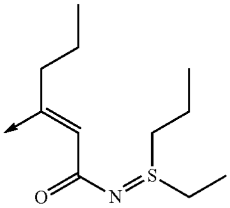
Q-2.91
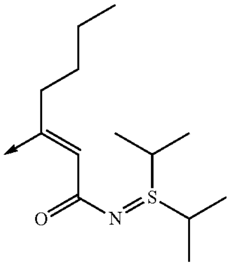
Q-2.92
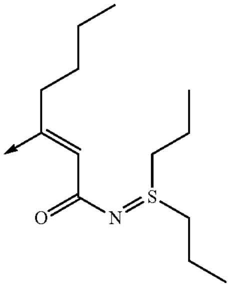

-continued
Q-2.93
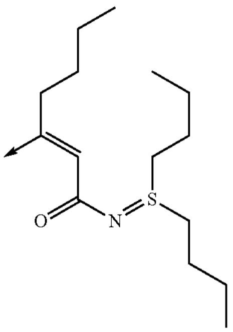
Q-2.94
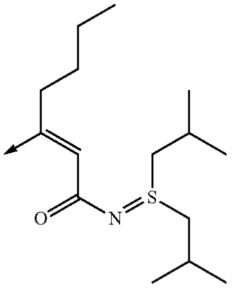
Q-2.95
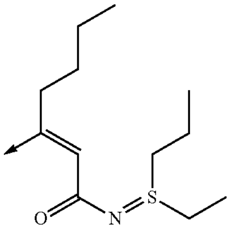
Q-2.96
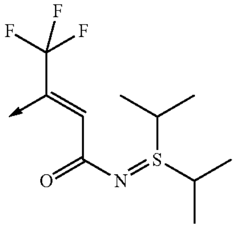
Q-2.97
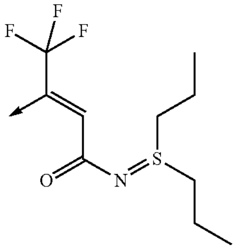
-continued
Q-2.98
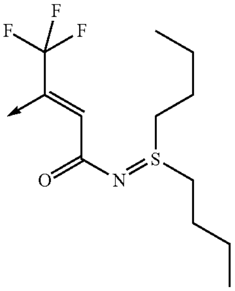
Q-2.99
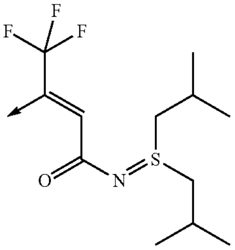
Q-2.100
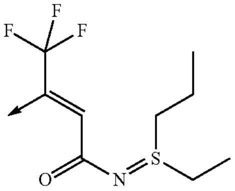
Q-2.101
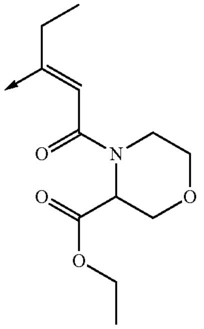
Q-2.102
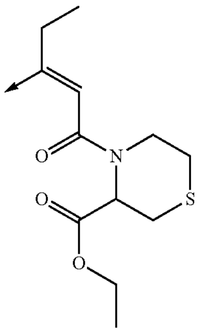

-continued
Q-2.103
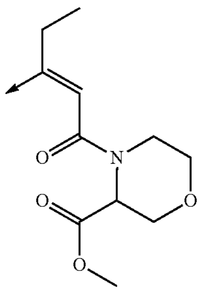
Q-2.104
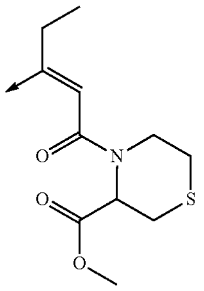
Q-2.105
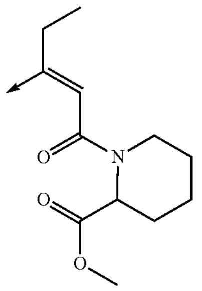
Q-2.106
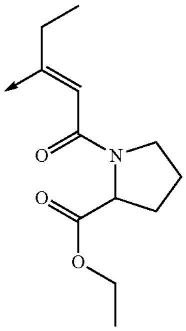
Q-2.107
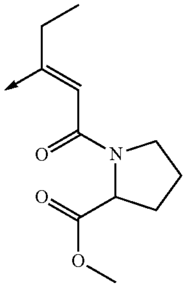
-continued
Q-2.108
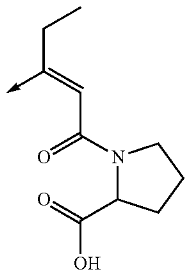
Q-2.109
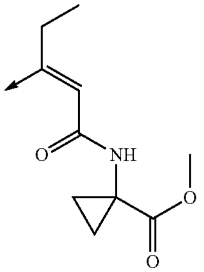
Q-2.110
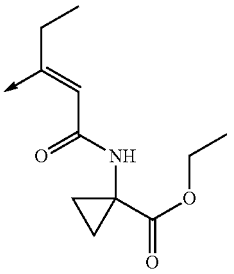
Q-2.111
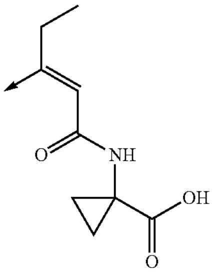
Q-2.112
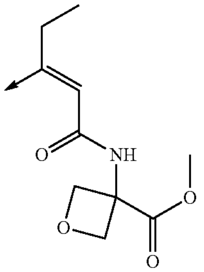

Q-2.113
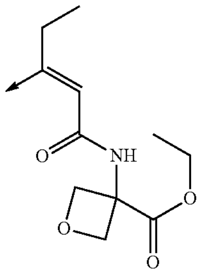
Q-2.114
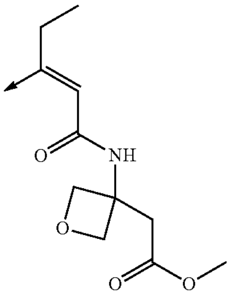
Q-2.115
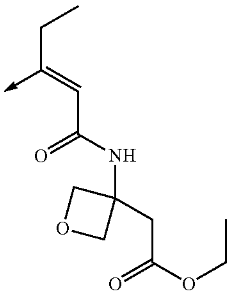
Q-2.116
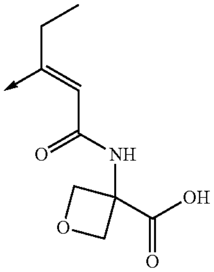
Q-2.117
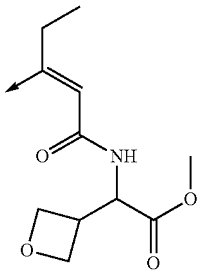
Q-2.118
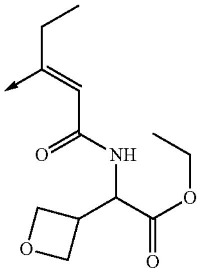
Q-2.119
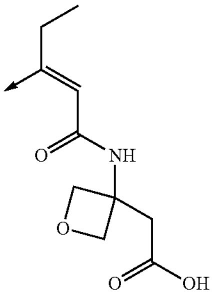
Q-2.120
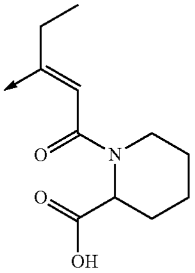
Q-2.121
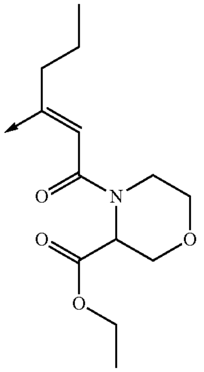
Q-2.122
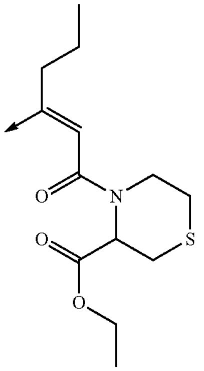

-continued
Q-2.123
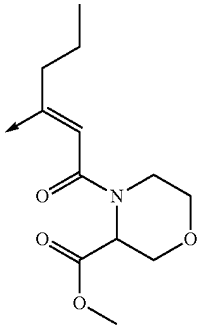
Q-2.124
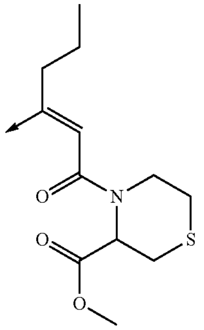
Q-2.125
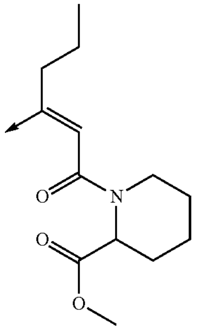
Q-2.126
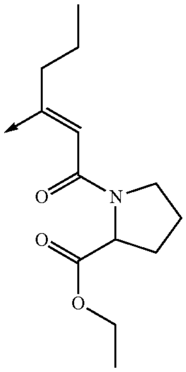
-continued
Q-2.127
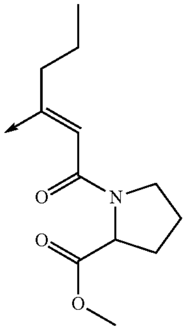
Q-2.128
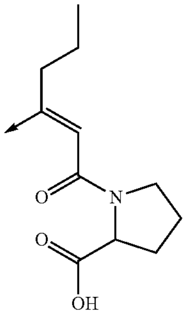
Q-2.129
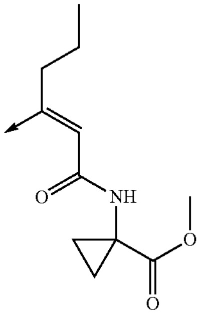
Q-2.130
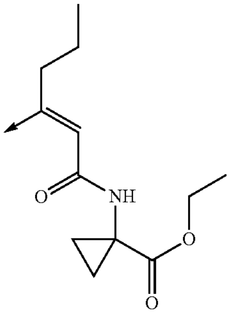
Q-2.131
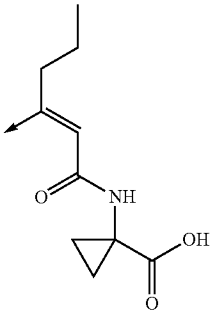

-continued
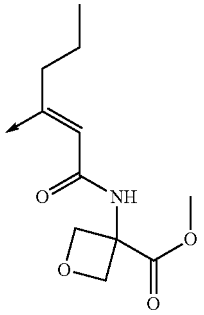
Q-2.132
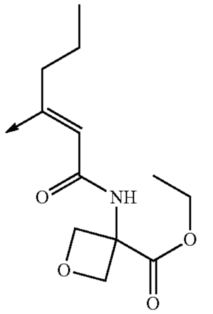
Q-2.133
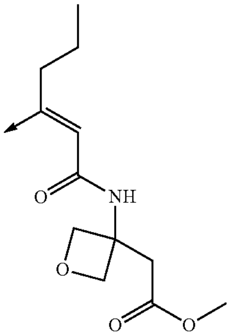
Q-2.134
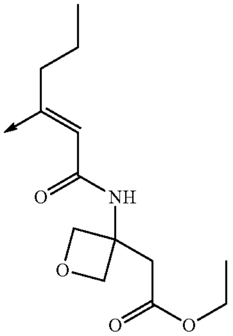
Q-2.135
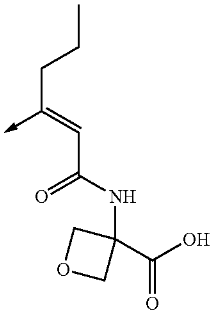
Q-2.136
-continued
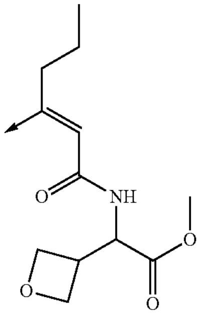
Q-2.137
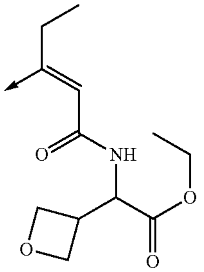
Q-2.138
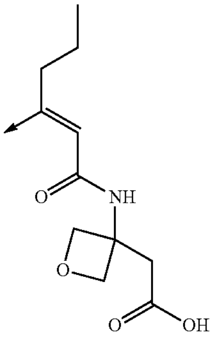
Q-2.139
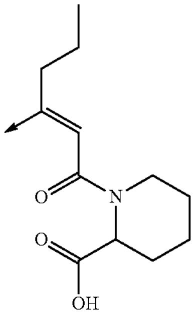
Q-2.140
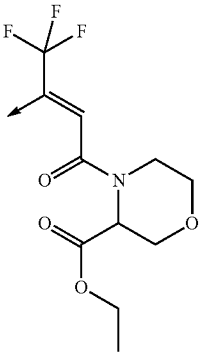
Q-2.141

Q-2.142
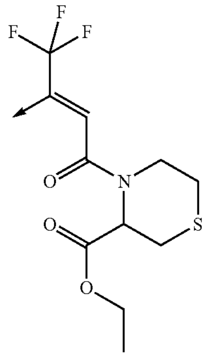
Q-2.143
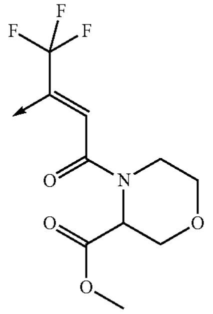
Q-2.144
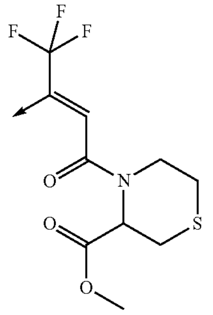
Q-2.145
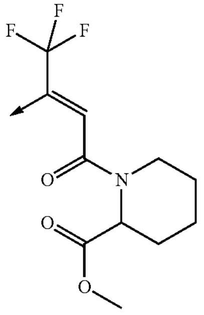
Q-2.146
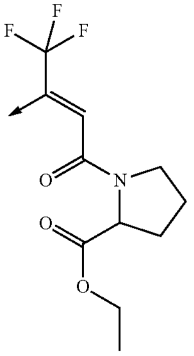
Q-2.147
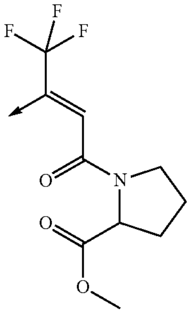
Q-2.148
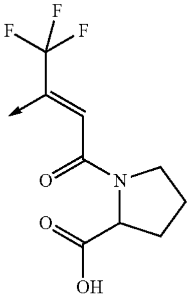
Q-2.149
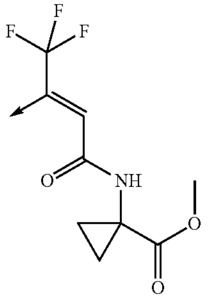
Q-2.150
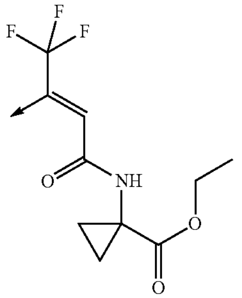

-continued
Q-2.151
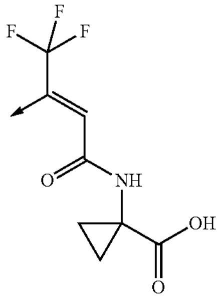
Q-2.152
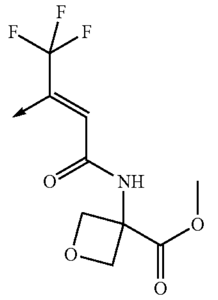
Q-2.153
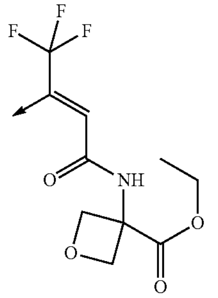
Q-2.154
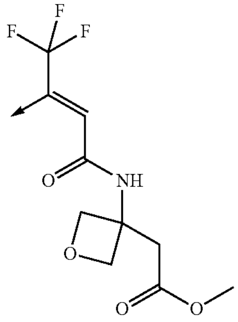
Q-2.155
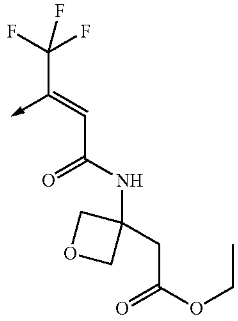
-continued
Q-2.156
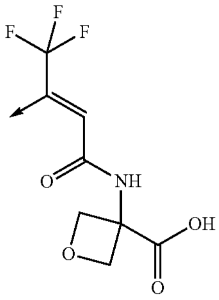
Q-2.157
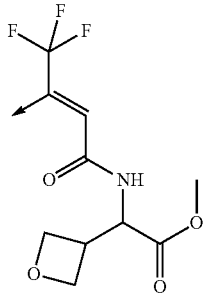
Q-2.158
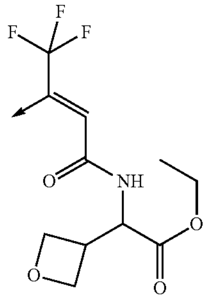
Q-2.159
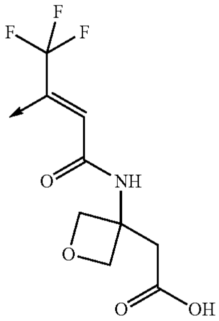
Q-2.160
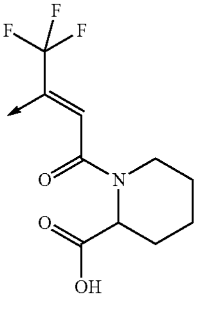

-continued
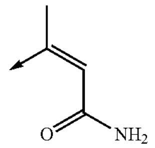
Q-2.161
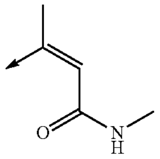
Q-2.162
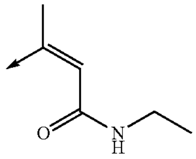
Q-2.163
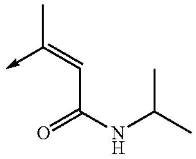
Q-2.164
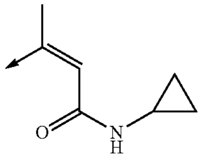
Q-2.165
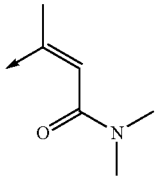
Q-2.166
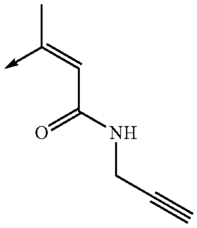
Q-2.167
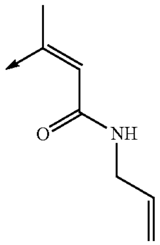
Q-2.168
-continued
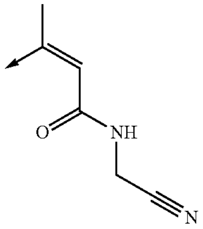
Q-2.169
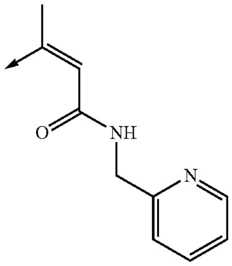
Q-2.170
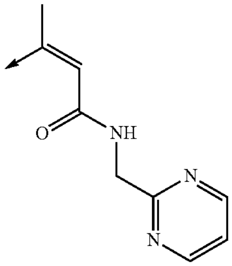
Q-2.171
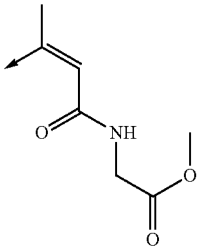
Q-2.172
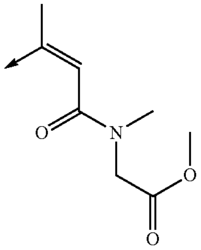
Q-2.173
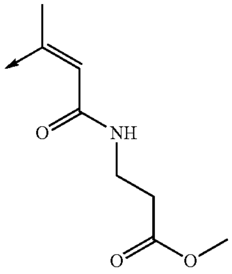
Q-2.174

-continued
Q-2.175
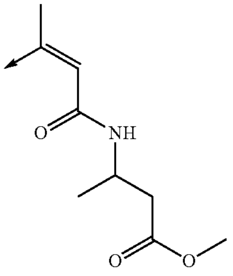
Q-2.176
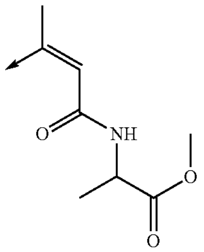
Q-2.177
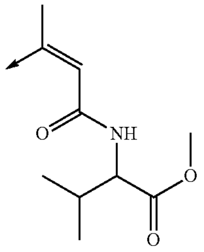
Q-2.178
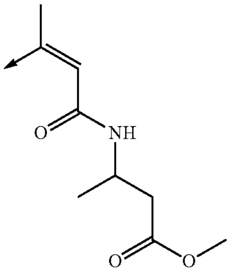
Q-2.179
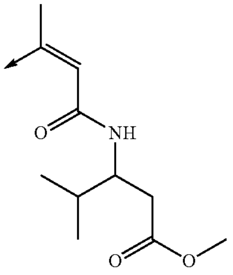
-continued
Q-2.180
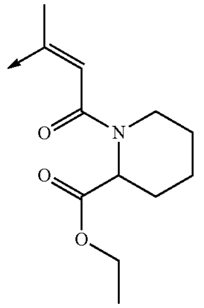
Q-2.181
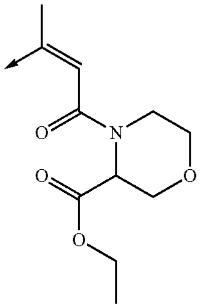
Q-2.182
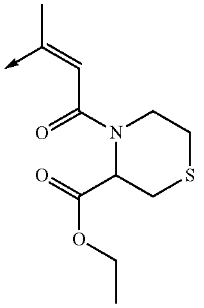
Q-2.183
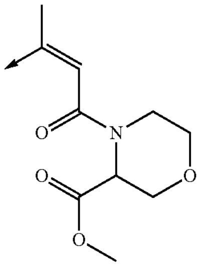
Q-2.184
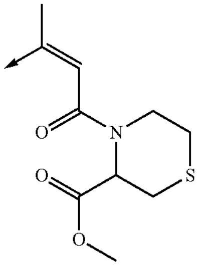

Q-2.185
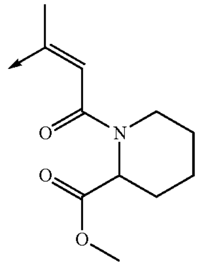
Q-2.186
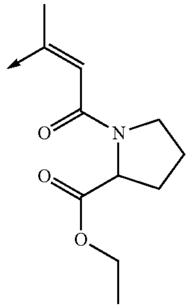
Q-2.187
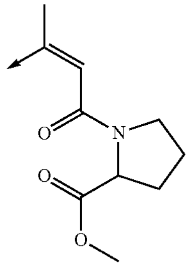
Q-2.188
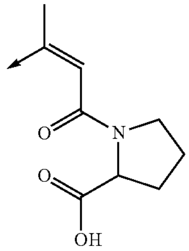
Q-2.189
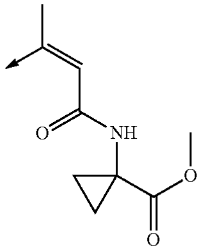
Q-2.190
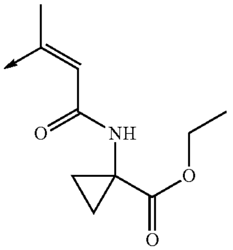
Q-2.191
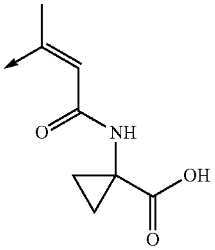
Q-2.192
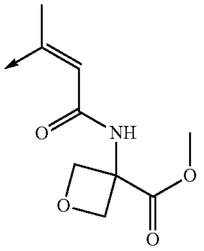
Q-2.193
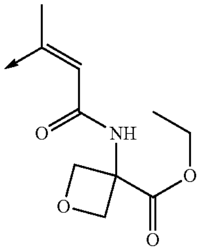
Q-2.194
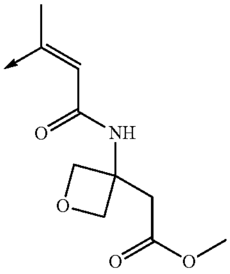
Q-2.195
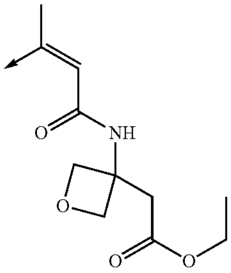
Q-2.196
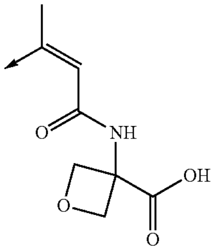

-continued
Q-2.197
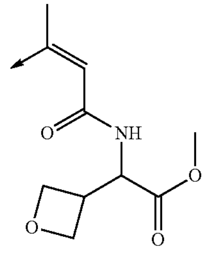
Q-2.198
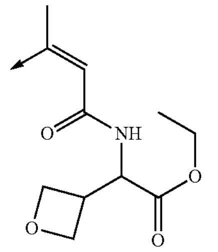
Q-2.199
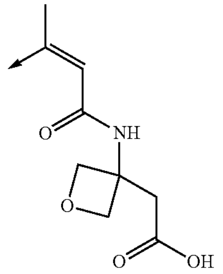
Q-2.200
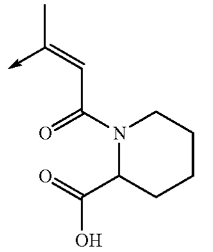
Q-2.201
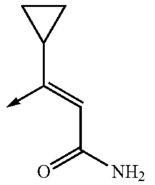
Q-2.202
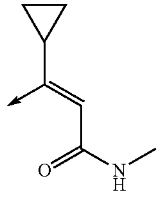
-continued
Q-2.203
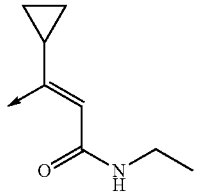
Q-2.204
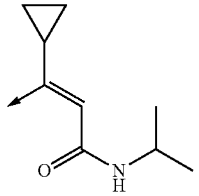
Q-2.205
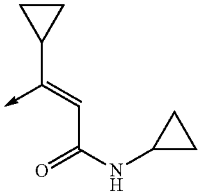
Q-3.1
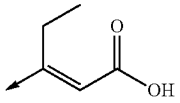
Q-3.2
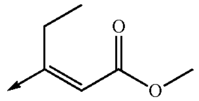
Q-3.3
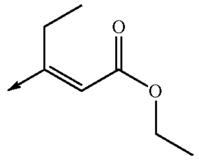
Q-3.4
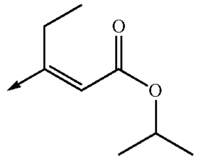
Q-3.5
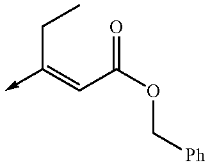
Q-3.6
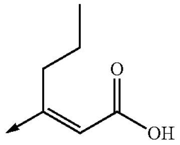

-continued
Q-3.7
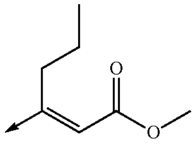
Q-3.8
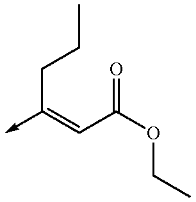
Q-3.9
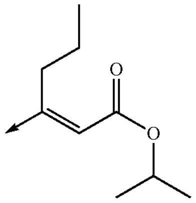
Q-3.10
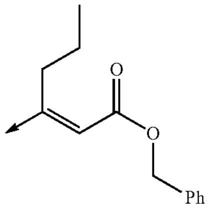
Q-3.11
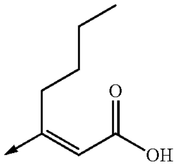
Q-3.12
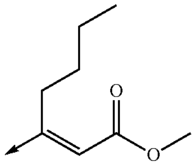
Q-3.13
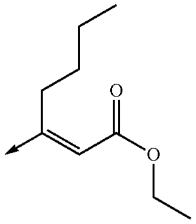
Q-3.14
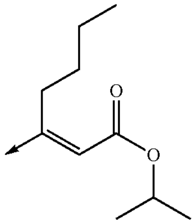
-continued
Q-3.15
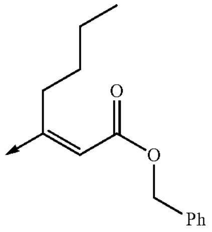
Q-3.16
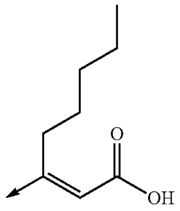
Q-3.17
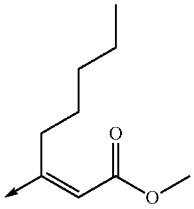
Q-3.18
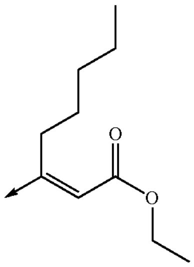
Q-3.19
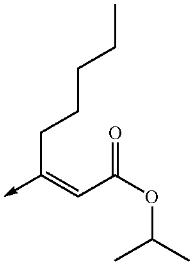
Q-3.20
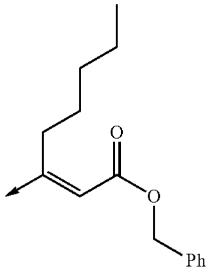

-continued
Q-3.21
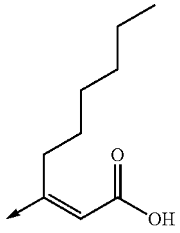
Q-3.22
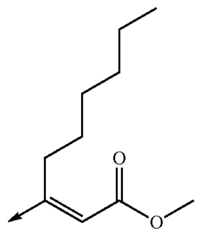
Q-3.23
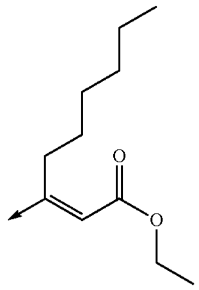
Q-3.24
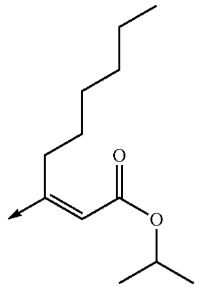
Q-3.25
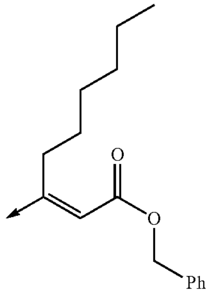
Q-3.26
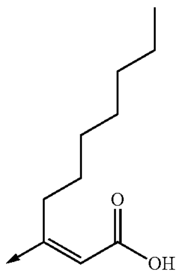
-continued
Q-3.27
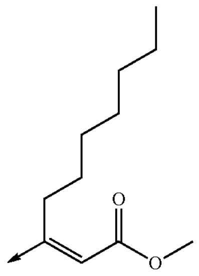
Q-3.28
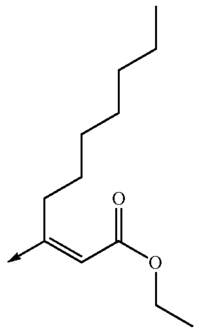
Q-3.29
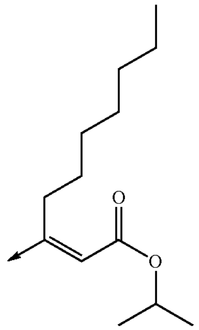
Q-3.30
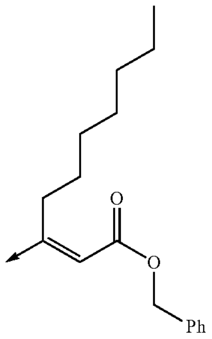
Q-3.31
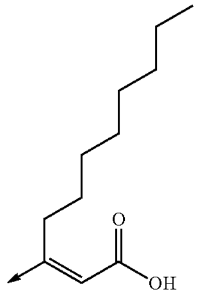

-continued
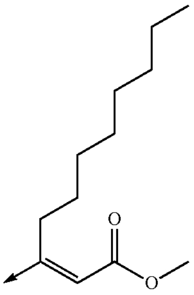
Q-3.32
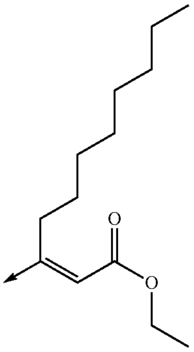
Q-3.33
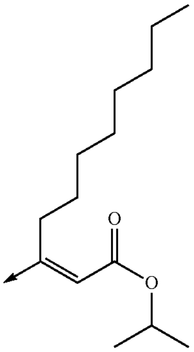
Q-3.34
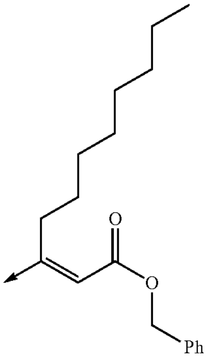
Q-3.35
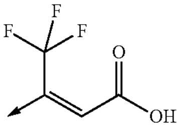
Q-3.36
-continued
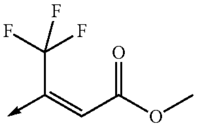
Q-3.37
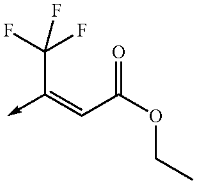
Q-3.38
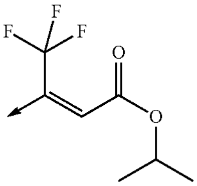
Q-3.39
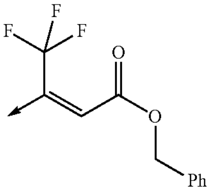
Q-3.40
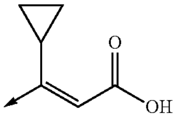
Q-3.41
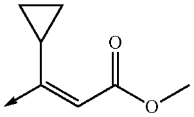
Q-3.42
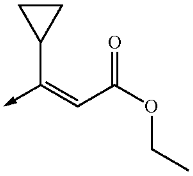
Q-3.43
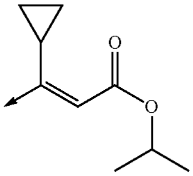
Q-3.44
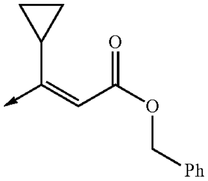
Q-3.45

-continued

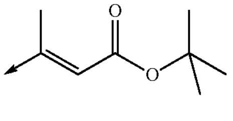

Q-3.46

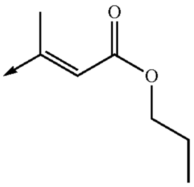

Q-3.47

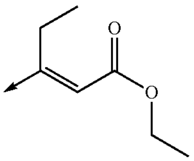

Q-3.48

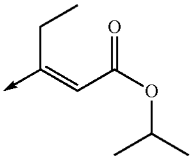

Q-3.49

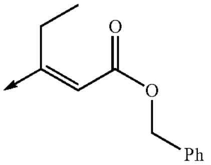

Q-3.50

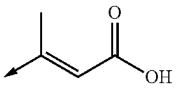

Q-3.51

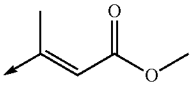

Q-3.52

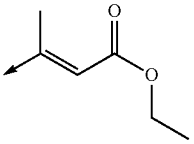

Q-3.53

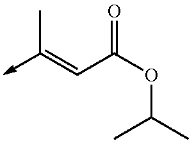

Q-3.54

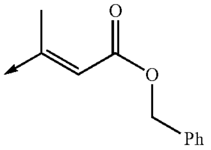

Q-3.55

Very specific preference is given to compounds of the general formula (I) in which

[X-Y] represents the moieties and $[X-Y]^1$

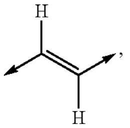

$[X-Y]^2$ $R^1$ is methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-methylcyclohexyl, 2-methylcyclohexyl, 3-methylcyclohexyl, 1-methoxycyclohexyl, 2-methoxycyclohexyl, 3-methoxycyclohexyl, aryl-($C_1$-$C_8$)-alkyl, heterocyclyl-($C_1$-$C_{85}$)-alkyl, $R^2$ is hydrogen, tert-butyldimethylsilyl, trimethylsilyl, triethylsilyl, tri(isopropyl)silyl, tri(n-propyl)silyl, dimethyl(phenyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, methyl, ethyl, allyl, methylcarbonyl, ethylcarbonyl, n-propylcarbonyl, isopropylcarbonyl, n-butylcarbonyl, tert-butylcarbonyl, isobutylcarbonyl, isopentylcarbonyl, neopentylcarbonyl, arylcarbonyl, heteroarylcarbonyl, cyclopropylcarbonyl, cyclobutylcarbonyl, cyclopentylcarbonyl, cyclohexylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, ethylthio-n-propyl, $A^1$, V, W are each independently a $CR^3R^4$ group, $A^2$ is a $CR^3R^4$ group or oxygen, m is 0, n is 0, 1, $R^3$ and $R^4$ are each independently hydrogen, methyl, ethyl, n-propyl, isopropyl, n-butyl, isobutyl, tert-butyl, fluorine, chlorine, bromine, iodine, cyclopropyl, cyclobutyl, cyclopentyl, cyclohexyl, methoxy, optionally substituted phenyl, heterocyclyl, heteroaryl, methylthio, trifluoromethyl, difluoromethyl, vinyl, prop-1-en-1-yl, but-1-en-1-yl, allyl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methylthiomethyl and $R^3$ and $R^4$ together with the atom to which they are bonded form a fully saturated 3- to 6-membered ring optionally interrupted by heteroatoms and optionally having further substitution, and Q is one of the Q-1.1 to Q-3.55 moieties described in the table above.

The definitions of radicals listed above in general terms or within areas of preference apply both to the end products of the formula (I) and correspondingly to the starting materials or intermediates required for preparation in each case. These radical definitions can be combined with one another as desired, i.e. including combinations between the given preferred ranges.

Likewise as yet unknown and thus forming a further part of the invention are compounds of the formula (II) or salts thereof (II)

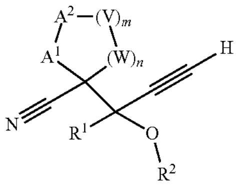

which serve as intermediates for preparation of the inventive compounds of the general formula (I), where $R^1$ is hydrogen, $(C_1-C_8)$-alkyl, aryl, heteroaryl, heterocyclyl, $(C_3-C_8)$-cycloalkyl, $(C_2-C_8)$-alkenyl, $(C_2-C_8)$-alkynyl, $(C_2-C_8)$-alkynyl-$(C_1-C_8)$-alkyl, $(C_1-C_8)$-alkoxy-$(C_1-C_8)$-alkyl, hydroxy-$(C_1-C_8)$-alkyl, $(C_1-C_8)$-haloalkyl, $(C_2-C_8)$-haloalkenyl, $(C_1-C_8)$-haloalkoxy-$(C_1-C_8)$-alkyl, $(C_1-C_8)$-alkylthio-$(C_1-C_8)$-alkyl, aryl-$(C_1-C_8)$-alkyl, heterocyclyl-$(C_1-C_8)$-alkyl, $(C_3-C_8)$-halocycloalkyl, $(C_4-C_8)$-cycloalkenyl, $(C_1-C_8)$-alkoxy-$(C_1-C_8)$-alkoxy-$(C_1-C_8)$-alkyl, $(C_1-C_8)$-alkoxy-$(C_1-C_8)$-haloalkyl, $(C_1-C_8)$-haloalkoxy-$(C_1-C_8)$-haloalkyl, $(C_3-C_8)$-cycloalkyl-$(C_1-C_8)$-alkyl, $R^2$ is hydrogen, $(C_1-C_8)$-alkyl, $(C_1-C_8)$-alkoxy-$(C_1-C_8)$-alkyl, $(C_1-C_8)$-alkoxy-$(C_1-C_8)$-alkoxy-$(C_1-C_8)$-alkyl, $(C_2-C_8)$-alkenyl, $(C_2-C_8)$-alkynyl, $(C_1-C_8)$-alkylcarbonyl, arylcarbonyl, heteroarylcarbonyl, $(C_3-C_8)$-cycloalkylcarbonyl, $(C_2-C_8)$-alkenylcarbonyl, heterocyclylcarbonyl, $(C_1-C_8)$-alkoxycarbonyl, $(C_2-C_8)$-alkenyloxycarbonyl, aryloxy-$(C_1-C_8)$-alkyl, aryl-$(C_1-C_8)$-alkoxycarbonyl, $(C_3-C_8)$-cycloalkoxycarbonyl, $(C_3-C_8)$-cycloalkyl-$(C_1-C_8)$-alkoxycarbonyl, aryl-$(C_1-C_8)$-alkoxy-$(C_1-C_8)$-alkyl, aryl-$(C_1-C_8)$-alkyl, $(C_1-C_8)$-alkoxy-$(C_1-C_8)$-alkoxy-$(C_1-C_8)$-alkyl, $(C_1-C_8)$-alkylthio-$(C_1-C_8)$-alkyl, tris[$(C_1-C_8)$-alkyl]silyl, $(C_1-C_8)$-alkylbis-[$(C_1-C_8)$-alkyl]silyl, $(C_1-C_8)$-alkylbis(aryl)silyl, arylbis[$(C_1-C_8)$-alkyl]silyl, $(C_3-C_8)$-cycloalkylbis[$(C_1-C_8)$-alkyl]silyl, halobis[$(C_1-C_8)$-alkyl]silyl, tris[$(C_1-C_8)$-alkyl]silyl-$(C_1-C_8)$-alkoxy-$(C_1-C_8)$-alkyl, tris[$(C_1-C_8)$-alkyl]silyl-$(C_1-C_8)$-alkyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, 2, n is 0, 1, 2, $R^3$ and $R^4$ are each independently hydrogen, $(C_1-C_8)$-alkyl, halogen, $(C_3-C_8)$-cycloalkyl, $(C_1-C_8)$-alkoxy, aryl, heterocyclyl, heteroaryl, aryl-$(C_1-C_8)$-alkyl, $(C_1-C_8)$-alkylthio, $(C_1-C_8)$-haloalkyl, $(C_1-C_8)$-haloalkyloxy, $(C_1-C_8)$-haloalkylthio, $(C_1-C_8)$-alkoxy-$(C_1-C_8)$-alkyl, $(C_1-C_8)$-alkylthio-$(C_1-C_8)$-alkyl, heteroaryl-$(C_1-C_8)$-alkyl, heterocyclyl-$(C_1-C_8)$-alkyl, $(C_1-C_8)$-alkoxy-$(C_1-C_8)$-haloalkyl, $(C_1-C_8)$-haloalkoxy-$(C_1-C_8)$-haloalkyl, $(C_2-C_8)$-alkenyl, $(C_2-C_8)$-alkynyl and $R^3$ and $R^4$ together with the atom to which they are bonded form a fully saturated 3- to 6-membered ring optionally interrupted by heteroatoms and optionally having further substitution.

Preference is given to compounds of the formula (II) where $R^1$ is hydrogen, $(C_1-C_6)$-alkyl, aryl, heteroaryl, heterocyclyl, $(C_3-C_6)$-cycloalkyl, $(C_2-C_6)$-alkenyl, $(C_2-C_6)$-alkynyl, $(C_2-C_6)$-alkynyl-$(C_1-C_6)$-alkyl, $(C_1-C_6)$-alkoxy-$(C_1-C_6)$-alkyl, hydroxy-$(C_1-C_6)$-alkyl, $(C_1-C_6)$-haloalkyl, $(C_2-C_6)$-haloalkenyl, $(C_1-C_6)$-haloalkoxy-$(C_1-C_6)$-alkyl, $(C_1-C_6)$-alkylthio-$(C_1-C_6)$-alkyl, aryl-$(C_1-C_6)$-alkyl, heterocyclyl-$(C_1-C_6)$-alkyl, $(C_3-C_6)$-halocycloalkyl, $(C_4-C_6)$-cycloalkenyl, $(C_1-C_6)$-alkoxy-$(C_1-C_6)$-alkoxy-$(C_1-C_6)$-alkyl, $(C_1-C_6)$-alkoxy-$(C_1-C_6)$-haloalkyl, $(C_1-C_6)$-haloalkoxy-$(C_1-C_6)$-haloalkyl, $(C_3-C_6)$-cycloalkyl-$(C_1-C_6)$-alkyl, $R^2$ is hydrogen, $(C_1-C_6)$-alkyl, $(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_2-C_6)$-alkenyl, $(C_2-C_6)$-alkynyl, $(C_1-C_6)$-alkylcarbonyl, arylcarbonyl, heteroarylcarbonyl, $(C_3-C_6)$-cycloalkylcarbonyl, $(C_2-C_6)$-alkenylcarbonyl, heterocyclylcarbonyl, $(C_1-C_6)$-alkoxycarbonyl, $(C_2-C_6)$-alkenyloxycarbonyl, aryloxy-$(C_1-C_6)$-alkyl, aryl-$(C_1-C_6)$-alkoxycarbonyl, $(C_3-C_6)$-cycloalkoxycarbonyl, $(C_3-C_6)$-cycloalkyl-$(C_1-C_6)$-alkoxycarbonyl, aryl-$(C_1-C_6)$-alkoxy-$(C_1-C_6)$-alkyl, aryl-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, tris[$(C_1-C_6)$-alkyl]silyl, $(C_1-C_6)$-alkylbis-[$(C_1-C_6)$-alkyl]silyl, $(C_1-C_6)$-alkylbis(aryl)silyl, arylbis[$(C_1-C_6)$-alkyl]silyl, $(C_3-C_6)$-cycloalkylbis[$(C_1-C_6)$-alkyl]silyl, halobis[$(C_1-C_6)$-alkyl]silyl, tris[$(C_1-C_6)$-alkyl]silyl-$(C_1-C_6)$-alkoxy-$(C_1-C_6)$-alkyl, tris[$(C_1-C_6)$-alkyl]silyl-$(C_1-C_6)$-alkyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, 2, n is 0, 1, 2, $R^3$ and $R^4$ are each independently hydrogen, $(C_1-C_6)$-alkyl, halogen, $(C_3-C_6)$-cycloalkyl, $(C_1-C_6)$-alkoxy, aryl, heterocyclyl, heteroaryl, aryl-$(C_1-C_6)$-alkyl, $(C_1-C_6)$-alkylthio, $(C_1-C_6)$-haloalkyl, $(C_1-C_6)$-haloalkyloxy, $(C_1-C_6)$-haloalkylthio, $(C_1-C_6)$-alkoxy-$(C_1-C_6)$-alkyl, $(C_1-C_6)$-alkylthio-$(C_1-C_6)$-alkyl, heteroaryl-$(C_1-C_6)$-alkyl, heterocyclyl-$(C_1-C_6)$-alkyl, $(C_1-C_6)$-alkoxy-$(C_1-C_8)$-haloalkyl, $(C_1-C_6)$-haloalkoxy-$(C_1-C_6)$-haloalkyl, $(C_2-C_6)$-alkenyl, $(C_2-C_6)$-alkynyl and $R^3$ and $R^4$ together with the atom to which they are bonded form a fully saturated 3- to 6-membered ring optionally interrupted by heteroatoms and optionally having further substitution.

Particularly preferred compounds of the formula (II) are those in which $R^1$ is hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-methylcyclohexyl, 2-methylcyclohexyl, 3-methylcyclohexyl, 1-methoxycyclohexyl, 2-methoxycyclohexyl, 3-methoxycyclohexyl, aryl-($C_1$-$C_8$)-alkyl, heterocyclyl-($C_1$-$C_8$)-alkyl, $R^2$ is hydrogen, tert-butyldimethylsilyl, trimethylsilyl, triethylsilyl, tri(isopropyl)silyl, tri(n-propyl)silyl, dimethyl(phenyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, methyl, ethyl, allyl, methylcarbonyl, ethylcarbonyl, n-propylcarbonyl, isopropylcarbonyl, n-butylcarbonyl, tert-butylcarbonyl, isobutylcarbonyl, isopentylcarbonyl, neopentylcarbonyl, arylcarbonyl, heteroarylcarbonyl, cyclopropylcarbonyl, cyclobutylcarbonyl, cyclopentylcarbonyl, cyclohexylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, ethylthio-n-propyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, n is 0, 1, $R^3$ and $R^4$ are each independently hydrogen, methyl, ethyl, n-propyl, isopropyl, n-butyl, isobutyl, tert-butyl, fluorine, chlorine, bromine, iodine, cyclopropyl, cyclobutyl, cyclopentyl, cyclohexyl, methoxy, ethoxy, n-propoxy, isopropoxy, n-butyloxy, tert-butyloxy, isobutyloxy, n-pentyloxy, optionally substituted phenyl, heterocyclyl, heteroaryl, benzyl, p-Cl-benzyl, p-F-benzyl, p-methoxybenzyl, p-methylbenzyl, methylthio, ethylthio, n-propylthio, n-butylthio, n-pentylthio, isopropylthio, isobutylthio, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluoroethyl, 2-chloro-2,2-difluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, vinyl, prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, ethynyl, propargyl, 1-methylprop-2-yn-1-yl, 2-butynyl, 2-pentynyl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, methylthiomethyl and $R^3$ and $R^4$ together with the atom to which they are bonded form a fully saturated 3- to 6-membered ring optionally interrupted by heteroatoms and optionally having further substitution.

Very particularly preferred compounds of the formula (II) are those in which $R^1$ is methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-methylcyclohexyl, 2-methylcyclohexyl, 3-methylcyclohexyl, 1-methoxycyclohexyl, 2-methoxycyclohexyl, 3-methoxycyclohexyl, aryl-($C_1$-$C_8$)-alkyl, heterocyclyl-($C_1$-$C_8$)-alkyl, $R^2$ is hydrogen, tert-butyldimethylsilyl, trimethylsilyl, triethylsilyl, tri(isopropyl)silyl, tri(n-propyl)silyl, dimethyl(phenyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, methyl, ethyl, allyl, methylcarbonyl, ethylcarbonyl, n-propylcarbonyl, isopropylcarbonyl, n-butylcarbonyl, tert-butylcarbonyl, isobutylcarbonyl, isopentylcarbonyl, neopentylcarbonyl, arylcarbonyl, heteroarylcarbonyl, cyclopropylcarbonyl, cyclobutylcarbonyl, cyclopentylcarbonyl, cyclohexylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, ethylthio-n-propyl, $A^1$, V, W are each independently a $CR^3R^4$ group, $A^2$ is a $CR^3R^4$ group or oxygen, m is 0, n is 0, 1, $R^3$ and $R^4$ are each independently hydrogen, methyl, ethyl, n-propyl, isopropyl, n-butyl, isobutyl, tert-butyl, fluorine, chlorine, bromine, iodine, cyclopropyl, cyclobutyl, cyclopentyl, cyclohexyl, methoxy, optionally substituted phenyl, heterocyclyl, heteroaryl, methylthio, trifluoromethyl, difluoromethyl, vinyl, prop-1-en-1-yl, but-1-en-1-yl, allyl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methylthiomethyl and $R^3$ and $R^4$ together with the atom to which they are bonded form a fully saturated 3- to 6-membered ring optionally interrupted by heteroatoms and optionally having further substitution.

Since they are additionally as yet unknown, a further part of the invention is formed by compounds of the formula (III) or salts thereof (III)

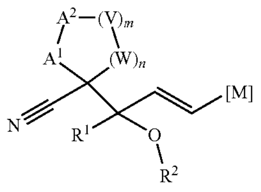

which serve as intermediates for preparation of the inventive compounds of the general formula (I), where $R^1$ is hydrogen, $(C_1-C_8)$-alkyl, aryl, heteroaryl, heterocyclyl, $(C_3-C_8)$-cycloalkyl, $(C_2-C_8)$-alkenyl, $(C_2-C_8)$-alkynyl, $(C_2-C_8)$-alkynyl-$(C_1-C_8)$-alkyl, $(C_1-C_8)$-alkoxy-$(C_1-C_8)$-alkyl, hydroxy-$(C_1-C_8)$-alkyl, $(C_1-C_8)$-haloalkyl, $(C_2-C_8)$-haloalkenyl, $(C_1-C_8)$-haloalkoxy-$(C_1-C_8)$-alkyl, $(C_1-C_8)$-alkylthio-$(C_1-C_8)$-alkyl, aryl-$(C_1-C_8)$-alkyl, heterocyclyl-$(C_1-C_8)$-alkyl, $(C_3-C_8)$-halocycloalkyl, $(C_4-C_8)$-cycloalkenyl, $(C_1-C_8)$-alkoxy-$(C_1-C_8)$-alkoxy-$(C_1-C_8)$-alkyl, $(C_1-C_8)$-alkoxy-$(C_1-C_8)$-haloalkyl, $(C_1-C_8)$-haloalkoxy-$(C_1-C_8)$-haloalkyl, $R^2$ is hydrogen, $(C_1-C_8)$-alkyl, $(C_1-C_8)$-alkoxy-$(C_1-C_8)$-alkyl, $(C_1-C_8)$-alkoxy-$(C_1-C_8)$-alkoxy-$(C_1-C_8)$-alkyl, $(C_2-C_8)$-alkenyl, $(C_2-C_8)$-alkynyl, $(C_1-C_8)$-alkylcarbonyl, arylcarbonyl, heteroarylcarbonyl, $(C_3-C_8)$-cycloalkylcarbonyl, $(C_2-C_8)$-alkenylcarbonyl, heterocyclylcarbonyl, $(C_1-C_8)$-alkoxycarbonyl, $(C_2-C_8)$-alkenyloxycarbonyl, aryloxy-$(C_1-C_8)$-alkyl, aryl-$(C_1-C_8)$-alkoxycarbonyl, $(C_3-C_8)$-cycloalkoxycarbonyl, $(C_3-C_8)$-cycloalkyl-$(C_1-C_8)$-alkoxycarbonyl, aryl-$(C_1-C_8)$-alkoxy-$(C_1-C_8)$-alkyl, aryl-$(C_1-C_8)$-alkyl, $(C_1-C_8)$-alkoxy-$(C_1-C_8)$-alkoxy-$(C_1-C_8)$-alkyl, $(C_1-C_8)$-alkylthio-$(C_1-C_8)$-alkyl, tris[$(C_1-C_8)$-alkyl]silyl, $(C_1-C_8)$-alkylbis-[$(C_1-C_8)$-alkyl]silyl, $(C_1-C_8)$-alkylbis(aryl)silyl, arylbis[$(C_1-C_8)$-alkyl]silyl, $(C_3-C_8)$-cycloalkylbis[$(C_1-C_8)$-alkyl]silyl, halobis[$(C_1-C_8)$-alkyl]silyl, tris[$(C_1-C_8)$-alkyl]silyl-$(C_1-C_8)$-alkoxy-$(C_1-C_8)$-alkyl, tris[$(C_1-C_8)$-alkyl]silyl-$(C_1-C_8)$-alkyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, 2, n is 0, 1, 2, $R^3$ and $R^4$ are each independently hydrogen, $(C_1-C_8)$-alkyl, halogen, $(C_3-C_8)$-cycloalkyl, $(C_1-C_8)$-alkoxy, aryl, heterocyclyl, heteroaryl, aryl-$(C_1-C_8)$-alkyl, $(C_1-C_8)$-alkylthio, $(C_1-C_8)$-haloalkyl, $(C_1-C_8)$-haloalkyloxy, $(C_1-C_8)$-haloalkylthio, $(C_1-C_8)$-alkoxy-$(C_1-C_8)$-alkyl, $(C_1-C_8)$-alkylthio-$(C_1-C_8)$-alkyl, heteroaryl-$(C_1-C_8)$-alkyl, heterocyclyl-$(C_1-C_8)$-alkyl, $(C_1-C_8)$-alkoxy-$(C_1-C_8)$-haloalkyl, $(C_1-C_8)$-haloalkoxy-$(C_1-C_8)$-haloalkyl, $(C_2-C_8)$-alkenyl, $(C_2-C_8)$-alkynyl, $R^3$ and $R^4$ together with the atom to which they are bonded form a fully saturated 3- to 6-membered ring optionally interrupted by heteroatoms and optionally having further substitution and

[M] is tris[$(C_1-C_6)$-alkyl]stannyl, tris[$(C_3-C_8)$-cycloalkyl]stannyl, tris-[$(C_1-C_6)$-alkyl]germanyl, tris-[$(C_3-C_8)$-cycloalkyl]germanyl, bis(cyclopentadienyl)zirconyl, bis(1,2,3,4,5-pentamethylcyclopentadienyl)zirconyl, bis(cyclopentadienyl)hafnyl, bis(1,2,3,4,5-pentamethylcyclopentadienyl)hafnyl, bis(hydroxy)boryl, bis[$(C_1-C_6)$-alkoxy]boryl, $(C_1-C_6)$-alkyl-1,3,2-dioxaborolan-2-yl, bis[$(C_1-C_6)$-alkyl]-1,3,2-dioxaborolan-2-yl, tetrakis[$(C_1-C_6)$-alkyl]-1,3,2-dioxaborolan-2-yl, 1,3,2-dioxaborinan-2-yl, bis[$(C_1-C_6)$-alkyl]-1,3,2-dioxaborinan-2-yl, $(C_1-C_6)$-alkyl-1,3,2-dioxaborinan-2-yl, tris[$(C_1-C_6)$-alkyl]-1,3,2-dioxaborinan-2-yl, 2,6,7-trioxa-1-boranuidabicyclo[2.2.2]octanyl, $(C_1-C_6)$-alkyl-2,6,7-trioxa-1-boranuidabicyclo[2.2.2]octanyl, tris[$(C_1-C_6)$-alkyl]plumbanyl, tris[$(C_3-C_8)$-cycloalkyl]plumbanyl, tris[$(C_1-C_6)$-alkylcarbonyloxy]plumbanyl, trisarylplumbanyl, bis[$(C_1-C_6)$-alkylcarbonyloxy]arylplumbanyl, bis[$(C_1-C_6)$-alkyl]alanyl, bis[$(C_1-C_6)$-cycloalkyl]alanyl, dichloroalanyl, chloromagnesyl, bromomagnesyl, chlorozincyl, chlorohydrargyl, bromohydrargyl, $(C_1-C_6)$-alkylhydrargyl, $(C_3-C_6)$-cycloalkylhydrargyl, tris[$(C_1-C_6)$-alkyl]silyl, $(C_1-C_6)$-alkyl-[bis-$(C_1-C_6)$-alkyl]silyl, $(C_1-C_6)$-alkylbis(aryl)silyl, arylbis[$(C_1-C_6)$-alkyl)]silyl, $(C_3-C_7)$-cycloalkylbis[$(C_1-C_6)$-alkyl]silyl.

Preference is given to compounds of the formula (III) where $R^1$ is hydrogen, $(C_1-C_6)$-alkyl, aryl, heteroaryl, heterocyclyl, $(C_3-C_6)$-cycloalkyl, $(C_2-C_6)$-alkenyl, $(C_2-C_6)$-alkynyl, $(C_2-C_6)$-alkynyl-$(C_1-C_6)$-alkyl, $(C_1-C_6)$-alkoxy-$(C_1-C_6)$-alkyl, hydroxy-$(C_1-C_6)$-alkyl, $(C_1-C_6)$-haloalkyl, $(C_2-C_6)$-haloalkenyl, $(C_1-C_6)$-haloalkoxy-$(C_1-C_6)$-alkyl, $(C_1-C_6)$-alkylthio-$(C_1-C_6)$-alkyl, aryl-$(C_1-C_6)$-alkyl, heterocyclyl-$(C_1-C_6)$-alkyl, $(C_3-C_6)$-halocycloalkyl, $(C_4-C_6)$-cycloalkenyl, $(C_1-C_6)$-alkoxy-$(C_1-C_6)$-alkoxy-$(C_1-C_6)$-alkyl, $(C_1-C_8)$-alkoxy-$(C_1-C_8)$-haloalkyl, $(C_1-C_8)$-haloalkoxy-$(C_1-C_8)$-haloalkyl, $R^2$ is hydrogen, $(C_1-C_6)$-alkyl, $(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_2-C_6)$-alkenyl, $(C_2-C_6)$-alkynyl, $(C_1-C_6)$-alkylcarbonyl, arylcarbonyl, heteroarylcarbonyl, $(C_3-C_6)$-cycloalkylcarbonyl, $(C_2-C_6)$-alkenylcarbonyl, heterocyclylcarbonyl, $(C_1-C_6)$-alkoxycarbonyl, $(C_2-C_6)$-alkenyloxycarbonyl, aryloxy-$(C_1-C_6)$-alkyl, aryl-$(C_1-C_6)$-alkoxycarbonyl, $(C_3-C_6)$-cycloalkoxycarbonyl, $(C_3-C_6)$-cycloalkyl-$(C_1-C_6)$-alkoxycarbonyl, aryl-$(C_1-C_6)$-alkoxy-$(C_1-C_6)$-alkyl, aryl-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, tris[$(C_1-C_6)$-alkyl]silyl, $(C_1-C_6)$-alkylbis-[$(C_1-C_6)$-alkyl]silyl, $(C_1-C_6)$-alkylbis(aryl)silyl, arylbis[$(C_1-C_6)$-alkyl]silyl, $(C_3-C_6)$-cycloalkylbis[$(C_1-C_6)$-alkyl]silyl, halobis[$(C_1-C_6)$-alkyl]silyl, tris[$(C_1-C_6)$-alkyl]silyl-$(C_1-C_6)$-alkoxy-$(C_1-C_6)$-alkyl, tris[$(C_1-C_6)$-alkyl]silyl-$(C_1-C_6)$-alkyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, 2, n is 0, 1, 2, $R^3$ and $R^4$ are each independently hydrogen, $(C_1-C_6)$-alkyl, halogen, $(C_3-C_6)$-cycloalkyl, $(C_1-C_6)$-alkoxy, aryl, heterocyclyl, heteroaryl, aryl-$(C_1-C_6)$-alkyl, $(C_1-C_6)$-alkylthio, $(C_1-C_6)$-haloalkyl, $(C_1-C_6)$-haloalkyloxy, $(C_1-C_6)$-haloalkylthio, $(C_1-C_6)$-alkoxy-$(C_1-C_6)$-alkyl, $(C_1-C_6)$-alkylthio-$(C_1-C_6)$-alkyl, heteroaryl-$(C_1-C_6)$-alkyl, heterocyclyl-$(C_1-C_6)$-alkyl, $(C_1-C_6)$-alkoxy-$(C_1-C_6)$-haloalkyl, $(C_1-C_6)$-haloalkoxy-$(C_1-C_6)$-haloalkyl, $(C_2-C_6)$-alkenyl, $(C_2-C_6)$-alkynyl, $R^3$ and $R^4$ together with the atom to which they are bonded form a fully saturated 3- to 6-membered ring optionally interrupted by heteroatoms and optionally having further substitution and

[M] is tris[$(C_1-C_6)$-alkyl]stannyl, tris[$(C_3-C_6)$-cycloalkyl]stannyl, tris-[$(C_1-C_6)$-alkyl]germanyl, tris-[$(C_3-C_6)$-cycloalkyl]germanyl, bis(cyclopentadienyl)zirconyl, bis(1,2,3,4,5-pentamethylcyclopentadienyl)zirconyl, bis(cyclopentadienyl)hafnyl, bis(1,2,3,4,5-pentamethylcyclopentadienyl)hafnyl, bis(hydroxy)boryl, bis[$(C_1-C_6)$-alkoxy]boryl, $(C_1-C_6)$-alkyl-1,3,2-dioxaborolan-2-yl, bis[$(C_1-C_6)$-alkyl]-1,3,2-dioxaborolan-2-yl, tetrakis[$(C_1-C_6)$-alkyl]-1,3,2-dioxaborolan-2-yl, 1,3,2-dioxaborinan-2-yl, bis[$(C_1-C_6)$-alkyl]-1,3,2-dioxaborinan-2-yl, $(C_1-C_6)$-alkyl-1,3,2-dioxaborinan-2-yl, tris[$(C_1-C_6)$-alkyl]-1,3,2-dioxaborinan-2-yl, 2,6,7-trioxa-1-boranuidabicyclo[2.2.2]octanyl, $(C_1-C_6)$-alkyl-2,6,7-trioxa-1-boranuidabicyclo[2.2.2]octanyl, tris[$(C_1-C_6)$-alkyl]plumbanyl, tris[$(C_3-C_6)$-cycloalkyl]plumbanyl, tris[$(C_1-C_6)$-alkylcarbonyloxy]plumbanyl, trisarylplumbanyl, bis[$(C_1-C_6)$-alkylcarbonyloxy]arylplumbanyl, bis[$(C_1-C_6)$-alkyl]alanyl, bis[$(C_1-C_6)$-cycloalkyl]alanyl, dichloroalanyl, chloromagnesyl, bromomagnesyl, chlorozincyl, chlorohydrargyl, bromohydrargyl, $(C_1-C_6)$-alkylhydrargyl, $(C_3-C_6)$-cycloalkylhydrargyl, tris[$(C_1-C_6)$-alkyl]silyl, $(C_1-C_6)$-alkyl-[bis-$(C_1-C_6)$-alkyl]silyl, $(C_1-C_6)$-alkylbis(aryl)silyl, aryl-bis[$(C_1-C_6)$-alkyl)]silyl, $(C_3-C_7)$-cycloalkylbis[$(C_1-C_6)$-alkyl]silyl.

Particular preference is given to compounds of the formula (III) where $R^1$ is hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-methylcyclohexyl, 2-methylcyclohexyl, 3-methylcyclohexyl, 1-methoxycyclohexyl, 2-methoxycyclohexyl, 3-methoxycyclohexyl, aryl-$(C_1-C_8)$-alkyl, heterocyclyl-$(C_1-C_8)$-alkyl, $R^2$ is hydrogen, tert-butyldimethylsilyl, trimethylsilyl, triethylsilyl, tri(isopropyl)silyl, tri(n-propyl)silyl, dimethyl(phenyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, methyl, ethyl, allyl, methylcarbonyl, ethylcarbonyl, n-propylcarbonyl, isopropylcarbonyl, n-butylcarbonyl, tert-butylcarbonyl, isobutylcarbonyl, isopentylcarbonyl, neopentylcarbonyl, arylcarbonyl, heteroarylcarbonyl, cyclopropylcarbonyl, cyclobutylcarbonyl, cyclopentylcarbonyl, cyclohexylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, ethylthio-n-propyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0, 1, n is 0, 1, $R^3$ and $R^4$ are each independently hydrogen, methyl, ethyl, n-propyl, isopropyl, n-butyl, isobutyl, tert-butyl, fluorine, chlorine, bromine, iodine, cyclopropyl, cyclobutyl, cyclopentyl, cyclohexyl, methoxy, ethoxy, n-propoxy, isopropoxy, n-butyloxy, tert-butyloxy, isobutyloxy, n-pentyloxy, optionally substituted phenyl, heterocyclyl, heteroaryl, benzyl, p-Cl-benzyl, p-F-benzyl, p-methoxybenzyl, p-methylbenzyl, methylthio, ethylthio, n-propylthio, n-butylthio, n-pentylthio, isopropylthio, isobutylthio, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluoroethyl, 2-chloro-2,2-difluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, vinyl, prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, ethynyl, propargyl, 1-methylprop-2-yn-1-yl, 2-butynyl, 2-pentynyl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, methylthiomethyl, $R^3$ and $R^4$ together with the atom to which they are bonded form a fully saturated 3- to 6-membered ring optionally interrupted by heteroatoms and optionally having further substitution and

[M] is trimethylstannyl, triethylstannyl, tris(n-propyl)stannyl, tris(isopropyl)stannyl, tris(n-butyl)stannyl, tris(sec-butyl)stannyl, tris(tert-butyl)stannyl, tris(n-pentyl)stannyl, tris(n-hexyl)stannyl, trimethylgermanyl, triethylgermanyl, tris(n-propyl)germanyl, tris(isopropyl)germanyl, tris(n-butyl)germanyl, tris(sec-butyl)germanyl, tris(tert-butyl)germanyl, tris(n-pentyl)germanyl, tris(n-hexyl)germanyl, tris(cyclohexyl)stannyl, tris(cyclohexyl)germanyl, bis(cyclopentadienyl)zirconyl, bis(1,2,3,4,5-pentamethylcyclopentadienyl)zirconyl, bis(cyclopentadienyl)hafnyl, bis(1,2,3,4,5-pentamethylcyclopentadienyl)hafnyl, bis(hydroxy)boryl, bis(methoxy)boryl, bis(ethoxy)boryl, bis(n-propyloxy)boryl, bis(isopropyloxy)boryl, bis(n-butyloxy)boryl, bis(sec-butyloxy)boryl, bis(tert-butyloxy)boryl, bis(n-pentyloxy)boryl, bis(isopentyloxy)boryl, bis(neopentyloxy)boryl, bis(n-hexyloxy)boryl, $(C_1-C_6)$-alkyl-1,3,2-dioxaborolan-2-yl, bis[$(C_1-C_6)$-alkyl]-1,3,2-dioxaborolan-2-yl, tetrakis[$(C_1-C_6)$-alkyl]-1,3,2-dioxaborolan-2-yl, 1,3,2-dioxaborinan-2-yl, bis[$(C_1-C_6)$-alkyl]-1,3,2-dioxaborinan-2-yl, $(C_1-C_6)$-alkyl-1,3,2-dioxaborinan-2-yl, tris-[$(C_1-C_6)$-alkyl]-1,3,2-dioxaborinan-2-yl, 2,6,7-trioxa-1-boranuidabicyclo[2.2.2]octanyl, $(C_1-C_6)$-alkyl-2,6,7-trioxa-1-boranuidabicyclo[2.2.2]octanyl, tris[$(C_1-C_6)$-alkyl]plumbanyl, tris(cycloalkyl)plumbanyl, tris[$(C_1-C_6)$-alkylcarbonyloxy]plumbanyl, trisarylplumbanyl, bis[$(C_1-C_6)$-alkylcarbonyloxy]arylplumbanyl, bis[$(C_1-C_6)$-alkyl]alanyl, bis[$(C_1-C_6)$-cycloalkyl]alanyl, dichloroalanyl, chloromagnesyl, bromomagnesyl, chlorozincyl, chlorohydrargyl, bromohydrargyl, $(C_1-C_6)$-alkylhydrargyl, $(C_3-C_6)$-cycloalkylhydrargyl, tris[$(C_1-C_6)$-alkyl]silyl, $(C_1-C_6)$-alkyl[bis-$(C_1-C_6)$-alkyl]silyl, $(C_1-C_6)$-alkylbis(aryl)silyl, arylbis[$(C_1-C_6)$-alkyl)]silyl, $(C_3-C_7)$-cycloalkylbis[$(C_1-C_6)$-alkyl]silyl.

Very particular preference is given to compounds of the formula (III) where $R^1$ is methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-methylcyclohexyl, 2-methylcyclohexyl, 3-methylcyclohexyl, 1-methoxycyclohexyl, 2-methoxycyclohexyl, 3-methoxycyclohexyl, aryl-$(C_1-C_8)$-alkyl, heterocyclyl-$(C_1-C_{85})$-alkyl, $R^2$ is hydrogen, tert-butyldimethylsilyl, trimethylsilyl, triethylsilyl, tri(isopropyl)silyl, tri(n-propyl)silyl, dimethyl(phenyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, methyl, ethyl, allyl, methylcarbonyl, ethylcarbonyl, n-propylcarbonyl, isopropylcarbonyl, n-butylcarbonyl, tert-butylcarbonyl, isobutylcarbonyl, isopentylcarbonyl, neopentylcarbonyl, arylcarbonyl, heteroarylcarbonyl, cyclopropylcarbonyl, cyclobutylcarbonyl, cyclopentylcarbonyl, cyclohexylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, ethylthio-n-propyl, $A^1$, V, W are each independently a $CR^3R^4$ group, $A^2$ is a $CR^3R^4$ group or oxygen, m is 0, n is 0, 1, $R^3$ and $R^4$ are each independently hydrogen, methyl, ethyl, n-propyl, isopropyl, n-butyl, isobutyl, tert-butyl, fluorine, chlorine, bromine, iodine, cyclopropyl, cyclobutyl, cyclopentyl, cyclohexyl, methoxy, optionally substituted phenyl, heterocyclyl, heteroaryl, methylthio, trifluoromethyl, difluoromethyl, vinyl, prop-1-en-1-yl, but-1-en-1-yl, allyl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methylthiomethyl, $R^3$ and $R^4$ together with the atom to which they are bonded form a fully saturated 3- to 6-membered ring optionally interrupted by heteroatoms and optionally having further substitution and

[M] is trimethylstannyl, triethylstannyl, tris(n-propyl)stannyl, tris(isopropyl)stannyl, tris(n-butyl)stannyl, tris(sec-butyl)stannyl, tris(tert-butyl)stannyl, tris(n-pentyl)stannyl, tris(n-hexyl)stannyl, trimethylgermanyl, triethylgermanyl, tris(n-propyl)germanyl, tris(isopropyl)germanyl, tris(n-butyl)germanyl, tris(sec-butyl)germanyl, tris(tert-butyl)germanyl, tris(n-pentyl)germanyl, tris(n-hexyl)germanyl, tris(cyclohexyl)stannyl, tris(cyclohexyl)germanyl, bis(cyclopentadienyl)zirconyl, bis(1,2,3,4,5-pentamethylcyclopentadienyl)zirconyl, bis (cyclopentadienyl)hafnyl, bis(1,2,3,4,5-pentamethylcyclopentadienyl)hafnyl, bis(hydroxy)boryl, bis(methoxy)boryl, bis(ethoxy)boryl, bis(n-propyloxy)boryl, bis(isopropyloxy)boryl, bis(n-butyloxy)boryl, bis(sec-butyloxy)boryl, bis(tert-butyloxy)boryl, bis(n-pentyloxy)boryl, bis(isopentyloxy)boryl, bis(neopentyloxy)boryl, bis(n-hexyloxy)boryl, $(C_1-C_6)$-alkyl-1,3,2-dioxaborolan-2-yl, bis[$(C_1-C_6)$-alkyl]-1,3,2-dioxaborolan-2-yl, tetrakis-[$(C_1-C_6)$-alkyl]-1,3,2-dioxaborolan-2-yl, 1,3,2-dioxaborinan-2-yl, bis[$(C_1-C_6)$-alkyl]-1,3,2-dioxaborinan-2-yl, $(C_1-C_6)$-alkyl-1,3,2-dioxaborinan-2-yl, tris-[$(C_1-C_6)$-alkyl]-1,3,2-dioxaborinan-2-yl, 2,6,7-trioxa-1-boranuidabicyclo[2.2.2]octanyl, $(C_1-C_6)$-alkyl-2,6,7-trioxa-1-boranuidabicyclo[2.2.2]octanyl, tris[$(C_1-C_6)$-alkyl]plumbanyl, tris(cycloalkyl)plumbanyl, tris[$(C_1-C_6)$-alkylcarbonyloxy]plumbanyl, trisarylplumbanyl, bis[$(C_1-C_6)$-alkylcarbonyloxy]arylplumbanyl, bis[$(C_1-C_6)$-alkyl]alanyl, bis[$(C_1-C_6)$-cycloalkyl]alanyl, dichloroalanyl, chloromagnesyl, bromomagnesyl, chlorozincyl, chlorohydrargyl, bromohydrargyl, $(C_1-C_6)$-alkylhydrargyl, $(C_3-C_6)$-cycloalkylhydrargyl, tris[$(C_1-C_6)$-alkyl]silyl, $(C_1-C_6)$-alkyl[bis-$(C_1-C_6)$-alkyl]silyl, $(C_1-C_6)$-alkylbis(aryl)silyl, arylbis[$(C_1-C_6)$-alkyl)]silyl, $(C_3-C_7)$-cycloalkylbis[$(C_1-C_6)$-alkyl]silyl.

With regard to the compounds according to the invention, the terms used above and further below will be elucidated. These are familiar to the person skilled in the art and especially have the definitions elucidated hereinafter:

According to the invention, "arylsulphonyl" is optionally substituted phenylsulphonyl or optionally substituted polycyclic arylsulphonyl, here especially optionally substituted naphthylsulphonyl, for example substituted by fluorine, chlorine, bromine, iodine, cyano, nitro, alkyl, haloalkyl, haloalkoxy, amino, alkylamino, alkylcarbonylamino, dialkylamino or alkoxy groups.

According to the invention, "cycloalkylsulphonyl"—alone or as part of a chemical group—is optionally substituted cycloalkylsulphonyl, preferably having 3 to 6 carbon atoms, for example cyclopropylsulphonyl, cyclobutylsulphonyl, cyclopentylsulphonyl or cyclohexylsulphonyl.

According to the invention, "alkylsulphonyl"—alone or as part of a chemical group—is straight-chain or branched alkylsulphonyl, preferably having 1 to 8 or having 1 to 6 carbon atoms, for example methylsulphonyl, ethylsulphonyl, n-propylsulphonyl, isopropylsulphonyl, n-butylsulphonyl, isobutylsulphonyl, sec-butylsulphonyl and tert-butylsulphonyl.

According to the invention, "heteroarylsulphonyl" is optionally substituted pyridylsulphonyl, pyrimidinylsulphonyl, pyrazinylsulphonyl or optionally substituted polycyclic heteroarylsulphonyl, here in particular optionally substituted quinolinylsulphonyl, for example substituted by fluorine, chlorine, bromine, iodine, cyano, nitro, alkyl, haloalkyl, haloalkoxy, amino, alkylamino, alkylcarbonylamino, dialkylamino or alkoxy groups.

According to the invention, "alkylthio"—alone or as part of a chemical group—is straight-chain or branched S-alkyl, preferably having 1 to 8 or having 1 to 6 carbon atoms, for example methylthio, ethylthio, n-propylthio, isopropylthio, n-butylthio, isobutylthio, sec-butylthio and tert-butylthio. Alkenylthio is an alkenyl radical bonded via a sulphur atom, alkynylthio is an alkynyl radical bonded via a sulphur atom, cycloalkylthio is a cycloalkyl radical bonded via a sulphur atom, and cycloalkenylthio is a cycloalkenyl radical bonded via a sulphur atom.

"Alkoxy" is an alkyl radical bonded via an oxygen atom, alkenyloxy is an alkenyl radical bonded via an oxygen atom, alkynyloxy is an alkynyl radical bonded via an oxygen atom, cycloalkyloxy is a cycloalkyl radical bonded via an oxygen atom, and cycloalkenyloxy is a cycloalkenyl radical bonded via an oxygen atom.

The term "aryl" means an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl".

A heterocyclic radical (heterocyclyl) contains at least one heterocyclic ring (=carbocyclic ring in which at least one carbon atom has been replaced by a heteroatom, preferably by a heteroatom from the group of N, O, S, P) which is saturated, unsaturated, partly saturated or heteroaromatic and may be unsubstituted or substituted, in which case the bonding site is localized on a ring atom. If the heterocyclyl radical or the heterocyclic ring is optionally substituted, it may be fused to other carbocyclic or heterocyclic rings. In the case of optionally substituted heterocyclyl, polycyclic systems are also included, for example 8-azabicyclo[3.2.1]octanyl, 8-azabicyclo[2.2.2]octanyl or 1-azabicyclo[2.2.1]heptyl. In the case of optionally substituted heterocyclyl, spirocyclic systems are also included, for example 1-oxa-5-azaspiro[2.3]hexyl. Unless defined differently, the heterocyclic ring contains preferably 3 to 9 ring atoms and especially 3 to 6 ring atoms and one or more, preferably 1 to 4 and especially 1, 2 or 3 heteroatoms in the heterocyclic ring, preferably from the group of N, O and S, although no two oxygen atoms should be directly adjacent, for example, with one heteroatom from the group of N, O and S, 1- or 2- or 3-pyrrolidinyl, 3,4-dihydro-2H-pyrrol-2- or 3-yl, 2,3-dihydro-1H-pyrrol-1- or 2- or 3- or 4- or 5-yl; 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl; 2,5-dihydropyridin-2- or 3- or 4- or 5- or 6-yl, 1- or 2- or 3- or 4-azepanyl; 2,3,4,5-tetrahydro-1H-azepin-1- or 2- or 3- or 4- or 5- or 6- or 7-yl; 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl; 2,5-dihydro-1H-azepin-1- or -2- or 3- or 4- or 5- or 6- or 7-yl; 2,7-dihydro-1H-azepin-1- or -2- or 3- or 4-yl; 2,3-dihydro-1H-azepin-1- or -2- or 3- or 4- or 5- or 6- or 7-yl; 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl, 2- or 3-oxolanyl (=2- or 3-tetrahydrofuranyl); 2,3-dihydrofuran-2- or 3- or 4- or 5-yl; 2,5-dihydrofuran-2- or 3-yl, 2- or 3- or 4-oxanyl (=2- or 3- or 4-tetrahydropyranyl); 3,4-dihydro-2H-pyran-2- or 3- or 4- or 5- or 6-yl; 3,6-dihydro-2H-pyran-2- or 3- or 4- or 5- or 6-yl; 2H-pyran-2- or 3- or 4- or 5- or 6-yl; 4H-pyran-2- or 3- or 4-yl, 2- or 3- or 4-oxepanyl; 2,3,4,5-tetrahydrooxepin-2- or 3- or 4- or 5- or 6- or 7-yl; 2,3,4,7-tetrahydrooxepin-2- or 3- or 4- or 5- or 6- or 7-yl; 2,3,6,7-tetrahydrooxepin-2- or 3- or 4-yl; 2,3-dihydrooxepin-2- or 3- or 4- or 5- or 6- or 7-yl; 4,5-dihydrooxepin-2- or 3- or 4-yl; 2,5-dihydrooxepin-2- or 3- or 4- or 5- or 6- or 7-yl; oxepin-2- or 3- or 4- or 5- or 6- or 7-yl; 2- or 3-tetrahydrothiophenyl; 2,3-dihydrothiophen-2- or 3- or 4- or 5-yl; 2,5-dihydrothiophen-2- or 3-yl; tetrahydro-2H-thiopyran-2- or 3- or 4-yl; 3,4-dihydro-2H-thiopyran-2- or 3- or 4- or 5- or 6-yl; 3,6-dihydro-2H-thiopyran-2- or 3- or 4- or 5- or 6-yl; 2H-thiopyran-2- or 3- or 4- or 5- or 6-yl; 4H-thiopyran-2- or 3- or 4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partly or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 2- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyriazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or 5- or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl; 2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5-dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or 5- or 6- or 7-yl; 1,4-oxazepan-2- or 3- or 5- or 6- or 7-yl; 2,3,4,5-tetrahydro-1,4-oxazepin-2- or 3- or 4- or 5- or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl.

Further examples of "heterocyclyl" are a partly or fully hydrogenated heterocyclic radical having 3 heteroatoms from the group of N, O and S, for example 1,4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl; 1,4,2-dioxazepan-2- or 3- or 5- or 6- or 7-yl; 6,7-dihydro-5H-1,4,2-dioxazepin-3- or 5- or 6- or 7-yl; 2,3-dihydro-7H-1,4, 2-dioxazepin-2- or 3- or 5- or 6- or 7-yl; 2,3-dihydro-5H-1,4,2-dioxazepin-2- or 3- or 5- or 6- or 7-yl; 5H-1,4,2-dioxazepin-3- or 5- or 6- or 7-yl; 7H-1,4,2-dioxazepin-3- or 5- or 6- or 7-yl. Structural examples of heterocycles which are optionally substituted further are also listed below:
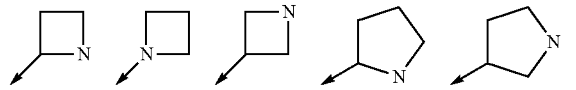
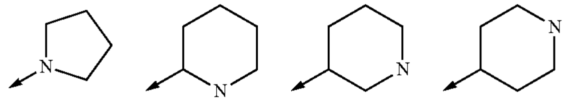
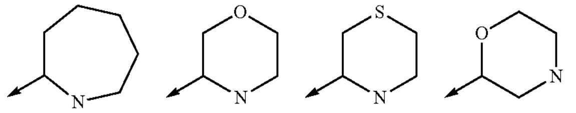
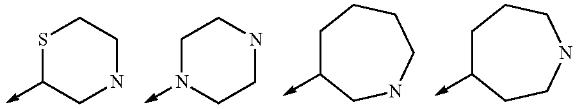
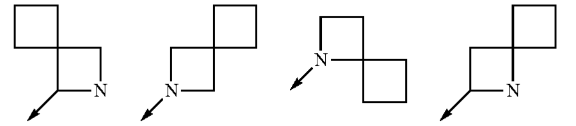
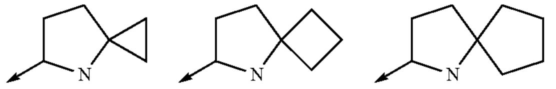
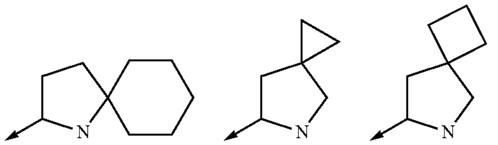
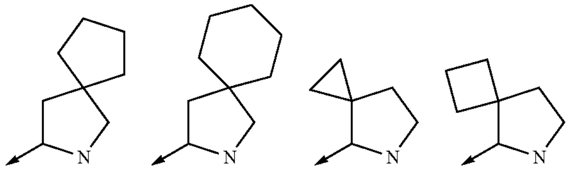
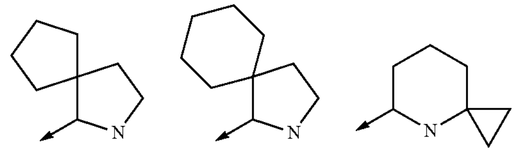
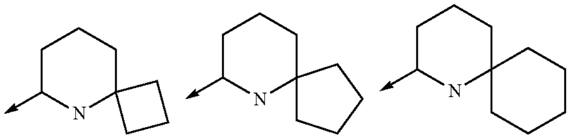
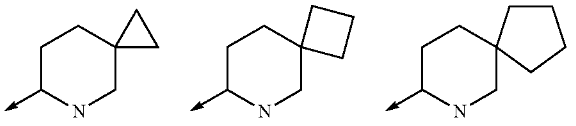
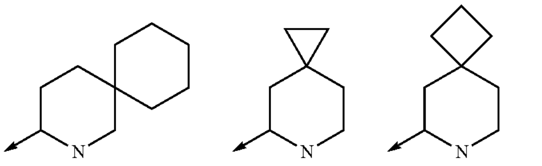
-continued
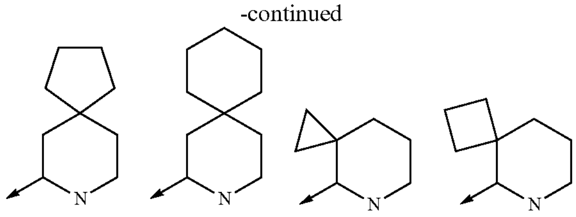
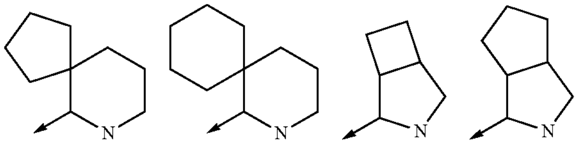
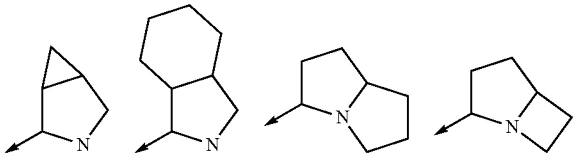
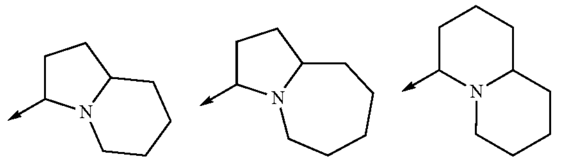
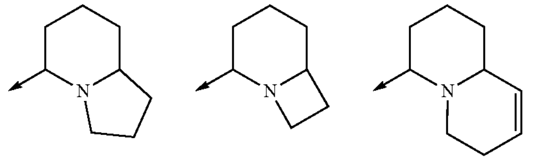
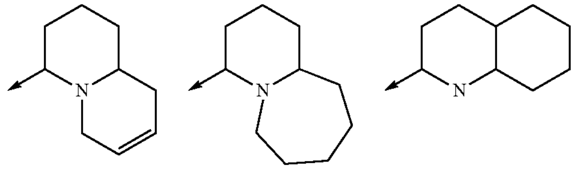
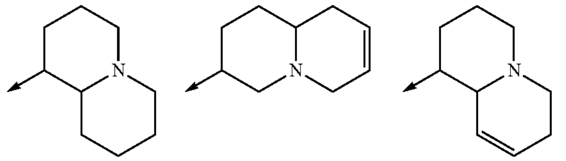
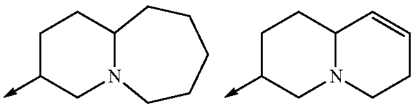
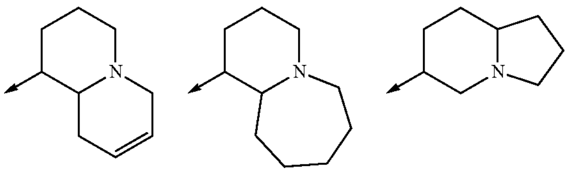
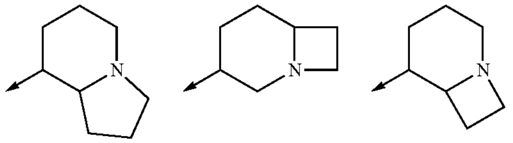
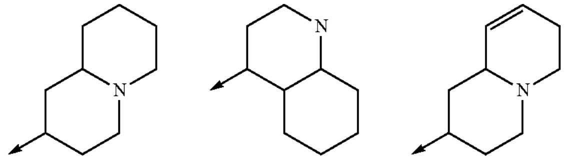

-continued

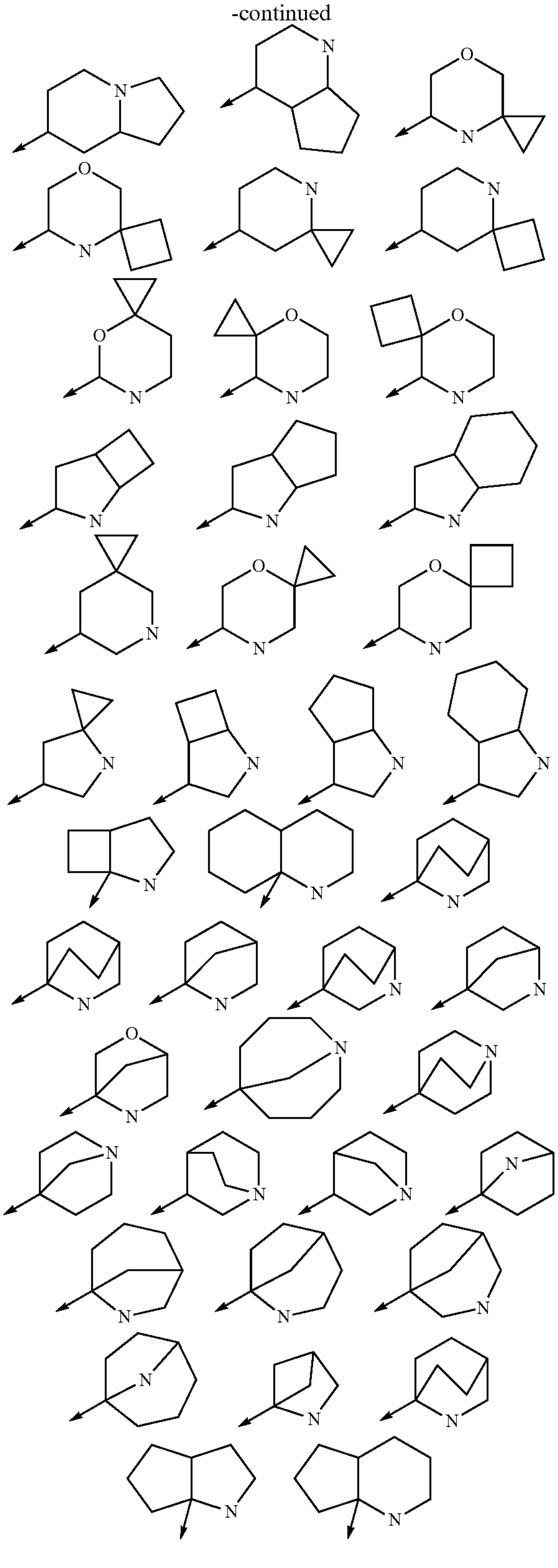

The heterocycles listed above are preferably substituted, for example, by hydrogen, halogen, alkyl, haloalkyl, hydroxyl, alkoxy, cycloalkoxy, aryloxy, alkoxyalkyl, alkoxyalkoxy, cycloalkyl, halocycloalkyl, aryl, arylalkyl, heteroaryl, heterocyclyl, alkenyl, alkylcarbonyl, cycloalkylcarbonyl, arylcarbonyl, heteroarylcarbonyl, alkoxycarbonyl, hydroxycarbonyl, cycloalkoxycarbonyl, cycloalkylalkoxycarbonyl, alkoxycarbonylalkyl, arylalkoxycarbonyl, arylalkoxycarbonylalkyl, alkynyl, alkynylalkyl, alkylalkynyl, trisalkylsilylalkynyl, nitro, amino, cyano, haloalkoxy, haloalkylthio, alkylthio, hydrothio, hydroxyalkyl, oxo, heteroarylalkoxy, arylalkoxy, heterocyclylalkoxy, heterocyclylalkylthio, heterocyclyloxy, heterocyclylthio, heteroaryloxy, bisalkylamino, alkylamino, cycloalkylamino, hydroxycarbonylalkylamino, alkoxycarbonylalkylamino, arylalkoxycarbonylalkylamino, alkoxycarbonylalkyl(alkyl)amino, aminocarbonyl, alkylaminocarbonyl, bisalkylaminocarbonyl, cycloalkylaminocarbonyl, hydroxycarbonylalkylaminocarbonyl, alkoxycarbonylalkylaminocarbonyl, arylalkoxycarbonylalkylaminocarbonyl.

When a base structure is substituted "by one or more radicals" from a list of radicals (=group) or a generically defined group of radicals, this in each case includes simultaneous substitution by a plurality of identical and/or structurally different radicals.

In the case of a partly or fully saturated nitrogen heterocycle, this may be joined to the remainder of the molecule either via carbon or via the nitrogen.

Suitable substituents for a substituted heterocyclic radical are the substituents specified further down, and additionally also oxo and thioxo. The oxo group as a substituent on a ring carbon atom is then, for example, a carbonyl group in the heterocyclic ring. As a result, lactones and lactams are preferably also included. The oxo group may also be present on the ring heteroatoms, which can exist in various oxidation states, for example on N and S, in which case they form, for example, the divalent groups N(O), S(O) (also SO for short) and S(O)2 (also SO2 for short) in the heterocyclic ring. In the case of —N(O)— and —S(O)— groups, both enantiomers in each case are included.

According to the invention, the expression "heteroaryl" represents heteroaromatic compounds, i.e. fully unsaturated aromatic heterocyclic compounds, preferably 5- to 7-membered rings having 1 to 4, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl.

The heteroaryl groups according to the invention may also be substituted by one or more identical or different radicals. If two adjacent carbon atoms are part of a further aromatic ring, the systems are fused heteroaromatic systems, such as benzofused or polyannulated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" means, for example, fluorine, chlorine, bromine or iodine. If the term is used for a radical, "halogen" means, for example, a fluorine, chlorine, bromine or iodine atom.

According to the invention, "alkyl" means a straight-chain or branched open-chain, saturated hydrocarbon radical which is optionally mono- or polysubstituted, and in the latter case is referred to as "substituted alkyl". Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine.

"Haloalkyl", "-alkenyl" and "-alkynyl" are alkyl, alkenyl and alkynyl, respectively, which are partially or fully substituted by identical or different halogen atoms, for example monohaloalkyl such as $CH_2CH_2Cl$, $CH_2CH_2Br$, $CHClCH_3$, $CH_2Cl$, $CH_2F$; perhaloalkyl such as $CCl_3$, $CClF_2$, $CFCl_2$, $CF_2CClF_2$, $CF_2CClFCF_3$; polyhaloalkyl such as $CH_2CHFCl$, $CF_2CClFH$, $CF_2CBrFH$, $CH_2CF_3$; here, the term perhaloalkyl also comprises the term perfluoroalkyl.

Partly fluorinated alkyl means a straight-chain or branched, saturated hydrocarbon which is mono- or polysubstituted by fluorine, where the fluorine atoms in question may be present as substituents on one or more different carbon atoms of the straight-chain or branched hydrocarbon chain, for example $CHFCH_3$, $CH_2CH_2F$, $CH_2CH_2CF_3$, $CHF_2$, $CH_2F$, $CHFCF_2CF_3$.

Partly fluorinated haloalkyl means a straight-chain or branched, saturated hydrocarbon which is substituted by different halogen atoms with at least one fluorine atom, where any other halogen atoms optionally present are selected from the group consisting of fluorine, chlorine or bromine, iodine. The corresponding halogen atoms may be present as substituents on one or more different carbon atoms of the straight-chain or branched hydrocarbon chain. Partly fluorinated haloalkyl also includes full substitution of the straight or branched chain by halogen including at least one fluorine atom.

Haloalkoxy is, for example, $OCF_3$, $OCHF_2$, $OCH_2F$, $OCF_2CF_3$, $OCH_2CF_3$ and $OCH_2CH_2Cl$; the situation is equivalent for haloalkenyl and other halogen-substituted radicals.

The expression "$(C_1-C_4)$-alkyl" mentioned here by way of example is a brief notation for straight-chain or branched alkyl having one to 4 carbon atoms according to the range stated for carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals having a greater number of carbon atoms, i.e. according to the example also the alkyl radicals having 5 and 6 carbon atoms.

Unless stated specifically, in the case of the hydrocarbyl radicals such as alkyl, alkenyl and alkynyl radicals, including in composite radicals, preference is given to the lower carbon skeletons, for example having 1 to 6 carbon atoms, or in the case of unsaturated groups having 2 to 6 carbon atoms. Alkyl radicals, including in the combined radicals such as alkoxy, haloalkyl, etc., mean, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

The term "alkenyl" also includes, in particular, straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl is, for example, vinyl which may be optionally substituted by further alkyl radicals, for example prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

The term "alkynyl" also includes, in particular, straight-chain or branched open-chain hydrocarbon radicals having more than one triple bond, or else having one or more triple bonds and one or more double bonds, for example 1,3-butatrienyl or 3-penten-1-yn-1-yl. $(C_2-C_6)$-Alkynyl means, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

The term "cycloalkyl" means a carbocyclic, saturated and optionally substituted ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene. Optionally substituted cycloalkyl also includes polycyclic aliphatic systems, for example bicyclo[1.1.0]

butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl. The term "($C_3$-$C_7$)-cycloalkyl" is a brief notation for cycloalkyl having three to 7 carbon atoms, corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

"Cycloalkenyl" means a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "alkylidene", also, for example, in the form ($C_1$-$C_{10}$)-alkylidene, means the radical of a straight-chain or branched open-chain hydrocarbon radical which is attached via a double bond. Possible bonding sites for alkylidene are naturally only positions on the base structure where two hydrogen atoms can be replaced by the double bond; examples of radicals include $=CH_2$, $=CH-CH_3$, $=C(CH_3)-CH_3$, $=C(CH_3)-C_2H_5$ and $=C(C_2H_5)-C_2H_5$. Cycloalkylidene is a carbocyclic radical bonded via a double bond.

The term "stannyl" is a further-substituted radical containing a tin atom; "germanyl", analogously, is a further-substituted radical containing a germanium atom. "Zirconyl" is a further-substituted radical containing a zirconium atom. "Hafnyl" is a further-substituted radical containing a hafnium atom. "Boryl", "borolanyl" and "borinanyl" are further-substituted and optionally cyclic groups each containing a boron atom. "Plumbanyl" is a further-substituted radical containing a lead atom. "Hydrargyl" is a further-substituted radical containing a mercury atom. "Alanyl" is a further-substituted radical containing an aluminium atom. "Magnesyl" is a further-substituted radical containing a magnesium atom. "Zincyl" is a further-substituted radical containing a zinc atom.

Depending on the nature of the substituents and the manner in which they are attached, the compounds of the general formula (I) may be present as stereoisomers. The formula (I) embraces all possible stereoisomers defined by the specific three-dimensional form thereof, such as enantiomers, diastereomers, Z and E isomers. If, for example, one or more alkenyl groups are present, diastereomers (Z and E isomers) may occur. If, for example, one or more asymmetric carbon atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomeric excess, or else on the preparative scale to produce test specimens for biological testing. It is likewise possible to selectively prepare stereoisomers through use of stereoselective reactions using optically active starting materials and/or auxiliaries. The invention thus also relates to all stereoisomers which are embraced by the general formula (I) but are not shown in their specific stereomeric form, and to mixtures thereof.

Synthesis of Substituted cyanocycloalkylpenta-2,4-dienes and cyanocycloalkylpent-2-en-4-ynes, cyanoheterocyclylpenta-2,4-dienes and cyanoheterocyclylpent-2-en-4-ynes of the General Formula (I)

The inventive substituted cyanocycloalkylpenta-2,4-dienes, cyanocycloalkylpent-2-en-4-ynes, cyanoheterocyclylpenta-2,4-dienes and cyanoheterocyclylpent-2-en-4-ynes of the general formula (I) can be prepared proceeding from known processes. The known and structurally related plant-derived natural substance abscisic acid can be obtained by various synthetic routes (cf. Hanson et al. J. Chem. Res. (S), 2003, 426; Constantino et al. J. Org. Chem. 1986, 51, 253; Constantino et al. 1989, 54, 681; Marsh et al. Org. Biomol. Chem. 2006, 4, 4186; WO94/15467). Some of the processes described therein for the synthesis of the abscisic acid skeleton have been optimized and replaced by alternative synthesis steps. The synthesis routes used and examined proceed from commercially available or easily preparable ketones and alkynoic acid derivatives. The first key intermediate prepared for the synthesis of the inventive compounds of the general formula (I) is an optionally substituted 1-(2-hydroxybut-3-yn-2-yl)cycloalkylcarbonitrile of the general formula (II).

Scheme 1

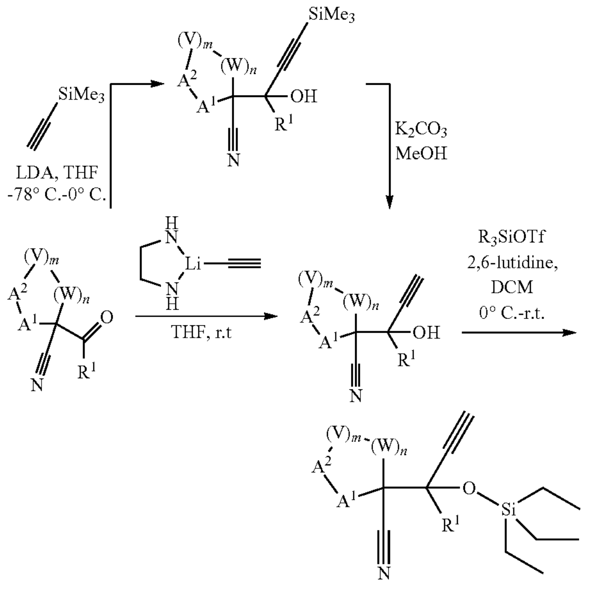

This is effected by reaction of an appropriate ketone with a lithium acetylide/ethylenediamine complex in a suitable polar-aprotic solvent (for example tetrahydrofuran) or in two steps by reaction with trimethylsilylacetylene and LDA (lithium diisopropylamide) within a temperature range from −78° C. to 0° C. in a suitable polar-aprotic solvent (for example tetrahydrofuran) and subsequent elimination of the trimethylsilyl group with the aid of a suitable trialkylammonium fluoride (for example tetrabutylammonium fluoride) in a polar-aprotic solvent or with a suitable carbonate base (for example potassium carbonate) in a polar-protic solvent (for example methanol) (cf. J. Chem. Res. (S) 2003, 426) to give a correspondingly substituted inventive 1-(2-hydroxybut-3-yn-2-yl)cycloalkylcarbonitrile of the general formula II (Scheme 1). $A^1$, $A^2$, V, W, m, n, and $R^1$ in the above Scheme 1 are each as defined above. $R^2$ in Scheme 1 is, by way of example, a hydrogen atom or a triethylsilyl group. The ketone reactants used for the reactions in Schemes 1 and 2 are prepared via synthesis routes described in the literature (cf. J. Org. Chem. 1992, 57, 436; Zh. Org. Khim. 1992, 28, 256).

Proceeding from correspondingly substituted 1-(2-hydroxybut-3-yn-2-yl)cycloalkylcarbonitriles II, it is possible to prepare the inventive substituted cyanocycloalkylpent-2-en-4-ynes I(a) by transition metal-catalysed coupling with suitable substituted iodoalkenoic acid or alkynoic acid derivatives (cf. J. Chem. Res. (S), 2003, 426; J. Chem. Soc., Perkin Trans. 1 2001, 47; Adv. Synth. Catal. 2005, 347, 872), using a suitable transition metal catalyst system (e.g. bis(triphenylphosphine)palladium dichloride, palladium(II) acetate together with triphenylphosphine or bis(cycloacta-1,5-dienyl)iridium chloride in combination with a bidentate ligand, e.g. 2,2'-bis(diphenylphosphino)-1,1'-binaphthyl or 1,4-bis(diphenylphosphino)butane) and a suitable copper(I) halide (e.g. copper(I) iodide) in a suitable solvent mixture of an amine and a polar aprotic solvent (e.g. diisopropylamine and toluene or triethylamine and tetrahydrofuran) (Scheme 2). $A^1$, $A^2$, V, W, $R^1$, $R^2$, $R^5$, $R^6$, $R^7$ and $R^8$ in Scheme 2 below are each as defined above.

Scheme 2

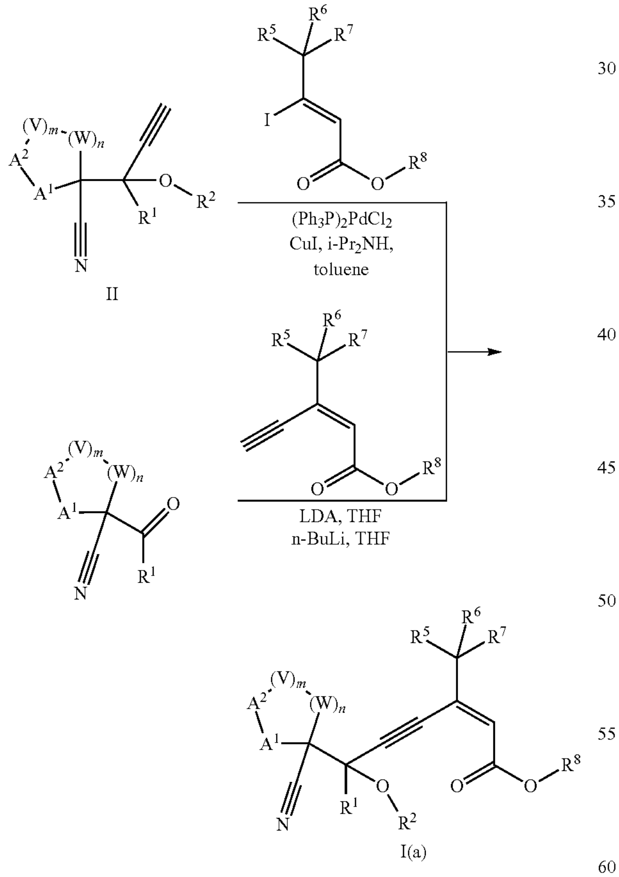

The corresponding (Z)-iodoalkenoic acid derivatives can be prepared, for example, by reacting a terminal alkyne with chloroformic esters using a suitable base (for example n-butyllithium) and subsequent reaction with sodium iodide (cf. J. Fluorine Chem. 1981, 17, 249; Org. Lett. 2000, 2, 3407; Tetrahedron Lett. 2008, 49, 794; Tetrahedron Lett.

1997, 38, 6729) (Scheme 3). Alternatively, the inventive substituted cyanocycloalkylpent-2-en-4-ynes I(a) can also be prepared by reacting a suitable substituted ketone with appropriate substituted (Z)-pent-2-en-4-ynoic acid derivatives using a suitable base (for example lithium diisopropylamide or n-butyllithium) in a suitable polar-aprotic solvent (for example tetrahydrofuran) (Scheme 3). The corresponding (Z)-pent-2-en-4-ynoic acid derivatives are obtainable by transition metal-catalysed coupling of a trialkylsilylalkyne with a (Z)-iodoalkenoic acid derivative (cf. J. Chem. Res. (S), 2003, 426; J. Chem. Soc., Perkin Trans. 1 2001, 47) using a suitable palladium catalyst (for example bis(triphenylphosphine)palladium dichloride) and a suitable copper (I) halide (for example copper(I) iodide) in a suitable solvent mixture of an amine and a polar aprotic solvent (for example diisopropylamine and toluene or triethylamine and tetrahydrofuran) and subsequent treatment with a suitable tetraalkylammonium fluoride (Scheme 3). Substituted (Z)-iodoalkenamides are obtainable from the corresponding (Z)-iodoalkenoic acids by reaction with thionyl chloride and subsequent addition of the relevant amino component or by EDC and HOBt-mediated coupling with the amine component (Scheme 3). EDC here is 1-ethyl-3-(3-dimethylaminopropyl)carbodiimide, and HOBt in this context is hydroxybenzotriazole. $R^5$, $R^6$, $R^7$, $R^8$, $R^9$ and $R^{10}$ in Scheme 3 below are each as defined above.

Scheme 3

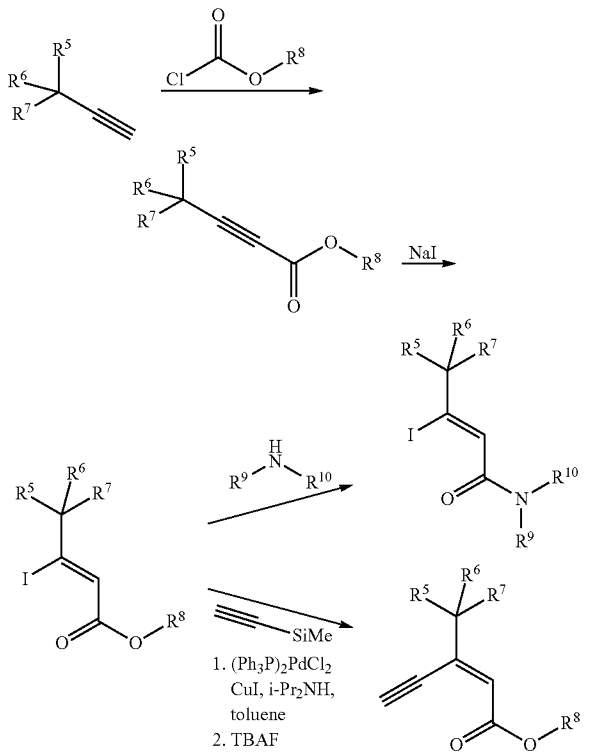

The inventive substituted cyanocycloalkylpent-2-en-4-ynecarboxamides I(b) are therefore obtainable via two possible synthesis routes (Scheme 4), a) the conversion of the inventive substituted cyanocycloalkylpent-2-en-4-ynoic acids I(a) by reaction with thionyl chloride and subsequent addition of the relevant amino component or by EDC- and HOBt-mediated coupling of the amine component or b) the transition metal-catalysed coupling of an appropriately substituted 1-(2-hydroxybut-3-yn-2-yl)cycloalkylcarbonitrile II and a (Z)-iodoalkenamide (cf. J. Chem. Res. (S), 2003, 426; J. Chem. Soc., Perkin Trans. 1 2001, 47) using a suitable palladium catalyst (for example bis(triphenylphosphine)palladium dichloride) and a suitable copper(I) halide (for example copper(I) iodide) in a suitable solvent mixture of an amine and a polar aprotic solvent (for example diisopropylamine and toluene or triethylamine and tetrahydrofuran). $A^1$, $A^2$, V, W, $R^1$, $R^2$, $R^5$, $R^6$, $R^7$, $R^8$, $R^9$ and $R^{10}$, and also m and n, in Scheme 4 below are each as defined above.

Scheme 4

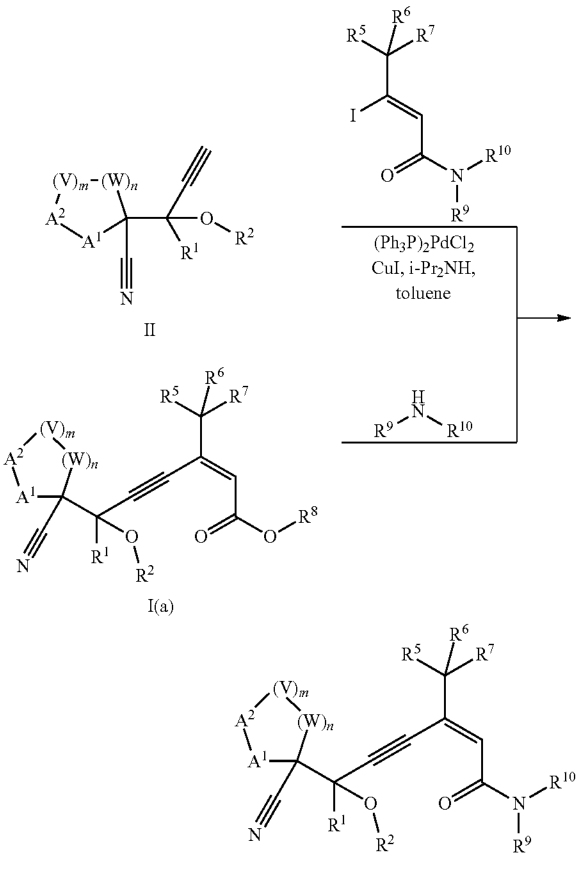

II

I(a)

I(b)

The inventive substituted (E,Z)-configured cyanocycloalkylpenta-2,4-dienes I(c) can be prepared by reduction of the alkyne group of the inventive compounds I(a) using suitable aluminium hydride reagents (e.g. sodium bis(2-methoxyethoxy)alumino-hydride or lithium aluminium-hydride) in a suitable polar-aprotic solvent (e.g. tetrahydrofuran) (cf. Org. Biomol. Chem. 2006, 4, 4186; Bioorg. Med. Chem. 2004, 12, 363-370; Tetrahedron 2003, 59, 9091-9100; Org. Biomol. Chem. 2006, 4, 1400-1412; Synthesis 1977, 561; Tetrahedron Letters 1992, 33, 3477 and Tetrahedron Letters 1974, 1593), using borohydride reagents (e.g. sodium borohydride) in a suitable polar-protic solvent (e.g. methanol) (cf. Org. Lett. 2004, 6, 1785), using lithium dissolved in a mixture of ethylamine and tert-butanol (e.g. Helvetica Chimica Acta 1986, 69, 368), or utilizing a suitable trialkoxysilane, in the presence of a suitable transition metal catalyst (e.g. tris(acetonitrile)ruthenium 1,2,3,4,5-pentamethylcyclopentadienylhexafluorophosphate or tris(acetonitrile)ruthenium cyclopentadienylhexafluorophosphate; cf. J. Am. Chem. Soc. 2002, 124, 7622; J. Am. Chem. Soc. 2005, 127, 17645) (Scheme 5). Depending on the reaction conditions, the hydrogenations of the triple bond can also give, as further reaction products, the corresponding inventive (E,E)-configured cyanocycloalkylpenta-2,4-dienes I(d). $A^1$, $A^2$, V, W, $R^1$, $R^2$, $R^5$, $R^6$, $R^7$ and $R^8$, and also m and n, in Scheme 5 below are each as defined above.

Scheme 5

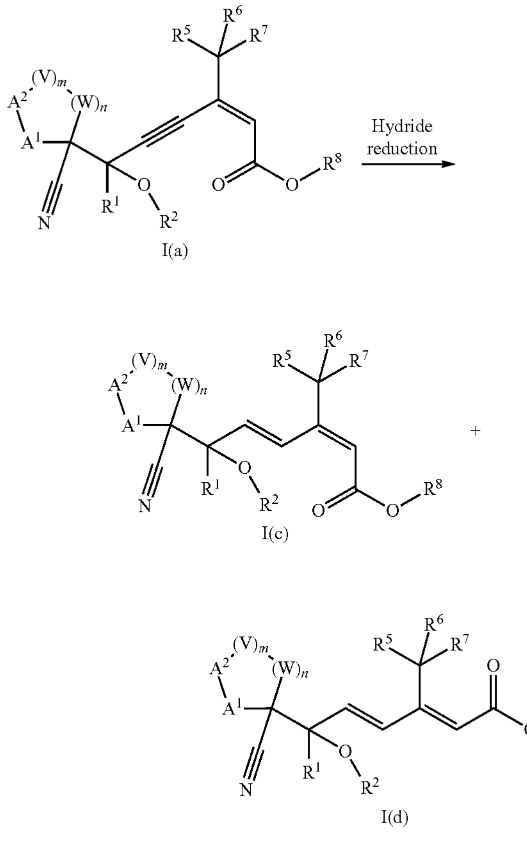

I(a)

I(c)

I(d)

An alternative route to the inventive substituted (E,Z)-configured cyanocycloalkylpenta-2,4-dienes I(c) is the metal or semimetal hydride-mediated conversion of the above-described substituted 1-(2-hydroxybut-3-yn-2-yl)cycloalkylcarbonitriles in a suitable polar-aprotic solvent (e.g. tetrahydrofuran or dichloromethane) to corresponding substituted 1-[(3E)-2-hydroxy-4-[M]-but-3-en-2-yl]cycloalkylcarbonitriles of the general formula III (cf. Org. Lett. 2002, 4, 703; Angew. Int. Ed. 2006, 45, 2916) where [M] is, for example, a further-substituted metal or semimetal component from the group of tin, germanium, lead, boron, aluminium or zirconium (e.g. [M]=tri-n-butylstannyl or biscyclopentadienylchlorozirconyl) (cf. also Org. Lett. 2010, 12, 1056; Org. Lett 2005, 7, 5191, J. Am. Chem. Soc. 2010, 132, 10961; Tetrahedron 1994, 50, 5189; Angew. Chem. Int. Ed. 2000, 39, 1930). The substituted 1-[(3E)-2-hydroxy-4-[M]-but-3-en-2-yl]cycloalkylcarbonitriles thus obtained can be converted by coupling with an appropriate substituted (Z)-haloalkenoic acid derivative in a suitable solvent (for example tetrahydrofuran or N,N-dimethylformamide) using suitable transition metal catalysts (for example bis(triphenylphosphine)palladium dicyanide, tetrakis(triphenylphosphine)palladium or bis(triphenylphosphine)palladium dichloride) to give the inventive substituted (E,Z)-configured cyanocycloalkylpenta-2,4-dienes I(c) (Scheme 6). $A^1$, $A^2$, V, W, [M], $R^1$, $R^2$, $R^5$, $R^6$, $R^7$ and $R^8$, and also m and n, in Scheme 6 below are each as defined above.

Scheme 6

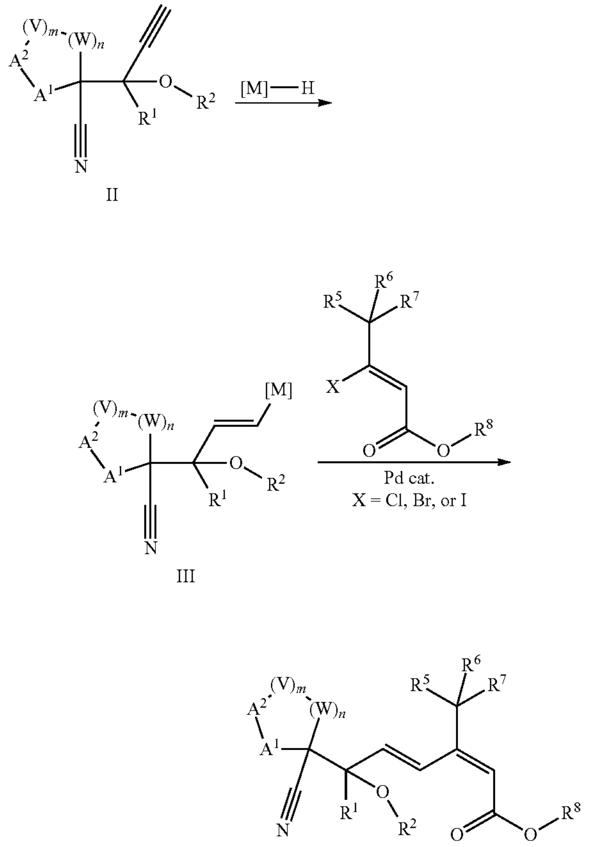

II

III

I(c)

The corresponding inventive substituted (E,Z)-configured cyanocycloalkylpenta-2,4-dienamides I(e) are preparable by reacting inventive compounds I(c) with thionyl chloride and subsequently adding the amino component in question or by EDC- and HOBt-mediated coupling of the amine component (Scheme 7). $A^1$, $A^2$, V, W, [M], $R^1$, $R^2$, $R^5$, $R^6$, $R^7$, $R^8$, $R^9$ and $R^{10}$, and also m and n, in Scheme 7 below are each as defined above.

Scheme 7

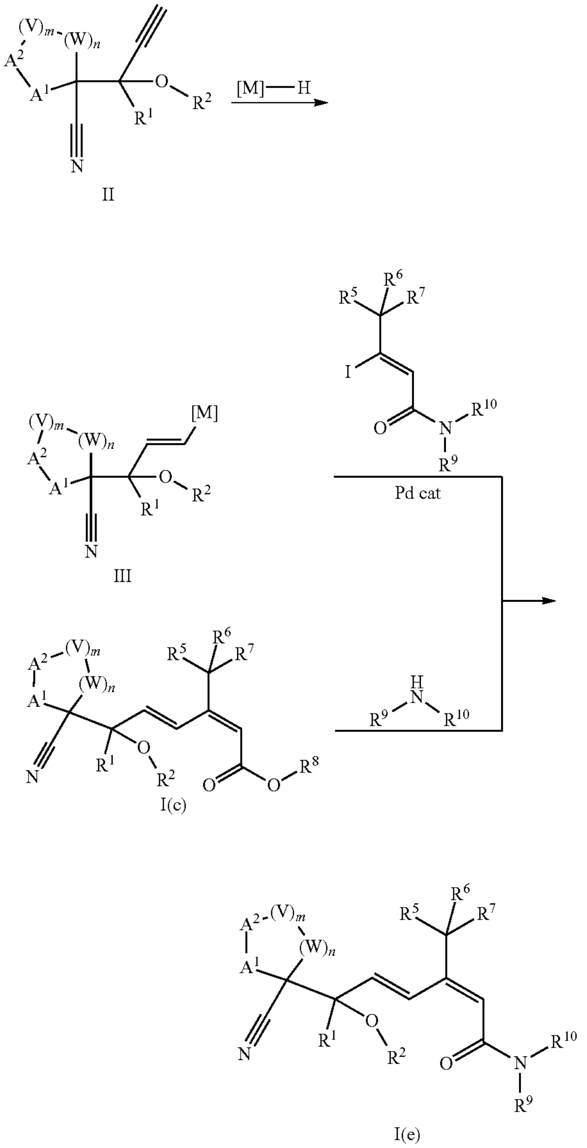

II

III

I(c)

I(e)

A further possible route to the inventive substituted (E,Z)-configured cyanocycloalkylpenta-2,4-dienamides I(e) is the coupling of substituted 1-[(3E)-2-hydroxy-4-[M]-but-3-en-2-yl]cycloalkylcarbonitriles III where [M] is as defined above with an appropriate substituted (Z)-haloalkenamide in a suitable solvent (for example tetrahydrofuran or N,N-dimethylformamide) using suitable transition metal catalysts (for example bis(triphenylphosphine)palladium dicyanide, tetrakis(triphenylphosphine)palladium or bis(triphenylphosphine)palladium dichloride) (Scheme 7).

Scheme 8

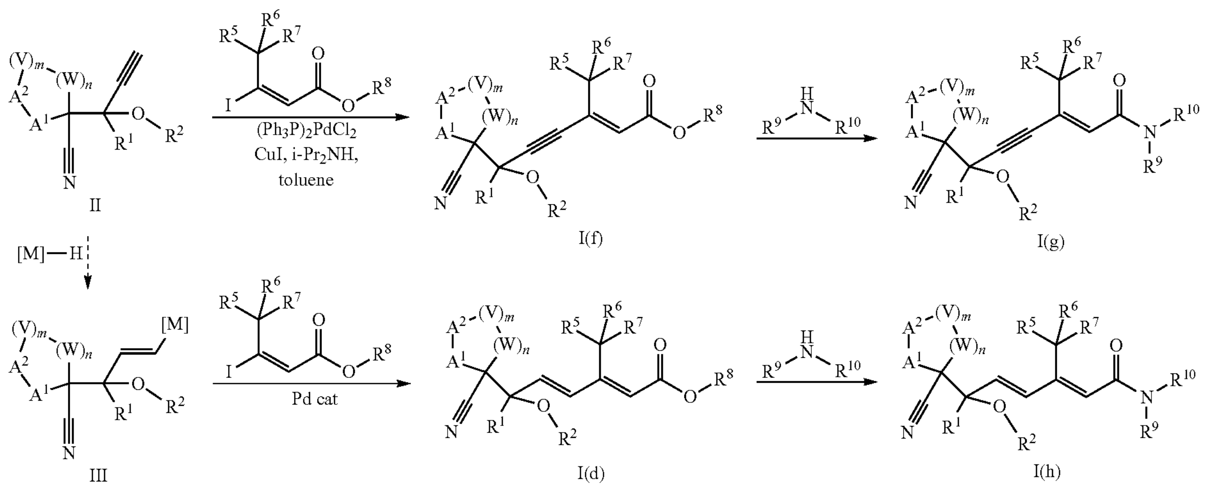

II, I(f), I(g), III, I(d), I(h)

The inventive substituted (E)-cyanocycloalkylpent-2-en-4-ynoic acid derivatives I(f), the corresponding amide analogues thereof I(g) and the (E,E)-configured cyanocycloalkylpenta-2,4-dienoic acid derivatives I(d) and the analogous amides I(h) can be prepared using the corresponding (E)-haloalkenoic acid derivatives and utilizing the synthesis methods described above (Scheme 8). $A^1$, $A^2$, V, W, $R^1$, $R^2$, $R^5$, $R^6$, $R^7$, $R^8$, $R^9$ and $R^{10}$, and also m and n, in Scheme 8 shown above are each as defined above.

Scheme 9

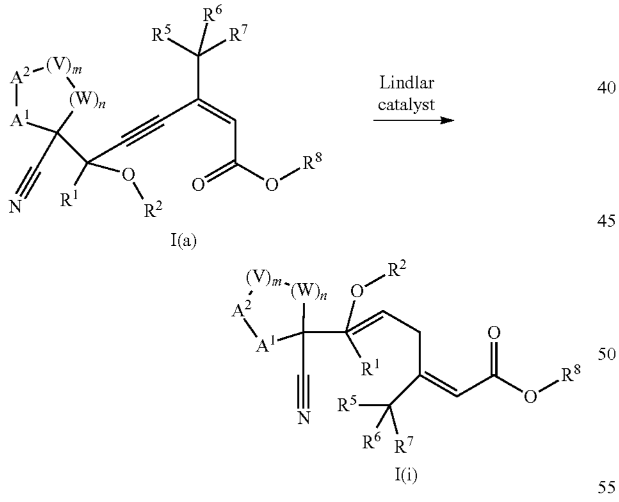

I(a), I(i)

The reduction of inventive substituted (Z)-cyanocycloalkylpent-2-en-4-ynoic acid derivatives I(a) to the inventive substituted (Z,Z)-configured cyanocycloalkylpenta-2,4-dienoic acid derivatives I(i) can be performed in the presence of a transition metal catalyst, for example Lindlar's catalyst, with hydrogen in a suitable polar-aprotic solvent (for example n-butanol) (cf. Tetrahedron 1987, 43, 4107; Tetrahedron 1983, 39, 2315; J. Org. Synth. 1983, 48, 4436 and J. Am. Chem. Soc. 1984, 106, 2735) (Scheme 9). The preparation of inventive substituted cyanocycloalkylpenta-2,4-dienoic acid derivatives I(k) having substituents $R^{11}$, in which $R^{11}$ is not hydrogen, is possible through reaction of inventive substituted 1-[(3E)-2-hydroxy-4-[M]-but-3-en-2-yl]cycloalkylcarbonitriles Ill with an appropriate substituted vinyl trifluoromethanesulphonate in a suitable solvent (for example tetrahydrofuran or N,N-dimethylformamide) using suitable transition metal catalysts (for example bis(triphenylphosphine)palladium dicyanide, tetrakis(triphenylphosphine)palladium or bis(triphenylphosphine)palladium dichloride). Scheme 10 below shows this reaction, using the example of the conversion of methyl (2Z)-2-methyl-3-{[(trifluoromethyl)sulphonyl]oxy}but-2-enoate. $A^1$, $A^2$, V, W, [M], $R^1$, $R^2$ and $R^8$, and also m and n, are each as defined above, and $R^5$, $R^6$, $R^7$ are hydrogen by way of example but without restriction, in Scheme 10 below, and $R^{11}$ is methyl by way of example.

Scheme 10

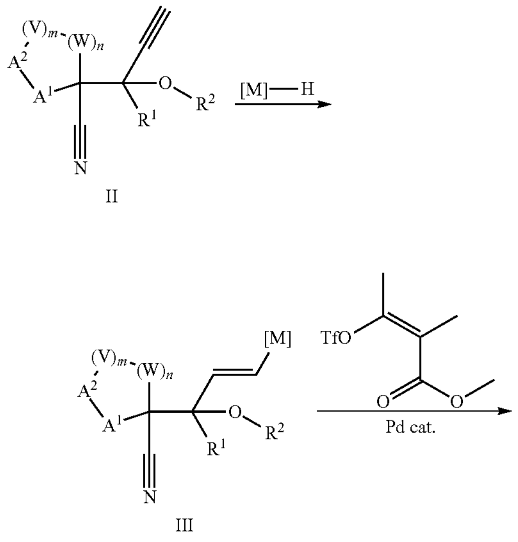

II, III

-continued

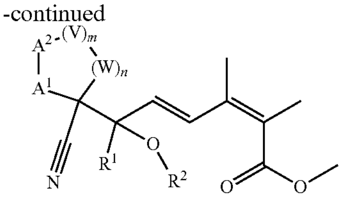

I(k)

Selected detailed synthesis examples for the inventive compounds of the general formulae (I), (II) and (III) are given below. The example numbers mentioned correspond to the numbering scheme in Tables 1 to 5 below. The $^1H$ NMR, $^{13}C$ NMR and $^{19}F$ NMR spectroscopy data reported for the chemical examples described in the paragraphs which follow (400 MHz for $^1H$ NMR and 150 MHz for $^{13}C$ NMR and 375 MHz for $^{19}F$ NMR, solvent: $CDC_3$, $CD_3OD$ or $d_6$-DMSO, internal standard: tetramethylsilane δ=0.00 ppm), were obtained with a Bruker instrument, and the signals identified are defined as follows: br=broad; s=singlet, d=doublet, t=triplet, dd=double doublet, ddd=doublet of a double doublet, m=multiplet, q=quartet, quint=quintet, sext=sextet, sept=septet, dq=double quartet, dt=double triplet. The abbreviations used for chemical groups are defined as follows: Me=$CH_3$, Et=$CH_2CH_3$, t-Hex=$C(CH_3)_2CH(CH_3)_2$, t-Bu=$C(CH_3)_3$, n-Bu=unbranched butyl, n-Pr=unbranched propyl, c-Hex=cyclohexyl. In the case of diastereomer mixtures, either the significant signals for each of the two diastereomers are reported or the characteristic signal of the main diastereomer is reported.

SYNTHESIS EXAMPLES

No. I.1-124: Ethyl (2Z)-6-(1-cyanocyclopropyl)-3-cyclopropyl-6-hydroxy-7-methyloct-2-en-4-ynoate

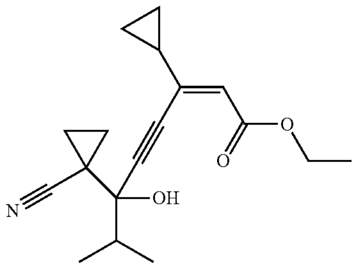 [SMILES: CCOC(=O)/C=C(\C#CC(O)(C(C)C)C1(C#N)CC1)C1CC1]

Ethyl 3-cyclopropylprop-2-ynoate (2.00 g, 14.48 mmol) was dissolved in conc. acetic acid (15 ml), finely powdered sodium iodide (6.51 g, 43.43 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain ethyl (2Z)-3-cyclopropyl-3-iodoacrylate (3.01 g, 74% of theory) in the form of a viscous oil. Copper(I) iodide (47 mg, 0.25 mmol) and bis(triphenylphosphine)palladium(II) chloride (129 mg, 0.18 mmol) were initially charged under argon in a baked-out round-bottom flask, and abs. toluene (6 ml) and ethyl (2Z)-3-cyclopropyl-3-iodoacrylate (326 mg, 1.23 mmol) were added. Stirring at room temperature for 10 min was followed by the dropwise addition of a solution of 1-(3-hydroxy-4-methylpent-1-yn-3-yl)cyclopropanecarbonitrile (200 mg, 1.23 mmol) in abs. toluene (9 ml) and of diisopropylamine (0.34 ml, 2.45 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), ethyl (2Z)-6-(1-cyanocyclopropyl)-3-cyclopropyl-6-hydroxy-7-methyloct-2-en-4-ynoate (190 mg, 47% of theory) was isolated in the form of a colourless oil. $^1H$ NMR (400 MHz, $CDCl_3$ δ, ppm) 6.17 (s, 1H), 4.17 (q, 2H), 2.46 (sept, 1H), 2.01 (br. s, 1H, OH), 1.68 (m, 1H), 1.47 (m, 1H), 1.39 (m, 1H), 1.30 (m, 1H), 1.28 (t, 3H), 1.21 (m, 1H), 1.12 (d, 3H), 1.09 (d, 3H), 0.87 (m, 4H).

No. I.1-157: (2Z)-6-(1-Cyanocyclopropyl)-N-cyclopropyl-3-ethyl-6-hydroxy-7-methyloct-2-en-4-ynamide

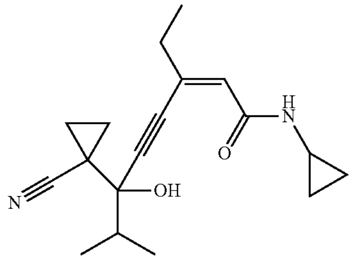 [SMILES: CC/C(C#CC(O)(C(C)C)C1(C#N)CC1)=C/C(=O)NC1CC1]

N-Cyclopropylpent-2-ynamide (1 equiv) was dissolved in conc. acetic acid (2 ml/mmol), finely powdered sodium iodide (3 equiv) was added and the mixture was stirred at a temperature of 110° C. for 4 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain (2Z)—N-cyclopropyl-3-iodopent-2-enamide (77% of theory) in the form of a waxy solid. Copper(I) iodide (4 mg, 0.02 mmol) and bis(triphenylphosphine)palladium(II) chloride (10 mg, 0.02 mmol) were initially charged under argon in a thoroughly baked-out round-bottom flask, and toluene (3 ml) which had been rendered absolute and stored over molecular sieves and (2Z)—N-cyclopropyl-3-iodopent-2-enamide (130 mg, 0.49 mmol) were added. Stirring at room temperature for 10 min was followed by the dropwise addition of a solution of 1-(3-hydroxy-4-methylpent-1-yn-3-yl)cyclopropanecarbonitrile (80 mg, 0.49 mmol) in abs. N,N-dimethylformamide (2 ml) and of diisopropylamine (0.21 ml, 1.47 mmol). The resulting reaction mixture was stirred at room temperature for 17 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), (2Z)-6-(1-cyanocyclopropyl)-N-cyclopropyl-3-ethyl-6-hydroxy-7-methyloct-2-en-4-ynamide (132 mg, 89% of theory) was isolated in the form of a waxy solid. $^{1}H$ NMR (400 MHz, $CDCl_3$ δ, ppm) 6.20 (br. m, 1H, NH), 5.95 (s, 1H), 2.82-2.70 (m, 2H), 2.46 (sept, 1H), 2.27 (q, 2H), 1.41 (m, 1H), 1.33 (m, 2H), 1.27 (m, 1H), 1.15 (t, 3H), 1.13 (d, 3H), 1.11 (d, 3H), 0.82 (m, 2H), 0.57 (m, 2H).

No. I.1-236: Ethyl (2Z)-6-(1-cyanocyclopropyl)-6-hydroxy-3-methyl-6-phenylhex-2-en-4-ynoate

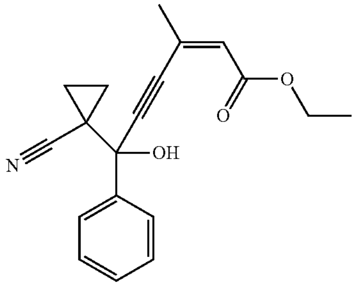 [SMILES: CCOC(=O)/C=C(/C)C#CC(O)(c1ccccc1)C1(C#N)CC1]

Copper(I) iodide (31 mg, 0.16 mmol) and bis(triphenylphosphine)palladium(II)chloride (85 mg, 0.12 mmol) were initially charged under argon in a round-bottom flask which had been dried by heating, and abs. toluene (4 ml) and ethyl (2Z)-3-iodobut-2-enoate (195 mg, 0.81 mmol) were added. Stirring at room temperature for 10 min was followed by the dropwise addition of a solution of 1-(1-hydroxy-1-phenylprop-2-yn-1-yl)cyclopropanecarbonitrile (160 mg, 0.81 mmol) in abs. toluene (6 ml) and of diisopropylamine (0.23 ml, 1.62 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), ethyl (2Z)-6-(1-cyanocyclopropyl)-6-hydroxy-3-methyl-6-phenylhex-2-en-4-ynoate (320 mg, 42% of theory) was isolated in the form of a colourless oil. $^{1}H$ NMR (400 MHz, $CDCl_3$ δ, ppm) 7.77 (m, 2H), 7.43-7.37 (m, 3H), 6.07 (s, 1H), 4.17 (q, 2H), 3.33 (br. s, 1H, OH), 2.07 (s, 3H), 1.59 (m, 2H), 1.39 (m, 1H), 1.28 (t, 3H), 1.27 (m, 1H).

No. I.1-503: Ethyl (2Z)-6-(1-cyanocyclopropyl)-3-ethyl-6-(4-fluorophenyl)-6-hydroxyhex-2-en-4-ynoate

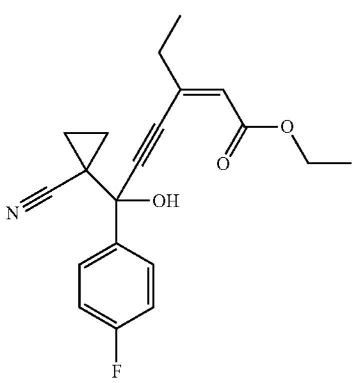 [SMILES: CCOC(=O)/C=C(\C#CC(O)(c1ccc(F)cc1)C1(C#N)CC1)CC]

Ethyl 3-ethylprop-2-ynoate (700 mg, 5.55 mmol) was dissolved in conc. acetic acid (7 ml), finely powdered sodium iodide (2.49 g, 16.65 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain ethyl (2Z)-3-ethyl-3-iodoacrylate (1000 mg, 67% of theory) in the form of a viscous oil. Copper(I) iodide (4 mg, 0.02 mmol) and bis(triphenylphosphine)palladium(II) chloride (12 mg, 0.02 mmol) were then initially charged under argon in a thoroughly baked-out round-bottom flask, and abs. toluene (3 ml) and ethyl (2Z)-3-ethyl-3-iodoacrylate (148 mg, 0.58 mmol) were added. Stirring at room temperature for 10 min was followed by the dropwise addition of a solution of 1-[1-(4-fluorophenyl)-1-hydroxyprop-2-yn-1-yl]cyclopropanecarbonitrile (125 mg, 0.58 mmol) in abs. toluene (2 ml) and of diisopropylamine (0.24 ml, 1.74 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), ethyl (2Z)-6-(1-cyanocyclopropyl)-3-ethyl-6-(4-fluorophenyl)-6-hydroxyhex-2-en-4-ynoate (80 mg, 40% of theory) was isolated in the form of a colourless solid. $^{1}H$ NMR (400 MHz, $CDCl_3$ δ, ppm) 7.75 (m, 2H), 7.10 (m, 2H), 6.08 (s, 1H), 4.20 (q, 2H), 3.42 (br. s, 1H, OH), 2.35 (q, 2H), 1.56 (m, 2H), 1.31-1.27 (m, 5H), 1.17 (t, 3H).

No. I.1-606: 2-Methoxyethyl (2Z)-6-(1-cyanocyclopropyl)-3-ethyl-6-hydroxy-7-methyloct-2-en-4-ynoate

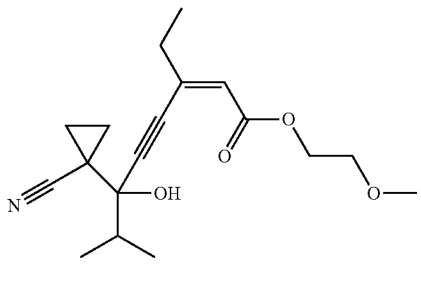 [SMILES: CC/C(C#CC(O)(C(C)C)C1(C#N)CC1)=C/C(=O)OCCOC]

2-Methoxyethyl pent-2-ynoate (1 equiv) was dissolved in conc. acetic acid (1.5 ml/mmol), finely powdered sodium iodide (3 equiv) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain 2-methoxyethyl (2Z)-3-iodopent-2-enoate (69% of theory) in the form of a viscous oil. Copper(I) iodide (6 mg, 0.03 mmol) and bis(triphenylphosphine)palladium(II) chloride (15 mg, 0.02 mmol) were initially charged under argon in a thoroughly baked-out round-bottom flask, and toluene (3 ml) which had been rendered absolute and stored over molecular sieves and 2-methoxyethyl (2Z)-3-iodopent-2-enoate (209 mg, 0.74 mmol) were added. Stirring at room temperature for 10 min was followed by the dropwise addition of a solution of 1-(3-hydroxy-4-methylpent-1-yn-3-yl)cyclopropanecarbonitrile (120 mg, 0.74 mmol) in abs. toluene (3 ml) and of diisopropylamine (0.31 ml, 2.21 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), 2-methoxyethyl (2Z)-6-(1-cyanocyclopropyl)-3-ethyl-6-hydroxy-7-methyloct-2-en-4-ynoate (176 mg, 75% of theory) was isolated in the form of a colourless, viscous oil. $^1$H NMR (400 MHz, $CDCl_3$ δ, ppm) 6.04 (s, 1H), 4.31 (m, 2H), 3.66 (m, 2H), 3.61 (br. s, 1H, OH), 3.41 (s, 3H), 2.44 (sept, 1H), 2.29 (q, 2H), 1.41 (m, 1H), 1.32 (m, 1H), 1.29 (m, 1H), 1.20 (m, 1H), 1.15 (t, 3H), 1.13 (d, 3H), 1.10 (d, 3H).

No. I.1-708: Methyl (2Z)-6-(1-cyanocyclopropyl)-3, 7-diethyl-6-hydroxynon-2-en-4-ynoate

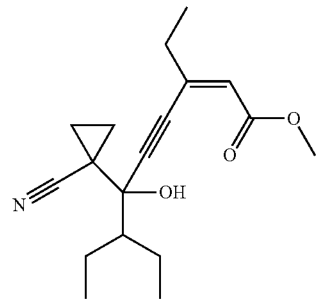 [SMILES: CC/C(C#CC(O)(C(CC)CC)C1(C#N)CC1)=C/C(=O)OC]

Methyl pent-2-ynoate (14.48 mmol) was dissolved in conc. acetic acid (15 ml), finely powdered sodium iodide (43.43 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-3-iodopent-2-enoate (about 3.0 g, 72% of theory) in the form of a viscous oil. Copper(I) iodide (5 mg, 0.25 mmol) and bis(triphenylphosphine)palladium(II) chloride (13 mg, 0.02 mmol) were initially charged under argon in a baked-out round-bottom flask, and abs. toluene (2 ml) and methyl (2Z)-3-iodopent-2-enoate (151 mg, 0.63 mmol) were added. Stirring at room temperature for 10 min was followed by the dropwise addition of a solution of 1-(4-ethyl-3-hydroxyhex-1-yn-3-yl)cyclopropanecarbonitrile (120 mg, 0.63 mmol) in abs. toluene (3 ml) and of diisopropylamine (0.26 ml, 1.88 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), methyl (2Z)-6-(1-cyanocyclopropyl)-3,7-diethyl-6-hydroxynon-2-en-4-ynoate (149 mg, 78% of theory) was isolated in the form of a colourless oil. $^1$H NMR (400 MHz, $CDCl_3$ δ, ppm) 6.02 (s, 1H), 3.72 (s, 3H), 2.63 (br. s, 1H, OH), 2.28 (q, 2H), 1.99 (m, 1H), 1.88 (m, 1H), 1.78 (m, 1H), 1.50-1.41 (m, 4H), 1.34 (m, 1H), 1.24 (m, 1H), 1.15 (t, 3H), 1.06 (t, 6H).

No. I.1-828: Methyl (2Z)-6-(1-cyanocyclopropyl)-6-cyclopentyl-3-ethyl-6-hydroxyhex-2-en-4-ynoate

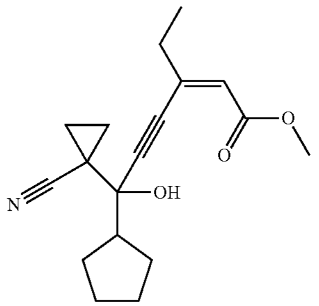 [SMILES: CC/C(C#CC(O)(C1CCCC1)C1(C#N)CC1)=C/C(=O)OC]

Methyl pent-2-ynoate (14.48 mmol) was dissolved in conc. acetic acid (15 ml), finely powdered sodium iodide (43.43 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-3-iodopent-2-enoate (about 3.0 g, 72% of theory) in the form of a viscous oil. Copper(I) iodide (4 mg, 0.21 mmol) and bis(triphenylphosphine)palladium(II) chloride (11 mg, 0.02 mmol) were initially charged under argon in a baked-out round-bottom flask, and abs. toluene (2 ml) and methyl (2Z)-3-iodopent-2-enoate (127 mg, 0.53 mmol) were added. Stirring at room temperature for 10 min was followed by the dropwise addition of a solution of 1-(1-cyclopentyl-1-hydroxyprop-2-yn-1-yl)cyclopropanecarbonitrile (100 mg, 0.53 mmol) in abs. toluene (3 ml) and of diisopropylamine (0.22 ml, 1.58 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), methyl (2Z)-6-(1-cyanocyclopropyl)-6-cyclopentyl-3-ethyl-6-hydroxyhex-2-en-4-ynoate (128 mg, 80% of theory) was isolated in the form of a colourless oil. $^1$H NMR (400 MHz, $CDCl_3$ δ, ppm) 6.02 (s, 1H), 3.72 (s, 3H), 2.70 (m, 1H), 2.64 (br. s, 1H, OH), 2.29 (q, 2H), 1.94 (m, 2H), 1.72-1.58 (m, 6H), 1.48-1.41 (m, 2H), 1.28 (m, 1H), 1.21 (m, 1H), 1.14 (t, 3H).

No. I.2-101: (2Z,4E)-6-(1-Cyanocyclopropyl)-3-ethyl-6-hydroxy-7-methylocta-2,4-dienoic Acid

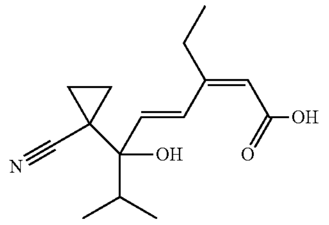 [SMILES: CCC(=C/C(=O)O)/C=C/C(O)(C(C)C)C1(C#N)CC1]

Pent-2-ynecarboxylic acid (1500 mg, 15.2 mmol) was dissolved in conc. acetic acid (15 ml), finely powdered sodium iodide (6876 mg, 45.8 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain (2Z)-3-iodopent-2-enoic acid (2100 mg, 58% of theory) in the form of a colourless solid. 1-[(1E)-3-Hydroxy-4-methyl-1-(tributylstannyl)pent-1-en-3-yl]cyclopropanecarbonitrile (390 mg, 0.86 mmol) and (2Z)-3-iodopent-2-enoic acid (194 mg, 0.86 mmol) were dissolved in abs. N,N-dimethylformamide (4 ml) under argon in a baked-out round-bottom flask, dichlorobis(acetonitrile)palladium(II) (7 mg, 0.03 mmol) and copper(I) iodide (131 mg, 0.80 mmol) were added and the mixture was stirred at room temperature for 8 h. After the addition of aqueous potassium fluoride solution, stirring of the reaction mixture continued at room temperature for 1 h. The aqueous phase was then repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain (2Z,4E)-6-(1-cyanocyclopropyl)-3-ethyl-6-hydroxy-7-methylocta-2,4-dienoic acid (83 mg, 37% of theory) in the form of a colourless viscous oil. $^{1}$H NMR (400 MHz, $CDCl_3$ δ, ppm) 7.63 (d, 1H), 6.28 (d, 1H), 5.81 (s, 1H), 2.97 (br. s, 1H, OH), 2.89 (br. s, 1H, OH), (s, 3H), 2.43 (q, 2H), 2.38 (sept, 1H), 1.33 (m, 1H) 1.21 (m, 1H), 1.18 (t, 3H), 1.09 (d, 3H), 1.05 (m, 1H), 0.97 (d, 3H).

No. I.2-120: Methyl (2E,4E)-6-(1-cyanocyclopropyl)-6-hydroxy-7-methyl-3-(trifluoro-methyl)octa-2,4-dienoate

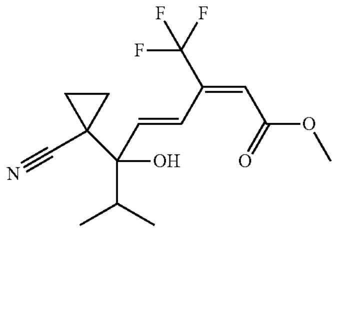 [SMILES: COC(=O)/C=C(\C=C\C(O)(C(C)C)C1(C#N)CC1)C(F)(F)F]

Methyl 4,4,4-trifluorobut-2-ynoate (500 mg, 3.01 mmol) was dissolved in conc. acetic acid (6 ml), finely powdered sodium iodide (1353 mg, 9.03 mmol) was added and the mixture was stirred at a temperature of 110° C. for 4 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-4,4,4-trifluoro-3-iodobut-2-enoate (380 mg, 43% of theory) in the form of a viscous oil. 1-[(1E)-3-Hydroxy-4-methyl-1-(tributylstannyl)pent-1-en-3-yl]cyclopropanecarbonitrile (300 mg, 0.66 mmol) and methyl (2Z)-4,4,4-trifluoro-3-iodobut-2-enoate (185 mg, 0.66 mmol) were dissolved in abs. N,N-dimethylformamide (20 ml) under argon in a baked-out round-bottom flask, tetrakis(triphenylphosphine)palladium(0) (76 mg, 0.07 mmol) and copper(I) iodide (94 mg, 0.49 mmol) were added and the mixture was stirred at room temperature for 16 h. After the addition of aqueous potassium fluoride solution, stirring of the reaction mixture continued at room temperature for 1 h. The aqueous phase was then repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain methyl (2E,4E)-6-(1-cyanocyclopropyl)-6-hydroxy-7-methyl-3-(trifluoromethyl)octa-2,4-dienoate (53 mg, 25% of theory) in the form of a colourless viscous oil. $^{1}$H NMR (400 MHz, $CDCl_3$ δ, ppm) 7.44 (d, 1H), 6.36 (d, 1H), 6.32 (s, 1H), 3.80 (s, 3H), 2.42 (sept, 1H), 1.63 (br. s, 1H, OH), 1.27 (m, 1H) 1.22 (m, 1H), 1.12 (m, 1H), 1.05 (d, 3H), 0.99 (m, 1H), 0.97 (d, 3H).

No. I.2-136: Ethyl (2Z,4E)-6-(1-cyanocyclopropyl)-6-hydroxy-3,7-dimethylocta-2,4-dienoate

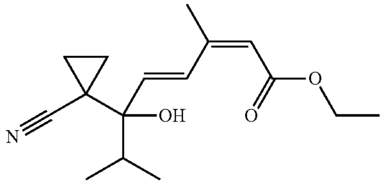 [SMILES: CCOC(=O)/C=C(C)\C=C\C(O)(C(C)C)C1(C#N)CC1]

Ethyl 2-butynoate (3.00 g, 26.76 mmol) was dissolved in conc. acetic acid (25 ml), finely powdered sodium iodide (12.03 g, 80.27 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain ethyl (2Z)-3-iodobut-2-enoate (5.58 g, 79% of theory) in the form of a viscous oil. 1-[(1E)-3-Hydroxy-4-methyl-1-(tributylstannyl)pent-1-en-3-yl]cyclopropanecarbonitrile (160 mg, 0.35 mmol) and ethyl (2Z)-3-iodobut-2-enoate (85 mg, 0.35 mmol) were dissolved in abs.

tetrahydrofuran (5 ml) under argon in a baked-out round-bottom flask, dichlorobis(acetonitrile)palladium(II) (5 mg, 0.02 mmol) was added and the mixture was stirred at room temperature for 4 h. After the addition of potassium fluoride solution, stirring of the reaction mixture continued at room temperature for 1 h. The aqueous phase was then repeatedly extracted thoroughly with diethyl ether, and the combined organic phases were then dried over magnesium sulphate, filtered and concentrated under reduced pressure. By final column chromatography purification of the resulting crude product (ethyl acetate/heptane gradient), it was possible to obtain ethyl (2Z,4E)-6-(1-cyanocyclopropyl)-6-hydroxy-3,7-dimethylocta-2,4-dienoate (30 mg, 29% of theory) in the form of a colourless oil. $^1$H NMR (400 MHz, $CDCl_3$ δ, ppm) 7.77 (d, 1H), 6.25 (d, 1H), 5.74 (s, 1H), 4.29 (q, 2H), 2.39 (sept, 1H), 2.22 (br. s, 1H, OH), 2.04 (s, 3H), 1.34 (m, 1H), 1.29 (t, 3H), 1.20 (m, 1H), 1.06 (d, 3H), 1.03 (m, 1H), 0.97 (m, 1H), 0.93 (d, 3H).

No. I.2-534: Methyl (2E,4E)-6-(1-cyanocyclopropyl)-6-cyclopropyl-6-hydroxy-3-(trifluoromethyl)hexa-2,4-dienoate

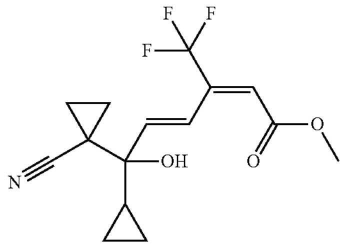 [SMILES: COC(=O)/C=C(\C=C\C(O)(C1CC1)C1(C#N)CC1)C(F)(F)F]

Methyl 4,4,4-trifluorobut-2-ynoate (500 mg, 3.01 mmol) was dissolved in conc. acetic acid (6 ml), finely powdered sodium iodide (1353 mg, 9.03 mmol) was added and the mixture was stirred at a temperature of 110° C. for 4 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-4,4,4-trifluoro-3-iodobut-2-enoate (380 mg, 43% of theory) in the form of a viscous oil. 1-[(2E)-1-Cyclopropyl-1-hydroxy-3-(tributylstannyl)prop-2-en-1-yl]cyclopropanecarbonitrile (200 mg, 0.44 mmol) and methyl (2Z)-4,4,4-trifluoro-3-iodobut-2-enoate (124 mg, 0.44 mmol) were dissolved in abs. N,N-dimethylformamide (5 ml) under argon in a baked-out round-bottom flask, dichlorobis(acetonitrile)palladium(II) (4 mg, 0.01 mmol) and copper(I) iodide (67 mg, 0.35 mmol) were added and the mixture was stirred at room temperature for 12 h. After the addition of aqueous potassium fluoride solution, stirring of the reaction mixture continued at room temperature for 1 h. The aqueous phase was then repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain methyl (2E,4E)-6-(1-cyanocyclopropyl)-6-cyclopropyl-6-hydroxy-3-(trifluoromethyl)hexa-2,4-dienoate (79 mg, 57% of theory) in the form of a colourless viscous oil. $^1$H NMR (400 MHz, $CDCl_3$ δ, ppm) 7.56 (d, 1H), 6.33 (s, 1H), 6.27 (d, 1H), 3.80 (s, 3H), 1.63 (br. s, 1H, OH), 1.32-1.24 (m, 4H) 1.22-1.13 (m, 3H), 0.51 (m, 2H).

No. I.2-579: Methyl (2Z,4E)-6-(1-cyanocyclopropyl)-6-cyclohexyl-3-ethyl-6-hydroxyhexa-2,4-dienoate

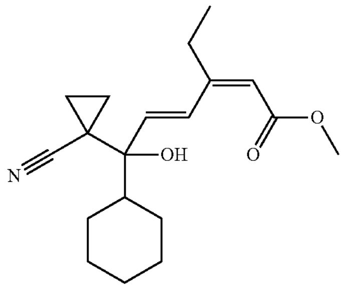 [SMILES: CCC(=C/C(=O)OC)/C=C/C(O)(C1CCCCC1)C1(C#N)CC1]

Methyl pent-2-ynoate (14.48 mmol) was dissolved in conc. acetic acid (15 ml), finely powdered sodium iodide (43.43 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-3-iodopent-2-enoate (about 3.0 g, 72% of theory) in the form of a viscous oil. 1-[(2E)-1-Cyclohexyl-1-hydroxy-3-(tributylstannyl)prop-2-en-1-yl]cyclopropanecarbonitrile (Ex. No. III.1-66, 450 mg, 0.91 mmol) and methyl (2Z)-3-iodopent-2-enoate (219 mg, 0.91 mmol) were dissolved in abs. N,N-dimethylformamide (5 ml) under argon in a baked-out round-bottom flask, dichlorobis(acetonitrile)palladium(II) (7 mg, 0.03 mmol) and copper(I) iodide (139 mg, 0.73 mmol) were added and the mixture was stirred at room temperature for 12 h. After the addition of aqueous potassium fluoride solution, stirring of the reaction mixture continued at room temperature for 1 h. The aqueous phase was then repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain methyl (2Z,4E)-6-(1-cyanocyclopropyl)-6-cyclohexyl-3-ethyl-6-hydroxyhexa-2,4-dienoate (105 mg, 36% of theory) in the form of a colourless viscous oil. $^1$H NMR (400 MHz, $CDCl_3$ δ, ppm) 7.66 (d, 1H), 6.26 (d, 1H), 5.73 (s, 1H), 3.72 (s, 3H), 2.43 (m, 2H), 2.08-1.97 (m, 2H), 1.81 (m, 2H), 1.71 (m, 2H), 1.64 (br. s, 1H, OH), 1.39-1.26 (m, 4H), 1.19 (m, 1H), 1.16 (t, 3H), 1.09 (m, 1H), 1.02-0.93 (m, 3H).

No. I.2-585: Methyl (2E,4E)-6-(1-cyanocyclopropyl)-7-ethyl-6-hydroxy-3-(trifluoromethyl)nona-2,4-dienoate

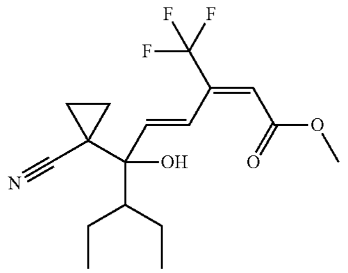 [SMILES: CCC(CC)C(O)(/C=C/C(=C\C(=O)OC)C(F)(F)F)C1(C#N)CC1]

Methyl 4,4,4-trifluorobut-2-ynoate (500 mg, 3.01 mmol) was dissolved in conc. acetic acid (6 ml), finely powdered sodium iodide (1353 mg, 9.03 mmol) was added and the mixture was stirred at a temperature of 110° C. for 4 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-4,4,4-trifluoro-3-iodobut-2-enoate (380 mg, 43% of theory) in the form of a viscous oil. 1-[(1E)-4-Ethyl-3-hydroxy-1-(tributylstannyl)hex-1-en-3-yl]cyclopropanecarbonitrile (325 mg, 0.67 mmol) and methyl (2Z)-4,4,4-trifluoro-3-iodobut-2-enoate (189 mg, 0.67 mmol) were dissolved in abs. N,N-dimethylformamide (5 ml) under argon in a baked-out round-bottom flask, dichlorobis(acetonitrile)palladium(II) (5 mg, 0.02 mmol) and copper(I) iodide (103 mg, 0.54 mmol) were added and the mixture was stirred at room temperature for 12 h. After the addition of aqueous potassium fluoride solution, stirring of the reaction mixture continued at room temperature for 1 h. The aqueous phase was then repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain methyl (2E,4E)-6-(1-cyanocyclopropyl)-7-ethyl-6-hydroxy-3-(trifluoromethyl)nona-2,4-dienoate (88 mg, 38% of theory) in the form of a colourless viscous oil. $^1$H NMR (400 MHz, $CDCl_3$ δ, ppm) 7.45 (d, 1H), 6.35 (d, 1H), 6.31 (s, 1H), 3.80 (s, 3H), 1.93 (m, 1H), 1.78 (m, 1H), 1.64 (m, 1H), 1.59 (br. s, 1H, OH), 1.38 (m, 1H), 1.32-1.22 (m, 4H) 1.13 (m, 1H), 1.06 (t, 3H), 0.99 (t, 3H).

No. I.2-618: Ethyl (2E,4E)-6-(1-cyanocyclopropyl)-6-cyclopentyl-6-hydroxy-3-(trifluoromethyl)hexa-2,4-dienoate

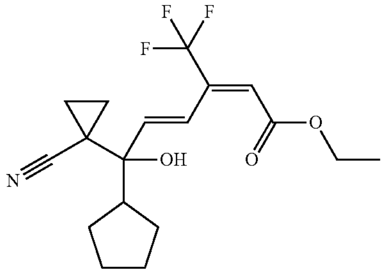 [SMILES: CCOC(=O)/C=C(\C=C\C(O)(C1CCCC1)C1(C#N)CC1)C(F)(F)F]

Ethyl 4,4,4-trifluorobut-2-ynoate (500 mg, 3.01 mmol) was dissolved in conc. acetic acid (6 ml), finely powdered sodium iodide (1353 mg, 9.03 mmol) was added and the mixture was stirred at a temperature of 110° C. for 4 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain ethyl (2Z)-4,4,4-trifluoro-3-iodobut-2-enoate (380 mg, 45% of theory) in the form of a viscous oil. 1-[(2E)-1-Cyclopentyl-1-hydroxy-3-(tributylstannyl)prop-2-en-1-yl]cyclopropanecarbonitrile (350 mg, 0.73 mmol) and ethyl (2Z)-4,4,4-trifluoro-3-iodobut-2-enoate (214 mg, 0.73 mmol) were dissolved in abs. N,N-dimethylformamide (4 ml) under argon in a baked-out round-bottom flask, dichlorobis(acetonitrile)palladium(II) (6 mg, 0.02 mmol) and copper(I) iodide (111 mg, 0.58 mmol) were added and the mixture was stirred at room temperature for 12 h. After the addition of aqueous potassium fluoride solution, stirring of the reaction mixture continued at room temperature for 1 h. The aqueous phase was then repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain ethyl (2E,4E)-6-(1-cyanocyclopropyl)-6-cyclopentyl-6-hydroxy-3-(trifluoromethyl)hexa-2,4-dienoate (84 mg, 32% of theory) in the form of a colourless viscous oil. $^1$H NMR (400 MHz, $CDCl_3$, δ, ppm) 7.49 (d, 1H), 6.41 (d, 1H), 6.31 (s, 1H), 4.26 (q, 2H), 2.69-2.63 (m, 1H), 1.95-1.88 (m, 1H), 1.68-1.60 (m, 4H), 1.58 (br. s, 1H, OH), 1.48-1.26 (m, 6H) 1.19 (m, 1H), 1.12 (m, 1H), 1.03 (m, 1H).

No. I.3-32: Methyl (2Z)-6-(1-cyanocyclobutyl)-6-hydroxy-7-methyl-3-trifluoromethyloct-2-en-4-ynoate

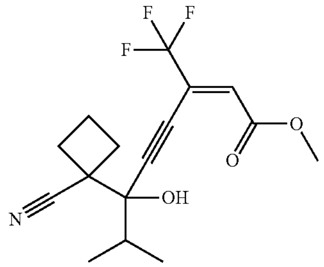 [SMILES: COC(=O)/C=C(\C#CC(O)(C(C)C)C1(C#N)CCC1)C(F)(F)F]

Methyl 4,4,4-trifluorobut-2-ynoate (500 mg, 3.01 mmol) was dissolved in conc. acetic acid (6 ml), finely powdered sodium iodide (1353 mg, 9.03 mmol) was added and the mixture was stirred at a temperature of 110° C. for 4 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-4,4,4-trifluoro-3-iodobut-2-enoate (380 mg, 43% of theory) in the form of a viscous oil. Copper(I) iodide (6 mg, 0.03 mmol) and bis(triphenylphosphine)palladium(II) chloride (18 mg, 0.03 mmol) were initially charged under argon in a baked-out round-bottom flask, and abs. toluene (6 ml) and methyl (2Z)-4,4,4-trifluoro-3-iodobut-2-enoate (237 mg, 0.85 mmol) were added. Stirring at room temperature for 10 min was followed by the dropwise addition of a solution of 1-(3-hydroxy-4-methylpent-1-yn-3-yl)cyclobutanecarbonitrile (150 mg, 0.85 mmol) in abs. toluene (7 ml) and of diisopropylamine (0.36 ml, 2.54 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), methyl (2Z)-6-(1-cyanocyclobutyl)-6-hydroxy-7-methyl-3-trifluoromethyloct-2-en-4-ynoate (147 mg, 53% of theory) was isolated in the form of a colourless oil. $^1$H NMR (400 MHz, $CDCl_3$ δ, ppm) 6.71 (s, 1H), 3.83 (s, 3H), 2.79-2.68 (m, 2H), 2.47 (br. s, 1H, OH), 2.41 (m, 4H), 2.32 (m, 2H), 1.94 (m, 1H), 1.13 (d, 3H), 1.03 (d, 3H).

No. I.3-44: Methyl (2Z)-6-(1-cyanocyclobutyl)-3-ethyl-6-hydroxy-6-phenylhex-2-en-4-ynoate

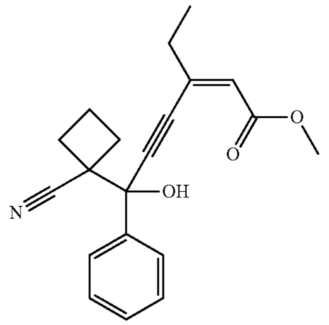 [SMILES: CC/C(C#CC(O)(c1ccccc1)C1(C#N)CCC1)=C/C(=O)OC]

Methyl pent-2-ynoate (14.48 mmol) was dissolved in conc. acetic acid (15 ml), finely powdered sodium iodide (43.43 mmol) was added and the mixture was stirred at a temperature of 110° C. for 3 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-3-iodopent-2-enoate (about 3.0 g, 72% of theory) in the form of a viscous oil. Copper(I) iodide (4 mg, 0.23 mmol) and bis(triphenylphosphine)palladium(II) chloride (12 mg, 0.02 mmol) were initially charged under argon in a baked-out round-bottom flask, and abs. toluene (3 ml) and methyl (2Z)-3-iodopent-2-enoate (136 mg, 0.57 mmol) were added. Stirring at room temperature for 10 min was followed by the dropwise addition of a solution of 1-(1-hydroxy-1-phenylprop-2-yn-1-yl)cyclobutanecarbonitrile (120 mg, 0.57 mmol) in abs. toluene (3 ml) and of diisopropylamine (0.24 ml, 1.70 mmol). The resulting reaction mixture was stirred at room temperature for 3 h and then water was added. The aqueous phase was extracted repeatedly with dichloromethane. The combined organic phases were dried over magnesium sulphate, filtered and concentrated under reduced pressure. By final column chromatography purification of the crude product obtained (using an ethyl acetate/heptane gradient), methyl (2Z)-6-(1-cyanocyclobutyl)-3-ethyl-6-hydroxy-6-phenylhex-2-en-4-ynoate (128 mg, 80% of theory) was isolated in the form of a colourless oil. $^1$H NMR (400 MHz, $CDCl_3$ δ, ppm) 7.76 (m, 2H), 7.42-7.37 (m, 3H), 6.10 (s, 1H), 3.73 (s, 3H), 3.34 (br. s, 1H, OH), 2.88-2.75 (m, 2H), 2.42-2.38 (q, 2H), 2.34-2.25 (m, 2H), 2.23-2.14 (m, 1H), 1.95-1.88 (m, 1H), 1.21 (t, 3H).

No. 1.4-32: Methyl (2E,4E)-6-(1-cyanocyclobutyl)-6-hydroxy-7-methyl-3-(trifluoromethyl)octa-2,4-dienoate

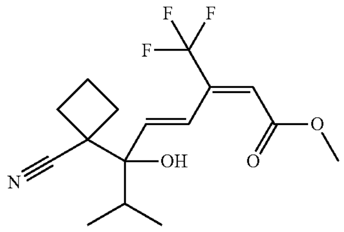 [SMILES: COC(=O)/C=C(\C=C\C(O)(C(C)C)C1(C#N)CCC1)C(F)(F)F]

Methyl 4,4,4-trifluorobut-2-ynoate (500 mg, 3.01 mmol) was dissolved in conc. acetic acid (6 ml), finely powdered sodium iodide (1353 mg, 9.03 mmol) was added and the mixture was stirred at a temperature of 110° C. for 4 h. After cooling to room temperature, methyl tert-butyl ether (MTBE) and saturated sodium thiosulphate solution were added. The aqueous phase was extracted repeatedly with MTBE, and the combined organic phases were dried over magnesium sulphate, filtered and concentrated under reduced pressure. By column chromatography purification of the resulting crude product (ethyl acetate/heptane gradient), it was possible to obtain methyl (2Z)-4,4,4-trifluoro-3-iodobut-2-enoate (380 mg, 43% of theory) in the form of a viscous oil. 1-[(1E)-3-Hydroxy-4-methyl-1-(tributylstannyl)pent-1-en-3-yl]cyclobutanecarbonitrile (300 mg, 0.64 mmol) and methyl (2Z)-4,4,4-trifluoro-3-iodobut-2-enoate (179 mg, 0.64 mmol) were dissolved in abs. N,N-dimethylformamide (5 ml) under argon in a baked-out round-bottom flask, dichlorobis(acetonitrile)palladium(II) (5 mg, 0.02 mmol) and copper(I) iodide (98 mg, 0.51 mmol) were added and the mixture was stirred at room temperature for 12 h. After the addition of potassium fluoride solution, stirring of the reaction mixture continued at room temperature for 1 h. The aqueous phase was then repeatedly extracted thoroughly with diethyl ether, and the combined organic phases were then dried over magnesium sulphate, filtered and concentrated under reduced pressure. By final column chromatography purification of the resulting crude product (ethyl acetate/heptane gradient), it was possible to obtain methyl (2E,4E)-6-(1-cyanocyclobutyl)-6-hydroxy-7-methyl-3-(trifluoromethyl)octa-2,4-dienoate (46 mg, 21% of theory) in the form of a colourless oil. $^1$H NMR (400 MHz, $CDCl_3$ δ, ppm) 7.53 (d, 1H), 6.31 (s, 1H), 6.30 (d, 1H), 3.80 (s, 3H), 2.65 (m, 1H), 2.40 (m, 1H), 2.29 (m, 2H), 2.11 (m, 1H), 1.80 (m, 1H), 1.73 (br. s, 1H, OH), 1.30 (m, 1H), 0.94 (d, 3H), 0.91 (d, 3H).

No. II.1-2: 1-(3-hydroxy-4-methylpent-1-yn-3-yl)cyclopropanecarbonitrile

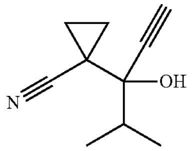

1-Isobutyrylcyclopropanecarbonitrile (4.00 g, 29.16 mmol) was dissolved in abs. tetrahydrofuran (120 ml) in a round-bottom flask under argon and added dropwise to a solution, cooled to 0° C., of a lithium acetylide-ethylenediamine complex (4.11 g, 37.91 mmol, content 85%) in abs. tetrahydrofuran (80 ml). On completion of addition, the reaction solution was stirred at room temperature for 4 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-(3-hydroxy-4-methylpent-1-yn-3-yl)cyclopropanecarbonitrile (2.59 g, 54% of theory) was isolated as a colourless solid. $^{1}$H NMR (400 MHz, $CDCl_3$ δ, ppm) 2.48 (s, 1H), 2.41 (sept, 1H), 2.19 (br. s, 1H, OH), 1.34-1.28 (m, 3H), 1.21 (m, 1H), 1.12 (d, 3H), 1.09 (d, 3H).

No. II.1-3: 1-(1-Hydroxy-1-phenylprop-2-yn-1-yl)cyclopropanecarbonitrile

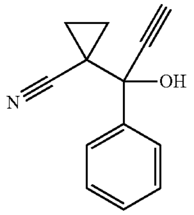

1-Benzoylcyclopropanecarbonitrile (4.00 g, 23.37 mmol) was dissolved in abs. tetrahydrofuran (160 ml) in a round-bottom flask under argon and added dropwise to a solution, cooled to 0° C., of a lithium acetylide-ethylenediamine complex (3.29 g, 37.37 mmol, content 85%) in abs. tetrahydrofuran (80 ml). On completion of addition, the reaction solution was stirred at room temperature for 4 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-(1-hydroxy-1-phenylprop-2-yn-3-yl)cyclopropanecarbonitrile (3.16 g, 69% of theory) was isolated as a colourless solid. $^{1}$H NMR (400 MHz, $CDCl_3$ δ, ppm) 7.70 (m, 2H), 7.41 (m, 2H), 7.29 (m, 1H), 2.78 (s, 1H), 2.62 (br. s, 1H, OH), 1.51 (m, 1H), 1.39 (m, 1H), 1.28 (m, 2H); $^{13}$C NMR (150 MHz, $CDCl_3$ δ, ppm) 140.1, 129.0, 128.5, 127.2, 125.8, 122.3, 120.9, 86.1, 76.8, 72.0, 22.8, 13.2, 12.7.

No. II.1-5: 1-(1-Cyclopropyl-1-hydroxyprop-2-yn-1-yl)cyclopropanecarbonitrile

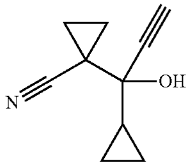

1-(Cyclopropylcarbonyl)cyclopropanecarbonitrile (9.0 g, 66.59 mmol) was dissolved in abs. tetrahydrofuran (70 ml) in a round-bottom flask under argon and added dropwise to a solution, cooled to 0° C., of a lithium acetylide-ethylenediamine complex (8.86 g, 86.56 mmol, content 90%) in abs. tetrahydrofuran (50 ml). On completion of addition, the reaction solution was stirred at room temperature for 4 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-(1-cyclopropyl-1-hydroxyprop-2-yn-3-yl)cyclopropanecarbonitrile (0.77 g, 7% of theory) was isolated as a colourless solid. $^{1}$H NMR (400 MHz, $CDCl_3$ δ, ppm) 2.46 (s, 1H), 2.15 (br. s, 1H, OH), 1.57 (m, 1H), 1.47-1.34 (m, 2H), 1.28-1.23 (m, 2H), 0.75-0.55 (m, 4H).

No. II.1-7: 1-[1-(4-Fluorophenyl)-1-hydroxyprop-2-yn-1-yl]cyclopropanecarbonitrile

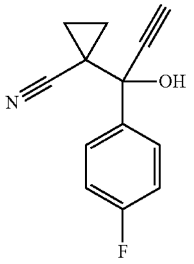 [SMILES: C#CC(O)(c1ccc(F)cc1)C1(C#N)CC1]

1-(4-Fluorobenzoyl)cyclopropanecarbonitrile (7.00 g, 37.00 mmol) was dissolved in abs. tetrahydrofuran (40 ml) in a round-bottom flask under argon and added dropwise to a solution, cooled to 0° C., of a lithium acetylide-ethylenediamine complex (4.92 g, 48.10 mmol, content 90%) in abs. tetrahydrofuran (20 ml). On completion of addition, the reaction solution was stirred at room temperature for 4 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-[1-(4-fluorophenyl)-1-hydroxyprop-2-yn-1-yl]cyclopropanecarbonitrile (0.84 g, 11% of theory) was isolated as a colourless waxy solid. $^1H$ NMR (400 MHz, $CDCl_3$ δ, ppm) 7.69 (m, 2H), 7.11 (m, 2H), 2.79 (s, 1H), 2.62 (br. s, 1H, OH), 1.51 (m, 1H), 1.39 (m, 1H), 1.28 (m, 2H).

No. II.1-81: 1-(1-Cyclopentyl-1-hydroxyprop-2-yn-1-yl)cyclopropanecarbonitrile

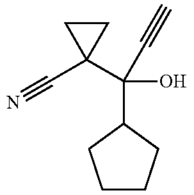

1-(Cyclopentylcarbonyl)cyclopropanecarbonitrile (9.00 g, 55.14 mmol) was dissolved in abs. tetrahydrofuran (50 ml) in a round-bottom flask under argon and added dropwise to a solution, cooled to 0° C., of a lithium acetylide-ethylenediamine complex (6.59 g, 71.68 mmol) in abs. tetrahydrofuran (40 ml). On completion of addition, the reaction solution was stirred at room temperature for 2 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-(1-cyclopentyl-1-hydroxyprop-2-yn-1-yl)cyclopropanecarbonitrile (2.55 g, 25% of theory) was isolated as a colourless solid. $^1H$ NMR (400 MHz, $CDCl_3$ δ, ppm) 2.65 (m, 1H), 2.47 (s, 1H), 2.18 (br. s, 1H, OH), 1.97-1.85 (m, 2H), 1.73-1.59 (m, 4H), 1.45-1.39 (m, 1H), 1.37-1.33 (m, 2H), 1.30-1.26 (m, 2H), 1.22-1.19 (m, 1H).

No. II.1-84: 1-(4-Ethyl 3-hydroxyhex-1-yn-3-yl)cyclopropanecarbonitrile

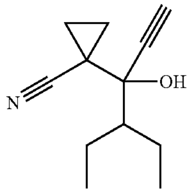

1-(2-Ethylbutanoyl)cyclopropanecarbonitrile (14.00 g, 84.73 mmol) was dissolved in abs. tetrahydrofuran (50 ml) in a round-bottom flask under argon and added dropwise to a solution, cooled to 0° C., of a lithium acetylide-ethylenediamine complex (10.14 g, 110.15 mmol, content 85%) in abs. tetrahydrofuran (40 ml). On completion of addition, the reaction solution was stirred at room temperature for 3 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-(4-ethyl 3-hydroxyhex-1-yn-3-yl)cyclopropanecarbonitrile (6.15 g, 38% of theory) was isolated as a colourless solid. $^1H$ NMR (400 MHz, $CDCl_3$ δ, ppm) 2.31 (s, 1H), 2.02 (br. s, 1H, OH), 1.77 (m, 1H), 1.67 (m, 1H), 1.58 (m, 1H), 1.33 (m, 1H), 1.25 (m, 1H), 1.19 (m, 2H), 1.08 (m, 2H), 0.89 (m, 6H).

No. 11.2-2: 1-(3-Hydroxy-4-methylpent-1-yn-3-yl)cyclobutanecarbonitrile

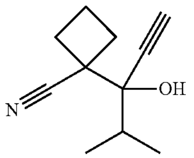

1-Isobutyrylcyclobutanecarbonitrile (9.00 g, 60.0 mmol) was dissolved in abs. tetrahydrofuran (50 ml) in a round-bottom flask under argon and added dropwise to a solution, cooled to 0° C., of a lithium acetylide-ethylenediamine complex (7.92 g, 77.0 mmol, content 90%) in abs. tetrahydrofuran (20 ml). On completion of addition, the reaction solution was stirred at room temperature for 2 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-(3-hydroxy-4-methylpent-1-yn-3-yl)cyclobutanecarbonitrile (2.50 g, 24% of theory) was isolated as a colourless waxy solid. $^1H$ NMR (400 MHz, $CDCl_3$ δ, ppm) 2.70 (m, 2H), 2.64 (s, 1H), 2.36 (m, 2H), 2.24 (m, 2H), 2.12 (br. s, 1H, OH), 1.08 (d, 3H), 0.98 (d, 3H).

No. 11.2-3:1-(1-Hydroxy-1-phenylprop-2-yn-1-yl)cyclobutanecarbonitrile

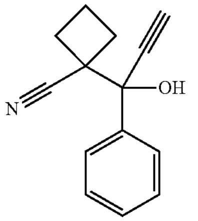 [SMILES: C#CC(O)(c1ccccc1)C1(C#N)CCC1]

1-Benzoylcyclobutanecarbonitrile (10.00 g, 53.99 mmol) was dissolved in abs. tetrahydrofuran (50 ml) in a round-bottom flask under argon and added dropwise to a solution, cooled to 0° C., of a lithium acetylide-ethylenediamine complex (7.18 g, 70.19 mmol, content 90%) in abs. tetrahydrofuran (20 ml). On completion of addition, the reaction solution was stirred at room temperature for 3 h, then water was added and the mixture was concentrated under reduced pressure. The remaining residue was admixed with water and dichloromethane, and the aqueous phase was extracted repeatedly with dichloromethane. The combined organic phases were dried over magnesium sulphate, filtered and concentrated under reduced pressure. By column chromatography purification of the crude product obtained (ethyl acetate/heptane gradient), 1-(1-hydroxy-1-phenylprop-2-yn-1-yl)cyclobutanecarbonitrile (740 mg, 6% of theory) was isolated as a colourless waxy solid. $^1$H NMR (400 MHz, $CDCl_3$ δ, ppm) 7.69 (m, 2H), 7.42-7.37 (m, 3H), 2.83 (br. s, 1H, OH), 2.80-2.65 (m, 2H), 2.62 (s, 1H), 2.36-2.15 (m, 4H), 1.91-1.84 (m, 2H).

No. III.1-2: 1-[(1E)-3-Hydroxy-4-methyl-1-(tributylstannyl)pent-1-en-3-yl]cyclopropanecarbonitrile

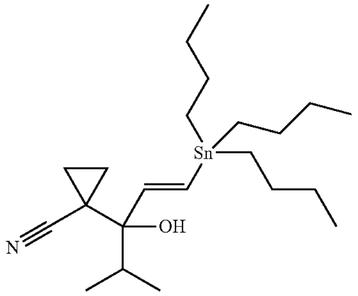 [SMILES: CCC[CH2][Sn](/[CH]=C/C(O)(C(C)C)C1(C#N)CC1)([CH2]CCC)[CH2]CCC]

Tetrakis(triphenylphosphine)palladium(0) (198 mg, 0.17 mmol) was initially charged under argon in a baked-out round-bottom flask, and abs. tetrahydrofuran (20 ml) and 1-(3-hydroxy-4-methylpent-1-yn-3-yl)cyclopropanecarbonitrile (560 mg, 3.41 mmol) were added. Stirring at room temperature for 5 minutes was followed by the addition of tributyltin hydride (1.10 ml, 4.12 mmol). The resulting reaction mixture was stirred at room temperature for 1 h and then water was added. The aqueous phase was repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain 1-[(1E)-3-hydroxy-4-methyl-1-(tributylstannyl)pent-1-en-3-yl]cyclopropanecarbonitrile (0.38 mg, 24% of theory) in the form of a colourless oil. $^1$H NMR (400 MHz, $CDCl_3$ δ, ppm) 6.18 (d, 1H), 6.03 (d, 1H), 2.32 (sept, 1H), 1.53-1.45 (m, 6H), 1.35-1.29 (m, 6H), 1.28 (m, 1H), 1.14 (m, 1H), 1.03 (d, 3H), 0.94-0.88 (m, 18H), 0.72 (m, 2H).

No. III.1-5: 1-[(2E)-1-Cyclopropyl-1-hydroxy-3-(tributylstannyl)prop-2-en-1-yl]cyclopropanecarbonitrile

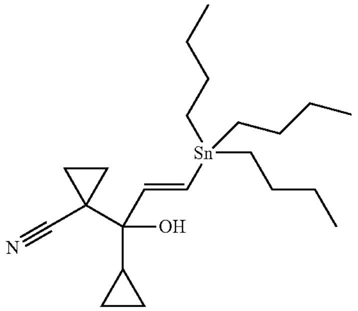 [SMILES: CCC[CH2][Sn](/[CH]=C/C(O)(C1CC1)C1(C#N)CC1)([CH2]CCC)[CH2]CCC]

Tetrakis(triphenylphosphine)palladium(0) (107 mg, 0.09 mmol) was initially charged under argon in a baked-out round-bottom flask, and abs. tetrahydrofuran (10 ml) and 1-(1-cyclopropyl-1-hydroxyprop-2-yn-1-yl)cyclopropanecarbonitrile (370 mg, 2.29 mmol) were added. Stirring at room temperature for 5 minutes was followed by the addition of tributyltin hydride (0.74 ml, 2.75 mmol). The resulting reaction mixture was stirred at room temperature for 1 h and at a temperature of 50° C. for 30 minutes, and then water was added. The aqueous phase was repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain 1-[(2E)-1-cyclopropyl-1-hydroxy-3-(tributylstannyl)prop-2-en-1-yl]cyclopropanecarbonitrile (202 mg, 19% of theory) in the form of a colourless oil. $^1$H NMR (400 MHz, $CDCl_3$ δ, ppm) 6.33 (d, 1H), 6.00 (d, 1H), 1.56 (br. s, 1H, OH), 1.53-1.45 (m, 7H), 1.35-1.28 (m, 6H), 1.24 (m, 1H), 1.17-1.08 (m, 2H), 1.03 (m, 1H), 0.96-0.86 (m, 15H), 0.57 (m, 1H), 0.47 (m, 2H), 0.41 (m, 1H).

No. III.1-76: 1-[(2E)-1-Cyclopentyl-1-hydroxy-3-(tributylstannyl)prop-2-en-1-yl]cyclopropanecarbonitrile

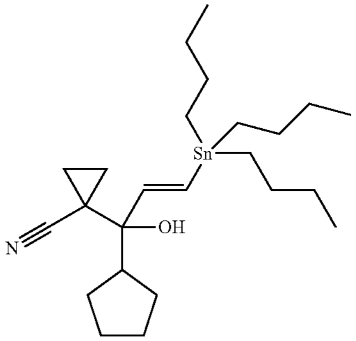 [SMILES: CCC[CH2][Sn](/[CH]=C/C(O)(C1CCCC1)C1(C#N)CC1)([CH2]CCC)[CH2]CCC]

Tetrakis(triphenylphosphine)palladium(0) (464 mg, 0.40 mmol) was initially charged under argon in a baked-out round-bottom flask, and abs. tetrahydrofuran (30 ml) and 1-(1-cyclopentyl-1-hydroxyprop-2-yn-1-yl)cyclopropanecarbonitrile (1900 mg, 10.04 mmol) were added. Stirring at room temperature for 5 minutes was followed by the addition of tributyltin hydride (3.24 ml, 12.05 mmol). The resulting reaction mixture was stirred at room temperature for 1 h and then water was added. The aqueous phase was repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain 1-[(2E)-1-cyclopentyl-1-hydroxy-3-(tributylstannyl)prop-2-en-1-yl]cyclopropanecarbonitrile (1650 mg, 34% of theory) in the form of a colourless oil. $^1$H NMR (400 MHz, $CDCl_3$ δ, ppm) 6.19 (d, 1H), 6.13 (d, 1H), 2.63-2.57 (m, 1H), 1.88-1.80 (br. s, 1H, OH), 1.73-1.58 (m, 4H), 1.56-1.47 (m, 8H), 1.37-1.27 (m, 8H), 1.26 (m, 1H), 1.13 (m, 1H), 1.05-0.98 (m, 2H), 0.94-0.86 (m, 15H).

No. III.1-67: 1-[(1E)-4-Ethyl-3-hydroxy-1-(tributylstannyl)hex-1-en-3-yl]cyclopropanecarbonitrile

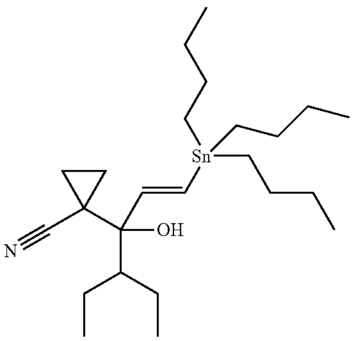 [SMILES: CCC[CH2][Sn](/[CH]=C/C(O)(C(CC)CC)C1(C#N)CC1)([CH2]CCC)[CH2]CCC]

Tetrakis(triphenylphosphine)palladium(0) (242 mg, 0.21 mmol) was initially charged under argon in a baked-out round-bottom flask, and abs. tetrahydrofuran (20 ml) and 1-(4-ethyl-3-hydroxyhex-1-yn-3-yl)cyclopropanecarbonitrile (1.00 g, 5.23 mmol) were added. Stirring at room temperature for 5 minutes was followed by the addition of tributyltin hydride (1.69 ml, 6.27 mmol). The resulting reaction mixture was stirred at room temperature for 1 h and at a temperature of 50° C. for 30 minutes, and then water was added. The aqueous phase was repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain 1-[(1E)-4-ethyl-3-hydroxy-1-(tributylstannyl)hex-1-en-3-yl]cyclopropanecarbonitrile (1.34 mg, 53% of theory) in the form of a colourless oil. $^1H$ NMR (400 MHz, $CDCl_3$ δ, ppm) 6.16 (d, 1H), 6.07 (d, 1H), 1.83 (m, 1H), 1.74 (m, 1H), 1.60 (m, 1H), 1.53 (br. s, 1H, OH), 1.52-1.46 (m, 4H), 1.37-1.29 (m, 9H), 1.25 (m, 1H), 1.18 (m, 1H), 1.08-0.95 (m, 7H), 0.93-0.87 (m, 16H), 0.82 (m, 1H).

No. III.2-2: 1-[(1E)-3-Hydroxy-4-methyl-1-(tributylstannyl)pent-1-en-3-yl]cyclobutanecarbonitrile

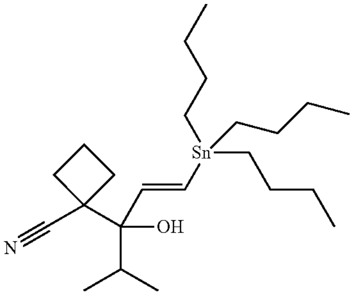 [SMILES: CCC[CH2][Sn](/[CH]=C/C(O)(C(C)C)C1(C#N)CCC1)([CH2]CCC)[CH2]CCC]

Tetrakis(triphenylphosphine)palladium(0) (261 mg, 0.23 mmol) was initially charged under argon in a baked-out round-bottom flask, and abs. tetrahydrofuran (20 ml) and 1-(3-hydroxy-4-methylpent-1-yn-3-yl)cyclobutanecarbonitrile (1000 mg, 5.64 mmol) were added. Stirring at room temperature for 5 minutes was followed by the addition of tributyltin hydride (1.82 ml, 6.77 mmol). The resulting reaction mixture was stirred at room temperature for 1 h and then water was added. The aqueous phase was repeatedly extracted thoroughly with dichloromethane, and the combined organic phases were then dried over magnesium sulphate, filtered and concentrated under reduced pressure. By final column chromatography purification of the resulting crude product (ethyl acetate/heptane gradient), it was possible to obtain 1-[(1E)-3-hydroxy-4-methyl-1-(tributylstannyl)pent-1-en-3-yl]cyclobutanecarbonitrile (1.40 mg, 53% of theory) in the form of a colourless oil. $^1H$ NMR (400 MHz, $CDCl_3$ δ, ppm) 6.23 (d, 1H), 5.98 (d, 1H), 2.78 (m, 1H), 2.30 (m, 1H), 2.22 (m, 3H), 2.02 (m, 1H), 1.77 (m, 1H), 1.67 (br. s, 1H, OH), 1.53-1.45 (m, 6H), 1.35-1.27 (m, 6H), 0.96-0.85 (m, 21H).

In analogy to the preparation examples cited above and recited in the tables below, and taking into account the general details regarding the preparation of substituted cyanocycloalkylpenta-2,4-dienes, cyanocycloalkylpent-2-en-4-ynes, cyanoheterocyclylpenta-2,4-dienes and cyanoheterocyclylpent-2-en-4-ynes of the general formula (I) and of the compounds of the general formulae (II) and (III), the following compounds specified in Tables 1 to 8 are obtained:

TABLE 1

(I)

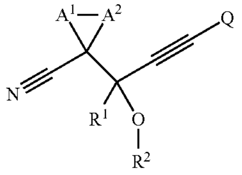

The Q radicals here correspond to the structures defined as very particularly preferred earlier in the document

| No. | $R^1$ | $R^2$ | $A^1$ | $A^2$ | Q |
|---|---|---|---|---|---|
| I.1-1 | $CH_3$ | H | $CH_2$ | $CH_2$ | Q-1.1 |
| I.1-2 | $CH_3$ | H | $CH_2$ | $CH_2$ | Q-1.2 |
| I.1-3 | $CH_3$ | H | $CH_2$ | $CH_2$ | Q-1.3 |
| I.1-4 | $CH_3$ | H | $CH_2$ | $CH_2$ | Q-1.16 |
| I.1-5 | $CH_3$ | H | $CH_2$ | $CH_2$ | Q-1.17 |
| I.1-6 | $CH_3$ | H | $CH_2$ | $CH_2$ | Q-1.18 |
| I.1-7 | $CH_3$ | H | $CH_2$ | $CH_2$ | Q-1.31 |
| I.1-8 | $CH_3$ | H | $CH_2$ | $CH_2$ | Q-1.32 |
| I.1-9 | $CH_3$ | H | $CH_2$ | $CH_2$ | Q-1.33 |
| I.1-10 | $CH_3$ | H | $CH_2$ | $CH_2$ | Q-1.91 |
| I.1-11 | $CH_3$ | H | $CH_2$ | $CH_2$ | Q-1.92 |
| I.1-12 | $CH_3$ | H | $CH_2$ | $CH_2$ | Q-1.93 |
| I.1-13 | $CH_3$ | H | $CH_2$ | $CH_2$ | Q-1.106 |
| I.1-14 | $CH_3$ | H | $CH_2$ | $CH_2$ | Q-1.107 |
| I.1-15 | $CH_3$ | H | $CH_2$ | $CH_2$ | Q-1.108 |
| I.1-16 | $CH_3$ | H | $CH_2$ | $CH_2$ | Q-1.121 |
| I.1-17 | $CH_3$ | H | $CH_2$ | $CH_2$ | Q-1.122 |
| I.1-18 | $CH_3$ | H | $CH_2$ | $CH_2$ | Q-1.123 |
| I.1-19 | $CH_3$ | H | $CH_2$ | $CH_2$ | Q-1.136 |
| I.1-20 | $CH_3$ | H | $CH_2$ | $CH_2$ | Q-1.137 |
| I.1-21 | $CH_3$ | H | $CH_2$ | $CH_2$ | Q-1.138 |
| I.1-22 | $CH_3$ | H | $CH_2$ | $CH_2$ | Q-1.166 |
| I.1-23 | $CH_3$ | H | $CH_2$ | $CH_2$ | Q-1.167 |
| I.1-24 | $CH_3$ | H | $CH_2$ | $CH_2$ | Q-1.168 |
| I.1-25 | $CH_3$ | H | $CH_2$ | $CH_2$ | Q-1.171 |
| I.1-26 | $CH_3$ | H | $CH_2$ | $CH_2$ | Q-1.172 |
| I.1-27 | $CH_3$ | H | $CH_2$ | $CH_2$ | Q-1.173 |
| I.1-28 | $CH_3$ | H | $CH_2$ | $CH_2$ | Q-1.176 |
| I.1-29 | $CH_3$ | H | $CH_2$ | $CH_2$ | Q-1.177 |
| I.1-30 | $CH_3$ | H | $CH_2$ | $CH_2$ | Q-1.178 |
| I.1-31 | $CH_3$ | H | $CH_2$ | $CH_2$ | Q-1.181 |
| I.1-32 | $CH_3$ | H | $CH_2$ | $CH_2$ | Q-1.182 |
| I.1-33 | $CH_3$ | H | $CH_2$ | $CH_2$ | Q-1.183 |
| I.1-34 | $CH_3$ | H | $CH_2$ | $CH_2$ | Q-1.201 |
| I.1-35 | $CH_3$ | H | $CH_2$ | $CH_2$ | Q-1.202 |

TABLE 1-continued (I)

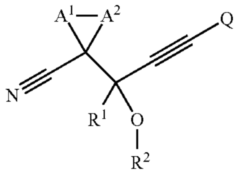

The Q radicals here correspond to the structures defined as very particularly preferred earlier in the document

| No. | $R^1$ | $R^2$ | $A^1$ | $A^2$ | Q |
|---|---|---|---|---|---|
| I.1-36 | $CH_3$ | H | $CH_2$ | $CH_2$ | Q-1.203 |
| I.1-37 | $CH_3$ | H | $CH_2$ | $CH_2$ | Q-1.204 |
| I.1-38 | $CH_3$ | H | $CH_2$ | $CH_2$ | Q-1.205 |
| I.1-39 | $CH_3$ | H | $CH_2$ | $CH_2$ | Q-1.206 |
| I.1-41 | $CH_3$ | H | $CH_2$ | $CH_2$ | Q-1.207 |
| I.1-42 | $CH_3$ | H | $CH_2$ | $CH_2$ | Q-1.208 |
| I.1-43 | $CH_3$ | H | $CH_2$ | $CH_2$ | Q-1.209 |
| I.1-44 | $CH_3$ | H | $CH_2$ | $CH_2$ | Q-1.210 |
| I.1-45 | $CH_3$ | H | $CH_2$ | $CH_2$ | Q-1.211 |
| I.1-46 | $CH_3$ | H | $CH_2$ | $CH_2$ | Q-1.212 |
| I.1-47 | $CH_3$ | H | $CH_2$ | $CH_2$ | Q-1.213 |
| I.1-48 | $CH_3$ | H | $CH_2$ | $CH_2$ | Q-1.216 |
| I.1-49 | $CH_3$ | H | $CH_2$ | $CH_2$ | Q-1.217 |
| I.1-50 | $CH_3$ | H | $CH_2$ | $CH_2$ | Q-1.218 |
| I.1-51 | $CH_3$ | H | $CH_2$ | $CH_2$ | Q-1.246 |
| I.1-52 | $CH_3$ | H | $CH_2$ | $CH_2$ | Q-1.247 |
| I.1-53 | $CH_3$ | H | $CH_2$ | $CH_2$ | Q-1.248 |
| I.1-54 | $CH_3$ | H | $CH_2$ | $CH_2$ | Q-2.1 |
| I.1-55 | $CH_3$ | H | $CH_2$ | $CH_2$ | Q-2.2 |
| I.1-56 | $CH_3$ | H | $CH_2$ | $CH_2$ | Q-2.3 |
| I.1-57 | $CH_3$ | H | $CH_2$ | $CH_2$ | Q-2.5 |
| I.1-58 | $CH_3$ | H | $CH_2$ | $CH_2$ | Q-2.4 |
| I.1-59 | $CH_3$ | H | $CH_2$ | $CH_2$ | Q-2.7 |
| I.1-60 | $CH_3$ | H | $CH_2$ | $CH_2$ | Q-2.9 |
| I.1-61 | $CH_3$ | H | $CH_2$ | $CH_2$ | Q-2.12 |
| I.1-62 | $CH_3$ | H | $CH_2$ | $CH_2$ | Q-2.13 |
| I.1-63 | $CH_3$ | H | $CH_2$ | $CH_2$ | Q-2.14 |
| I.1-64 | $CH_3$ | H | $CH_2$ | $CH_2$ | Q-2.61 |
| I.1-65 | $CH_3$ | H | $CH_2$ | $CH_2$ | Q-2.62 |
| I.1-66 | $CH_3$ | H | $CH_2$ | $CH_2$ | Q-2.63 |
| I.1-67 | $CH_3$ | H | $CH_2$ | $CH_2$ | Q-2.64 |
| I.1-68 | $CH_3$ | H | $CH_2$ | $CH_2$ | Q-2.65 |
| I.1-69 | $CH_3$ | H | $CH_2$ | $CH_2$ | Q-2.67 |
| I.1-70 | $CH_3$ | H | $CH_2$ | $CH_2$ | Q-2.69 |
| I.1-71 | $CH_3$ | H | $CH_2$ | $CH_2$ | Q-2.72 |
| I.1-72 | $CH_3$ | H | $CH_2$ | $CH_2$ | Q-2.73 |
| I.1-73 | $CH_3$ | H | $CH_2$ | $CH_2$ | Q-2.74 |
| I.1-74 | $CH_3$ | H | $CH_2$ | $CH_2$ | Q-2.80 |
| I.1-75 | $CH_3$ | H | $CH_2$ | $CH_2$ | Q-2.105 |
| I.1-76 | $CH_3$ | H | $CH_2$ | $CH_2$ | Q-2.106 |
| I.1-77 | $CH_3$ | H | $CH_2$ | $CH_2$ | Q-2.108 |
| I.1-78 | $CH_3$ | H | $CH_2$ | $CH_2$ | Q-2.145 |
| I.1-79 | $CH_3$ | H | $CH_2$ | $CH_2$ | Q-2.146 |
| I.1-80 | $CH_3$ | H | $CH_2$ | $CH_2$ | Q-2.147 |
| I.1-81 | $CH_3$ | H | $CH_2$ | $CH_2$ | Q-2.161 |
| I.1-82 | $CH_3$ | H | $CH_2$ | $CH_2$ | Q-2.162 |
| I.1-83 | $CH_3$ | H | $CH_2$ | $CH_2$ | Q-2.163 |
| I.1-84 | $CH_3$ | H | $CH_2$ | $CH_2$ | Q-2.164 |
| I.1-85 | $CH_3$ | H | $CH_2$ | $CH_2$ | Q-2.165 |
| I.1-86 | $CH_3$ | H | $CH_2$ | $CH_2$ | Q-2.167 |
| I.1-87 | $CH_3$ | H | $CH_2$ | $CH_2$ | Q-2.168 |
| I.1-88 | $CH_3$ | H | $CH_2$ | $CH_2$ | Q-2.169 |
| I.1-89 | $CH_3$ | H | $CH_2$ | $CH_2$ | Q-2.172 |
| I.1-90 | $CH_3$ | H | $CH_2$ | $CH_2$ | Q-2.173 |
| I.1-91 | $CH_3$ | H | $CH_2$ | $CH_2$ | Q-2.174 |
| I.1-92 | $CH_3$ | H | $CH_2$ | $CH_2$ | Q-2.180 |
| I.1-93 | $CH_3$ | H | $CH_2$ | $CH_2$ | Q-2.185 |
| I.1-94 | $CH_3$ | H | $CH_2$ | $CH_2$ | Q-2.189 |
| I.1-95 | $CH_3$ | H | $CH_2$ | $CH_2$ | Q-2.190 |
| I.1-96 | $CH_3$ | H | $CH_2$ | $CH_2$ | Q-2.201 |
| I.1-97 | $CH_3$ | H | $CH_2$ | $CH_2$ | Q-2.202 |
| I.1-98 | $CH_3$ | H | $CH_2$ | $CH_2$ | Q-2.203 |
| I.1-99 | $CH_3$ | H | $CH_2$ | $CH_2$ | Q-2.204 |
| I.1-100 | $CH_3$ | H | $CH_2$ | $CH_2$ | Q-2.205 |

TABLE 1-continued (I)

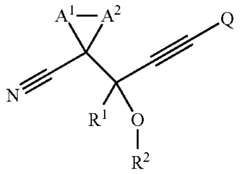

The Q radicals here correspond to the structures defined as very particularly preferred earlier in the document

| No. | $R^1$ | $R^2$ | $A^1$ | $A^2$ | Q |
|---|---|---|---|---|---|
| I.1-101 | i-Pr | H | $CH_2$ | $CH_2$ | Q-1.1 |
| I.1-102 | i-Pr | H | $CH_2$ | $CH_2$ | Q-1.2 |
| I.1-103 | i-Pr | H | $CH_2$ | $CH_2$ | Q-1.3 |
| I.1-104 | i-Pr | H | $CH_2$ | $CH_2$ | Q-1.16 |
| I.1-105 | i-Pr | H | $CH_2$ | $CH_2$ | Q-1.17 |
| I.1-106 | i-Pr | H | $CH_2$ | $CH_2$ | Q-1.18 |
| I.1-107 | i-Pr | H | $CH_2$ | $CH_2$ | Q-1.31 |
| I.1-108 | i-Pr | H | $CH_2$ | $CH_2$ | Q-1.32 |
| I.1-109 | i-Pr | H | $CH_2$ | $CH_2$ | Q-1.33 |
| I.1-110 | i-Pr | H | $CH_2$ | $CH_2$ | Q-1.91 |
| I.1-111 | i-Pr | H | $CH_2$ | $CH_2$ | Q-1.92 |
| I.1-112 | i-Pr | H | $CH_2$ | $CH_2$ | Q-1.93 |
| I.1-113 | i-Pr | H | $CH_2$ | $CH_2$ | Q-1.106 |
| I.1-114 | i-Pr | H | $CH_2$ | $CH_2$ | Q-1.107 |
| I.1-115 | i-Pr | H | $CH_2$ | $CH_2$ | Q-1.108 |
| I.1-116 | i-Pr | H | $CH_2$ | $CH_2$ | Q-1.121 |
| I.1-117 | i-Pr | H | $CH_2$ | $CH_2$ | Q-1.122 |
| I.1-118 | i-Pr | H | $CH_2$ | $CH_2$ | Q-1.123 |
| I.1-119 | i-Pr | H | $CH_2$ | $CH_2$ | Q-1.136 |
| I.1-120 | i-Pr | H | $CH_2$ | $CH_2$ | Q-1.137 |
| I.1-121 | i-Pr | H | $CH_2$ | $CH_2$ | Q-1.138 |
| I.1-122 | i-Pr | H | $CH_2$ | $CH_2$ | Q-1.166 |
| I.1-123 | i-Pr | H | $CH_2$ | $CH_2$ | Q-1.167 |
| I.1-124 | i-Pr | H | $CH_2$ | $CH_2$ | Q-1.168 |
| I.1-125 | i-Pr | H | $CH_2$ | $CH_2$ | Q-1.171 |
| I.1-126 | i-Pr | H | $CH_2$ | $CH_2$ | Q-1.172 |
| I.1-127 | i-Pr | H | $CH_2$ | $CH_2$ | Q-1.173 |
| I.1-128 | i-Pr | H | $CH_2$ | $CH_2$ | Q-1.176 |
| I.1-129 | i-Pr | H | $CH_2$ | $CH_2$ | Q-1.177 |
| I.1-130 | i-Pr | H | $CH_2$ | $CH_2$ | Q-1.178 |
| I.1-131 | i-Pr | H | $CH_2$ | $CH_2$ | Q-1.181 |
| I.1-132 | i-Pr | H | $CH_2$ | $CH_2$ | Q-1.182 |
| I.1-133 | i-Pr | H | $CH_2$ | $CH_2$ | Q-1.183 |
| I.1-134 | i-Pr | H | $CH_2$ | $CH_2$ | Q-1.201 |
| I.1-135 | i-Pr | H | $CH_2$ | $CH_2$ | Q-1.202 |
| I.1-136 | i-Pr | H | $CH_2$ | $CH_2$ | Q-1.203 |
| I.1-137 | i-Pr | H | $CH_2$ | $CH_2$ | Q-1.204 |
| I.1-138 | i-Pr | H | $CH_2$ | $CH_2$ | Q-1.205 |
| I.1-139 | i-Pr | H | $CH_2$ | $CH_2$ | Q-1.206 |
| I.1-141 | i-Pr | H | $CH_2$ | $CH_2$ | Q-1.207 |
| I.1-142 | i-Pr | H | $CH_2$ | $CH_2$ | Q-1.208 |
| I.1-143 | i-Pr | H | $CH_2$ | $CH_2$ | Q-1.209 |
| I.1-144 | i-Pr | H | $CH_2$ | $CH_2$ | Q-1.210 |
| I.1-145 | i-Pr | H | $CH_2$ | $CH_2$ | Q-1.211 |
| I.1-146 | i-Pr | H | $CH_2$ | $CH_2$ | Q-1.212 |
| I.1-147 | i-Pr | H | $CH_2$ | $CH_2$ | Q-1.213 |
| I.1-148 | i-Pr | H | $CH_2$ | $CH_2$ | Q-1.216 |
| I.1-149 | i-Pr | H | $CH_2$ | $CH_2$ | Q-1.217 |
| I.1-150 | i-Pr | H | $CH_2$ | $CH_2$ | Q-1.218 |
| I.1-151 | i-Pr | H | $CH_2$ | $CH_2$ | Q-1.246 |
| I.1-152 | i-Pr | H | $CH_2$ | $CH_2$ | Q-1.247 |
| I.1-153 | i-Pr | H | $CH_2$ | $CH_2$ | Q-1.248 |
| I.1-154 | i-Pr | H | $CH_2$ | $CH_2$ | Q-2.1 |
| I.1-155 | i-Pr | H | $CH_2$ | $CH_2$ | Q-2.2 |
| I.1-156 | i-Pr | H | $CH_2$ | $CH_2$ | Q-2.3 |
| I.1-157 | i-Pr | H | $CH_2$ | $CH_2$ | Q-2.5 |
| I.1-158 | i-Pr | H | $CH_2$ | $CH_2$ | Q-2.4 |
| I.1-159 | i-Pr | H | $CH_2$ | $CH_2$ | Q-2.7 |
| I.1-160 | i-Pr | H | $CH_2$ | $CH_2$ | Q-2.9 |
| I.1-161 | i-Pr | H | $CH_2$ | $CH_2$ | Q-2.12 |
| I.1-162 | i-Pr | H | $CH_2$ | $CH_2$ | Q-2.13 |
| I.1-163 | i-Pr | H | $CH_2$ | $CH_2$ | Q-2.14 |
| I.1-164 | i-Pr | H | $CH_2$ | $CH_2$ | Q-2.61 |
| I.1-165 | i-Pr | H | $CH_2$ | $CH_2$ | Q-2.62 |

TABLE 1-continued (I)

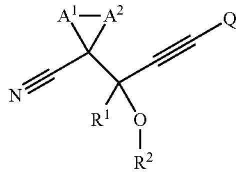

The Q radicals here correspond to the structures defined as very particularly preferred earlier in the document

| No. | $R^1$ | $R^2$ | $A^1$ | $A^2$ | Q |
|---|---|---|---|---|---|
| I.1-166 | i-Pr | H | $CH_2$ | $CH_2$ | Q-2.63 |
| I.1-167 | i-Pr | H | $CH_2$ | $CH_2$ | Q-2.64 |
| I.1-168 | i-Pr | H | $CH_2$ | $CH_2$ | Q-2.65 |
| I.1-169 | i-Pr | H | $CH_2$ | $CH_2$ | Q-2.67 |
| I.1-170 | i-Pr | H | $CH_2$ | $CH_2$ | Q-2.69 |
| I.1-171 | i-Pr | H | $CH_2$ | $CH_2$ | Q-2.72 |
| I.1-172 | i-Pr | H | $CH_2$ | $CH_2$ | Q-2.73 |
| I.1-173 | i-Pr | H | $CH_2$ | $CH_2$ | Q-2.74 |
| I.1-174 | i-Pr | H | $CH_2$ | $CH_2$ | Q-2.80 |
| I.1-175 | i-Pr | H | $CH_2$ | $CH_2$ | Q-2.105 |
| I.1-176 | i-Pr | H | $CH_2$ | $CH_2$ | Q-2.106 |
| I.1-177 | i-Pr | H | $CH_2$ | $CH_2$ | Q-2.108 |
| I.1-178 | i-Pr | H | $CH_2$ | $CH_2$ | Q-2.145 |
| I.1-179 | i-Pr | H | $CH_2$ | $CH_2$ | Q-2.146 |
| I.1-180 | i-Pr | H | $CH_2$ | $CH_2$ | Q-2.147 |
| I.1-181 | i-Pr | H | $CH_2$ | $CH_2$ | Q-2.161 |
| I.1-182 | i-Pr | H | $CH_2$ | $CH_2$ | Q-2.162 |
| I.1-183 | i-Pr | H | $CH_2$ | $CH_2$ | Q-2.163 |
| I.1-184 | i-Pr | H | $CH_2$ | $CH_2$ | Q-2.164 |
| I.1-185 | i-Pr | H | $CH_2$ | $CH_2$ | Q-2.165 |
| I.1-186 | i-Pr | H | $CH_2$ | $CH_2$ | Q-2.167 |
| I.1-187 | i-Pr | H | $CH_2$ | $CH_2$ | Q-2.168 |
| I.1-188 | i-Pr | H | $CH_2$ | $CH_2$ | Q-2.169 |
| I.1-189 | i-Pr | H | $CH_2$ | $CH_2$ | Q-2.172 |
| I.1-190 | i-Pr | H | $CH_2$ | $CH_2$ | Q-2.173 |
| I.1-191 | i-Pr | H | $CH_2$ | $CH_2$ | Q-2.174 |
| I.1-192 | i-Pr | H | $CH_2$ | $CH_2$ | Q-2.180 |
| I.1-193 | i-Pr | H | $CH_2$ | $CH_2$ | Q-2.185 |
| I.1-194 | i-Pr | H | $CH_2$ | $CH_2$ | Q-2.189 |
| I.1-195 | i-Pr | H | $CH_2$ | $CH_2$ | Q-2.190 |
| I.1-196 | i-Pr | H | $CH_2$ | $CH_2$ | Q-2.201 |
| I.1-197 | i-Pr | H | $CH_2$ | $CH_2$ | Q-2.202 |
| I.1-198 | i-Pr | H | $CH_2$ | $CH_2$ | Q-2.203 |
| I.1-199 | i-Pr | H | $CH_2$ | $CH_2$ | Q-2.204 |
| I.1-200 | i-Pr | H | $CH_2$ | $CH_2$ | Q-2.205 |
| I.1-201 | Ph | H | $CH_2$ | $CH_2$ | Q-1.1 |
| I.1-202 | Ph | H | $CH_2$ | $CH_2$ | Q-1.2 |
| I.1-203 | Ph | H | $CH_2$ | $CH_2$ | Q-1.3 |
| I.1-204 | Ph | H | $CH_2$ | $CH_2$ | Q-1.16 |
| I.1-205 | Ph | H | $CH_2$ | $CH_2$ | Q-1.17 |
| I.1-206 | Ph | H | $CH_2$ | $CH_2$ | Q-1.18 |
| I.1-207 | Ph | H | $CH_2$ | $CH_2$ | Q-1.31 |
| I.1-208 | Ph | H | $CH_2$ | $CH_2$ | Q-1.32 |
| I.1-209 | Ph | H | $CH_2$ | $CH_2$ | Q-1.33 |
| I.1-210 | Ph | H | $CH_2$ | $CH_2$ | Q-1.91 |
| I.1-211 | Ph | H | $CH_2$ | $CH_2$ | Q-1.92 |
| I.1-212 | Ph | H | $CH_2$ | $CH_2$ | Q-1.93 |
| I.1-213 | Ph | H | $CH_2$ | $CH_2$ | Q-1.106 |
| I.1-214 | Ph | H | $CH_2$ | $CH_2$ | Q-1.107 |
| I.1-215 | Ph | H | $CH_2$ | $CH_2$ | Q-1.108 |
| I.1-216 | Ph | H | $CH_2$ | $CH_2$ | Q-1.121 |
| I.1-217 | Ph | H | $CH_2$ | $CH_2$ | Q-1.122 |
| I.1-218 | Ph | H | $CH_2$ | $CH_2$ | Q-1.123 |
| I.1-219 | Ph | H | $CH_2$ | $CH_2$ | Q-1.136 |
| I.1-220 | Ph | H | $CH_2$ | $CH_2$ | Q-1.137 |
| I.1-221 | Ph | H | $CH_2$ | $CH_2$ | Q-1.138 |
| I.1-222 | Ph | H | $CH_2$ | $CH_2$ | Q-1.166 |
| I.1-223 | Ph | H | $CH_2$ | $CH_2$ | Q-1.167 |
| I.1-224 | Ph | H | $CH_2$ | $CH_2$ | Q-1.168 |
| I.1-225 | Ph | H | $CH_2$ | $CH_2$ | Q-1.171 |
| I.1-226 | Ph | H | $CH_2$ | $CH_2$ | Q-1.172 |
| I.1-227 | Ph | H | $CH_2$ | $CH_2$ | Q-1.173 |
| I.1-228 | Ph | H | $CH_2$ | $CH_2$ | Q-1.176 |
| I.1-229 | Ph | H | $CH_2$ | $CH_2$ | Q-1.177 |

TABLE 1-continued (I)

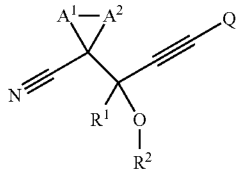

The Q radicals here correspond to the structures defined as very particularly preferred earlier in the document

| No. | $R^1$ | $R^2$ | $A^1$ | $A^2$ | Q |
|---|---|---|---|---|---|
| I.1-230 | Ph | H | $CH_2$ | $CH_2$ | Q-1.178 |
| I.1-231 | Ph | H | $CH_2$ | $CH_2$ | Q-1.181 |
| I.1-232 | Ph | H | $CH_2$ | $CH_2$ | Q-1.182 |
| I.1-233 | Ph | H | $CH_2$ | $CH_2$ | Q-1.183 |
| I.1-234 | Ph | H | $CH_2$ | $CH_2$ | Q-1.201 |
| I.1-235 | Ph | H | $CH_2$ | $CH_2$ | Q-1.202 |
| I.1-236 | Ph | H | $CH_2$ | $CH_2$ | Q-1.203 |
| I.1-237 | Ph | H | $CH_2$ | $CH_2$ | Q-1.204 |
| I.1-238 | Ph | H | $CH_2$ | $CH_2$ | Q-1.205 |
| I.1-239 | Ph | H | $CH_2$ | $CH_2$ | Q-1.206 |
| I.1-241 | Ph | H | $CH_2$ | $CH_2$ | Q-1.207 |
| I.1-242 | Ph | H | $CH_2$ | $CH_2$ | Q-1.208 |
| I.1-243 | Ph | H | $CH_2$ | $CH_2$ | Q-1.209 |
| I.1-244 | Ph | H | $CH_2$ | $CH_2$ | Q-1.210 |
| I.1-245 | Ph | H | $CH_2$ | $CH_2$ | Q-1.211 |
| I.1-246 | Ph | H | $CH_2$ | $CH_2$ | Q-1.212 |
| I.1-247 | Ph | H | $CH_2$ | $CH_2$ | Q-1.213 |
| I.1-248 | Ph | H | $CH_2$ | $CH_2$ | Q-1.216 |
| I.1-249 | Ph | H | $CH_2$ | $CH_2$ | Q-1.217 |
| I.1-250 | Ph | H | $CH_2$ | $CH_2$ | Q-1.218 |
| I.1-251 | Ph | H | $CH_2$ | $CH_2$ | Q-1.246 |
| I.1-252 | Ph | H | $CH_2$ | $CH_2$ | Q-1.247 |
| I.1-253 | Ph | H | $CH_2$ | $CH_2$ | Q-1.248 |
| I.1-254 | Ph | H | $CH_2$ | $CH_2$ | Q-2.1 |
| I.1-255 | Ph | H | $CH_2$ | $CH_2$ | Q-2.2 |
| I.1-256 | Ph | H | $CH_2$ | $CH_2$ | Q-2.3 |
| I.1-257 | Ph | H | $CH_2$ | $CH_2$ | Q-2.5 |
| I.1-258 | Ph | H | $CH_2$ | $CH_2$ | Q-2.4 |
| I.1-259 | Ph | H | $CH_2$ | $CH_2$ | Q-2.7 |
| I.1-260 | Ph | H | $CH_2$ | $CH_2$ | Q-2.9 |
| I.1-261 | Ph | H | $CH_2$ | $CH_2$ | Q-2.12 |
| I.1-262 | Ph | H | $CH_2$ | $CH_2$ | Q-2.13 |
| I.1-263 | Ph | H | $CH_2$ | $CH_2$ | Q-2.14 |
| I.1-264 | Ph | H | $CH_2$ | $CH_2$ | Q-2.61 |
| I.1-265 | Ph | H | $CH_2$ | $CH_2$ | Q-2.62 |
| I.1-266 | Ph | H | $CH_2$ | $CH_2$ | Q-2.63 |
| I.1-267 | Ph | H | $CH_2$ | $CH_2$ | Q-2.64 |
| I.1-268 | Ph | H | $CH_2$ | $CH_2$ | Q-2.65 |
| I.1-269 | Ph | H | $CH_2$ | $CH_2$ | Q-2.67 |
| I.1-270 | Ph | H | $CH_2$ | $CH_2$ | Q-2.69 |
| I.1-271 | Ph | H | $CH_2$ | $CH_2$ | Q-2.72 |
| I.1-272 | Ph | H | $CH_2$ | $CH_2$ | Q-2.73 |
| I.1-273 | Ph | H | $CH_2$ | $CH_2$ | Q-2.74 |
| I.1-274 | Ph | H | $CH_2$ | $CH_2$ | Q-2.80 |
| I.1-275 | Ph | H | $CH_2$ | $CH_2$ | Q-2.105 |
| I.1-276 | Ph | H | $CH_2$ | $CH_2$ | Q-2.106 |
| I.1-277 | Ph | H | $CH_2$ | $CH_2$ | Q-2.108 |
| I.1-278 | Ph | H | $CH_2$ | $CH_2$ | Q-2.145 |
| I.1-279 | Ph | H | $CH_2$ | $CH_2$ | Q-2.146 |
| I.1-280 | Ph | H | $CH_2$ | $CH_2$ | Q-2.147 |
| I.1-281 | Ph | H | $CH_2$ | $CH_2$ | Q-2.161 |
| I.1-282 | Ph | H | $CH_2$ | $CH_2$ | Q-2.162 |
| I.1-283 | Ph | H | $CH_2$ | $CH_2$ | Q-2.163 |
| I.1-284 | Ph | H | $CH_2$ | $CH_2$ | Q-2.164 |
| I.1-285 | Ph | H | $CH_2$ | $CH_2$ | Q-2.165 |
| I.1-286 | Ph | H | $CH_2$ | $CH_2$ | Q-2.167 |
| I.1-287 | Ph | H | $CH_2$ | $CH_2$ | Q-2.168 |
| I.1-288 | Ph | H | $CH_2$ | $CH_2$ | Q-2.169 |
| I.1-289 | Ph | H | $CH_2$ | $CH_2$ | Q-2.172 |
| I.1-290 | Ph | H | $CH_2$ | $CH_2$ | Q-2.173 |
| I.1-291 | Ph | H | $CH_2$ | $CH_2$ | Q-2.174 |
| I.1-292 | Ph | H | $CH_2$ | $CH_2$ | Q-2.180 |
| I.1-293 | Ph | H | $CH_2$ | $CH_2$ | Q-2.185 |
| I.1-294 | Ph | H | $CH_2$ | $CH_2$ | Q-2.189 |

TABLE 1-continued (I)

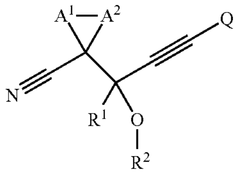

The Q radicals here correspond to the structures defined as very particularly preferred earlier in the document

| No. | $R^1$ | $R^2$ | $A^1$ | $A^2$ | Q |
|---|---|---|---|---|---|
| I.1-295 | Ph | H | $CH_2$ | $CH_2$ | Q-2.190 |
| I.1-296 | Ph | H | $CH_2$ | $CH_2$ | Q-2.201 |
| I.1-297 | Ph | H | $CH_2$ | $CH_2$ | Q-2.202 |
| I.1-298 | Ph | H | $CH_2$ | $CH_2$ | Q-2.203 |
| I.1-299 | Ph | H | $CH_2$ | $CH_2$ | Q-2.204 |
| I.1-300 | Ph | H | $CH_2$ | $CH_2$ | Q-2.205 |
| I.1-301 | $CH_3$ | $CH_3$ | $CH_2$ | $CH_2$ | Q-1.1 |
| I.1-302 | $CH_3$ | $CH_3$ | $CH_2$ | $CH_2$ | Q-1.2 |
| I.1-303 | $CH_3$ | $CH_3$ | $CH_2$ | $CH_2$ | Q-1.3 |
| I.1-304 | $CH_3$ | $CH_3$ | $CH_2$ | $CH_2$ | Q-1.16 |
| I.1-305 | $CH_3$ | $CH_3$ | $CH_2$ | $CH_2$ | Q-1.17 |
| I.1-306 | $CH_3$ | $CH_3$ | $CH_2$ | $CH_2$ | Q-1.18 |
| I.1-307 | $CH_3$ | $CH_3$ | $CH_2$ | $CH_2$ | Q-1.136 |
| I.1-308 | $CH_3$ | $CH_3$ | $CH_2$ | $CH_2$ | Q-1.137 |
| I.1-309 | $CH_3$ | $CH_3$ | $CH_2$ | $CH_2$ | Q-1.138 |
| I.1-310 | $CH_3$ | $CH_3$ | $CH_2$ | $CH_2$ | Q-1.166 |
| I.1-311 | $CH_3$ | $CH_3$ | $CH_2$ | $CH_2$ | Q-1.167 |
| I.1-312 | $CH_3$ | $CH_3$ | $CH_2$ | $CH_2$ | Q-1.168 |
| I.1-313 | $CH_3$ | $CH_3$ | $CH_2$ | $CH_2$ | Q-1.201 |
| I.1-314 | $CH_3$ | $CH_3$ | $CH_2$ | $CH_2$ | Q-1.202 |
| I.1-315 | $CH_3$ | $CH_3$ | $CH_2$ | $CH_2$ | Q-1.203 |
| I.1-316 | $CH_3$ | $CH_3$ | $CH_2$ | $CH_2$ | Q-1.206 |
| I.1-317 | $CH_3$ | $CH_3$ | $CH_2$ | $CH_2$ | Q-1.207 |
| I.1-318 | $CH_3$ | $CH_3$ | $CH_2$ | $CH_2$ | Q-1.210 |
| I.1-319 | $CH_3$ | $CH_3$ | $CH_2$ | $CH_2$ | Q-1.211 |
| I.1-320 | $CH_3$ | $CH_3$ | $CH_2$ | $CH_2$ | Q-1.213 |
| I.1-321 | $CH_3$ | $C(=)CH_3$ | $CH_2$ | $CH_2$ | Q-1.1 |
| I.1-322 | $CH_3$ | $C(=)CH_3$ | $CH_2$ | $CH_2$ | Q-1.2 |
| I.1-323 | $CH_3$ | $C(=)CH_3$ | $CH_2$ | $CH_2$ | Q-1.3 |
| I.1-324 | $CH_3$ | $C(=)CH_3$ | $CH_2$ | $CH_2$ | Q-1.16 |
| I.1-325 | $CH_3$ | $C(=)CH_3$ | $CH_2$ | $CH_2$ | Q-1.17 |
| I.1-326 | $CH_3$ | $C(=)CH_3$ | $CH_2$ | $CH_2$ | Q-1.18 |
| I.1-327 | $CH_3$ | $C(=)CH_3$ | $CH_2$ | $CH_2$ | Q-1.136 |
| I.1-328 | $CH_3$ | $C(=)CH_3$ | $CH_2$ | $CH_2$ | Q-1.137 |
| I.1-329 | $CH_3$ | $C(=)CH_3$ | $CH_2$ | $CH_2$ | Q-1.138 |
| I.1-330 | $CH_3$ | $C(=)CH_3$ | $CH_2$ | $CH_2$ | Q-1.166 |
| I.1-331 | $CH_3$ | $C(=)CH_3$ | $CH_2$ | $CH_2$ | Q-1.167 |
| I.1-332 | $CH_3$ | $C(=)CH_3$ | $CH_2$ | $CH_2$ | Q-1.168 |
| I.1-333 | $CH_3$ | $C(=)CH_3$ | $CH_2$ | $CH_2$ | Q-1.201 |
| I.1-334 | $CH_3$ | $C(=)CH_3$ | $CH_2$ | $CH_2$ | Q-1.202 |
| I.1-335 | $CH_3$ | $C(=)CH_3$ | $CH_2$ | $CH_2$ | Q-1.203 |
| I.1-336 | $CH_3$ | $C(=)CH_3$ | $CH_2$ | $CH_2$ | Q-1.206 |
| I.1-337 | $CH_3$ | $C(=)CH_3$ | $CH_2$ | $CH_2$ | Q-1.207 |
| I.1-338 | $CH_3$ | $C(=)CH_3$ | $CH_2$ | $CH_2$ | Q-1.210 |
| I.1-339 | $CH_3$ | $C(=)CH_3$ | $CH_2$ | $CH_2$ | Q-1.211 |
| I.1-340 | $CH_3$ | $C(=)CH_3$ | $CH_2$ | $CH_2$ | Q-1.213 |
| I.1-341 | $CH_3$ | $SiEt_3$ | $CH_2$ | $CH_2$ | Q-1.1 |
| I.1-342 | $CH_3$ | $SiEt_3$ | $CH_2$ | $CH_2$ | Q-1.2 |
| I.1-343 | $CH_3$ | $SiEt_3$ | $CH_2$ | $CH_2$ | Q-1.3 |
| I.1-344 | $CH_3$ | $SiEt_3$ | $CH_2$ | $CH_2$ | Q-1.16 |
| I.1-345 | $CH_3$ | $SiEt_3$ | $CH_2$ | $CH_2$ | Q-1.17 |
| I.1-346 | $CH_3$ | $SiEt_3$ | $CH_2$ | $CH_2$ | Q-1.18 |
| I.1-347 | $CH_3$ | $SiEt_3$ | $CH_2$ | $CH_2$ | Q-1.136 |
| I.1-348 | $CH_3$ | $SiEt_3$ | $CH_2$ | $CH_2$ | Q-1.137 |
| I.1-349 | $CH_3$ | $SiEt_3$ | $CH_2$ | $CH_2$ | Q-1.138 |
| I.1-350 | $CH_3$ | $SiEt_3$ | $CH_2$ | $CH_2$ | Q-1.166 |
| I.1-351 | $CH_3$ | $SiEt_3$ | $CH_2$ | $CH_2$ | Q-1.167 |
| I.1-352 | $CH_3$ | $SiEt_3$ | $CH_2$ | $CH_2$ | Q-1.168 |
| I.1-353 | $CH_3$ | $SiEt_3$ | $CH_2$ | $CH_2$ | Q-1.201 |
| I.1-354 | $CH_3$ | $SiEt_3$ | $CH_2$ | $CH_2$ | Q-1.202 |
| I.1-355 | $CH_3$ | $SiEt_3$ | $CH_2$ | $CH_2$ | Q-1.203 |
| I.1-356 | $CH_3$ | $SiEt_3$ | $CH_2$ | $CH_2$ | Q-1.206 |
| I.1-357 | $CH_3$ | $SiEt_3$ | $CH_2$ | $CH_2$ | Q-1.207 |
| I.1-358 | $CH_3$ | $SiEt_3$ | $CH_2$ | $CH_2$ | Q-1.210 |

TABLE 1-continued (I)

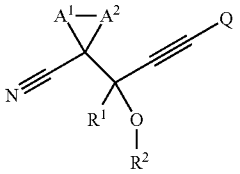

The Q radicals here correspond to the structures defined as very particularly preferred earlier in the document

| No. | $R^1$ | $R^2$ | $A^1$ | $A^2$ | Q |
|---|---|---|---|---|---|
| I.1-359 | $CH_3$ | $SiEt_3$ | $CH_2$ | $CH_2$ | Q-1.211 |
| I.1-360 | $CH_3$ | $SiEt_3$ | $CH_2$ | $CH_2$ | Q-1.213 |
| I.1-361 | Ph | $CH_3$ | $CH_2$ | $CH_2$ | Q-1.1 |
| I.1-362 | Ph | $CH_3$ | $CH_2$ | $CH_2$ | Q-1.2 |
| I.1-363 | Ph | $CH_3$ | $CH_2$ | $CH_2$ | Q-1.3 |
| I.1-364 | Ph | $CH_3$ | $CH_2$ | $CH_2$ | Q-1.16 |
| I.1-365 | Ph | $CH_3$ | $CH_2$ | $CH_2$ | Q-1.17 |
| I.1-366 | Ph | $CH_3$ | $CH_2$ | $CH_2$ | Q-1.18 |
| I.1-367 | Ph | $CH_3$ | $CH_2$ | $CH_2$ | Q-1.136 |
| I.1-368 | Ph | $CH_3$ | $CH_2$ | $CH_2$ | Q-1.137 |
| I.1-369 | Ph | $CH_3$ | $CH_2$ | $CH_2$ | Q-1.138 |
| I.1-370 | Ph | $CH_3$ | $CH_2$ | $CH_2$ | Q-1.166 |
| I.1-371 | Ph | $CH_3$ | $CH_2$ | $CH_2$ | Q-1.167 |
| I.1-372 | Ph | $CH_3$ | $CH_2$ | $CH_2$ | Q-1.168 |
| I.1-373 | Ph | $CH_3$ | $CH_2$ | $CH_2$ | Q-1.201 |
| I.1-374 | Ph | $CH_3$ | $CH_2$ | $CH_2$ | Q-1.202 |
| I.1-375 | Ph | $CH_3$ | $CH_2$ | $CH_2$ | Q-1.203 |
| I.1-376 | Ph | $CH_3$ | $CH_2$ | $CH_2$ | Q-1.206 |
| I.1-377 | Ph | $CH_3$ | $CH_2$ | $CH_2$ | Q-1.207 |
| I.1-378 | Ph | $CH_3$ | $CH_2$ | $CH_2$ | Q-1.210 |
| I.1-379 | Ph | $CH_3$ | $CH_2$ | $CH_2$ | Q-1.211 |
| I.1-380 | Ph | $CH_3$ | $CH_2$ | $CH_2$ | Q-1.213 |
| I.1-381 | Ph | $C(=)CH_3$ | $CH_2$ | $CH_2$ | Q-1.1 |
| I.1-382 | Ph | $C(=)CH_3$ | $CH_2$ | $CH_2$ | Q-1.2 |
| I.1-383 | Ph | $C(=)CH_3$ | $CH_2$ | $CH_2$ | Q-1.3 |
| I.1-384 | Ph | $C(=)CH_3$ | $CH_2$ | $CH_2$ | Q-1.16 |
| I.1-385 | Ph | $C(=)CH_3$ | $CH_2$ | $CH_2$ | Q-1.17 |
| I.1-386 | Ph | $C(=)CH_3$ | $CH_2$ | $CH_2$ | Q-1.18 |
| I.1-387 | Ph | $C(=)CH_3$ | $CH_2$ | $CH_2$ | Q-1.136 |
| I.1-388 | Ph | $C(=)CH_3$ | $CH_2$ | $CH_2$ | Q-1.137 |
| I.1-389 | Ph | $C(=)CH_3$ | $CH_2$ | $CH_2$ | Q-1.138 |
| I.1-390 | Ph | $C(=)CH_3$ | $CH_2$ | $CH_2$ | Q-1.166 |
| I.1-391 | Ph | $C(=)CH_3$ | $CH_2$ | $CH_2$ | Q-1.167 |
| I.1-392 | Ph | $C(=)CH_3$ | $CH_2$ | $CH_2$ | Q-1.168 |
| I.1-393 | Ph | $C(=)CH_3$ | $CH_2$ | $CH_2$ | Q-1.201 |
| I.1-394 | Ph | $C(=)CH_3$ | $CH_2$ | $CH_2$ | Q-1.202 |
| I.1-395 | Ph | $C(=)CH_3$ | $CH_2$ | $CH_2$ | Q-1.203 |
| I.1-396 | Ph | $C(=)CH_3$ | $CH_2$ | $CH_2$ | Q-1.206 |
| I.1-397 | Ph | $C(=)CH_3$ | $CH_2$ | $CH_2$ | Q-1.207 |
| I.1-398 | Ph | $C(=)CH_3$ | $CH_2$ | $CH_2$ | Q-1.210 |
| I.1-399 | Ph | $C(=)CH_3$ | $CH_2$ | $CH_2$ | Q-1.211 |
| I.1-400 | Ph | $C(=)CH_3$ | $CH_2$ | $CH_2$ | Q-1.213 |
| I.1-401 | Ph | $SiEt_3$ | $CH_2$ | $CH_2$ | Q-1.1 |
| I.1-402 | Ph | $SiEt_3$ | $CH_2$ | $CH_2$ | Q-1.2 |
| I.1-403 | Ph | $SiEt_3$ | $CH_2$ | $CH_2$ | Q-1.3 |
| I.1-404 | Ph | $SiEt_3$ | $CH_2$ | $CH_2$ | Q-1.16 |
| I.1-405 | Ph | $SiEt_3$ | $CH_2$ | $CH_2$ | Q-1.17 |
| I.1-406 | Ph | $SiEt_3$ | $CH_2$ | $CH_2$ | Q-1.18 |
| I.1-407 | Ph | $SiEt_3$ | $CH_2$ | $CH_2$ | Q-1.136 |
| I.1-408 | Ph | $SiEt_3$ | $CH_2$ | $CH_2$ | Q-1.137 |
| I.1-409 | Ph | $SiEt_3$ | $CH_2$ | $CH_2$ | Q-1.138 |
| I.1-410 | Ph | $SiEt_3$ | $CH_2$ | $CH_2$ | Q-1.166 |
| I.1-411 | Ph | $SiEt_3$ | $CH_2$ | $CH_2$ | Q-1.167 |
| I.1-412 | Ph | $SiEt_3$ | $CH_2$ | $CH_2$ | Q-1.168 |
| I.1-413 | Ph | $SiEt_3$ | $CH_2$ | $CH_2$ | Q-1.201 |
| I.1-414 | Ph | $SiEt_3$ | $CH_2$ | $CH_2$ | Q-1.202 |
| I.1-415 | Ph | $SiEt_3$ | $CH_2$ | $CH_2$ | Q-1.203 |
| I.1-416 | Ph | $SiEt_3$ | $CH_2$ | $CH_2$ | Q-1.206 |
| I.1-417 | Ph | $SiEt_3$ | $CH_2$ | $CH_2$ | Q-1.207 |
| I.1-418 | Ph | $SiEt_3$ | $CH_2$ | $CH_2$ | Q-1.210 |
| I.1-419 | Ph | $SiEt_3$ | $CH_2$ | $CH_2$ | Q-1.211 |
| I.1-420 | Ph | $SiEt_3$ | $CH_2$ | $CH_2$ | Q-1.213 |
| I.1-421 | i-Pr | $CH_3$ | $CH_2$ | $CH_2$ | Q-1.1 |
| I.1-422 | i-Pr | $CH_3$ | $CH_2$ | $CH_2$ | Q-1.2 |

TABLE 1-continued (I)

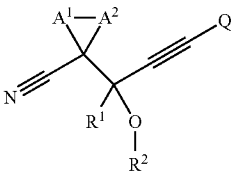

The Q radicals here correspond to the structures defined as very particularly preferred earlier in the document

| No. | $R^1$ | $R^2$ | $A^1$ | $A^2$ | Q |
|---|---|---|---|---|---|
| I.1-423 | i-Pr | $CH_3$ | $CH_2$ | $CH_2$ | Q-1.3 |
| I.1-424 | i-Pr | $CH_3$ | $CH_2$ | $CH_2$ | Q-1.16 |
| I.1-425 | i-Pr | $CH_3$ | $CH_2$ | $CH_2$ | Q-1.17 |
| I.1-426 | i-Pr | $CH_3$ | $CH_2$ | $CH_2$ | Q-1.18 |
| I.1-427 | i-Pr | $CH_3$ | $CH_2$ | $CH_2$ | Q-1.136 |
| I.1-428 | i-Pr | $CH_3$ | $CH_2$ | $CH_2$ | Q-1.137 |
| I.1-429 | i-Pr | $CH_3$ | $CH_2$ | $CH_2$ | Q-1.138 |
| I.1-430 | i-Pr | $CH_3$ | $CH_2$ | $CH_2$ | Q-1.166 |
| I.1-431 | i-Pr | $CH_3$ | $CH_2$ | $CH_2$ | Q-1.167 |
| I.1-432 | i-Pr | $CH_3$ | $CH_2$ | $CH_2$ | Q-1.168 |
| I.1-433 | i-Pr | $CH_3$ | $CH_2$ | $CH_2$ | Q-1.201 |
| I.1-434 | i-Pr | $CH_3$ | $CH_2$ | $CH_2$ | Q-1.202 |
| I.1-435 | i-Pr | $CH_3$ | $CH_2$ | $CH_2$ | Q-1.203 |
| I.1-436 | i-Pr | $CH_3$ | $CH_2$ | $CH_2$ | Q-1.206 |
| I.1-437 | i-Pr | $CH_3$ | $CH_2$ | $CH_2$ | Q-1.207 |
| I.1-438 | i-Pr | $CH_3$ | $CH_2$ | $CH_2$ | Q-1.210 |
| I.1-439 | i-Pr | $CH_3$ | $CH_2$ | $CH_2$ | Q-1.211 |
| I.1-440 | i-Pr | $CH_3$ | $CH_2$ | $CH_2$ | Q-1.213 |
| I.1-441 | i-Pr | $C(=)CH_3$ | $CH_2$ | $CH_2$ | Q-1.1 |
| I.1-442 | i-Pr | $C(=)CH_3$ | $CH_2$ | $CH_2$ | Q-1.2 |
| I.1-443 | i-Pr | $C(=)CH_3$ | $CH_2$ | $CH_2$ | Q-1.3 |
| I.1-444 | i-Pr | $C(=)CH_3$ | $CH_2$ | $CH_2$ | Q-1.16 |
| I.1-445 | i-Pr | $C(=)CH_3$ | $CH_2$ | $CH_2$ | Q-1.17 |
| I.1-446 | i-Pr | $C(=)CH_3$ | $CH_2$ | $CH_2$ | Q-1.18 |
| I.1-447 | i-Pr | $C(=)CH_3$ | $CH_2$ | $CH_2$ | Q-1.136 |
| I.1-448 | i-Pr | $C(=)CH_3$ | $CH_2$ | $CH_2$ | Q-1.137 |
| I.1-449 | i-Pr | $C(=)CH_3$ | $CH_2$ | $CH_2$ | Q-1.138 |
| I.1-450 | i-Pr | $C(=)CH_3$ | $CH_2$ | $CH_2$ | Q-1.166 |
| I.1-451 | i-Pr | $C(=)CH_3$ | $CH_2$ | $CH_2$ | Q-1.167 |
| I.1-452 | i-Pr | $C(=)CH_3$ | $CH_2$ | $CH_2$ | Q-1.168 |
| I.1-453 | i-Pr | $C(=)CH_3$ | $CH_2$ | $CH_2$ | Q-1.201 |
| I.1-454 | i-Pr | $C(=)CH_3$ | $CH_2$ | $CH_2$ | Q-1.202 |
| I.1-455 | i-Pr | $C(=)CH_3$ | $CH_2$ | $CH_2$ | Q-1.203 |
| I.1-456 | i-Pr | $C(=)CH_3$ | $CH_2$ | $CH_2$ | Q-1.206 |
| I.1-457 | i-Pr | $C(=)CH_3$ | $CH_2$ | $CH_2$ | Q-1.207 |
| I.1-458 | i-Pr | $C(=)CH_3$ | $CH_2$ | $CH_2$ | Q-1.210 |
| I.1-459 | i-Pr | $C(=)CH_3$ | $CH_2$ | $CH_2$ | Q-1.211 |
| I.1-460 | i-Pr | $C(=)CH_3$ | $CH_2$ | $CH_2$ | Q-1.213 |
| I.1-461 | i-Pr | $SiEt_3$ | $CH_2$ | $CH_2$ | Q-1.1 |
| I.1-462 | i-Pr | $SiEt_3$ | $CH_2$ | $CH_2$ | Q-1.2 |
| I.1-463 | i-Pr | $SiEt_3$ | $CH_2$ | $CH_2$ | Q-1.3 |
| I.1-464 | i-Pr | $SiEt_3$ | $CH_2$ | $CH_2$ | Q-1.16 |
| I.1-465 | i-Pr | $SiEt_3$ | $CH_2$ | $CH_2$ | Q-1.17 |
| I.1-466 | i-Pr | $SiEt_3$ | $CH_2$ | $CH_2$ | Q-1.18 |
| I.1-467 | i-Pr | $SiEt_3$ | $CH_2$ | $CH_2$ | Q-1.136 |
| I.1-468 | i-Pr | $SiEt_3$ | $CH_2$ | $CH_2$ | Q-1.137 |
| I.1-469 | i-Pr | $SiEt_3$ | $CH_2$ | $CH_2$ | Q-1.138 |
| I.1-470 | i-Pr | $SiEt_3$ | $CH_2$ | $CH_2$ | Q-1.166 |
| I.1-471 | i-Pr | $SiEt_3$ | $CH_2$ | $CH_2$ | Q-1.167 |
| I.1-472 | i-Pr | $SiEt_3$ | $CH_2$ | $CH_2$ | Q-1.168 |
| I.1-473 | i-Pr | $SiEt_3$ | $CH_2$ | $CH_2$ | Q-1.201 |
| I.1-474 | i-Pr | $SiEt_3$ | $CH_2$ | $CH_2$ | Q-1.202 |
| I.1-475 | i-Pr | $SiEt_3$ | $CH_2$ | $CH_2$ | Q-1.203 |
| I.1-476 | i-Pr | $SiEt_3$ | $CH_2$ | $CH_2$ | Q-1.206 |
| I.1-477 | i-Pr | $SiEt_3$ | $CH_2$ | $CH_2$ | Q-1.207 |
| I.1-478 | i-Pr | $SiEt_3$ | $CH_2$ | $CH_2$ | Q-1.210 |
| I.1-479 | i-Pr | $SiEt_3$ | $CH_2$ | $CH_2$ | Q-1.211 |
| I.1-480 | i-Pr | $SiEt_3$ | $CH_2$ | $CH_2$ | Q-1.213 |
| I.1-481 | i-Pr | $CH_3$ | CHF | $CH_2$ | Q-1.3 |
| I.1-482 | i-Pr | $CH_3$ | CHF | $CH_2$ | Q-1.168 |
| I.1-483 | i-Pr | $CH_3$ | CHF | $CH_2$ | Q-1.203 |
| I.1-484 | Ph | $CH_3$ | CHF | $CH_2$ | Q-1.3 |
| I.1-485 | Ph | $CH_3$ | CHF | $CH_2$ | Q-1.168 |
| I.1-486 | Ph | $CH_3$ | CHF | $CH_2$ | Q-1.203 |

TABLE 1-continued (I)

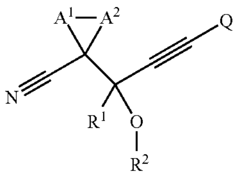

The Q radicals here correspond to the structures defined as very particularly preferred earlier in the document

| No. | $R^1$ | $R^2$ | $A^1$ | $A^2$ | Q |
|---|---|---|---|---|---|
| I.1-487 | $CH_3$ | $CH_3$ | CHF | $CH_2$ | Q-1.3 |
| I.1-488 | $CH_3$ | $CH_3$ | CHF | $CH_2$ | Q-1.168 |
| I.1-489 | $CH_3$ | $CH_3$ | CHF | $CH_2$ | Q-1.203 |
| I.1-490 | i-Pr | $CH_3$ | $CH(CH_3)$ | $CH_2$ | Q-1.3 |
| I.1-491 | i-Pr | $CH_3$ | $CH(CH_3)$ | $CH_2$ | Q-1.168 |
| I.1-492 | i-Pr | $CH_3$ | $CH(CH_3)$ | $CH_2$ | Q-1.203 |
| I.1-493 | Ph | $CH_3$ | $CH(CH_3)$ | $CH_2$ | Q-1.3 |
| I.1-494 | Ph | $CH_3$ | $CH(CH_3)$ | $CH_2$ | Q-1.168 |
| I.1-495 | Ph | $CH_3$ | $CH(CH_3)$ | $CH_2$ | Q-1.203 |
| I.1-496 | $CH_3$ | $CH_3$ | $CH(CH_3)$ | $CH_2$ | Q-1.3 |
| I.1-497 | $CH_3$ | $CH_3$ | $CH(CH_3)$ | $CH_2$ | Q-1.168 |
| I.1-498 | $CH_3$ | $CH_3$ | $CH(CH_3)$ | $CH_2$ | Q-1.203 |
| I.1-499 | i-Pr | $CH_3$ | CH(i-Pr) | $CH_2$ | Q-1.168 |
| I.1-500 | i-Pr | $CH_3$ | CH(i-Pr) | $CH_2$ | Q-1.203 |
| I.1-501 | 4-F-Ph | H | $CH_2$ | $CH_2$ | Q-1.1 |
| I.1-502 | 4-F-Ph | H | $CH_2$ | $CH_2$ | Q-1.2 |
| I.1-503 | 4-F-Ph | H | $CH_2$ | $CH_2$ | Q-1.3 |
| I.1-504 | 4-F-Ph | H | $CH_2$ | $CH_2$ | Q-1.16 |
| I.1-505 | 4-F-Ph | H | $CH_2$ | $CH_2$ | Q-1.17 |
| I.1-506 | 4-F-Ph | H | $CH_2$ | $CH_2$ | Q-1.18 |
| I.1-507 | 4-F-Ph | H | $CH_2$ | $CH_2$ | Q-1.31 |
| I.1-508 | 4-F-Ph | H | $CH_2$ | $CH_2$ | Q-1.32 |
| I.1-509 | 4-F-Ph | H | $CH_2$ | $CH_2$ | Q-1.33 |
| I.1-510 | 4-F-Ph | H | $CH_2$ | $CH_2$ | Q-1.91 |
| I.1-511 | 4-F-Ph | H | $CH_2$ | $CH_2$ | Q-1.92 |
| I.1-512 | 4-F-Ph | H | $CH_2$ | $CH_2$ | Q-1.93 |
| I.1-513 | 4-F-Ph | H | $CH_2$ | $CH_2$ | Q-1.106 |
| I.1-514 | 4-F-Ph | H | $CH_2$ | $CH_2$ | Q-1.107 |
| I.1-515 | 4-F-Ph | H | $CH_2$ | $CH_2$ | Q-1.108 |
| I.1-516 | 4-F-Ph | H | $CH_2$ | $CH_2$ | Q-1.121 |
| I.1-517 | 4-F-Ph | H | $CH_2$ | $CH_2$ | Q-1.122 |
| I.1-518 | 4-F-Ph | H | $CH_2$ | $CH_2$ | Q-1.123 |
| I.1-519 | 4-F-Ph | H | $CH_2$ | $CH_2$ | Q-1.136 |
| I.1-520 | 4-F-Ph | H | $CH_2$ | $CH_2$ | Q-1.137 |
| I.1-521 | 4-F-Ph | H | $CH_2$ | $CH_2$ | Q-1.138 |
| I.1-522 | 4-F-Ph | H | $CH_2$ | $CH_2$ | Q-1.166 |
| I.1-523 | 4-F-Ph | H | $CH_2$ | $CH_2$ | Q-1.167 |
| I.1-524 | 4-F-Ph | H | $CH_2$ | $CH_2$ | Q-1.168 |
| I.1-525 | 4-F-Ph | H | $CH_2$ | $CH_2$ | Q-1.171 |
| I.1-526 | 4-F-Ph | H | $CH_2$ | $CH_2$ | Q-1.172 |
| I.1-527 | 4-F-Ph | H | $CH_2$ | $CH_2$ | Q-1.173 |
| I.1-528 | 4-F-Ph | H | $CH_2$ | $CH_2$ | Q-1.176 |
| I.1-529 | 4-F-Ph | H | $CH_2$ | $CH_2$ | Q-1.177 |
| I.1-530 | 4-F-Ph | H | $CH_2$ | $CH_2$ | Q-1.178 |
| I.1-531 | 4-F-Ph | H | $CH_2$ | $CH_2$ | Q-1.181 |
| I.1-532 | 4-F-Ph | H | $CH_2$ | $CH_2$ | Q-1.182 |
| I.1-533 | 4-F-Ph | H | $CH_2$ | $CH_2$ | Q-1.183 |
| I.1-534 | 4-F-Ph | H | $CH_2$ | $CH_2$ | Q-1.201 |
| I.1-535 | 4-F-Ph | H | $CH_2$ | $CH_2$ | Q-1.202 |
| I.1-536 | 4-F-Ph | H | $CH_2$ | $CH_2$ | Q-1.203 |
| I.1-537 | 4-F-Ph | H | $CH_2$ | $CH_2$ | Q-1.204 |
| I.1-538 | 4-F-Ph | H | $CH_2$ | $CH_2$ | Q-1.205 |
| I.1-539 | 4-F-Ph | H | $CH_2$ | $CH_2$ | Q-1.206 |
| I.1-541 | 4-F-Ph | H | $CH_2$ | $CH_2$ | Q-1.207 |
| I.1-542 | 4-F-Ph | H | $CH_2$ | $CH_2$ | Q-1.208 |
| I.1-543 | 4-F-Ph | H | $CH_2$ | $CH_2$ | Q-1.209 |
| I.1-544 | 4-F-Ph | H | $CH_2$ | $CH_2$ | Q-1.210 |
| I.1-545 | 4-F-Ph | H | $CH_2$ | $CH_2$ | Q-1.211 |
| I.1-546 | 4-F-Ph | H | $CH_2$ | $CH_2$ | Q-1.212 |
| I.1-547 | 4-F-Ph | H | $CH_2$ | $CH_2$ | Q-1.213 |
| I.1-548 | 4-F-Ph | H | $CH_2$ | $CH_2$ | Q-1.216 |
| I.1-549 | 4-F-Ph | H | $CH_2$ | $CH_2$ | Q-1.217 |
| I.1-550 | 4-F-Ph | H | $CH_2$ | $CH_2$ | Q-1.218 |
| I.1-551 | 4-F-Ph | H | $CH_2$ | $CH_2$ | Q-1.246 |

TABLE 1-continued (I)

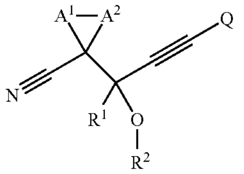

The Q radicals here correspond to the structures defined as very particularly preferred earlier in the document

| No. | $R^1$ | $R^2$ | $A^1$ | $A^2$ | Q |
|---|---|---|---|---|---|
| I.1-552 | 4-F-Ph | H | $CH_2$ | $CH_2$ | Q-1.247 |
| I.1-553 | 4-F-Ph | H | $CH_2$ | $CH_2$ | Q-1.248 |
| I.1-554 | 4-F-Ph | H | $CH_2$ | $CH_2$ | Q-2.1 |
| I.1-555 | 4-F-Ph | H | $CH_2$ | $CH_2$ | Q-2.2 |
| I.1-556 | 4-F-Ph | H | $CH_2$ | $CH_2$ | Q-2.3 |
| I.1-557 | 4-F-Ph | H | $CH_2$ | $CH_2$ | Q-2.5 |
| I.1-558 | 4-F-Ph | H | $CH_2$ | $CH_2$ | Q-2.4 |
| I.1-559 | 4-F-Ph | H | $CH_2$ | $CH_2$ | Q-2.7 |
| I.1-560 | 4-F-Ph | H | $CH_2$ | $CH_2$ | Q-2.9 |
| I.1-561 | 4-F-Ph | H | $CH_2$ | $CH_2$ | Q-2.12 |
| I.1-562 | 4-F-Ph | H | $CH_2$ | $CH_2$ | Q-2.13 |
| I.1-563 | 4-F-Ph | H | $CH_2$ | $CH_2$ | Q-2.14 |
| I.1-564 | 4-F-Ph | H | $CH_2$ | $CH_2$ | Q-2.61 |
| I.1-565 | 4-F-Ph | H | $CH_2$ | $CH_2$ | Q-2.62 |
| I.1-566 | 4-F-Ph | H | $CH_2$ | $CH_2$ | Q-2.63 |
| I.1-567 | 4-F-Ph | H | $CH_2$ | $CH_2$ | Q-2.64 |
| I.1-568 | 4-F-Ph | H | $CH_2$ | $CH_2$ | Q-2.65 |
| I.1-569 | 4-F-Ph | H | $CH_2$ | $CH_2$ | Q-2.67 |
| I.1-570 | 4-F-Ph | H | $CH_2$ | $CH_2$ | Q-2.69 |
| I.1-571 | 4-F-Ph | H | $CH_2$ | $CH_2$ | Q-2.72 |
| I.1-572 | 4-F-Ph | H | $CH_2$ | $CH_2$ | Q-2.73 |
| I.1-573 | 4-F-Ph | H | $CH_2$ | $CH_2$ | Q-2.74 |
| I.1-574 | 4-F-Ph | H | $CH_2$ | $CH_2$ | Q-2.80 |
| I.1-575 | 4-F-Ph | H | $CH_2$ | $CH_2$ | Q-2.105 |
| I.1-576 | 4-F-Ph | H | $CH_2$ | $CH_2$ | Q-2.106 |
| I.1-577 | 4-F-Ph | H | $CH_2$ | $CH_2$ | Q-2.108 |
| I.1-578 | 4-F-Ph | H | $CH_2$ | $CH_2$ | Q-2.145 |
| I.1-579 | 4-F-Ph | H | $CH_2$ | $CH_2$ | Q-2.146 |
| I.1-580 | 4-F-Ph | H | $CH_2$ | $CH_2$ | Q-2.147 |
| I.1-581 | 4-F-Ph | H | $CH_2$ | $CH_2$ | Q-2.161 |
| I.1-582 | 4-F-Ph | H | $CH_2$ | $CH_2$ | Q-2.162 |
| I.1-583 | 4-F-Ph | H | $CH_2$ | $CH_2$ | Q-2.163 |
| I.1-584 | 4-F-Ph | H | $CH_2$ | $CH_2$ | Q-2.164 |
| I.1-585 | 4-F-Ph | H | $CH_2$ | $CH_2$ | Q-2.165 |
| I.1-586 | 4-F-Ph | H | $CH_2$ | $CH_2$ | Q-2.167 |
| I.1-587 | 4-F-Ph | H | $CH_2$ | $CH_2$ | Q-2.168 |
| I.1-588 | 4-F-Ph | H | $CH_2$ | $CH_2$ | Q-2.169 |
| I.1-589 | 4-F-Ph | H | $CH_2$ | $CH_2$ | Q-2.172 |
| I.1-590 | 4-F-Ph | H | $CH_2$ | $CH_2$ | Q-2.173 |
| I.1-591 | 4-F-Ph | H | $CH_2$ | $CH_2$ | Q-2.174 |
| I.1-592 | 4-F-Ph | H | $CH_2$ | $CH_2$ | Q-2.180 |
| I.1-593 | 4-F-Ph | H | $CH_2$ | $CH_2$ | Q-2.185 |
| I.1-594 | 4-F-Ph | H | $CH_2$ | $CH_2$ | Q-2.189 |
| I.1-595 | 4-F-Ph | H | $CH_2$ | $CH_2$ | Q-2.190 |
| I.1-596 | 4-F-Ph | H | $CH_2$ | $CH_2$ | Q-2.201 |
| I.1-597 | 4-F-Ph | H | $CH_2$ | $CH_2$ | Q-2.202 |
| I.1-598 | 4-F-Ph | H | $CH_2$ | $CH_2$ | Q-2.203 |
| I.1-599 | 4-F-Ph | H | $CH_2$ | $CH_2$ | Q-2.204 |
| I.1-600 | 4-F-Ph | H | $CH_2$ | $CH_2$ | Q-2.205 |
| I.1-601 | $CH_3$ | H | $CH_2$ | $CH_2$ | Q-1.6 |
| I.1-602 | $CH_3$ | H | $CH_2$ | $CH_2$ | Q-1.10 |
| I.1-603 | $CH_3$ | H | $CH_2$ | $CH_2$ | Q-1.11 |
| I.1-604 | $CH_3$ | H | $CH_2$ | $CH_2$ | Q-1.141 |
| I.1-605 | i-Pr | H | $CH_2$ | $CH_2$ | Q-1.6 |
| I.1-606 | i-Pr | H | $CH_2$ | $CH_2$ | Q-1.10 |
| I.1-607 | i-Pr | H | $CH_2$ | $CH_2$ | Q-1.11 |
| I.1-608 | i-Pr | H | $CH_2$ | $CH_2$ | Q-1.141 |
| I.1-609 | Ph | H | $CH_2$ | $CH_2$ | Q-1.6 |
| I.1-610 | Ph | H | $CH_2$ | $CH_2$ | Q-1.10 |
| I.1-611 | Ph | H | $CH_2$ | $CH_2$ | Q-1.11 |
| I.1-612 | Ph | H | $CH_2$ | $CH_2$ | Q-1.141 |
| I.1-613 | 4-F-Ph | H | $CH_2$ | $CH_2$ | Q-1.6 |
| I.1-614 | 4-F-Ph | H | $CH_2$ | $CH_2$ | Q-1.10 |
| I.1-615 | 4-F-Ph | H | $CH_2$ | $CH_2$ | Q-1.11 |

TABLE 1-continued (I)

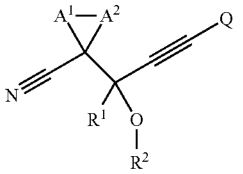

The Q radicals here correspond to the structures defined as very particularly preferred earlier in the document

| No. | $R^1$ | $R^2$ | $A^1$ | $A^2$ | Q |
|---|---|---|---|---|---|
| I.1-616 | 4-F-Ph | H | $CH_2$ | $CH_2$ | Q-1.141 |
| I.1-617 | c-Pr | H | $CH_2$ | $CH_2$ | Q-1.1 |
| I.1-618 | c-Pr | H | $CH_2$ | $CH_2$ | Q-1.2 |
| I.1-619 | c-Pr | H | $CH_2$ | $CH_2$ | Q-1.3 |
| I.1-620 | c-Pr | H | $CH_2$ | $CH_2$ | Q-1.6 |
| I.1-621 | c-Pr | H | $CH_2$ | $CH_2$ | Q-1.10 |
| I.1-622 | c-Pr | H | $CH_2$ | $CH_2$ | Q-1.11 |
| I.1-623 | c-Pr | H | $CH_2$ | $CH_2$ | Q-1.16 |
| I.1-624 | c-Pr | H | $CH_2$ | $CH_2$ | Q-1.17 |
| I.1-625 | c-Pr | H | $CH_2$ | $CH_2$ | Q-1.18 |
| I.1-626 | c-Pr | H | $CH_2$ | $CH_2$ | Q-1.21 |
| I.1-627 | c-Pr | H | $CH_2$ | $CH_2$ | Q-1.91 |
| I.1-628 | c-Pr | H | $CH_2$ | $CH_2$ | Q-1.92 |
| I.1-629 | c-Pr | H | $CH_2$ | $CH_2$ | Q-1.93 |
| I.1-630 | c-Pr | H | $CH_2$ | $CH_2$ | Q-1.96 |
| I.1-631 | c-Pr | H | $CH_2$ | $CH_2$ | Q-1.136 |
| I.1-632 | c-Pr | H | $CH_2$ | $CH_2$ | Q-1.137 |
| I.1-633 | c-Pr | H | $CH_2$ | $CH_2$ | Q-1.138 |
| I.1-634 | c-Pr | H | $CH_2$ | $CH_2$ | Q-1.166 |
| I.1-635 | c-Pr | H | $CH_2$ | $CH_2$ | Q-1.167 |
| I.1-636 | c-Pr | H | $CH_2$ | $CH_2$ | Q-1.168 |
| I.1-637 | c-Pr | H | $CH_2$ | $CH_2$ | Q-1.171 |
| I.1-638 | c-Pr | H | $CH_2$ | $CH_2$ | Q-1.172 |
| I.1-639 | c-Pr | H | $CH_2$ | $CH_2$ | Q-1.173 |
| I.1-640 | c-Pr | H | $CH_2$ | $CH_2$ | Q-1.201 |
| I.1-641 | c-Pr | H | $CH_2$ | $CH_2$ | Q-1.202 |
| I.1-642 | c-Pr | H | $CH_2$ | $CH_2$ | Q-1.203 |
| I.1-643 | c-Pr | H | $CH_2$ | $CH_2$ | Q-1.206 |
| I.1-644 | c-Pr | H | $CH_2$ | $CH_2$ | Q-1.207 |
| I.1-645 | c-Pr | H | $CH_2$ | $CH_2$ | Q-1.210 |
| I.1-646 | c-Pr | H | $CH_2$ | $CH_2$ | Q-1.211 |
| I.1-647 | c-Bu | H | $CH_2$ | $CH_2$ | Q-1.1 |
| I.1-648 | c-Bu | H | $CH_2$ | $CH_2$ | Q-1.2 |
| I.1-649 | c-Bu | H | $CH_2$ | $CH_2$ | Q-1.3 |
| I.1-650 | c-Bu | H | $CH_2$ | $CH_2$ | Q-1.6 |
| I.1-651 | c-Bu | H | $CH_2$ | $CH_2$ | Q-1.10 |
| I.1-652 | c-Bu | H | $CH_2$ | $CH_2$ | Q-1.11 |
| I.1-653 | c-Bu | H | $CH_2$ | $CH_2$ | Q-1.16 |
| I.1-654 | c-Bu | H | $CH_2$ | $CH_2$ | Q-1.17 |
| I.1-655 | c-Bu | H | $CH_2$ | $CH_2$ | Q-1.18 |
| I.1-656 | c-Bu | H | $CH_2$ | $CH_2$ | Q-1.21 |
| I.1-657 | c-Bu | H | $CH_2$ | $CH_2$ | Q-1.91 |
| I.1-658 | c-Bu | H | $CH_2$ | $CH_2$ | Q-1.92 |
| I.1-659 | c-Bu | H | $CH_2$ | $CH_2$ | Q-1.93 |
| I.1-660 | c-Bu | H | $CH_2$ | $CH_2$ | Q-1.96 |
| I.1-661 | c-Bu | H | $CH_2$ | $CH_2$ | Q-1.136 |
| I.1-662 | c-Bu | H | $CH_2$ | $CH_2$ | Q-1.137 |
| I.1-663 | c-Bu | H | $CH_2$ | $CH_2$ | Q-1.138 |
| I.1-664 | c-Bu | H | $CH_2$ | $CH_2$ | Q-1.166 |
| I.1-665 | c-Bu | H | $CH_2$ | $CH_2$ | Q-1.167 |
| I.1-666 | c-Bu | H | $CH_2$ | $CH_2$ | Q-1.168 |
| I.1-667 | c-Bu | H | $CH_2$ | $CH_2$ | Q-1.171 |
| I.1-668 | c-Bu | H | $CH_2$ | $CH_2$ | Q-1.172 |
| I.1-669 | c-Bu | H | $CH_2$ | $CH_2$ | Q-1.173 |
| I.1-670 | c-Bu | H | $CH_2$ | $CH_2$ | Q-1.201 |
| I.1-671 | c-Bu | H | $CH_2$ | $CH_2$ | Q-1.202 |
| I.1-672 | c-Bu | H | $CH_2$ | $CH_2$ | Q-1.203 |
| I.1-673 | c-Bu | H | $CH_2$ | $CH_2$ | Q-1.206 |
| I.1-674 | c-Bu | H | $CH_2$ | $CH_2$ | Q-1.207 |
| I.1-675 | c-Bu | H | $CH_2$ | $CH_2$ | Q-1.210 |
| I.1-676 | c-Bu | H | $CH_2$ | $CH_2$ | Q-1.211 |
| I.1-677 | c-Hexyl | H | $CH_2$ | $CH_2$ | Q-1.1 |
| I.1-678 | c-Hexyl | H | $CH_2$ | $CH_2$ | Q-1.2 |
| I.1-679 | c-Hexyl | H | $CH_2$ | $CH_2$ | Q-1.3 |

TABLE 1-continued (I)

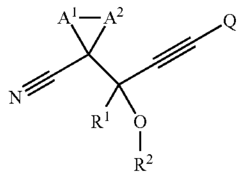

The Q radicals here correspond to the structures defined as very particularly preferred earlier in the document

| No. | $R^1$ | $R^2$ | $A^1$ | $A^2$ | Q |
|---|---|---|---|---|---|
| I.1-680 | c-Hexyl | H | $CH_2$ | $CH_2$ | Q-1.6 |
| I.1-681 | c-Hexyl | H | $CH_2$ | $CH_2$ | Q-1.10 |
| I.1-682 | c-Hexyl | H | $CH_2$ | $CH_2$ | Q-1.11 |
| I.1-683 | c-Hexyl | H | $CH_2$ | $CH_2$ | Q-1.16 |
| I.1-684 | c-Hexyl | H | $CH_2$ | $CH_2$ | Q-1.17 |
| I.1-685 | c-Hexyl | H | $CH_2$ | $CH_2$ | Q-1.18 |
| I.1-686 | c-Hexyl | H | $CH_2$ | $CH_2$ | Q-1.21 |
| I.1-687 | c-Hexyl | H | $CH_2$ | $CH_2$ | Q-1.91 |
| I.1-688 | c-Hexyl | H | $CH_2$ | $CH_2$ | Q-1.92 |
| I.1-689 | c-Hexyl | H | $CH_2$ | $CH_2$ | Q-1.93 |
| I.1-690 | c-Hexyl | H | $CH_2$ | $CH_2$ | Q-1.96 |
| I.1-691 | c-Hexyl | H | $CH_2$ | $CH_2$ | Q-1.136 |
| I.1-692 | c-Hexyl | H | $CH_2$ | $CH_2$ | Q-1.137 |
| I.1-693 | c-Hexyl | H | $CH_2$ | $CH_2$ | Q-1.138 |
| I.1-694 | c-Hexyl | H | $CH_2$ | $CH_2$ | Q-1.166 |
| I.1-695 | c-Hexyl | H | $CH_2$ | $CH_2$ | Q-1.167 |
| I.1-696 | c-Hexyl | H | $CH_2$ | $CH_2$ | Q-1.168 |
| I.1-697 | c-Hexyl | H | $CH_2$ | $CH_2$ | Q-1.171 |
| I.1-698 | c-Hexyl | H | $CH_2$ | $CH_2$ | Q-1.172 |
| I.1-699 | c-Hexyl | H | $CH_2$ | $CH_2$ | Q-1.173 |
| I.1-700 | c-Hexyl | H | $CH_2$ | $CH_2$ | Q-1.201 |
| I.1-701 | c-Hexyl | H | $CH_2$ | $CH_2$ | Q-1.202 |
| I.1-702 | c-Hexyl | H | $CH_2$ | $CH_2$ | Q-1.203 |
| I.1-703 | c-Hexyl | H | $CH_2$ | $CH_2$ | Q-1.206 |
| I.1-704 | c-Hexyl | H | $CH_2$ | $CH_2$ | Q-1.207 |
| I.1-705 | c-Hexyl | H | $CH_2$ | $CH_2$ | Q-1.210 |
| I.1-706 | c-Hexyl | H | $CH_2$ | $CH_2$ | Q-1.211 |
| I.1-707 | 1-Ethylpropyl | H | $CH_2$ | $CH_2$ | Q-1.1 |
| I.1-708 | 1-Ethylpropyl | H | $CH_2$ | $CH_2$ | Q-1.2 |
| I.1-709 | 1-Ethylpropyl | H | $CH_2$ | $CH_2$ | Q-1.3 |
| I.1-710 | 1-Ethylpropyl | H | $CH_2$ | $CH_2$ | Q-1.6 |
| I.1-711 | 1-Ethylpropyl | H | $CH_2$ | $CH_2$ | Q-1.10 |
| I.1-712 | 1-Ethylpropyl | H | $CH_2$ | $CH_2$ | Q-1.11 |
| I.1-713 | 1-Ethylpropyl | H | $CH_2$ | $CH_2$ | Q-1.16 |
| I.1-714 | 1-Ethylpropyl | H | $CH_2$ | $CH_2$ | Q-1.17 |
| I.1-715 | 1-Ethylpropyl | H | $CH_2$ | $CH_2$ | Q-1.18 |
| I.1-716 | 1-Ethylpropyl | H | $CH_2$ | $CH_2$ | Q-1.21 |
| I.1-717 | 1-Ethylpropyl | H | $CH_2$ | $CH_2$ | Q-1.91 |
| I.1-718 | 1-Ethylpropyl | H | $CH_2$ | $CH_2$ | Q-1.92 |
| I.1-719 | 1-Ethylpropyl | H | $CH_2$ | $CH_2$ | Q-1.93 |
| I.1-720 | 1-Ethylpropyl | H | $CH_2$ | $CH_2$ | Q-1.96 |
| I.1-721 | 1-Ethylpropyl | H | $CH_2$ | $CH_2$ | Q-1.136 |
| I.1-722 | 1-Ethylpropyl | H | $CH_2$ | $CH_2$ | Q-1.137 |
| I.1-723 | 1-Ethylpropyl | H | $CH_2$ | $CH_2$ | Q-1.138 |
| I.1-724 | 1-Ethylpropyl | H | $CH_2$ | $CH_2$ | Q-1.166 |
| I.1-725 | 1-Ethylpropyl | H | $CH_2$ | $CH_2$ | Q-1.167 |
| I.1-726 | 1-Ethylpropyl | H | $CH_2$ | $CH_2$ | Q-1.168 |
| I.1-727 | 1-Ethylpropyl | H | $CH_2$ | $CH_2$ | Q-1.171 |
| I.1-728 | 1-Ethylpropyl | H | $CH_2$ | $CH_2$ | Q-1.172 |
| I.1-729 | 1-Ethylpropyl | H | $CH_2$ | $CH_2$ | Q-1.173 |
| I.1-730 | 1-Ethylpropyl | H | $CH_2$ | $CH_2$ | Q-1.201 |
| I.1-731 | 1-Ethylpropyl | H | $CH_2$ | $CH_2$ | Q-1.202 |
| I.1-732 | 1-Ethylpropyl | H | $CH_2$ | $CH_2$ | Q-1.203 |
| I.1-733 | 1-Ethylpropyl | H | $CH_2$ | $CH_2$ | Q-1.206 |
| I.1-734 | 1-Ethylpropyl | H | $CH_2$ | $CH_2$ | Q-1.207 |
| I.1-735 | 1-Ethylpropyl | H | $CH_2$ | $CH_2$ | Q-1.210 |
| I.1-736 | 1-Ethylpropyl | H | $CH_2$ | $CH_2$ | Q-1.211 |
| I.1-737 | Adamantyl | H | $CH_2$ | $CH_2$ | Q-1.1 |
| I.1-738 | Adamantyl | H | $CH_2$ | $CH_2$ | Q-1.2 |
| I.1-739 | Adamantyl | H | $CH_2$ | $CH_2$ | Q-1.3 |
| I.1-740 | Adamantyl | H | $CH_2$ | $CH_2$ | Q-1.6 |
| I.1-741 | Adamantyl | H | $CH_2$ | $CH_2$ | Q-1.10 |
| I.1-742 | Adamantyl | H | $CH_2$ | $CH_2$ | Q-1.11 |
| I.1-743 | Adamantyl | H | $CH_2$ | $CH_2$ | Q-1.16 |

TABLE 1-continued (I)

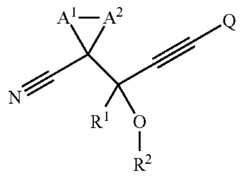

The Q radicals here correspond to the structures defined as very particularly preferred earlier in the document

| No. | $R^1$ | $R^2$ | $A^1$ | $A^2$ | Q |
|---|---|---|---|---|---|
| I.1-744 | Adamantyl | H | $CH_2$ | $CH_2$ | Q-1.17 |
| I.1-745 | Adamantyl | H | $CH_2$ | $CH_2$ | Q-1.18 |
| I.1-746 | Adamantyl | H | $CH_2$ | $CH_2$ | Q-1.21 |
| I.1-747 | Adamantyl | H | $CH_2$ | $CH_2$ | Q-1.91 |
| I.1-748 | Adamantyl | H | $CH_2$ | $CH_2$ | Q-1.92 |
| I.1-749 | Adamantyl | H | $CH_2$ | $CH_2$ | Q-1.93 |
| I.1-750 | Adamantyl | H | $CH_2$ | $CH_2$ | Q-1.96 |
| I.1-751 | Adamantyl | H | $CH_2$ | $CH_2$ | Q-1.136 |
| I.1-752 | Adamantyl | H | $CH_2$ | $CH_2$ | Q-1.137 |
| I.1-753 | Adamantyl | H | $CH_2$ | $CH_2$ | Q-1.138 |
| I.1-754 | Adamantyl | H | $CH_2$ | $CH_2$ | Q-1.166 |
| I.1-755 | Adamantyl | H | $CH_2$ | $CH_2$ | Q-1.167 |
| I.1-756 | Adamantyl | H | $CH_2$ | $CH_2$ | Q-1.168 |
| I.1-757 | Adamantyl | H | $CH_2$ | $CH_2$ | Q-1.171 |
| I.1-758 | Adamantyl | H | $CH_2$ | $CH_2$ | Q-1.172 |
| I.1-759 | Adamantyl | H | $CH_2$ | $CH_2$ | Q-1.173 |
| I.1-760 | Adamantyl | H | $CH_2$ | $CH_2$ | Q-1.201 |
| I.1-761 | Adamantyl | H | $CH_2$ | $CH_2$ | Q-1.202 |
| I.1-762 | Adamantyl | H | $CH_2$ | $CH_2$ | Q-1.203 |
| I.1-763 | Adamantyl | H | $CH_2$ | $CH_2$ | Q-1.206 |
| I.1-764 | Adamantyl | H | $CH_2$ | $CH_2$ | Q-1.207 |
| I.1-765 | Adamantyl | H | $CH_2$ | $CH_2$ | Q-1.210 |
| I.1-766 | Adamantyl | H | $CH_2$ | $CH_2$ | Q-1.211 |
| I.1-767 | 3-F-Ph | H | $CH_2$ | $CH_2$ | Q-1.1 |
| I.1-768 | 3-F-Ph | H | $CH_2$ | $CH_2$ | Q-1.2 |
| I.1-769 | 3-F-Ph | H | $CH_2$ | $CH_2$ | Q-1.3 |
| I.1-770 | 3-F-Ph | H | $CH_2$ | $CH_2$ | Q-1.6 |
| I.1-771 | 3-F-Ph | H | $CH_2$ | $CH_2$ | Q-1.10 |
| I.1-772 | 3-F-Ph | H | $CH_2$ | $CH_2$ | Q-1.11 |
| I.1-773 | 3-F-Ph | H | $CH_2$ | $CH_2$ | Q-1.16 |
| I.1-774 | 3-F-Ph | H | $CH_2$ | $CH_2$ | Q-1.17 |
| I.1-775 | 3-F-Ph | H | $CH_2$ | $CH_2$ | Q-1.18 |
| I.1-776 | 3-F-Ph | H | $CH_2$ | $CH_2$ | Q-1.21 |
| I.1-777 | 3-F-Ph | H | $CH_2$ | $CH_2$ | Q-1.91 |
| I.1-778 | 3-F-Ph | H | $CH_2$ | $CH_2$ | Q-1.92 |
| I.1-779 | 3-F-Ph | H | $CH_2$ | $CH_2$ | Q-1.93 |
| I.1-780 | 3-F-Ph | H | $CH_2$ | $CH_2$ | Q-1.96 |
| I.1-781 | 3-F-Ph | H | $CH_2$ | $CH_2$ | Q-1.136 |
| I.1-782 | 3-F-Ph | H | $CH_2$ | $CH_2$ | Q-1.137 |
| I.1-783 | 3-F-Ph | H | $CH_2$ | $CH_2$ | Q-1.138 |
| I.1-784 | 3-F-Ph | H | $CH_2$ | $CH_2$ | Q-1.166 |
| I.1-785 | 3-F-Ph | H | $CH_2$ | $CH_2$ | Q-1.167 |
| I.1-786 | 3-F-Ph | H | $CH_2$ | $CH_2$ | Q-1.168 |
| I.1-787 | 3-F-Ph | H | $CH_2$ | $CH_2$ | Q-1.171 |
| I.1-788 | 3-F-Ph | H | $CH_2$ | $CH_2$ | Q-1.172 |
| I.1-789 | 3-F-Ph | H | $CH_2$ | $CH_2$ | Q-1.173 |
| I.1-790 | 3-F-Ph | H | $CH_2$ | $CH_2$ | Q-1.201 |
| I.1-791 | 3-F-Ph | H | $CH_2$ | $CH_2$ | Q-1.202 |
| I.1-792 | 3-F-Ph | H | $CH_2$ | $CH_2$ | Q-1.203 |
| I.1-793 | 3-F-Ph | H | $CH_2$ | $CH_2$ | Q-1.206 |
| I.1-794 | 3-F-Ph | H | $CH_2$ | $CH_2$ | Q-1.207 |
| I.1-795 | 3-F-Ph | H | $CH_2$ | $CH_2$ | Q-1.210 |
| I.1-796 | 3-F-Ph | H | $CH_2$ | $CH_2$ | Q-1.211 |
| I.1-797 | 4-$CH_3$-Ph | H | $CH_2$ | $CH_2$ | Q-1.1 |
| I.1-798 | 4-$CH_3$-Ph | H | $CH_2$ | $CH_2$ | Q-1.2 |
| I.1-799 | 4-$CH_3$-Ph | H | $CH_2$ | $CH_2$ | Q-1.3 |
| I.1-800 | 4-$CH_3$-Ph | H | $CH_2$ | $CH_2$ | Q-1.6 |
| I.1-801 | 4-$CH_3$-Ph | H | $CH_2$ | $CH_2$ | Q-1.10 |
| I.1-802 | 4-$CH_3$-Ph | H | $CH_2$ | $CH_2$ | Q-1.11 |
| I.1-803 | 4-$CH_3$-Ph | H | $CH_2$ | $CH_2$ | Q-1.16 |
| I.1-804 | 4-$CH_3$-Ph | H | $CH_2$ | $CH_2$ | Q-1.17 |
| I.1-805 | 4-$CH_3$-Ph | H | $CH_2$ | $CH_2$ | Q-1.18 |
| I.1-806 | 4-$CH_3$-Ph | H | $CH_2$ | $CH_2$ | Q-1.21 |
| I.1-807 | 4-$CH_3$-Ph | H | $CH_2$ | $CH_2$ | Q-1.91 |

TABLE 1-continued (I)

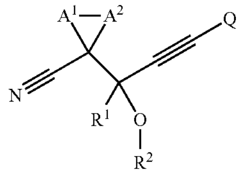

The Q radicals here correspond to the structures defined as very particularly preferred earlier in the document

| No. | $R^1$ | $R^2$ | $A^1$ | $A^2$ | Q |
|---|---|---|---|---|---|
| I.1-808 | 4-$CH_3$-Ph | H | $CH_2$ | $CH_2$ | Q-1.92 |
| I.1-809 | 4-$CH_3$-Ph | H | $CH_2$ | $CH_2$ | Q-1.93 |
| I.1-810 | 4-$CH_3$-Ph | H | $CH_2$ | $CH_2$ | Q-1.96 |
| I.1-811 | 4-$CH_3$-Ph | H | $CH_2$ | $CH_2$ | Q-1.136 |
| I.1-812 | 4-$CH_3$-Ph | H | $CH_2$ | $CH_2$ | Q-1.137 |
| I.1-813 | 4-$CH_3$-Ph | H | $CH_2$ | $CH_2$ | Q-1.138 |
| I.1-814 | 4-$CH_3$-Ph | H | $CH_2$ | $CH_2$ | Q-1.166 |
| I.1-815 | 4-$CH_3$-Ph | H | $CH_2$ | $CH_2$ | Q-1.167 |
| I.1-816 | 4-$CH_3$-Ph | H | $CH_2$ | $CH_2$ | Q-1.168 |
| I.1-817 | 4-$CH_3$-Ph | H | $CH_2$ | $CH_2$ | Q-1.171 |
| I.1-818 | 4-$CH_3$-Ph | H | $CH_2$ | $CH_2$ | Q-1.172 |
| I.1-819 | 4-$CH_3$-Ph | H | $CH_2$ | $CH_2$ | Q-1.173 |
| I.1-820 | 4-$CH_3$-Ph | H | $CH_2$ | $CH_2$ | Q-1.201 |
| I.1-821 | 4-$CH_3$-Ph | H | $CH_2$ | $CH_2$ | Q-1.202 |
| I.1-822 | 4-$CH_3$-Ph | H | $CH_2$ | $CH_2$ | Q-1.203 |
| I.1-823 | 4-$CH_3$-Ph | H | $CH_2$ | $CH_2$ | Q-1.206 |
| I.1-824 | 4-$CH_3$-Ph | H | $CH_2$ | $CH_2$ | Q-1.207 |
| I.1-825 | 4-$CH_3$-Ph | H | $CH_2$ | $CH_2$ | Q-1.210 |
| I.1-826 | 4-$CH_3$-Ph | H | $CH_2$ | $CH_2$ | Q-1.211 |
| I.1-827 | c-Pent | H | $CH_2$ | $CH_2$ | Q-1.1 |
| I.1-828 | c-Pent | H | $CH_2$ | $CH_2$ | Q-1.2 |
| I.1-829 | c-Pent | H | $CH_2$ | $CH_2$ | Q-1.3 |
| I.1-830 | c-Pent | H | $CH_2$ | $CH_2$ | Q-1.6 |
| I.1-831 | c-Pent | H | $CH_2$ | $CH_2$ | Q-1.10 |
| I.1-832 | c-Pent | H | $CH_2$ | $CH_2$ | Q-1.11 |
| I.1-833 | c-Pent | H | $CH_2$ | $CH_2$ | Q-1.16 |
| I.1-834 | c-Pent | H | $CH_2$ | $CH_2$ | Q-1.17 |
| I.1-835 | c-Pent | H | $CH_2$ | $CH_2$ | Q-1.18 |
| I.1-836 | c-Pent | H | $CH_2$ | $CH_2$ | Q-1.21 |
| I.1-837 | c-Pent | H | $CH_2$ | $CH_2$ | Q-1.91 |
| I.1-838 | c-Pent | H | $CH_2$ | $CH_2$ | Q-1.92 |
| I.1-839 | c-Pent | H | $CH_2$ | $CH_2$ | Q-1.93 |
| I.1-840 | c-Pent | H | $CH_2$ | $CH_2$ | Q-1.96 |
| I.1-841 | c-Pent | H | $CH_2$ | $CH_2$ | Q-1.136 |
| I.1-842 | c-Pent | H | $CH_2$ | $CH_2$ | Q-1.137 |
| I.1-843 | c-Pent | H | $CH_2$ | $CH_2$ | Q-1.138 |
| I.1-844 | c-Pent | H | $CH_2$ | $CH_2$ | Q-1.166 |
| I.1-845 | c-Pent | H | $CH_2$ | $CH_2$ | Q-1.167 |
| I.1-846 | c-Pent | H | $CH_2$ | $CH_2$ | Q-1.168 |
| I.1-847 | c-Pent | H | $CH_2$ | $CH_2$ | Q-1.171 |
| I.1-848 | c-Pent | H | $CH_2$ | $CH_2$ | Q-1.172 |
| I.1-849 | c-Pent | H | $CH_2$ | $CH_2$ | Q-1.173 |
| I.1-850 | c-Pent | H | $CH_2$ | $CH_2$ | Q-1.201 |
| I.1-851 | c-Pent | H | $CH_2$ | $CH_2$ | Q-1.202 |
| I.1-852 | c-Pent | H | $CH_2$ | $CH_2$ | Q-1.203 |
| I.1-853 | c-Pent | H | $CH_2$ | $CH_2$ | Q-1.206 |
| I.1-854 | c-Pent | H | $CH_2$ | $CH_2$ | Q-1.207 |
| I.1-855 | c-Pent | H | $CH_2$ | $CH_2$ | Q-1.210 |
| I.1-856 | c-Pent | H | $CH_2$ | $CH_2$ | Q-1.211 |
| I.1-857 | t-Bu | H | $CH_2$ | $CH_2$ | Q-1.1 |
| I.1-858 | t-Bu | H | $CH_2$ | $CH_2$ | Q-1.2 |
| I.1-859 | t-Bu | H | $CH_2$ | $CH_2$ | Q-1.3 |
| I.1-860 | t-Bu | H | $CH_2$ | $CH_2$ | Q-1.6 |
| I.1-861 | t-Bu | H | $CH_2$ | $CH_2$ | Q-1.10 |
| I.1-862 | t-Bu | H | $CH_2$ | $CH_2$ | Q-1.11 |
| I.1-863 | t-Bu | H | $CH_2$ | $CH_2$ | Q-1.16 |
| I.1-864 | t-Bu | H | $CH_2$ | $CH_2$ | Q-1.17 |
| I.1-865 | t-Bu | H | $CH_2$ | $CH_2$ | Q-1.18 |
| I.1-866 | t-Bu | H | $CH_2$ | $CH_2$ | Q-1.21 |
| I.1-867 | t-Bu | H | $CH_2$ | $CH_2$ | Q-1.91 |
| I.1-868 | t-Bu | H | $CH_2$ | $CH_2$ | Q-1.92 |
| I.1-869 | t-Bu | H | $CH_2$ | $CH_2$ | Q-1.93 |
| I.1-870 | t-Bu | H | $CH_2$ | $CH_2$ | Q-1.96 |
| I.1-871 | t-Bu | H | $CH_2$ | $CH_2$ | Q-1.136 |

TABLE 1-continued (I)

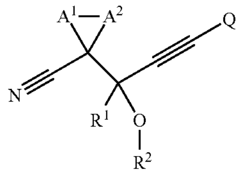

The Q radicals here correspond to the structures defined as very particularly preferred earlier in the document

| No. | $R^1$ | $R^2$ | $A^1$ | $A^2$ | Q |
|---|---|---|---|---|---|
| I.1-872 | t-Bu | H | $CH_2$ | $CH_2$ | Q-1.137 |
| I.1-873 | t-Bu | H | $CH_2$ | $CH_2$ | Q-1.138 |
| I.1-874 | t-Bu | H | $CH_2$ | $CH_2$ | Q-1.166 |
| I.1-875 | t-Bu | H | $CH_2$ | $CH_2$ | Q-1.167 |
| I.1-876 | t-Bu | H | $CH_2$ | $CH_2$ | Q-1.168 |
| I.1-877 | t-Bu | H | $CH_2$ | $CH_2$ | Q-1.171 |
| I.1-878 | t-Bu | H | $CH_2$ | $CH_2$ | Q-1.172 |
| I.1-879 | t-Bu | H | $CH_2$ | $CH_2$ | Q-1.173 |
| I.1-880 | t-Bu | H | $CH_2$ | $CH_2$ | Q-1.201 |
| I.1-881 | t-Bu | H | $CH_2$ | $CH_2$ | Q-1.202 |
| I.1-882 | t-Bu | H | $CH_2$ | $CH_2$ | Q-1.203 |
| I.1-883 | t-Bu | H | $CH_2$ | $CH_2$ | Q-1.206 |
| I.1-884 | t-Bu | H | $CH_2$ | $CH_2$ | Q-1.207 |
| I.1-885 | t-Bu | H | $CH_2$ | $CH_2$ | Q-1.210 |
| I.1-886 | t-Bu | H | $CH_2$ | $CH_2$ | Q-1.211 |
| I.1-887 | 1-Ethylpropyl | H | $CH_2$ | $CH_2$ | Q-1.141 |
| I.1-888 | 4-$CH_3$-Ph | H | $CH_2$ | $CH_2$ | Q-1.141 |
| I.1-889 | t-Bu | H | $CH_2$ | $CH_2$ | Q-1.141 |
| I.1-890 | c-Pent | H | $CH_2$ | $CH_2$ | Q-1.141 |
| I.1-891 | 4-Cl-Ph | H | $CH_2$ | $CH_2$ | Q-1.1 |
| I.1-892 | 4-Cl-Ph | H | $CH_2$ | $CH_2$ | Q-1.2 |
| I.1-893 | 4-Cl-Ph | H | $CH_2$ | $CH_2$ | Q-1.3 |
| I.1-894 | 4-Cl-Ph | H | $CH_2$ | $CH_2$ | Q-1.6 |
| I.1-895 | 4-Cl-Ph | H | $CH_2$ | $CH_2$ | Q-1.10 |
| I.1-896 | 4-Cl-Ph | H | $CH_2$ | $CH_2$ | Q-1.11 |
| I.1-897 | 4-Cl-Ph | H | $CH_2$ | $CH_2$ | Q-1.16 |
| I.1-898 | 4-Cl-Ph | H | $CH_2$ | $CH_2$ | Q-1.17 |
| I.1-899 | 4-Cl-Ph | H | $CH_2$ | $CH_2$ | Q-1.18 |
| I.1-900 | 4-Cl-Ph | H | $CH_2$ | $CH_2$ | Q-1.21 |
| I.1-901 | 4-Cl-Ph | H | $CH_2$ | $CH_2$ | Q-1.91 |
| I.1-902 | 4-Cl-Ph | H | $CH_2$ | $CH_2$ | Q-1.92 |
| I.1-903 | 4-Cl-Ph | H | $CH_2$ | $CH_2$ | Q-1.93 |
| I.1-904 | 4-Cl-Ph | H | $CH_2$ | $CH_2$ | Q-1.96 |
| I.1-905 | 4-Cl-Ph | H | $CH_2$ | $CH_2$ | Q-1.136 |
| I.1-906 | 4-Cl-Ph | H | $CH_2$ | $CH_2$ | Q-1.137 |
| I.1-907 | 4-Cl-Ph | H | $CH_2$ | $CH_2$ | Q-1.138 |
| I.1-908 | 4-Cl-Ph | H | $CH_2$ | $CH_2$ | Q-1.166 |
| I.1-909 | 4-Cl-Ph | H | $CH_2$ | $CH_2$ | Q-1.167 |
| I.1-910 | 4-Cl-Ph | H | $CH_2$ | $CH_2$ | Q-1.168 |
| I.1-911 | 4-Cl-Ph | H | $CH_2$ | $CH_2$ | Q-1.171 |
| I.1-912 | 4-Cl-Ph | H | $CH_2$ | $CH_2$ | Q-1.172 |
| I.1-913 | 4-Cl-Ph | H | $CH_2$ | $CH_2$ | Q-1.173 |
| I.1-914 | 4-Cl-Ph | H | $CH_2$ | $CH_2$ | Q-1.201 |
| I.1-915 | 4-Cl-Ph | H | $CH_2$ | $CH_2$ | Q-1.202 |
| I.1-916 | 4-Cl-Ph | H | $CH_2$ | $CH_2$ | Q-1.203 |
| I.1-917 | 4-Cl-Ph | H | $CH_2$ | $CH_2$ | Q-1.206 |
| I.1-918 | 4-Cl-Ph | H | $CH_2$ | $CH_2$ | Q-1.207 |
| I.1-919 | 4-Cl-Ph | H | $CH_2$ | $CH_2$ | Q-1.210 |
| I.1-920 | 4-Cl-Ph | H | $CH_2$ | $CH_2$ | Q-1.211 |
| I.1-921 | 4-Cl-Ph | H | $CH_2$ | $CH_2$ | Q-1.141 |

TABLE 2

(I)

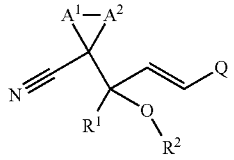

The Q radicals here correspond to the structures defined as particularly preferred earlier in the document

| No. | $R^1$ | $R^2$ | $A^1$ | $A^2$ | Q |
|---|---|---|---|---|---|
| I.2-1 | $CH_3$ | H | $CH_2$ | $CH_2$ | Q-1.1 |
| I.2-2 | $CH_3$ | H | $CH_2$ | $CH_2$ | Q-1.2 |
| I.2-3 | $CH_3$ | H | $CH_2$ | $CH_2$ | Q-1.3 |
| I.2-4 | $CH_3$ | H | $CH_2$ | $CH_2$ | Q-1.16 |
| I.2-5 | $CH_3$ | H | $CH_2$ | $CH_2$ | Q-1.17 |
| I.2-6 | $CH_3$ | H | $CH_2$ | $CH_2$ | Q-1.18 |
| I.2-7 | $CH_3$ | H | $CH_2$ | $CH_2$ | Q-1.31 |
| I.2-8 | $CH_3$ | H | $CH_2$ | $CH_2$ | Q-1.32 |
| I.2-9 | $CH_3$ | H | $CH_2$ | $CH_2$ | Q-1.33 |
| I.2-10 | $CH_3$ | H | $CH_2$ | $CH_2$ | Q-1.91 |
| I.2-11 | $CH_3$ | H | $CH_2$ | $CH_2$ | Q-1.92 |
| I.2-12 | $CH_3$ | H | $CH_2$ | $CH_2$ | Q-1.93 |
| I.2-13 | $CH_3$ | H | $CH_2$ | $CH_2$ | Q-1.106 |
| I.2-14 | $CH_3$ | H | $CH_2$ | $CH_2$ | Q-1.107 |
| I.2-15 | $CH_3$ | H | $CH_2$ | $CH_2$ | Q-1.108 |
| I.2-16 | $CH_3$ | H | $CH_2$ | $CH_2$ | Q-1.121 |
| I.2-17 | $CH_3$ | H | $CH_2$ | $CH_2$ | Q-1.122 |
| I.2-18 | $CH_3$ | H | $CH_2$ | $CH_2$ | Q-1.123 |
| I.2-19 | $CH_3$ | H | $CH_2$ | $CH_2$ | Q-1.136 |
| I.2-20 | $CH_3$ | H | $CH_2$ | $CH_2$ | Q-1.137 |
| I.2-21 | $CH_3$ | H | $CH_2$ | $CH_2$ | Q-1.138 |
| I.2-22 | $CH_3$ | H | $CH_2$ | $CH_2$ | Q-1.166 |
| I.2-23 | $CH_3$ | H | $CH_2$ | $CH_2$ | Q-1.167 |
| I.2-24 | $CH_3$ | H | $CH_2$ | $CH_2$ | Q-1.168 |
| I.2-25 | $CH_3$ | H | $CH_2$ | $CH_2$ | Q-1.171 |
| I.2-26 | $CH_3$ | H | $CH_2$ | $CH_2$ | Q-1.172 |
| I.2-27 | $CH_3$ | H | $CH_2$ | $CH_2$ | Q-1.173 |
| I.2-28 | $CH_3$ | H | $CH_2$ | $CH_2$ | Q-1.176 |
| I.2-29 | $CH_3$ | H | $CH_2$ | $CH_2$ | Q-1.177 |
| I.2-30 | $CH_3$ | H | $CH_2$ | $CH_2$ | Q-1.178 |
| I.2-31 | $CH_3$ | H | $CH_2$ | $CH_2$ | Q-1.181 |
| I.2-32 | $CH_3$ | H | $CH_2$ | $CH_2$ | Q-1.182 |
| I.2-33 | $CH_3$ | H | $CH_2$ | $CH_2$ | Q-1.183 |
| I.2-34 | $CH_3$ | H | $CH_2$ | $CH_2$ | Q-1.201 |
| I.2-35 | $CH_3$ | H | $CH_2$ | $CH_2$ | Q-1.202 |
| I.2-36 | $CH_3$ | H | $CH_2$ | $CH_2$ | Q-1.203 |
| I.2-37 | $CH_3$ | H | $CH_2$ | $CH_2$ | Q-1.204 |
| I.2-38 | $CH_3$ | H | $CH_2$ | $CH_2$ | Q-1.205 |
| I.2-39 | $CH_3$ | H | $CH_2$ | $CH_2$ | Q-1.206 |
| I.2-41 | $CH_3$ | H | $CH_2$ | $CH_2$ | Q-1.207 |
| I.2-42 | $CH_3$ | H | $CH_2$ | $CH_2$ | Q-1.208 |
| I.2-43 | $CH_3$ | H | $CH_2$ | $CH_2$ | Q-1.209 |
| I.2-44 | $CH_3$ | H | $CH_2$ | $CH_2$ | Q-1.210 |
| I.2-45 | $CH_3$ | H | $CH_2$ | $CH_2$ | Q-1.211 |
| I.2-46 | $CH_3$ | H | $CH_2$ | $CH_2$ | Q-1.212 |
| I.2-47 | $CH_3$ | H | $CH_2$ | $CH_2$ | Q-1.213 |
| I.2-48 | $CH_3$ | H | $CH_2$ | $CH_2$ | Q-1.216 |
| I.2-49 | $CH_3$ | H | $CH_2$ | $CH_2$ | Q-1.217 |
| I.2-50 | $CH_3$ | H | $CH_2$ | $CH_2$ | Q-1.218 |
| I.2-51 | $CH_3$ | H | $CH_2$ | $CH_2$ | Q-1.246 |
| I.2-52 | $CH_3$ | H | $CH_2$ | $CH_2$ | Q-1.247 |
| I.2-53 | $CH_3$ | H | $CH_2$ | $CH_2$ | Q-1.248 |
| I.2-54 | $CH_3$ | H | $CH_2$ | $CH_2$ | Q-2.1 |
| I.2-55 | $CH_3$ | H | $CH_2$ | $CH_2$ | Q-2.2 |
| I.2-56 | $CH_3$ | H | $CH_2$ | $CH_2$ | Q-2.3 |
| I.2-57 | $CH_3$ | H | $CH_2$ | $CH_2$ | Q-2.5 |
| I.2-58 | $CH_3$ | H | $CH_2$ | $CH_2$ | Q-2.4 |
| I.2-59 | $CH_3$ | H | $CH_2$ | $CH_2$ | Q-2.7 |
| I.2-60 | $CH_3$ | H | $CH_2$ | $CH_2$ | Q-2.9 |
| I.2-61 | $CH_3$ | H | $CH_2$ | $CH_2$ | Q-2.12 |
| I.2-62 | $CH_3$ | H | $CH_2$ | $CH_2$ | Q-2.13 |
| I.2-63 | $CH_3$ | H | $CH_2$ | $CH_2$ | Q-2.14 |
| I.2-64 | $CH_3$ | H | $CH_2$ | $CH_2$ | Q-2.61 |
| I.2-65 | $CH_3$ | H | $CH_2$ | $CH_2$ | Q-2.62 |

TABLE 2-continued (I)

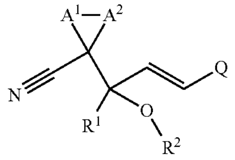

The Q radicals here correspond to the structures defined as particularly preferred earlier in the document

| No. | $R^1$ | $R^2$ | $A^1$ | $A^2$ | Q |
|---|---|---|---|---|---|
| I.2-66 | $CH_3$ | H | $CH_2$ | $CH_2$ | Q-2.63 |
| I.2-67 | $CH_3$ | H | $CH_2$ | $CH_2$ | Q-2.64 |
| I.2-68 | $CH_3$ | H | $CH_2$ | $CH_2$ | Q-2.65 |
| I.2-69 | $CH_3$ | H | $CH_2$ | $CH_2$ | Q-2.67 |
| I.2-70 | $CH_3$ | H | $CH_2$ | $CH_2$ | Q-2.69 |
| I.2-71 | $CH_3$ | H | $CH_2$ | $CH_2$ | Q-2.72 |
| I.2-72 | $CH_3$ | H | $CH_2$ | $CH_2$ | Q-2.73 |
| I.2-73 | $CH_3$ | H | $CH_2$ | $CH_2$ | Q-2.74 |
| I.2-74 | $CH_3$ | H | $CH_2$ | $CH_2$ | Q-2.80 |
| I.2-75 | $CH_3$ | H | $CH_2$ | $CH_2$ | Q-2.105 |
| I.2-76 | $CH_3$ | H | $CH_2$ | $CH_2$ | Q-2.106 |
| I.2-77 | $CH_3$ | H | $CH_2$ | $CH_2$ | Q-2.108 |
| I.2-78 | $CH_3$ | H | $CH_2$ | $CH_2$ | Q-2.145 |
| I.2-79 | $CH_3$ | H | $CH_2$ | $CH_2$ | Q-2.146 |
| I.2-80 | $CH_3$ | H | $CH_2$ | $CH_2$ | Q-2.147 |
| I.2-81 | $CH_3$ | H | $CH_2$ | $CH_2$ | Q-2.161 |
| I.2-82 | $CH_3$ | H | $CH_2$ | $CH_2$ | Q-2.162 |
| I.2-83 | $CH_3$ | H | $CH_2$ | $CH_2$ | Q-2.163 |
| I.2-84 | $CH_3$ | H | $CH_2$ | $CH_2$ | Q-2.164 |
| I.2-85 | $CH_3$ | H | $CH_2$ | $CH_2$ | Q-2.165 |
| I.2-86 | $CH_3$ | H | $CH_2$ | $CH_2$ | Q-2.167 |
| I.2-87 | $CH_3$ | H | $CH_2$ | $CH_2$ | Q-2.168 |
| I.2-88 | $CH_3$ | H | $CH_2$ | $CH_2$ | Q-2.169 |
| I.2-89 | $CH_3$ | H | $CH_2$ | $CH_2$ | Q-2.172 |
| I.2-90 | $CH_3$ | H | $CH_2$ | $CH_2$ | Q-2.173 |
| I.2-91 | $CH_3$ | H | $CH_2$ | $CH_2$ | Q-2.174 |
| I.2-92 | $CH_3$ | H | $CH_2$ | $CH_2$ | Q-2.180 |
| I.2-93 | $CH_3$ | H | $CH_2$ | $CH_2$ | Q-2.185 |
| I.2-94 | $CH_3$ | H | $CH_2$ | $CH_2$ | Q-2.189 |
| I.2-95 | $CH_3$ | H | $CH_2$ | $CH_2$ | Q-2.190 |
| I.2-96 | $CH_3$ | H | $CH_2$ | $CH_2$ | Q-2.201 |
| I.2-97 | $CH_3$ | H | $CH_2$ | $CH_2$ | Q-2.202 |
| I.2-98 | $CH_3$ | H | $CH_2$ | $CH_2$ | Q-2.203 |
| I.2-99 | $CH_3$ | H | $CH_2$ | $CH_2$ | Q-2.204 |
| I.2-100 | i-Pr | H | $CH_2$ | $CH_2$ | Q-1.10 |
| I.2-101 | i-Pr | H | $CH_2$ | $CH_2$ | Q-1.1 |
| I.2-102 | i-Pr | H | $CH_2$ | $CH_2$ | Q-1.2 |
| I.2-103 | i-Pr | H | $CH_2$ | $CH_2$ | Q-1.3 |
| I.2-104 | i-Pr | H | $CH_2$ | $CH_2$ | Q-1.16 |
| I.2-105 | i-Pr | H | $CH_2$ | $CH_2$ | Q-1.17 |
| I.2-106 | i-Pr | H | $CH_2$ | $CH_2$ | Q-1.18 |
| I.2-107 | i-Pr | H | $CH_2$ | $CH_2$ | Q-1.31 |
| I.2-108 | i-Pr | H | $CH_2$ | $CH_2$ | Q-1.32 |
| I.2-109 | i-Pr | H | $CH_2$ | $CH_2$ | Q-1.33 |
| I.2-110 | i-Pr | H | $CH_2$ | $CH_2$ | Q-1.91 |
| I.2-111 | i-Pr | H | $CH_2$ | $CH_2$ | Q-1.92 |
| I.2-112 | i-Pr | H | $CH_2$ | $CH_2$ | Q-1.93 |
| I.2-113 | i-Pr | H | $CH_2$ | $CH_2$ | Q-1.106 |
| I.2-114 | i-Pr | H | $CH_2$ | $CH_2$ | Q-1.107 |
| I.2-115 | i-Pr | H | $CH_2$ | $CH_2$ | Q-1.108 |
| I.2-116 | i-Pr | H | $CH_2$ | $CH_2$ | Q-1.121 |
| I.2-117 | i-Pr | H | $CH_2$ | $CH_2$ | Q-1.122 |
| I.2-118 | i-Pr | H | $CH_2$ | $CH_2$ | Q-1.123 |
| I.2-119 | i-Pr | H | $CH_2$ | $CH_2$ | Q-1.136 |
| I.2-120 | i-Pr | H | $CH_2$ | $CH_2$ | Q-1.137 |
| I.2-121 | i-Pr | H | $CH_2$ | $CH_2$ | Q-1.138 |
| I.2-122 | i-Pr | H | $CH_2$ | $CH_2$ | Q-1.166 |
| I.2-123 | i-Pr | H | $CH_2$ | $CH_2$ | Q-1.167 |
| I.2-124 | i-Pr | H | $CH_2$ | $CH_2$ | Q-1.168 |
| I.2-125 | i-Pr | H | $CH_2$ | $CH_2$ | Q-1.171 |
| I.2-126 | i-Pr | H | $CH_2$ | $CH_2$ | Q-1.172 |
| I.2-127 | i-Pr | H | $CH_2$ | $CH_2$ | Q-1.173 |
| I.2-128 | i-Pr | H | $CH_2$ | $CH_2$ | Q-1.176 |
| I.2-129 | i-Pr | H | $CH_2$ | $CH_2$ | Q-1.177 |

TABLE 2-continued (I)

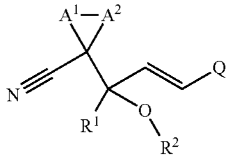

The Q radicals here correspond to the structures defined as particularly preferred earlier in the document

| No. | $R^1$ | $R^2$ | $A^1$ | $A^2$ | Q |
|---|---|---|---|---|---|
| I.2-130 | i-Pr | H | $CH_2$ | $CH_2$ | Q-1.178 |
| I.2-131 | i-Pr | H | $CH_2$ | $CH_2$ | Q-1.181 |
| I.2-132 | i-Pr | H | $CH_2$ | $CH_2$ | Q-1.182 |
| I.2-133 | i-Pr | H | $CH_2$ | $CH_2$ | Q-1.183 |
| I.2-134 | i-Pr | H | $CH_2$ | $CH_2$ | Q-1.201 |
| I.2-135 | i-Pr | H | $CH_2$ | $CH_2$ | Q-1.202 |
| I.2-136 | i-Pr | H | $CH_2$ | $CH_2$ | Q-1.203 |
| I.2-137 | i-Pr | H | $CH_2$ | $CH_2$ | Q-1.204 |
| I.2-138 | i-Pr | H | $CH_2$ | $CH_2$ | Q-1.205 |
| I.2-139 | i-Pr | H | $CH_2$ | $CH_2$ | Q-1.206 |
| I.2-141 | i-Pr | H | $CH_2$ | $CH_2$ | Q-1.207 |
| I.2-142 | i-Pr | H | $CH_2$ | $CH_2$ | Q-1.208 |
| I.2-143 | i-Pr | H | $CH_2$ | $CH_2$ | Q-1.209 |
| I.2-144 | i-Pr | H | $CH_2$ | $CH_2$ | Q-1.210 |
| I.2-145 | i-Pr | H | $CH_2$ | $CH_2$ | Q-1.211 |
| I.2-146 | i-Pr | H | $CH_2$ | $CH_2$ | Q-1.212 |
| I.2-147 | i-Pr | H | $CH_2$ | $CH_2$ | Q-1.213 |
| I.2-148 | i-Pr | H | $CH_2$ | $CH_2$ | Q-1.216 |
| I.2-149 | i-Pr | H | $CH_2$ | $CH_2$ | Q-1.217 |
| I.2-150 | i-Pr | H | $CH_2$ | $CH_2$ | Q-1.218 |
| I.2-151 | i-Pr | H | $CH_2$ | $CH_2$ | Q-1.246 |
| I.2-152 | i-Pr | H | $CH_2$ | $CH_2$ | Q-1.247 |
| I.2-153 | i-Pr | H | $CH_2$ | $CH_2$ | Q-1.248 |
| I.2-154 | i-Pr | H | $CH_2$ | $CH_2$ | Q-2.1 |
| I.2-155 | i-Pr | H | $CH_2$ | $CH_2$ | Q-2.2 |
| I.2-156 | i-Pr | H | $CH_2$ | $CH_2$ | Q-2.3 |
| I.2-157 | i-Pr | H | $CH_2$ | $CH_2$ | Q-2.5 |
| I.2-158 | i-Pr | H | $CH_2$ | $CH_2$ | Q-2.4 |
| I.2-159 | i-Pr | H | $CH_2$ | $CH_2$ | Q-2.7 |
| I.2-160 | i-Pr | H | $CH_2$ | $CH_2$ | Q-2.9 |
| I.2-161 | i-Pr | H | $CH_2$ | $CH_2$ | Q-2.12 |
| I.2-162 | i-Pr | H | $CH_2$ | $CH_2$ | Q-2.13 |
| I.2-163 | i-Pr | H | $CH_2$ | $CH_2$ | Q-2.14 |
| I.2-164 | i-Pr | H | $CH_2$ | $CH_2$ | Q-2.61 |
| I.2-165 | i-Pr | H | $CH_2$ | $CH_2$ | Q-2.62 |
| I.2-166 | i-Pr | H | $CH_2$ | $CH_2$ | Q-2.63 |
| I.2-167 | i-Pr | H | $CH_2$ | $CH_2$ | Q-2.64 |
| I.2-168 | i-Pr | H | $CH_2$ | $CH_2$ | Q-2.65 |
| I.2-169 | i-Pr | H | $CH_2$ | $CH_2$ | Q-2.67 |
| I.2-170 | i-Pr | H | $CH_2$ | $CH_2$ | Q-2.69 |
| I.2-171 | i-Pr | H | $CH_2$ | $CH_2$ | Q-2.72 |
| I.2-172 | i-Pr | H | $CH_2$ | $CH_2$ | Q-2.73 |
| I.2-173 | i-Pr | H | $CH_2$ | $CH_2$ | Q-2.74 |
| I.2-174 | i-Pr | H | $CH_2$ | $CH_2$ | Q-2.80 |
| I.2-175 | i-Pr | H | $CH_2$ | $CH_2$ | Q-2.105 |
| I.2-176 | i-Pr | H | $CH_2$ | $CH_2$ | Q-2.106 |
| I.2-177 | i-Pr | H | $CH_2$ | $CH_2$ | Q-2.108 |
| I.2-178 | i-Pr | H | $CH_2$ | $CH_2$ | Q-2.145 |
| I.2-179 | i-Pr | H | $CH_2$ | $CH_2$ | Q-2.146 |
| I.2-180 | i-Pr | H | $CH_2$ | $CH_2$ | Q-2.147 |
| I.2-181 | i-Pr | H | $CH_2$ | $CH_2$ | Q-2.161 |
| I.2-182 | i-Pr | H | $CH_2$ | $CH_2$ | Q-2.162 |
| I.2-183 | i-Pr | H | $CH_2$ | $CH_2$ | Q-2.163 |
| I.2-184 | i-Pr | H | $CH_2$ | $CH_2$ | Q-2.164 |
| I.2-185 | i-Pr | H | $CH_2$ | $CH_2$ | Q-2.165 |
| I.2-186 | i-Pr | H | $CH_2$ | $CH_2$ | Q-2.167 |
| I.2-187 | i-Pr | H | $CH_2$ | $CH_2$ | Q-2.168 |
| I.2-188 | i-Pr | H | $CH_2$ | $CH_2$ | Q-2.169 |
| I.2-189 | i-Pr | H | $CH_2$ | $CH_2$ | Q-2.172 |
| I.2-190 | i-Pr | H | $CH_2$ | $CH_2$ | Q-2.173 |
| I.2-191 | i-Pr | H | $CH_2$ | $CH_2$ | Q-2.174 |
| I.2-192 | i-Pr | H | $CH_2$ | $CH_2$ | Q-2.180 |
| I.2-193 | i-Pr | H | $CH_2$ | $CH_2$ | Q-2.185 |
| I.2-194 | i-Pr | H | $CH_2$ | $CH_2$ | Q-2.189 |

TABLE 2-continued (I)

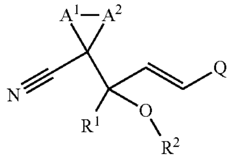

The Q radicals here correspond to the structures defined as particularly preferred earlier in the document

| No. | $R^1$ | $R^2$ | $A^1$ | $A^2$ | Q |
|---|---|---|---|---|---|
| I.2-195 | i-Pr | H | $CH_2$ | $CH_2$ | Q-2.190 |
| I.2-196 | i-Pr | H | $CH_2$ | $CH_2$ | Q-2.201 |
| I.2-197 | i-Pr | H | $CH_2$ | $CH_2$ | Q-2.202 |
| I.2-198 | i-Pr | H | $CH_2$ | $CH_2$ | Q-2.203 |
| I.2-199 | i-Pr | H | $CH_2$ | $CH_2$ | Q-2.204 |
| I.2-200 | i-Pr | H | $CH_2$ | $CH_2$ | Q-2.205 |
| I.2-201 | Ph | H | $CH_2$ | $CH_2$ | Q-1.1 |
| I.2-202 | Ph | H | $CH_2$ | $CH_2$ | Q-1.2 |
| I.2-203 | Ph | H | $CH_2$ | $CH_2$ | Q-1.3 |
| I.2-204 | Ph | H | $CH_2$ | $CH_2$ | Q-1.16 |
| I.2-205 | Ph | H | $CH_2$ | $CH_2$ | Q-1.17 |
| I.2-206 | Ph | H | $CH_2$ | $CH_2$ | Q-1.18 |
| I.2-207 | Ph | H | $CH_2$ | $CH_2$ | Q-1.31 |
| I.2-208 | Ph | H | $CH_2$ | $CH_2$ | Q-1.32 |
| I.2-209 | Ph | H | $CH_2$ | $CH_2$ | Q-1.33 |
| I.2-210 | Ph | H | $CH_2$ | $CH_2$ | Q-1.91 |
| I.2-211 | Ph | H | $CH_2$ | $CH_2$ | Q-1.92 |
| I.2-212 | Ph | H | $CH_2$ | $CH_2$ | Q-1.93 |
| I.2-213 | Ph | H | $CH_2$ | $CH_2$ | Q-1.106 |
| I.2-214 | Ph | H | $CH_2$ | $CH_2$ | Q-1.107 |
| I.2-215 | Ph | H | $CH_2$ | $CH_2$ | Q-1.108 |
| I.2-216 | Ph | H | $CH_2$ | $CH_2$ | Q-1.121 |
| I.2-217 | Ph | H | $CH_2$ | $CH_2$ | Q-1.122 |
| I.2-218 | Ph | H | $CH_2$ | $CH_2$ | Q-1.123 |
| I.2-219 | Ph | H | $CH_2$ | $CH_2$ | Q-1.136 |
| I.2-220 | Ph | H | $CH_2$ | $CH_2$ | Q-1.137 |
| I.2-221 | Ph | H | $CH_2$ | $CH_2$ | Q-1.138 |
| I.2-222 | Ph | H | $CH_2$ | $CH_2$ | Q-1.166 |
| I.2-223 | Ph | H | $CH_2$ | $CH_2$ | Q-1.167 |
| I.2-224 | Ph | H | $CH_2$ | $CH_2$ | Q-1.168 |
| I.2-225 | Ph | H | $CH_2$ | $CH_2$ | Q-1.171 |
| I.2-226 | Ph | H | $CH_2$ | $CH_2$ | Q-1.172 |
| I.2-227 | Ph | H | $CH_2$ | $CH_2$ | Q-1.173 |
| I.2-228 | Ph | H | $CH_2$ | $CH_2$ | Q-1.176 |
| I.2-229 | Ph | H | $CH_2$ | $CH_2$ | Q-1.177 |
| I.2-230 | Ph | H | $CH_2$ | $CH_2$ | Q-1.178 |
| I.2-231 | Ph | H | $CH_2$ | $CH_2$ | Q-1.181 |
| I.2-232 | Ph | H | $CH_2$ | $CH_2$ | Q-1.182 |
| I.2-233 | Ph | H | $CH_2$ | $CH_2$ | Q-1.183 |
| I.2-234 | Ph | H | $CH_2$ | $CH_2$ | Q-1.201 |
| I.2-235 | Ph | H | $CH_2$ | $CH_2$ | Q-1.202 |
| I.2-236 | Ph | H | $CH_2$ | $CH_2$ | Q-1.203 |
| I.2-237 | Ph | H | $CH_2$ | $CH_2$ | Q-1.204 |
| I.2-238 | Ph | H | $CH_2$ | $CH_2$ | Q-1.205 |
| I.2-239 | Ph | H | $CH_2$ | $CH_2$ | Q-1.206 |
| I.2-241 | Ph | H | $CH_2$ | $CH_2$ | Q-1.207 |
| I.2-242 | Ph | H | $CH_2$ | $CH_2$ | Q-1.208 |
| I.2-243 | Ph | H | $CH_2$ | $CH_2$ | Q-1.209 |
| I.2-244 | Ph | H | $CH_2$ | $CH_2$ | Q-1.210 |
| I.2-245 | Ph | H | $CH_2$ | $CH_2$ | Q-1.211 |
| I.2-246 | Ph | H | $CH_2$ | $CH_2$ | Q-1.212 |
| I.2-247 | Ph | H | $CH_2$ | $CH_2$ | Q-1.213 |
| I.2-248 | Ph | H | $CH_2$ | $CH_2$ | Q-1.216 |
| I.2-249 | Ph | H | $CH_2$ | $CH_2$ | Q-1.217 |
| I.2-250 | Ph | H | $CH_2$ | $CH_2$ | Q-1.218 |
| I.2-251 | Ph | H | $CH_2$ | $CH_2$ | Q-1.246 |
| I.2-252 | Ph | H | $CH_2$ | $CH_2$ | Q-1.247 |
| I.2-253 | Ph | H | $CH_2$ | $CH_2$ | Q-1.248 |
| I.2-254 | Ph | H | $CH_2$ | $CH_2$ | Q-2.1 |
| I.2-255 | Ph | H | $CH_2$ | $CH_2$ | Q-2.2 |
| I.2-256 | Ph | H | $CH_2$ | $CH_2$ | Q-2.3 |
| I.2-257 | Ph | H | $CH_2$ | $CH_2$ | Q-2.5 |
| I.2-258 | Ph | H | $CH_2$ | $CH_2$ | Q-2.4 |
| I.2-259 | Ph | H | $CH_2$ | $CH_2$ | Q-2.7 |

TABLE 2-continued

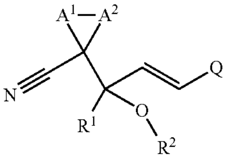

(I)

The Q radicals here correspond to the structures defined as particularly preferred earlier in the document

| No. | $R^1$ | $R^2$ | $A^1$ | $A^2$ | Q |
|---|---|---|---|---|---|
| I.2-260 | Ph | H | $CH_2$ | $CH_2$ | Q-2.9 |
| I.2-261 | Ph | H | $CH_2$ | $CH_2$ | Q-2.12 |
| I.2-262 | Ph | H | $CH_2$ | $CH_2$ | Q-2.13 |
| I.2-263 | Ph | H | $CH_2$ | $CH_2$ | Q-2.14 |
| I.2-264 | Ph | H | $CH_2$ | $CH_2$ | Q-2.61 |
| I.2-265 | Ph | H | $CH_2$ | $CH_2$ | Q-2.62 |
| I.2-266 | Ph | H | $CH_2$ | $CH_2$ | Q-2.63 |
| I.2-267 | Ph | H | $CH_2$ | $CH_2$ | Q-2.64 |
| I.2-268 | Ph | H | $CH_2$ | $CH_2$ | Q-2.65 |
| I.2-269 | Ph | H | $CH_2$ | $CH_2$ | Q-2.67 |
| I.2-270 | Ph | H | $CH_2$ | $CH_2$ | Q-2.69 |
| I.2-271 | Ph | H | $CH_2$ | $CH_2$ | Q-2.72 |
| I.2-272 | Ph | H | $CH_2$ | $CH_2$ | Q-2.73 |
| I.2-273 | Ph | H | $CH_2$ | $CH_2$ | Q-2.74 |
| I.2-274 | Ph | H | $CH_2$ | $CH_2$ | Q-2.80 |
| I.2-275 | Ph | H | $CH_2$ | $CH_2$ | Q-2.105 |
| I.2-276 | Ph | H | $CH_2$ | $CH_2$ | Q-2.106 |
| I.2-277 | Ph | H | $CH_2$ | $CH_2$ | Q-2.108 |
| I.2-278 | Ph | H | $CH_2$ | $CH_2$ | Q-2.145 |
| I.2-279 | Ph | H | $CH_2$ | $CH_2$ | Q-2.146 |
| I.2-280 | Ph | H | $CH_2$ | $CH_2$ | Q-2.147 |
| I.2-281 | Ph | H | $CH_2$ | $CH_2$ | Q-2.161 |
| I.2-282 | Ph | H | $CH_2$ | $CH_2$ | Q-2.162 |
| I.2-283 | Ph | H | $CH_2$ | $CH_2$ | Q-2.163 |
| I.2-284 | Ph | H | $CH_2$ | $CH_2$ | Q-2.164 |
| I.2-285 | Ph | H | $CH_2$ | $CH_2$ | Q-2.165 |
| I.2-286 | Ph | H | $CH_2$ | $CH_2$ | Q-2.167 |
| I.2-287 | Ph | H | $CH_2$ | $CH_2$ | Q-2.168 |
| I.2-288 | Ph | H | $CH_2$ | $CH_2$ | Q-2.169 |
| I.2-289 | Ph | H | $CH_2$ | $CH_2$ | Q-2.172 |
| I.2-290 | Ph | H | $CH_2$ | $CH_2$ | Q-2.173 |
| I.2-291 | Ph | H | $CH_2$ | $CH_2$ | Q-2.174 |
| I.2-292 | Ph | H | $CH_2$ | $CH_2$ | Q-2.180 |
| I.2-293 | Ph | H | $CH_2$ | $CH_2$ | Q-2.185 |
| I.2-294 | Ph | H | $CH_2$ | $CH_2$ | Q-2.189 |
| I.2-295 | Ph | H | $CH_2$ | $CH_2$ | Q-2.190 |
| I.2-296 | Ph | H | $CH_2$ | $CH_2$ | Q-2.201 |
| I.2-297 | Ph | H | $CH_2$ | $CH_2$ | Q-2.202 |
| I.2-298 | Ph | H | $CH_2$ | $CH_2$ | Q-2.203 |
| I.2-299 | Ph | H | $CH_2$ | $CH_2$ | Q-2.204 |
| I.2-300 | Ph | H | $CH_2$ | $CH_2$ | Q-2.205 |
| I.2-301 | $CH_3$ | $CH_3$ | $CH_2$ | $CH_2$ | Q-1.1 |
| I.2-302 | $CH_3$ | $CH_3$ | $CH_2$ | $CH_2$ | Q-1.2 |
| I.2-303 | $CH_3$ | $CH_3$ | $CH_2$ | $CH_2$ | Q-1.3 |
| I.2-304 | $CH_3$ | $CH_3$ | $CH_2$ | $CH_2$ | Q-1.16 |
| I.2-305 | $CH_3$ | $CH_3$ | $CH_2$ | $CH_2$ | Q-1.17 |
| I.2-306 | $CH_3$ | $CH_3$ | $CH_2$ | $CH_2$ | Q-1.18 |
| I.2-307 | $CH_3$ | $CH_3$ | $CH_2$ | $CH_2$ | Q-1.136 |
| I.2-308 | $CH_3$ | $CH_3$ | $CH_2$ | $CH_2$ | Q-1.137 |
| I.2-309 | $CH_3$ | $CH_3$ | $CH_2$ | $CH_2$ | Q-1.138 |
| I.2-310 | $CH_3$ | $CH_3$ | $CH_2$ | $CH_2$ | Q-1.166 |
| I.2-311 | $CH_3$ | $CH_3$ | $CH_2$ | $CH_2$ | Q-1.167 |
| I.2-312 | $CH_3$ | $CH_3$ | $CH_2$ | $CH_2$ | Q-1.168 |
| I.2-313 | $CH_3$ | $CH_3$ | $CH_2$ | $CH_2$ | Q-1.201 |
| I.2-314 | $CH_3$ | $CH_3$ | $CH_2$ | $CH_2$ | Q-1.202 |
| I.2-315 | $CH_3$ | $CH_3$ | $CH_2$ | $CH_2$ | Q-1.203 |
| I.2-316 | $CH_3$ | $CH_3$ | $CH_2$ | $CH_2$ | Q-1.206 |
| I.2-317 | $CH_3$ | $CH_3$ | $CH_2$ | $CH_2$ | Q-1.207 |
| I.2-318 | $CH_3$ | $CH_3$ | $CH_2$ | $CH_2$ | Q-1.210 |
| I.2-319 | $CH_3$ | $CH_3$ | $CH_2$ | $CH_2$ | Q-1.211 |
| I.2-320 | $CH_3$ | $CH_3$ | $CH_2$ | $CH_2$ | Q-1.213 |
| I.2-321 | $CH_3$ | C(=O)$CH_3$ | $CH_2$ | $CH_2$ | Q-1.1 |
| I.2-322 | $CH_3$ | C(=O)$CH_3$ | $CH_2$ | $CH_2$ | Q-1.2 |
| I.2-323 | $CH_3$ | C(=O)$CH_3$ | $CH_2$ | $CH_2$ | Q-1.3 |

TABLE 2-continued

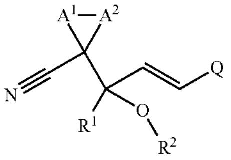

(I)

The Q radicals here correspond to the structures defined as particularly preferred earlier in the document

| No. | $R^1$ | $R^2$ | $A^1$ | $A^2$ | Q |
|---|---|---|---|---|---|
| I.2-324 | $CH_3$ | C(=O)$CH_3$ | $CH_2$ | $CH_2$ | Q-1.16 |
| I.2-325 | $CH_3$ | C(=O)$CH_3$ | $CH_2$ | $CH_2$ | Q-1.17 |
| I.2-326 | $CH_3$ | C(=O)$CH_3$ | $CH_2$ | $CH_2$ | Q-1.18 |
| I.2-327 | $CH_3$ | C(=O)$CH_3$ | $CH_2$ | $CH_2$ | Q-1.136 |
| I.2-328 | $CH_3$ | C(=O)$CH_3$ | $CH_2$ | $CH_2$ | Q-1.137 |
| I.2-329 | $CH_3$ | C(=O)$CH_3$ | $CH_2$ | $CH_2$ | Q-1.138 |
| I.2-330 | $CH_3$ | C(=O)$CH_3$ | $CH_2$ | $CH_2$ | Q-1.166 |
| I.2-331 | $CH_3$ | C(=O)$CH_3$ | $CH_2$ | $CH_2$ | Q-1.167 |
| I.2-332 | $CH_3$ | C(=O)$CH_3$ | $CH_2$ | $CH_2$ | Q-1.168 |
| I.2-333 | $CH_3$ | C(=O)$CH_3$ | $CH_2$ | $CH_2$ | Q-1.201 |
| I.2-334 | $CH_3$ | C(=O)$CH_3$ | $CH_2$ | $CH_2$ | Q-1.202 |
| I.2-335 | $CH_3$ | C(=O)$CH_3$ | $CH_2$ | $CH_2$ | Q-1.203 |
| I.2-336 | $CH_3$ | C(=O)$CH_3$ | $CH_2$ | $CH_2$ | Q-1.206 |
| I.2-337 | $CH_3$ | C(=O)$CH_3$ | $CH_2$ | $CH_2$ | Q-1.207 |
| I.2-338 | $CH_3$ | C(=O)$CH_3$ | $CH_2$ | $CH_2$ | Q-1.210 |
| I.2-339 | $CH_3$ | C(=O)$CH_3$ | $CH_2$ | $CH_2$ | Q-1.211 |
| I.2-340 | $CH_3$ | C(=O)$CH_3$ | $CH_2$ | $CH_2$ | Q-1.213 |
| I.2-341 | $CH_3$ | $SiEt_3$ | $CH_2$ | $CH_2$ | Q-1.1 |
| I.2-342 | $CH_3$ | $SiEt_3$ | $CH_2$ | $CH_2$ | Q-1.2 |
| I.2-343 | $CH_3$ | $SiEt_3$ | $CH_2$ | $CH_2$ | Q-1.3 |
| I.2-344 | $CH_3$ | $SiEt_3$ | $CH_2$ | $CH_2$ | Q-1.16 |
| I.2-345 | $CH_3$ | $SiEt_3$ | $CH_2$ | $CH_2$ | Q-1.17 |
| I.2-346 | $CH_3$ | $SiEt_3$ | $CH_2$ | $CH_2$ | Q-1.18 |
| I.2-347 | $CH_3$ | $SiEt_3$ | $CH_2$ | $CH_2$ | Q-1.136 |
| I.2-348 | $CH_3$ | $SiEt_3$ | $CH_2$ | $CH_2$ | Q-1.137 |
| I.2-349 | $CH_3$ | $SiEt_3$ | $CH_2$ | $CH_2$ | Q-1.138 |
| I.2-350 | $CH_3$ | $SiEt_3$ | $CH_2$ | $CH_2$ | Q-1.166 |
| I.2-351 | $CH_3$ | $SiEt_3$ | $CH_2$ | $CH_2$ | Q-1.167 |
| I.2-352 | $CH_3$ | $SiEt_3$ | $CH_2$ | $CH_2$ | Q-1.168 |
| I.2-353 | $CH_3$ | $SiEt_3$ | $CH_2$ | $CH_2$ | Q-1.201 |
| I.2-354 | $CH_3$ | $SiEt_3$ | $CH_2$ | $CH_2$ | Q-1.202 |
| I.2-355 | $CH_3$ | $SiEt_3$ | $CH_2$ | $CH_2$ | Q-1.203 |
| I.2-356 | $CH_3$ | $SiEt_3$ | $CH_2$ | $CH_2$ | Q-1.206 |
| I.2-357 | $CH_3$ | $SiEt_3$ | $CH_2$ | $CH_2$ | Q-1.207 |
| I.2-358 | $CH_3$ | $SiEt_3$ | $CH_2$ | $CH_2$ | Q-1.210 |
| I.2-359 | $CH_3$ | $SiEt_3$ | $CH_2$ | $CH_2$ | Q-1.211 |
| I.2-360 | $CH_3$ | $SiEt_3$ | $CH_2$ | $CH_2$ | Q-1.213 |
| I.2-361 | Ph | $CH_3$ | $CH_2$ | $CH_2$ | Q-1.1 |
| I.2-362 | Ph | $CH_3$ | $CH_2$ | $CH_2$ | Q-1.2 |
| I.2-363 | Ph | $CH_3$ | $CH_2$ | $CH_2$ | Q-1.3 |
| I.2-364 | Ph | $CH_3$ | $CH_2$ | $CH_2$ | Q-1.16 |
| I.2-365 | Ph | $CH_3$ | $CH_2$ | $CH_2$ | Q-1.17 |
| I.2-366 | Ph | $CH_3$ | $CH_2$ | $CH_2$ | Q-1.18 |
| I.2-367 | Ph | $CH_3$ | $CH_2$ | $CH_2$ | Q-1.136 |
| I.2-368 | Ph | $CH_3$ | $CH_2$ | $CH_2$ | Q-1.137 |
| I.2-369 | Ph | $CH_3$ | $CH_2$ | $CH_2$ | Q-1.138 |
| I.2-370 | Ph | $CH_3$ | $CH_2$ | $CH_2$ | Q-1.166 |
| I.2-371 | Ph | $CH_3$ | $CH_2$ | $CH_2$ | Q-1.167 |
| I.2-372 | Ph | $CH_3$ | $CH_2$ | $CH_2$ | Q-1.168 |
| I.2-373 | Ph | $CH_3$ | $CH_2$ | $CH_2$ | Q-1.201 |
| I.2-374 | Ph | $CH_3$ | $CH_2$ | $CH_2$ | Q-1.202 |
| I.2-375 | Ph | $CH_3$ | $CH_2$ | $CH_2$ | Q-1.203 |
| I.2-376 | Ph | $CH_3$ | $CH_2$ | $CH_2$ | Q-1.206 |
| I.2-377 | Ph | $CH_3$ | $CH_2$ | $CH_2$ | Q-1.207 |
| I.2-378 | Ph | $CH_3$ | $CH_2$ | $CH_2$ | Q-1.210 |
| I.2-379 | Ph | $CH_3$ | $CH_2$ | $CH_2$ | Q-1.211 |
| I.2-380 | Ph | $CH_3$ | $CH_2$ | $CH_2$ | Q-1.213 |
| I.2-381 | Ph | C(=O)$CH_3$ | $CH_2$ | $CH_2$ | Q-1.1 |
| I.2-382 | Ph | C(=O)$CH_3$ | $CH_2$ | $CH_2$ | Q-1.2 |
| I.2-383 | Ph | C(=O)$CH_3$ | $CH_2$ | $CH_2$ | Q-1.3 |
| I.2-384 | Ph | C(=O)$CH_3$ | $CH_2$ | $CH_2$ | Q-1.16 |
| I.2-385 | Ph | C(=O)$CH_3$ | $CH_2$ | $CH_2$ | Q-1.17 |
| I.2-386 | Ph | C(=O)$CH_3$ | $CH_2$ | $CH_2$ | Q-1.18 |
| I.2-387 | Ph | C(=O)$CH_3$ | $CH_2$ | $CH_2$ | Q-1.136 |

TABLE 2-continued

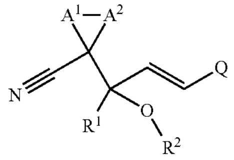

(I)

The Q radicals here correspond to the structures defined as particularly preferred earlier in the document

| No. | $R^1$ | $R^2$ | $A^1$ | $A^2$ | Q |
|---|---|---|---|---|---|
| I.2-388 | Ph | $C(=O)CH_3$ | $CH_2$ | $CH_2$ | Q-1.137 |
| I.2-389 | Ph | $C(=O)CH_3$ | $CH_2$ | $CH_2$ | Q-1.138 |
| I.2-390 | Ph | $C(=O)CH_3$ | $CH_2$ | $CH_2$ | Q-1.166 |
| I.2-391 | Ph | $C(=O)CH_3$ | $CH_2$ | $CH_2$ | Q-1.167 |
| I.2-392 | Ph | $C(=O)CH_3$ | $CH_2$ | $CH_2$ | Q-1.168 |
| I.2-393 | Ph | $C(=O)CH_3$ | $CH_2$ | $CH_2$ | Q-1.201 |
| I.2-394 | Ph | $C(=O)CH_3$ | $CH_2$ | $CH_2$ | Q-1.202 |
| I.2-395 | Ph | $C(=O)CH_3$ | $CH_2$ | $CH_2$ | Q-1.203 |
| I.2-396 | Ph | $C(=O)CH_3$ | $CH_2$ | $CH_2$ | Q-1.206 |
| I.2-397 | Ph | $C(=O)CH_3$ | $CH_2$ | $CH_2$ | Q-1.207 |
| I.2-398 | Ph | $C(=O)CH_3$ | $CH_2$ | $CH_2$ | Q-1.210 |
| I.2-399 | Ph | $C(=O)CH_3$ | $CH_2$ | $CH_2$ | Q-1.211 |
| I.2-400 | Ph | $C(=O)CH_3$ | $CH_2$ | $CH_2$ | Q-1.213 |
| I.2-401 | Ph | $SiEt_3$ | $CH_2$ | $CH_2$ | Q-1.1 |
| I.2-402 | Ph | $SiEt_3$ | $CH_2$ | $CH_2$ | Q-1.2 |
| I.2-403 | Ph | $SiEt_3$ | $CH_2$ | $CH_2$ | Q-1.3 |
| I.2-404 | Ph | $SiEt_3$ | $CH_2$ | $CH_2$ | Q-1.16 |
| I.2-405 | Ph | $SiEt_3$ | $CH_2$ | $CH_2$ | Q-1.17 |
| I.2-406 | Ph | $SiEt_3$ | $CH_2$ | $CH_2$ | Q-1.18 |
| I.2-407 | Ph | $SiEt_3$ | $CH_2$ | $CH_2$ | Q-1.136 |
| I.2-408 | Ph | $SiEt_3$ | $CH_2$ | $CH_2$ | Q-1.137 |
| I.2-409 | Ph | $SiEt_3$ | $CH_2$ | $CH_2$ | Q-1.138 |
| I.2-410 | Ph | $SiEt_3$ | $CH_2$ | $CH_2$ | Q-1.166 |
| I.2-411 | Ph | $SiEt_3$ | $CH_2$ | $CH_2$ | Q-1.167 |
| I.2-412 | Ph | $SiEt_3$ | $CH_2$ | $CH_2$ | Q-1.168 |
| I.2-413 | Ph | $SiEt_3$ | $CH_2$ | $CH_2$ | Q-1.201 |
| I.2-414 | Ph | $SiEt_3$ | $CH_2$ | $CH_2$ | Q-1.202 |
| I.2-415 | Ph | $SiEt_3$ | $CH_2$ | $CH_2$ | Q-1.203 |
| I.2-416 | Ph | $SiEt_3$ | $CH_2$ | $CH_2$ | Q-1.206 |
| I.2-417 | Ph | $SiEt_3$ | $CH_2$ | $CH_2$ | Q-1.207 |
| I.2-418 | Ph | $SiEt_3$ | $CH_2$ | $CH_2$ | Q-1.210 |
| I.2-419 | Ph | $SiEt_3$ | $CH_2$ | $CH_2$ | Q-1.211 |
| I.2-420 | Ph | $SiEt_3$ | $CH_2$ | $CH_2$ | Q-1.213 |
| I.2-421 | i-Pr | $CH_3$ | $CH_2$ | $CH_2$ | Q-1.1 |
| I.2-422 | i-Pr | $CH_3$ | $CH_2$ | $CH_2$ | Q-1.2 |
| I.2-423 | i-Pr | $CH_3$ | $CH_2$ | $CH_2$ | Q-1.3 |
| I.2-424 | i-Pr | $CH_3$ | $CH_2$ | $CH_2$ | Q-1.16 |
| I.2-425 | i-Pr | $CH_3$ | $CH_2$ | $CH_2$ | Q-1.17 |
| I.2-426 | i-Pr | $CH_3$ | $CH_2$ | $CH_2$ | Q-1.18 |
| I.2-427 | i-Pr | $CH_3$ | $CH_2$ | $CH_2$ | Q-1.136 |
| I.2-428 | i-Pr | $CH_3$ | $CH_2$ | $CH_2$ | Q-1.137 |
| I.2-429 | i-Pr | $CH_3$ | $CH_2$ | $CH_2$ | Q-1.138 |
| I.2-430 | i-Pr | $CH_3$ | $CH_2$ | $CH_2$ | Q-1.166 |
| I.2-431 | i-Pr | $CH_3$ | $CH_2$ | $CH_2$ | Q-1.167 |
| I.2-432 | i-Pr | $CH_3$ | $CH_2$ | $CH_2$ | Q-1.168 |
| I.2-433 | i-Pr | $CH_3$ | $CH_2$ | $CH_2$ | Q-1.201 |
| I.2-434 | i-Pr | $CH_3$ | $CH_2$ | $CH_2$ | Q-1.202 |
| I.2-435 | i-Pr | $CH_3$ | $CH_2$ | $CH_2$ | Q-1.203 |
| I.2-436 | i-Pr | $CH_3$ | $CH_2$ | $CH_2$ | Q-1.206 |
| I.2-437 | i-Pr | $CH_3$ | $CH_2$ | $CH_2$ | Q-1.207 |
| I.2-438 | i-Pr | $CH_3$ | $CH_2$ | $CH_2$ | Q-1.210 |
| I.2-439 | i-Pr | $CH_3$ | $CH_2$ | $CH_2$ | Q-1.211 |
| I.2-440 | i-Pr | $CH_3$ | $CH_2$ | $CH_2$ | Q-1.213 |
| I.2-441 | i-Pr | $C(=O)CH_3$ | $CH_2$ | $CH_2$ | Q-1.1 |
| I.2-442 | i-Pr | $C(=O)CH_3$ | $CH_2$ | $CH_2$ | Q-1.2 |
| I.2-443 | i-Pr | $C(=O)CH_3$ | $CH_2$ | $CH_2$ | Q-1.3 |
| I.2-444 | i-Pr | $C(=O)CH_3$ | $CH_2$ | $CH_2$ | Q-1.16 |
| I.2-445 | i-Pr | $C(=O)CH_3$ | $CH_2$ | $CH_2$ | Q-1.17 |
| I.2-446 | i-Pr | $C(=O)CH_3$ | $CH_2$ | $CH_2$ | Q-1.18 |
| I.2-447 | i-Pr | $C(=O)CH_3$ | $CH_2$ | $CH_2$ | Q-1.136 |
| I.2-448 | i-Pr | $C(=O)CH_3$ | $CH_2$ | $CH_2$ | Q-1.137 |
| I.2-449 | i-Pr | $C(=O)CH_3$ | $CH_2$ | $CH_2$ | Q-1.138 |
| I.2-450 | i-Pr | $C(=O)CH_3$ | $CH_2$ | $CH_2$ | Q-1.166 |
| I.2-451 | i-Pr | $C(=O)CH_3$ | $CH_2$ | $CH_2$ | Q-1.167 |

TABLE 2-continued

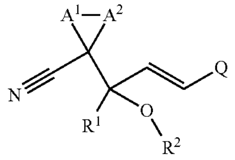

(I)

The Q radicals here correspond to the structures defined as particularly preferred earlier in the document

| No. | $R^1$ | $R^2$ | $A^1$ | $A^2$ | Q |
|---|---|---|---|---|---|
| I.2-452 | i-Pr | $C(=O)CH_3$ | $CH_2$ | $CH_2$ | Q-1.168 |
| I.2-453 | i-Pr | $C(=O)CH_3$ | $CH_2$ | $CH_2$ | Q-1.201 |
| I.2-454 | i-Pr | $C(=O)CH_3$ | $CH_2$ | $CH_2$ | Q-1.202 |
| I.2-455 | i-Pr | $C(=O)CH_3$ | $CH_2$ | $CH_2$ | Q-1.203 |
| I.2-456 | i-Pr | $C(=O)CH_3$ | $CH_2$ | $CH_2$ | Q-1.206 |
| I.2-457 | i-Pr | $C(=O)CH_3$ | $CH_2$ | $CH_2$ | Q-1.207 |
| I.2-458 | i-Pr | $C(=O)CH_3$ | $CH_2$ | $CH_2$ | Q-1.210 |
| I.2-459 | i-Pr | $C(=O)CH_3$ | $CH_2$ | $CH_2$ | Q-1.211 |
| I.2-460 | i-Pr | $C(=O)CH_3$ | $CH_2$ | $CH_2$ | Q-1.213 |
| I.2-461 | i-Pr | $SiEt_3$ | $CH_2$ | $CH_2$ | Q-1.1 |
| I.2-462 | i-Pr | $SiEt_3$ | $CH_2$ | $CH_2$ | Q-1.2 |
| I.2-463 | i-Pr | $SiEt_3$ | $CH_2$ | $CH_2$ | Q-1.3 |
| I.2-464 | i-Pr | $SiEt_3$ | $CH_2$ | $CH_2$ | Q-1.16 |
| I.2-465 | i-Pr | $SiEt_3$ | $CH_2$ | $CH_2$ | Q-1.17 |
| I.2-466 | i-Pr | $SiEt_3$ | $CH_2$ | $CH_2$ | Q-1.18 |
| I.2-467 | i-Pr | $SiEt_3$ | $CH_2$ | $CH_2$ | Q-1.136 |
| I.2-468 | i-Pr | $SiEt_3$ | $CH_2$ | $CH_2$ | Q-1.137 |
| I.2-469 | i-Pr | $SiEt_3$ | $CH_2$ | $CH_2$ | Q-1.138 |
| I.2-470 | i-Pr | $SiEt_3$ | $CH_2$ | $CH_2$ | Q-1.166 |
| I.2-471 | i-Pr | $SiEt_3$ | $CH_2$ | $CH_2$ | Q-1.167 |
| I.2-472 | i-Pr | $SiEt_3$ | $CH_2$ | $CH_2$ | Q-1.168 |
| I.2-473 | i-Pr | $SiEt_3$ | $CH_2$ | $CH_2$ | Q-1.201 |
| I.2-474 | i-Pr | $SiEt_3$ | $CH_2$ | $CH_2$ | Q-1.202 |
| I.2-475 | i-Pr | $SiEt_3$ | $CH_2$ | $CH_2$ | Q-1.203 |
| I.2-476 | i-Pr | $SiEt_3$ | $CH_2$ | $CH_2$ | Q-1.206 |
| I.2-477 | i-Pr | $SiEt_3$ | $CH_2$ | $CH_2$ | Q-1.207 |
| I.2-478 | i-Pr | $SiEt_3$ | $CH_2$ | $CH_2$ | Q-1.210 |
| I.2-479 | i-Pr | $SiEt_3$ | $CH_2$ | $CH_2$ | Q-1.211 |
| I.2-480 | i-Pr | $SiEt_3$ | $CH_2$ | $CH_2$ | Q-1.213 |
| I.2-481 | i-Pr | $CH_3$ | CHF | $CH_2$ | Q-1.3 |
| I.2-482 | i-Pr | $CH_3$ | CHF | $CH_2$ | Q-1.168 |
| I.2-483 | i-Pr | $CH_3$ | CHF | $CH_2$ | Q-1.203 |
| I.2-484 | Ph | $CH_3$ | CHF | $CH_2$ | Q-1.3 |
| I.2-485 | Ph | $CH_3$ | CHF | $CH_2$ | Q-1.168 |
| I.2-486 | Ph | $CH_3$ | CHF | $CH_2$ | Q-1.203 |
| I.2-487 | $CH_3$ | $CH_3$ | CHF | $CH_2$ | Q-1.3 |
| I.2-488 | $CH_3$ | $CH_3$ | CHF | $CH_2$ | Q-1.168 |
| I.2-489 | $CH_3$ | $CH_3$ | CHF | $CH_2$ | Q-1.203 |
| I.2-490 | i-Pr | $CH_3$ | $CH(CH_3)$ | $CH_2$ | Q-1.3 |
| I.2-491 | i-Pr | $CH_3$ | $CH(CH_3)$ | $CH_2$ | Q-1.168 |
| I.2-492 | i-Pr | $CH_3$ | $CH(CH_3)$ | $CH_2$ | Q-1.203 |
| I.2-493 | Ph | $CH_3$ | $CH(CH_3)$ | $CH_2$ | Q-1.3 |
| I.2-494 | Ph | $CH_3$ | $CH(CH_3)$ | $CH_2$ | Q-1.168 |
| I.2-495 | Ph | $CH_3$ | $CH(CH_3)$ | $CH_2$ | Q-1.203 |
| I.2-496 | $CH_3$ | $CH_3$ | $CH(CH_3)$ | $CH_2$ | Q-1.3 |
| I.2-497 | $CH_3$ | $CH_3$ | $CH(CH_3)$ | $CH_2$ | Q-1.168 |
| I.2-498 | $CH_3$ | $CH_3$ | $CH(CH_3)$ | $CH_2$ | Q-1.203 |
| I.2-499 | i-Pr | $CH_3$ | CH(i-Pr) | $CH_2$ | Q-1.168 |
| I.2-500 | i-Pr | $CH_3$ | CH(i-Pr) | $CH_2$ | Q-1.203 |
| I.2-501 | $CH_3$ | H | $CH_2$ | $CH_2$ | Q-1.6 |
| I.2-502 | $CH_3$ | H | $CH_2$ | $CH_2$ | Q-1.10 |
| I.2-503 | $CH_3$ | H | $CH_2$ | $CH_2$ | Q-1.11 |
| I.2-504 | $CH_3$ | H | $CH_2$ | $CH_2$ | Q-1.21 |
| I.2-505 | $CH_3$ | H | $CH_2$ | $CH_2$ | Q-1.96 |
| I.2-506 | $CH_3$ | H | $CH_2$ | $CH_2$ | Q-1.141 |
| I.2-507 | i-Pr | H | $CH_2$ | $CH_2$ | Q-1.6 |
| I.2-508 | i-Pr | H | $CH_2$ | $CH_2$ | Q-1.10 |
| I.2-509 | i-Pr | H | $CH_2$ | $CH_2$ | Q-1.11 |
| I.2-510 | i-Pr | H | $CH_2$ | $CH_2$ | Q-1.21 |
| I.2-511 | i-Pr | H | $CH_2$ | $CH_2$ | Q-1.96 |
| I.2-512 | i-Pr | H | $CH_2$ | $CH_2$ | Q-1.141 |
| I.2-513 | Ph | H | $CH_2$ | $CH_2$ | Q-1.6 |
| I.2-514 | Ph | H | $CH_2$ | $CH_2$ | Q-1.10 |
| I.2-515 | Ph | H | $CH_2$ | $CH_2$ | Q-1.11 |

TABLE 2-continued (I)

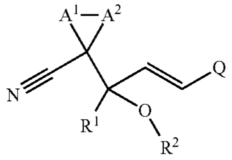

The Q radicals here correspond to the structures defined as particularly preferred earlier in the document

| No. | $R^1$ | $R^2$ | $A^1$ | $A^2$ | Q |
|---|---|---|---|---|---|
| I.2-516 | Ph | H | $CH_2$ | $CH_2$ | Q-1.21 |
| I.2-517 | Ph | H | $CH_2$ | $CH_2$ | Q-1.96 |
| I.2-518 | Ph | H | $CH_2$ | $CH_2$ | Q-1.141 |
| I.2-519 | c-Pr | H | $CH_2$ | $CH_2$ | Q-1.6 |
| I.2-520 | c-Pr | H | $CH_2$ | $CH_2$ | Q-1.10 |
| I.2-521 | c-Pr | H | $CH_2$ | $CH_2$ | Q-1.11 |
| I.2-522 | c-Pr | H | $CH_2$ | $CH_2$ | Q-1.21 |
| I.2-523 | c-Pr | H | $CH_2$ | $CH_2$ | Q-1.96 |
| I.2-524 | c-Pr | H | $CH_2$ | $CH_2$ | Q-1.141 |
| I.2-525 | c-Pr | H | $CH_2$ | $CH_2$ | Q-1.1 |
| I.2-526 | c-Pr | H | $CH_2$ | $CH_2$ | Q-1.2 |
| I.2-527 | c-Pr | H | $CH_2$ | $CH_2$ | Q-1.3 |
| I.2-528 | c-Pr | H | $CH_2$ | $CH_2$ | Q-1.16 |
| I.2-529 | c-Pr | H | $CH_2$ | $CH_2$ | Q-1.17 |
| I.2-530 | c-Pr | H | $CH_2$ | $CH_2$ | Q-1.18 |
| I.2-531 | c-Pr | H | $CH_2$ | $CH_2$ | Q-1.91 |
| I.2-532 | c-Pr | H | $CH_2$ | $CH_2$ | Q-1.92 |
| I.2-533 | c-Pr | H | $CH_2$ | $CH_2$ | Q-1.136 |
| I.2-534 | c-Pr | H | $CH_2$ | $CH_2$ | Q-1.137 |
| I.2-535 | c-Pr | H | $CH_2$ | $CH_2$ | Q-1.138 |
| I.2-536 | c-Pr | H | $CH_2$ | $CH_2$ | Q-1.166 |
| I.2-537 | c-Pr | H | $CH_2$ | $CH_2$ | Q-1.167 |
| I.2-538 | c-Pr | H | $CH_2$ | $CH_2$ | Q-1.168 |
| I.2-539 | c-Pr | H | $CH_2$ | $CH_2$ | Q-1.171 |
| I.2-540 | c-Pr | H | $CH_2$ | $CH_2$ | Q-1.172 |
| I.2-541 | c-Pr | H | $CH_2$ | $CH_2$ | Q-1.173 |
| I.2-542 | c-Pr | H | $CH_2$ | $CH_2$ | Q-1.201 |
| I.2-543 | c-Pr | H | $CH_2$ | $CH_2$ | Q-1.202 |
| I.2-544 | c-Pr | H | $CH_2$ | $CH_2$ | Q-1.203 |
| I.2-545 | c-Pr | H | $CH_2$ | $CH_2$ | Q-1.206 |
| I.2-546 | c-Pr | H | $CH_2$ | $CH_2$ | Q-1.210 |
| I.2-547 | c-Pr | H | $CH_2$ | $CH_2$ | Q-2.1 |
| I.2-548 | c-Pr | H | $CH_2$ | $CH_2$ | Q-2.5 |
| I.2-559 | c-Bu | H | $CH_2$ | $CH_2$ | Q-1.6 |
| I.2-550 | c-Bu | H | $CH_2$ | $CH_2$ | Q-1.10 |
| I.2-551 | c-Bu | H | $CH_2$ | $CH_2$ | Q-1.11 |
| I.2-552 | c-Bu | H | $CH_2$ | $CH_2$ | Q-1.21 |
| I.2-553 | c-Bu | H | $CH_2$ | $CH_2$ | Q-1.96 |
| I.2-554 | c-Bu | H | $CH_2$ | $CH_2$ | Q-1.141 |
| I.2-555 | c-Bu | H | $CH_2$ | $CH_2$ | Q-1.1 |
| I.2-556 | c-Bu | H | $CH_2$ | $CH_2$ | Q-1.2 |
| I.2-557 | c-Bu | H | $CH_2$ | $CH_2$ | Q-1.3 |
| I.2-558 | c-Bu | H | $CH_2$ | $CH_2$ | Q-1.16 |
| I.2-559 | c-Bu | H | $CH_2$ | $CH_2$ | Q-1.17 |
| I.2-560 | c-Bu | H | $CH_2$ | $CH_2$ | Q-1.18 |
| I.2-561 | c-Bu | H | $CH_2$ | $CH_2$ | Q-1.91 |
| I.2-562 | c-Bu | H | $CH_2$ | $CH_2$ | Q-1.92 |
| I.2-563 | c-Bu | H | $CH_2$ | $CH_2$ | Q-1.136 |
| I.2-564 | c-Bu | H | $CH_2$ | $CH_2$ | Q-1.137 |
| I.2-565 | c-Bu | H | $CH_2$ | $CH_2$ | Q-1.138 |
| I.2-566 | c-Bu | H | $CH_2$ | $CH_2$ | Q-1.166 |
| I.2-567 | c-Bu | H | $CH_2$ | $CH_2$ | Q-1.167 |
| I.2-568 | c-Bu | H | $CH_2$ | $CH_2$ | Q-1.168 |
| I.2-569 | c-Bu | H | $CH_2$ | $CH_2$ | Q-1.171 |
| I.2-570 | c-Bu | H | $CH_2$ | $CH_2$ | Q-1.172 |
| I.2-571 | c-Bu | H | $CH_2$ | $CH_2$ | Q-1.173 |
| I.2-572 | c-Bu | H | $CH_2$ | $CH_2$ | Q-1.201 |
| I.2-573 | c-Bu | H | $CH_2$ | $CH_2$ | Q-1.202 |
| I.2-574 | c-Bu | H | $CH_2$ | $CH_2$ | Q-1.203 |
| I.2-575 | c-Bu | H | $CH_2$ | $CH_2$ | Q-1.206 |
| I.2-576 | c-Bu | H | $CH_2$ | $CH_2$ | Q-1.210 |
| I.2-577 | c-Bu | H | $CH_2$ | $CH_2$ | Q-2.1 |
| I.2-578 | c-Bu | H | $CH_2$ | $CH_2$ | Q-2.5 |
| I.2-579 | c-Hex | H | $CH_2$ | $CH_2$ | Q-1.2 |

TABLE 2-continued (I)

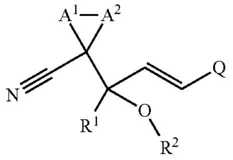

The Q radicals here correspond to the structures defined as particularly preferred earlier in the document

| No. | $R^1$ | $R^2$ | $A^1$ | $A^2$ | Q |
|---|---|---|---|---|---|
| I.2-580 | c-Hex | H | $CH_2$ | $CH_2$ | Q-1.10 |
| I.2-581 | c-Hex | H | $CH_2$ | $CH_2$ | Q-1.137 |
| I.2-582 | c-Hex | H | $CH_2$ | $CH_2$ | Q-1.141 |
| I.2-583 | 1-Ethylpropyl | H | $CH_2$ | $CH_2$ | Q-1.2 |
| I.2-584 | 1-Ethylpropyl | H | $CH_2$ | $CH_2$ | Q-1.10 |
| I.2-585 | 1-Ethylpropyl | H | $CH_2$ | $CH_2$ | Q-1.137 |
| I.2-586 | 1-Ethylpropyl | H | $CH_2$ | $CH_2$ | Q-1.141 |
| I.2-587 | Adamantyl | H | $CH_2$ | $CH_2$ | Q-1.2 |
| I.2-588 | Adamantyl | H | $CH_2$ | $CH_2$ | Q-1.10 |
| I.2-589 | Adamantyl | H | $CH_2$ | $CH_2$ | Q-1.137 |
| I.2-590 | Adamantyl | H | $CH_2$ | $CH_2$ | Q-1.141 |
| I.2-591 | 4-$CH_3$—Ph | H | $CH_2$ | $CH_2$ | Q-1.2 |
| I.2-592 | 4-$CH_3$—Ph | H | $CH_2$ | $CH_2$ | Q-1.10 |
| I.2-593 | 4-$CH_3$—Ph | H | $CH_2$ | $CH_2$ | Q-1.137 |
| I.2-594 | 4-$CH_3$—Ph | H | $CH_2$ | $CH_2$ | Q-1.141 |
| I.2-595 | 3-F—Ph | H | $CH_2$ | $CH_2$ | Q-1.2 |
| I.2-596 | 3-F—Ph | H | $CH_2$ | $CH_2$ | Q-1.10 |
| I.2-597 | 3-F—Ph | H | $CH_2$ | $CH_2$ | Q-1.137 |
| I.2-598 | 3-F—Ph | H | $CH_2$ | $CH_2$ | Q-1.141 |
| I.2-599 | c-Pent | H | $CH_2$ | $CH_2$ | Q-1.2 |
| I.2-600 | c-Pent | H | $CH_2$ | $CH_2$ | Q-1.10 |
| I.2-601 | c-Pent | H | $CH_2$ | $CH_2$ | Q-1.137 |
| I.2-602 | c-Pent | H | $CH_2$ | $CH_2$ | Q-1.141 |
| I.2-603 | t-Bu | H | $CH_2$ | $CH_2$ | Q-1.2 |
| I.2-604 | t-Bu | H | $CH_2$ | $CH_2$ | Q-1.10 |
| I.2-605 | t-Bu | H | $CH_2$ | $CH_2$ | Q-1.137 |
| I.2-606 | t-Bu | H | $CH_2$ | $CH_2$ | Q-1.141 |
| I.2-607 | 2-F—Ph | H | $CH_2$ | $CH_2$ | Q-1.2 |
| I.2-608 | 2-F—Ph | H | $CH_2$ | $CH_2$ | Q-1.10 |
| I.2-609 | 2-F—Ph | H | $CH_2$ | $CH_2$ | Q-1.137 |
| I.2-610 | 2-F—Ph | H | $CH_2$ | $CH_2$ | Q-1.141 |
| I.2-611 | 4-Cl—Ph | H | $CH_2$ | $CH_2$ | Q-1.2 |
| I.2-612 | 4-Cl—Ph | H | $CH_2$ | $CH_2$ | Q-1.10 |
| I.2-613 | 4-Cl—Ph | H | $CH_2$ | $CH_2$ | Q-1.137 |
| I.2-614 | 4-Cl—Ph | H | $CH_2$ | $CH_2$ | Q-1.141 |
| I.2-615 | 1-Ethylpropyl | H | $CH_2$ | $CH_2$ | Q-1.203 |
| I.2-616 | c-Hex | H | $CH_2$ | $CH_2$ | Q-1.203 |
| I.2-617 | 4-$CH_3$—Ph | H | $CH_2$ | $CH_2$ | Q-1.203 |
| I.2-618 | c-Pent | H | $CH_2$ | $CH_2$ | Q-1.138 |
| I.2-619 | t-Bu | H | $CH_2$ | $CH_2$ | Q-1.203 |
| I.2-620 | t-Bu | H | $CH_2$ | $CH_2$ | Q-1.138 |

TABLE 3

(I)

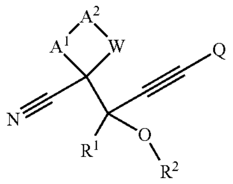

The Q radicals here correspond to the structures defined as particularly preferred earlier in the document

| No. | $R^1$ | $R^2$ | $A^1$ | $A^2$ | W | Q |
|---|---|---|---|---|---|---|
| I.3-1 | $CH_3$ | H | $CH_2$ | $CH_2$ | $CH_2$ | Q-1.1 |
| I.3-2 | $CH_3$ | H | $CH_2$ | $CH_2$ | $CH_2$ | Q-1.2 |

TABLE 3-continued

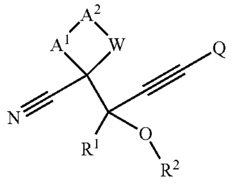

(I)

The Q radicals here correspond to the structures defined as particularly preferred earlier in the document

| No. | $R^1$ | $R^2$ | $A^1$ | $A^2$ | W | Q |
|---|---|---|---|---|---|---|
| I.3-3 | $CH_3$ | H | $CH_2$ | $CH_2$ | $CH_2$ | Q-1.3 |
| I.3-4 | $CH_3$ | H | $CH_2$ | $CH_2$ | $CH_2$ | Q-1.16 |
| I.3-5 | $CH_3$ | H | $CH_2$ | $CH_2$ | $CH_2$ | Q-1.17 |
| I.3-6 | $CH_3$ | H | $CH_2$ | $CH_2$ | $CH_2$ | Q-1.18 |
| I.3-7 | $CH_3$ | H | $CH_2$ | $CH_2$ | $CH_2$ | Q-1.91 |
| I.3-8 | $CH_3$ | H | $CH_2$ | $CH_2$ | $CH_2$ | Q-1.92 |
| I.3-9 | $CH_3$ | H | $CH_2$ | $CH_2$ | $CH_2$ | Q-1.93 |
| I.3-10 | $CH_3$ | H | $CH_2$ | $CH_2$ | $CH_2$ | Q-1.136 |
| I.3-11 | $CH_3$ | H | $CH_2$ | $CH_2$ | $CH_2$ | Q-1.137 |
| I.3-12 | $CH_3$ | H | $CH_2$ | $CH_2$ | $CH_2$ | Q-1.138 |
| I.3-13 | $CH_3$ | H | $CH_2$ | $CH_2$ | $CH_2$ | Q-1.166 |
| I.3-14 | $CH_3$ | H | $CH_2$ | $CH_2$ | $CH_2$ | Q-1.167 |
| I.3-15 | $CH_3$ | H | $CH_2$ | $CH_2$ | $CH_2$ | Q-1.168 |
| I.3-16 | $CH_3$ | H | $CH_2$ | $CH_2$ | $CH_2$ | Q-1.201 |
| I.3-17 | $CH_3$ | H | $CH_2$ | $CH_2$ | $CH_2$ | Q-1.202 |
| I.3-18 | $CH_3$ | H | $CH_2$ | $CH_2$ | $CH_2$ | Q-1.203 |
| I.3-19 | $CH_3$ | H | $CH_2$ | $CH_2$ | $CH_2$ | Q-1.246 |
| I.3-20 | $CH_3$ | H | $CH_2$ | $CH_2$ | $CH_2$ | Q-1.247 |
| I.3-21 | $CH_3$ | H | $CH_2$ | $CH_2$ | $CH_2$ | Q-1.248 |
| I.3-22 | i-Pr | H | $CH_2$ | $CH_2$ | $CH_2$ | Q-1.1 |
| I.3-23 | i-Pr | H | $CH_2$ | $CH_2$ | $CH_2$ | Q-1.2 |
| I.3-24 | i-Pr | H | $CH_2$ | $CH_2$ | $CH_2$ | Q-1.3 |
| I.3-25 | i-Pr | H | $CH_2$ | $CH_2$ | $CH_2$ | Q-1.16 |
| I.3-26 | i-Pr | H | $CH_2$ | $CH_2$ | $CH_2$ | Q-1.17 |
| I.3-27 | i-Pr | H | $CH_2$ | $CH_2$ | $CH_2$ | Q-1.18 |
| I.3-28 | i-Pr | H | $CH_2$ | $CH_2$ | $CH_2$ | Q-1.91 |
| I.3-29 | i-Pr | H | $CH_2$ | $CH_2$ | $CH_2$ | Q-1.92 |
| I.3-30 | i-Pr | H | $CH_2$ | $CH_2$ | $CH_2$ | Q-1.93 |
| I.3-31 | i-Pr | H | $CH_2$ | $CH_2$ | $CH_2$ | Q-1.136 |
| I.3-32 | i-Pr | H | $CH_2$ | $CH_2$ | $CH_2$ | Q-1.137 |
| I.3-33 | i-Pr | H | $CH_2$ | $CH_2$ | $CH_2$ | Q-1.138 |
| I.3-34 | i-Pr | H | $CH_2$ | $CH_2$ | $CH_2$ | Q-1.166 |
| I.3-35 | i-Pr | H | $CH_2$ | $CH_2$ | $CH_2$ | Q-1.167 |
| I.3-36 | i-Pr | H | $CH_2$ | $CH_2$ | $CH_2$ | Q-1.168 |
| I.3-37 | i-Pr | H | $CH_2$ | $CH_2$ | $CH_2$ | Q-1.201 |
| I.3-38 | i-Pr | H | $CH_2$ | $CH_2$ | $CH_2$ | Q-1.202 |
| I.3-39 | i-Pr | H | $CH_2$ | $CH_2$ | $CH_2$ | Q-1.203 |
| I.3-40 | i-Pr | H | $CH_2$ | $CH_2$ | $CH_2$ | Q-1.246 |
| I.3-41 | i-Pr | H | $CH_2$ | $CH_2$ | $CH_2$ | Q-1.247 |
| I.3-42 | i-Pr | H | $CH_2$ | $CH_2$ | $CH_2$ | Q-1.248 |
| I.3-43 | Ph | H | $CH_2$ | $CH_2$ | $CH_2$ | Q-1.1 |
| I.3-44 | Ph | H | $CH_2$ | $CH_2$ | $CH_2$ | Q-1.2 |
| I.3-45 | Ph | H | $CH_2$ | $CH_2$ | $CH_2$ | Q-1.3 |
| I.3-46 | Ph | H | $CH_2$ | $CH_2$ | $CH_2$ | Q-1.16 |
| I.3-47 | Ph | H | $CH_2$ | $CH_2$ | $CH_2$ | Q-1.17 |
| I.3-48 | Ph | H | $CH_2$ | $CH_2$ | $CH_2$ | Q-1.18 |
| I.3-49 | Ph | H | $CH_2$ | $CH_2$ | $CH_2$ | Q-1.91 |
| I.3-50 | Ph | H | $CH_2$ | $CH_2$ | $CH_2$ | Q-1.92 |
| I.3-51 | Ph | H | $CH_2$ | $CH_2$ | $CH_2$ | Q-1.93 |
| I.3-52 | Ph | H | $CH_2$ | $CH_2$ | $CH_2$ | Q-1.136 |
| I.3-53 | Ph | H | $CH_2$ | $CH_2$ | $CH_2$ | Q-1.137 |
| I.3-54 | Ph | H | $CH_2$ | $CH_2$ | $CH_2$ | Q-1.138 |
| I.3-55 | Ph | H | $CH_2$ | $CH_2$ | $CH_2$ | Q-1.166 |
| I.3-56 | Ph | H | $CH_2$ | $CH_2$ | $CH_2$ | Q-1.167 |
| I.3-57 | Ph | H | $CH_2$ | $CH_2$ | $CH_2$ | Q-1.168 |
| I.3-58 | Ph | H | $CH_2$ | $CH_2$ | $CH_2$ | Q-1.201 |
| I.3-59 | Ph | H | $CH_2$ | $CH_2$ | $CH_2$ | Q-1.202 |
| I.3-60 | Ph | H | $CH_2$ | $CH_2$ | $CH_2$ | Q-1.203 |
| I.3-61 | Ph | H | $CH_2$ | $CH_2$ | $CH_2$ | Q-1.246 |
| I.3-62 | Ph | H | $CH_2$ | $CH_2$ | $CH_2$ | Q-1.247 |
| I.3-63 | Ph | H | $CH_2$ | $CH_2$ | $CH_2$ | Q-1.248 |
| I.3-64 | $CH_3$ | H | $CH_2$ | O | $CH_2$ | Q-1.1 |
| I.3-65 | $CH_3$ | H | $CH_2$ | O | $CH_2$ | Q-1.2 |

TABLE 3-continued

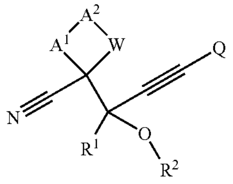

(I)

The Q radicals here correspond to the structures defined as particularly preferred earlier in the document

| No. | $R^1$ | $R^2$ | $A^1$ | $A^2$ | W | Q |
|---|---|---|---|---|---|---|
| I.3-66 | $CH_3$ | H | $CH_2$ | O | $CH_2$ | Q-1.3 |
| I.3-67 | $CH_3$ | H | $CH_2$ | O | $CH_2$ | Q-1.16 |
| I.3-68 | $CH_3$ | H | $CH_2$ | O | $CH_2$ | Q-1.17 |
| I.3-69 | $CH_3$ | H | $CH_2$ | O | $CH_2$ | Q-1.18 |
| I.3-70 | $CH_3$ | H | $CH_2$ | O | $CH_2$ | Q-1.91 |
| I.3-71 | $CH_3$ | H | $CH_2$ | O | $CH_2$ | Q-1.92 |
| I.3-72 | $CH_3$ | H | $CH_2$ | O | $CH_2$ | Q-1.93 |
| I.3-73 | $CH_3$ | H | $CH_2$ | O | $CH_2$ | Q-1.136 |
| I.3-74 | $CH_3$ | H | $CH_2$ | O | $CH_2$ | Q-1.137 |
| I.3-75 | $CH_3$ | H | $CH_2$ | O | $CH_2$ | Q-1.138 |
| I.3-76 | $CH_3$ | H | $CH_2$ | O | $CH_2$ | Q-1.166 |
| I.3-77 | $CH_3$ | H | $CH_2$ | O | $CH_2$ | Q-1.167 |
| I.3-78 | $CH_3$ | H | $CH_2$ | O | $CH_2$ | Q-1.168 |
| I.3-79 | $CH_3$ | H | $CH_2$ | O | $CH_2$ | Q-1.201 |
| I.3-80 | $CH_3$ | H | $CH_2$ | O | $CH_2$ | Q-1.202 |
| I.3-81 | $CH_3$ | H | $CH_2$ | O | $CH_2$ | Q-1.203 |
| I.3-82 | $CH_3$ | H | $CH_2$ | O | $CH_2$ | Q-1.246 |
| I.3-83 | $CH_3$ | H | $CH_2$ | O | $CH_2$ | Q-1.247 |
| I.3-84 | $CH_3$ | H | $CH_2$ | O | $CH_2$ | Q-1.248 |
| I.3-85 | i-Pr | H | $CH_2$ | O | $CH_2$ | Q-1.1 |
| I.3-86 | i-Pr | H | $CH_2$ | O | $CH_2$ | Q-1.2 |
| I.3-87 | i-Pr | H | $CH_2$ | O | $CH_2$ | Q-1.3 |
| I.3-88 | i-Pr | H | $CH_2$ | O | $CH_2$ | Q-1.16 |
| I.3-89 | i-Pr | H | $CH_2$ | O | $CH_2$ | Q-1.17 |
| I.3-90 | i-Pr | H | $CH_2$ | O | $CH_2$ | Q-1.18 |
| I.3-91 | i-Pr | H | $CH_2$ | O | $CH_2$ | Q-1.91 |
| I.3-92 | i-Pr | H | $CH_2$ | O | $CH_2$ | Q-1.92 |
| I.3-93 | i-Pr | H | $CH_2$ | O | $CH_2$ | Q-1.93 |
| I.3-94 | i-Pr | H | $CH_2$ | O | $CH_2$ | Q-1.136 |
| I.3-95 | i-Pr | H | $CH_2$ | O | $CH_2$ | Q-1.137 |
| I.3-96 | i-Pr | H | $CH_2$ | O | $CH_2$ | Q-1.138 |
| I.3-97 | i-Pr | H | $CH_2$ | O | $CH_2$ | Q-1.166 |
| I.3-98 | i-Pr | H | $CH_2$ | O | $CH_2$ | Q-1.167 |
| I.3-99 | i-Pr | H | $CH_2$ | O | $CH_2$ | Q-1.168 |
| I.3-100 | i-Pr | H | $CH_2$ | O | $CH_2$ | Q-1.201 |
| I.3-101 | i-Pr | H | $CH_2$ | O | $CH_2$ | Q-1.202 |
| I.3-102 | i-Pr | H | $CH_2$ | O | $CH_2$ | Q-1.203 |
| I.3-103 | i-Pr | H | $CH_2$ | O | $CH_2$ | Q-1.246 |
| I.3-104 | i-Pr | H | $CH_2$ | O | $CH_2$ | Q-1.247 |
| I.3-105 | i-Pr | H | $CH_2$ | O | $CH_2$ | Q-1.248 |
| I.3-106 | Ph | H | $CH_2$ | O | $CH_2$ | Q-1.1 |
| I.3-107 | Ph | H | $CH_2$ | O | $CH_2$ | Q-1.2 |
| I.3-108 | Ph | H | $CH_2$ | O | $CH_2$ | Q-1.3 |
| I.3-109 | Ph | H | $CH_2$ | O | $CH_2$ | Q-1.16 |
| I.3-110 | Ph | H | $CH_2$ | O | $CH_2$ | Q-1.17 |
| I.3-111 | Ph | H | $CH_2$ | O | $CH_2$ | Q-1.18 |
| I.3-112 | Ph | H | $CH_2$ | O | $CH_2$ | Q-1.91 |
| I.3-113 | Ph | H | $CH_2$ | O | $CH_2$ | Q-1.92 |
| I.3-114 | Ph | H | $CH_2$ | O | $CH_2$ | Q-1.93 |
| I.3-115 | Ph | H | $CH_2$ | O | $CH_2$ | Q-1.136 |
| I.3-116 | Ph | H | $CH_2$ | O | $CH_2$ | Q-1.137 |
| I.3-117 | Ph | H | $CH_2$ | O | $CH_2$ | Q-1.138 |
| I.3-118 | Ph | H | $CH_2$ | O | $CH_2$ | Q-1.166 |
| I.3-119 | Ph | H | $CH_2$ | O | $CH_2$ | Q-1.167 |
| I.3-120 | Ph | H | $CH_2$ | O | $CH_2$ | Q-1.168 |
| I.3-121 | Ph | H | $CH_2$ | O | $CH_2$ | Q-1.201 |
| I.3-122 | Ph | H | $CH_2$ | O | $CH_2$ | Q-1.202 |
| I.3-123 | Ph | H | $CH_2$ | O | $CH_2$ | Q-1.203 |
| I.3-124 | Ph | H | $CH_2$ | O | $CH_2$ | Q-1.246 |
| I.3-125 | Ph | H | $CH_2$ | O | $CH_2$ | Q-1.247 |
| I.3-126 | Ph | H | $CH_2$ | O | $CH_2$ | Q-1.248 |
| I.3-127 | i-Pr | H | $CH_2$ | $CH_2$ | $CH_2$ | Q-1.6 |
| I.3-128 | i-Pr | H | $CH_2$ | $CH_2$ | $CH_2$ | Q-1.10 |

TABLE 3-continued (I)

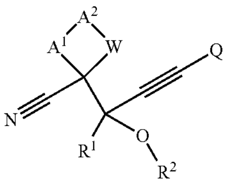

The Q radicals here correspond to the structures defined as particularly preferred earlier in the document

| No. | $R^1$ | $R^2$ | $A^1$ | $A^2$ | W | Q |
|---|---|---|---|---|---|---|
| I.3-129 | i-Pr | H | $CH_2$ | $CH_2$ | $CH_2$ | Q-1.11 |
| I.3-130 | i-Pr | H | $CH_2$ | $CH_2$ | $CH_2$ | Q-1.21 |
| I.3-131 | i-Pr | H | $CH_2$ | $CH_2$ | $CH_2$ | Q-1.96 |
| I.3-132 | i-Pr | H | $CH_2$ | $CH_2$ | $CH_2$ | Q-1.141 |
| I.3-133 | Ph | H | $CH_2$ | $CH_2$ | $CH_2$ | Q-1.6 |
| I.3-134 | Ph | H | $CH_2$ | $CH_2$ | $CH_2$ | Q-1.10 |
| I.3-135 | Ph | H | $CH_2$ | $CH_2$ | $CH_2$ | Q-1.11 |
| I.3-136 | Ph | H | $CH_2$ | $CH_2$ | $CH_2$ | Q-1.21 |
| I.3-137 | Ph | H | $CH_2$ | $CH_2$ | $CH_2$ | Q-1.96 |
| I.3-138 | Ph | H | $CH_2$ | $CH_2$ | $CH_2$ | Q-1.141 |

TABLE 4

(I)

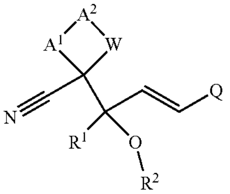

The Q radicals here correspond to the structures defined as particularly preferred earlier in the document

| No. | $R_1$ | $R_2$ | $A_1$ | $A_2$ | W | Q |
|---|---|---|---|---|---|---|
| I.4-1 | $CH_3$ | H | $CH_2$ | $CH_2$ | $CH_2$ | Q-1.1 |
| I.4-2 | $CH_3$ | H | $CH_2$ | $CH_2$ | $CH_2$ | Q-1.2 |
| I.4-3 | $CH_3$ | H | $CH_2$ | $CH_2$ | $CH_2$ | Q-1.3 |
| I.4-4 | $CH_3$ | H | $CH_2$ | $CH_2$ | $CH_2$ | Q-1.16 |
| I.4-5 | $CH_3$ | H | $CH_2$ | $CH_2$ | $CH_2$ | Q-1.17 |
| I.4-6 | $CH_3$ | H | $CH_2$ | $CH_2$ | $CH_2$ | Q-1.18 |
| I.4-7 | $CH_3$ | H | $CH_2$ | $CH_2$ | $CH_2$ | Q-1.91 |
| I.4-8 | $CH_3$ | H | $CH_2$ | $CH_2$ | $CH_2$ | Q-1.92 |
| I.4-9 | $CH_3$ | H | $CH_2$ | $CH_2$ | $CH_2$ | Q-1.93 |
| I.4-10 | $CH_3$ | H | $CH_2$ | $CH_2$ | $CH_2$ | Q-1.136 |
| I.4-11 | $CH_3$ | H | $CH_2$ | $CH_2$ | $CH_2$ | Q-1.137 |
| I.4-12 | $CH_3$ | H | $CH_2$ | $CH_2$ | $CH_2$ | Q-1.138 |
| I.4-13 | $CH_3$ | H | $CH_2$ | $CH_2$ | $CH_2$ | Q-1.166 |
| I.4-14 | $CH_3$ | H | $CH_2$ | $CH_2$ | $CH_2$ | Q-1.167 |
| I.4-15 | $CH_3$ | H | $CH_2$ | $CH_2$ | $CH_2$ | Q-1.168 |
| I.4-16 | $CH_3$ | H | $CH_2$ | $CH_2$ | $CH_2$ | Q-1.201 |
| I.4-17 | $CH_3$ | H | $CH_2$ | $CH_2$ | $CH_2$ | Q-1.202 |
| I.4-18 | $CH_3$ | H | $CH_2$ | $CH_2$ | $CH_2$ | Q-1.203 |
| I.4-19 | $CH_3$ | H | $CH_2$ | $CH_2$ | $CH_2$ | Q-1.246 |
| I.4-20 | $CH_3$ | H | $CH_2$ | $CH_2$ | $CH_2$ | Q-1.247 |
| I.4-21 | $CH_3$ | H | $CH_2$ | $CH_2$ | $CH_2$ | Q-1.248 |
| I.4-22 | i-Pr | H | $CH_2$ | $CH_2$ | $CH_2$ | Q-1.1 |
| I.4-23 | i-Pr | H | $CH_2$ | $CH_2$ | $CH_2$ | Q-1.2 |
| I.4-24 | i-Pr | H | $CH_2$ | $CH_2$ | $CH_2$ | Q-1.3 |
| I.4-25 | i-Pr | H | $CH_2$ | $CH_2$ | $CH_2$ | Q-1.16 |
| I.4-26 | i-Pr | H | $CH_2$ | $CH_2$ | $CH_2$ | Q-1.17 |
| I.4-27 | i-Pr | H | $CH_2$ | $CH_2$ | $CH_2$ | Q-1.18 |
| I.4-28 | i-Pr | H | $CH_2$ | $CH_2$ | $CH_2$ | Q-1.91 |
| I.4-29 | i-Pr | H | $CH_2$ | $CH_2$ | $CH_2$ | Q-1.92 |
| I.4-30 | i-Pr | H | $CH_2$ | $CH_2$ | $CH_2$ | Q-1.93 |
| I.4-31 | i-Pr | H | $CH_2$ | $CH_2$ | $CH_2$ | Q-1.136 |

TABLE 4-continued (I)

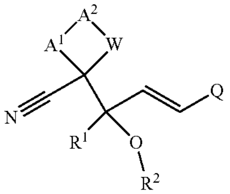

The Q radicals here correspond to the structures defined as particularly preferred earlier in the document

| No. | $R_1$ | $R_2$ | $A_1$ | $A_2$ | W | Q |
|---|---|---|---|---|---|---|
| I.4-32 | i-Pr | H | $CH_2$ | $CH_2$ | $CH_2$ | Q-1.137 |
| I.4-33 | i-Pr | H | $CH_2$ | $CH_2$ | $CH_2$ | Q-1.138 |
| I.4-34 | i-Pr | H | $CH_2$ | $CH_2$ | $CH_2$ | Q-1.166 |
| I.4-35 | i-Pr | H | $CH_2$ | $CH_2$ | $CH_2$ | Q-1.167 |
| I.4-36 | i-Pr | H | $CH_2$ | $CH_2$ | $CH_2$ | Q-1.168 |
| I.4-37 | i-Pr | H | $CH_2$ | $CH_2$ | $CH_2$ | Q-1.201 |
| I.4-38 | i-Pr | H | $CH_2$ | $CH_2$ | $CH_2$ | Q-1.202 |
| I.4-39 | i-Pr | H | $CH_2$ | $CH_2$ | $CH_2$ | Q-1.203 |
| I.4-40 | i-Pr | H | $CH_2$ | $CH_2$ | $CH_2$ | Q-1.246 |
| I.4-41 | i-Pr | H | $CH_2$ | $CH_2$ | $CH_2$ | Q-1.247 |
| I.4-42 | i-Pr | H | $CH_2$ | $CH_2$ | $CH_2$ | Q-1.248 |
| I.4-43 | Ph | H | $CH_2$ | $CH_2$ | $CH_2$ | Q-1.1 |
| I.4-44 | Ph | H | $CH_2$ | $CH_2$ | $CH_2$ | Q-1.2 |
| I.4-45 | Ph | H | $CH_2$ | $CH_2$ | $CH_2$ | Q-1.3 |
| I.4-46 | Ph | H | $CH_2$ | $CH_2$ | $CH_2$ | Q-1.16 |
| I.4-47 | Ph | H | $CH_2$ | $CH_2$ | $CH_2$ | Q-1.17 |
| I.4-48 | Ph | H | $CH_2$ | $CH_2$ | $CH_2$ | Q-1.18 |
| I.4-49 | Ph | H | $CH_2$ | $CH_2$ | $CH_2$ | Q-1.91 |
| I.4-50 | Ph | H | $CH_2$ | $CH_2$ | $CH_2$ | Q-1.92 |
| I.4-51 | Ph | H | $CH_2$ | $CH_2$ | $CH_2$ | Q-1.93 |
| I.4-52 | Ph | H | $CH_2$ | $CH_2$ | $CH_2$ | Q-1.136 |
| I.4-53 | Ph | H | $CH_2$ | $CH_2$ | $CH_2$ | Q-1.137 |
| I.4-54 | Ph | H | $CH_2$ | $CH_2$ | $CH_2$ | Q-1.138 |
| I.4-55 | Ph | H | $CH_2$ | $CH_2$ | $CH_2$ | Q-1.166 |
| I.4-56 | Ph | H | $CH_2$ | $CH_2$ | $CH_2$ | Q-1.167 |
| I.4-57 | Ph | H | $CH_2$ | $CH_2$ | $CH_2$ | Q-1.168 |
| I.4-58 | Ph | H | $CH_2$ | $CH_2$ | $CH_2$ | Q-1.201 |
| I.4-59 | Ph | H | $CH_2$ | $CH_2$ | $CH_2$ | Q-1.202 |
| I.4-60 | Ph | H | $CH_2$ | $CH_2$ | $CH_2$ | Q-1.203 |
| I.4-61 | Ph | H | $CH_2$ | $CH_2$ | $CH_2$ | Q-1.246 |
| I.4-62 | Ph | H | $CH_2$ | $CH_2$ | $CH_2$ | Q-1.247 |
| I.4-63 | Ph | H | $CH_2$ | $CH_2$ | $CH_2$ | Q-1.248 |
| I.4-64 | $CH_3$ | H | $CH_2$ | O | $CH_2$ | Q-1.1 |
| I.4-65 | $CH_3$ | H | $CH_2$ | O | $CH_2$ | Q-1.2 |
| I.4-66 | $CH_3$ | H | $CH_2$ | O | $CH_2$ | Q-1.3 |
| I.4-67 | $CH_3$ | H | $CH_2$ | O | $CH_2$ | Q-1.16 |
| I.4-68 | $CH_3$ | H | $CH_2$ | O | $CH_2$ | Q-1.17 |
| I.4-69 | $CH_3$ | H | $CH_2$ | O | $CH_2$ | Q-1.18 |
| I.4-70 | $CH_3$ | H | $CH_2$ | O | $CH_2$ | Q-1.91 |
| I.4-71 | $CH_3$ | H | $CH_2$ | O | $CH_2$ | Q-1.92 |
| I.4-72 | $CH_3$ | H | $CH_2$ | O | $CH_2$ | Q-1.93 |
| I.4-73 | $CH_3$ | H | $CH_2$ | O | $CH_2$ | Q-1.136 |
| I.4-74 | $CH_3$ | H | $CH_2$ | O | $CH_2$ | Q-1.137 |
| I.4-75 | $CH_3$ | H | $CH_2$ | O | $CH_2$ | Q-1.138 |
| I.4-76 | $CH_3$ | H | $CH_2$ | O | $CH_2$ | Q-1.166 |
| I.4-77 | $CH_3$ | H | $CH_2$ | O | $CH_2$ | Q-1.167 |
| I.4-78 | $CH_3$ | H | $CH_2$ | O | $CH_2$ | Q-1.168 |
| I.4-79 | $CH_3$ | H | $CH_2$ | O | $CH_2$ | Q-1.201 |
| I.4-80 | $CH_3$ | H | $CH_2$ | O | $CH_2$ | Q-1.202 |
| I.4-81 | $CH_3$ | H | $CH_2$ | O | $CH_2$ | Q-1.203 |
| I.4-82 | $CH_3$ | H | $CH_2$ | O | $CH_2$ | Q-1.246 |
| I.4-83 | $CH_3$ | H | $CH_2$ | O | $CH_2$ | Q-1.247 |
| I.4-84 | $CH_3$ | H | $CH_2$ | O | $CH_2$ | Q-1.248 |
| I.4-85 | i-Pr | H | $CH_2$ | O | $CH_2$ | Q-1.1 |
| I.4-86 | i-Pr | H | $CH_2$ | O | $CH_2$ | Q-1.2 |
| I.4-87 | i-Pr | H | $CH_2$ | O | $CH_2$ | Q-1.3 |
| I.4-88 | i-Pr | H | $CH_2$ | O | $CH_2$ | Q-1.16 |
| I.4-89 | i-Pr | H | $CH_2$ | O | $CH_2$ | Q-1.17 |
| I.4-90 | i-Pr | H | $CH_2$ | O | $CH_2$ | Q-1.18 |
| I.4-91 | i-Pr | H | $CH_2$ | O | $CH_2$ | Q-1.91 |
| I.4-92 | i-Pr | H | $CH_2$ | O | $CH_2$ | Q-1.92 |
| I.4-93 | i-Pr | H | $CH_2$ | O | $CH_2$ | Q-1.93 |
| I.4-94 | i-Pr | H | $CH_2$ | O | $CH_2$ | Q-1.136 |

TABLE 4-continued (I)

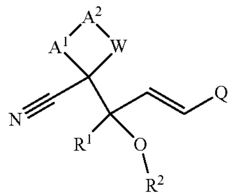

The Q radicals here correspond to the structures defined as particularly preferred earlier in the document

| No. | $R_1$ | $R_2$ | $A_1$ | $A_2$ | W | Q |
|---|---|---|---|---|---|---|
| I.4-95 | i-Pr | H | $CH_2$ | O | $CH_2$ | Q-1.137 |
| I.4-96 | i-Pr | H | $CH_2$ | O | $CH_2$ | Q-1.138 |
| I.4-97 | i-Pr | H | $CH_2$ | O | $CH_2$ | Q-1.166 |
| I.4-98 | i-Pr | H | $CH_2$ | O | $CH_2$ | Q-1.167 |
| I.4-99 | i-Pr | H | $CH_2$ | O | $CH_2$ | Q-1.168 |
| I.4-100 | i-Pr | H | $CH_2$ | O | $CH_2$ | Q-1.201 |
| I.4-101 | i-Pr | H | $CH_2$ | O | $CH_2$ | Q-1.202 |
| I.4-102 | i-Pr | H | $CH_2$ | O | $CH_2$ | Q-1.203 |
| I.4-103 | i-Pr | H | $CH_2$ | O | $CH_2$ | Q-1.246 |
| I.4-104 | i-Pr | H | $CH_2$ | O | $CH_2$ | Q-1.247 |
| I.4-105 | i-Pr | H | $CH_2$ | O | $CH_2$ | Q-1.248 |
| I.4-106 | Ph | H | $CH_2$ | O | $CH_2$ | Q-1.1 |
| I.4-107 | Ph | H | $CH_2$ | O | $CH_2$ | Q-1.2 |
| I.4-108 | Ph | H | $CH_2$ | O | $CH_2$ | Q-1.3 |
| I.4-109 | Ph | H | $CH_2$ | O | $CH_2$ | Q-1.16 |
| I.4-110 | Ph | H | $CH_2$ | O | $CH_2$ | Q-1.17 |
| I.4-111 | Ph | H | $CH_2$ | O | $CH_2$ | Q-1.18 |
| I.4-112 | Ph | H | $CH_2$ | O | $CH_2$ | Q-1.91 |
| I.4-113 | Ph | H | $CH_2$ | O | $CH_2$ | Q-1.92 |
| I.4-114 | Ph | H | $CH_2$ | O | $CH_2$ | Q-1.93 |
| I.4-115 | Ph | H | $CH_2$ | O | $CH_2$ | Q-1.136 |
| I.4-116 | Ph | H | $CH_2$ | O | $CH_2$ | Q-1.137 |
| I.4-117 | Ph | H | $CH_2$ | O | $CH_2$ | Q-1.138 |
| I.4-118 | Ph | H | $CH_2$ | O | $CH_2$ | Q-1.166 |
| I.4-119 | Ph | H | $CH_2$ | O | $CH_2$ | Q-1.167 |
| I.4-120 | Ph | H | $CH_2$ | O | $CH_2$ | Q-1.168 |
| I.4-121 | Ph | H | $CH_2$ | O | $CH_2$ | Q-1.201 |
| I.4-122 | Ph | H | $CH_2$ | O | $CH_2$ | Q-1.202 |
| I.4-123 | Ph | H | $CH_2$ | O | $CH_2$ | Q-1.203 |
| I.4-124 | Ph | H | $CH_2$ | O | $CH_2$ | Q-1.246 |
| I.4-125 | Ph | H | $CH_2$ | O | $CH_2$ | Q-1.247 |
| I.4-126 | Ph | H | $CH_2$ | O | $CH_2$ | Q-1.248 |
| I.4-127 | i-Pr | H | $CH_2$ | $CH_2$ | $CH_2$ | Q-1.6 |
| I.4-128 | i-Pr | H | $CH_2$ | $CH_2$ | $CH_2$ | Q-1.10 |
| I.4-129 | i-Pr | H | $CH_2$ | $CH_2$ | $CH_2$ | Q-1.11 |
| I.4-130 | i-Pr | H | $CH_2$ | $CH_2$ | $CH_2$ | Q-1.21 |
| I.4-131 | i-Pr | H | $CH_2$ | $CH_2$ | $CH_2$ | Q-1.96 |
| I.4-132 | i-Pr | H | $CH_2$ | $CH_2$ | $CH_2$ | Q-1.141 |
| I.4-133 | i-Pr | H | $CH_2$ | $CH_2$ | $CH_2$ | Q-1.6 |
| I.4-134 | i-Pr | H | $CH_2$ | $CH_2$ | $CH_2$ | Q-1.10 |
| I.4-135 | i-Pr | H | $CH_2$ | $CH_2$ | $CH_2$ | Q-1.11 |
| I.4-136 | i-Pr | H | $CH_2$ | $CH_2$ | $CH_2$ | Q-1.21 |
| I.4-137 | i-Pr | H | $CH_2$ | $CH_2$ | $CH_2$ | Q-1.96 |
| I.4-138 | i-Pr | H | $CH_2$ | $CH_2$ | $CH_2$ | Q-1.141 |

TABLE 5

(II)

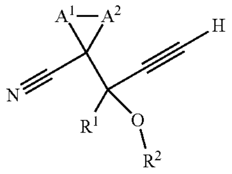

| No. | $R^1$ | $R^2$ | $A^1$ | $A^2$ |
|---|---|---|---|---|
| II.1-1 | $CH_3$ | H | $CH_2$ | $CH_2$ |
| II.1-2 | i-Pr | H | $CH_2$ | $CH_2$ |

TABLE 5-continued (II)

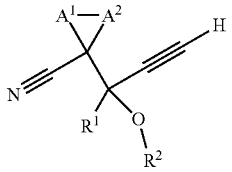

| No. | $R^1$ | $R^2$ | $A^1$ | $A^2$ |
|---|---|---|---|---|
| II.1-3 | Ph | H | $CH_2$ | $CH_2$ |
| II.1-4 | Et | H | $CH_2$ | $CH_2$ |
| II.1-5 | c-Pr | H | $CH_2$ | $CH_2$ |
| II.1-6 | n-Pr | H | $CH_2$ | $CH_2$ |
| II.1-7 | p—F—Ph | H | $CH_2$ | $CH_2$ |
| II.1-8 | m—F—Ph | H | $CH_2$ | $CH_2$ |
| II.1-9 | p—Cl—Ph | H | $CH_2$ | $CH_2$ |
| II.1-10 | m—Cl—Ph | H | $CH_2$ | $CH_2$ |
| II.1-11 | p—$CH_3$—Ph | H | $CH_2$ | $CH_2$ |
| II.1-12 | m—$CH_3$—Ph | H | $CH_2$ | $CH_2$ |
| II.1-13 | $CH_3$ | $CH_3$ | $CH_2$ | $CH_2$ |
| II.1-14 | i-Pr | $CH_3$ | $CH_2$ | $CH_2$ |
| II.1-15 | Ph | $CH_3$ | $CH_2$ | $CH_2$ |
| II.1-16 | Et | $CH_3$ | $CH_2$ | $CH_2$ |
| II.1-17 | c-Pr | $CH_3$ | $CH_2$ | $CH_2$ |
| II.1-18 | n-Pr | $CH_3$ | $CH_2$ | $CH_2$ |
| II.1-19 | p—F—Ph | $CH_3$ | $CH_2$ | $CH_2$ |
| II.1-20 | m—F—Ph | $CH_3$ | $CH_2$ | $CH_2$ |
| II.1-21 | p—Cl—Ph | $CH_3$ | $CH_2$ | $CH_2$ |
| II.1-22 | m—Cl—Ph | $CH_3$ | $CH_2$ | $CH_2$ |
| II.1-23 | p—$CH_3$—Ph | $CH_3$ | $CH_2$ | $CH_2$ |
| II.1-24 | m—$CH_3$—Ph | $CH_3$ | $CH_2$ | $CH_2$ |
| II.1-25 | $CH_3$ | C(═O)$CH_3$ | $CH_2$ | $CH_2$ |
| II.1-26 | i-Pr | C(═O)$CH_3$ | $CH_2$ | $CH_2$ |
| II.1-27 | Ph | C(═O)$CH_3$ | $CH_2$ | $CH_2$ |
| II.1-28 | Et | C(═O)$CH_3$ | $CH_2$ | $CH_2$ |
| II.1-29 | c-Pr | C(═O)$CH_3$ | $CH_2$ | $CH_2$ |
| II.1-30 | n-Pr | C(═O)$CH_3$ | $CH_2$ | $CH_2$ |
| II.1-31 | p—F—Ph | C(═O)$CH_3$ | $CH_2$ | $CH_2$ |
| II.1-32 | m—F—Ph | C(═O)$CH_3$ | $CH_2$ | $CH_2$ |
| II.1-33 | p—Cl—Ph | C(═O)$CH_3$ | $CH_2$ | $CH_2$ |
| II.1-34 | m—Cl—Ph | C(═O)$CH_3$ | $CH_2$ | $CH_2$ |
| II.1-35 | p—$CH_3$—Ph | C(═O)$CH_3$ | $CH_2$ | $CH_2$ |
| II.1-36 | m—$CH_3$—Ph | C(═O)$CH_3$ | $CH_2$ | $CH_2$ |
| II.1-37 | $CH_3$ | $SiEt_3$ | $CH_2$ | $CH_2$ |
| II.1-38 | i-Pr | $SiEt_3$ | $CH_2$ | $CH_2$ |
| II.1-39 | Ph | $SiEt_3$ | $CH_2$ | $CH_2$ |
| II.1-40 | Et | $SiEt_3$ | $CH_2$ | $CH_2$ |
| II.1-41 | c-Pr | $SiEt_3$ | $CH_2$ | $CH_2$ |
| II.1-42 | n-Pr | $SiEt_3$ | $CH_2$ | $CH_2$ |
| II.1-43 | p—F—Ph | $SiEt_3$ | $CH_2$ | $CH_2$ |
| II.1-44 | m—F—Ph | $SiEt_3$ | $CH_2$ | $CH_2$ |
| II.1-45 | p—Cl—Ph | $SiEt_3$ | $CH_2$ | $CH_2$ |
| II.1-46 | m—Cl—Ph | $SiEt_3$ | $CH_2$ | $CH_2$ |
| II.1-47 | p—$CH_3$—Ph | $SiEt_3$ | $CH_2$ | $CH_2$ |
| II.1-48 | m—$CH_3$—Ph | $SiEt_3$ | $CH_2$ | $CH_2$ |
| II.1-49 | $CH_3$ | H | CHF | $CH_2$ |
| II.1-50 | i-Pr | H | CHF | $CH_2$ |
| II.1-51 | Ph | H | CHF | $CH_2$ |
| II.1-52 | $CH_3$ | H | CH($CH_3$) | $CH_2$ |
| II.1-53 | i-Pr | H | CH($CH_3$) | $CH_2$ |
| II.1-54 | Ph | H | CH($CH_3$) | $CH_2$ |
| II.1-55 | $CH_3$ | H | CH(i-Pr) | $CH_2$ |
| II.1-56 | i-Pr | H | CH(i-Pr) | $CH_2$ |
| II.1-57 | Ph | H | CH(i-Pr) | $CH_2$ |
| II.1-58 | $CH_3$ | H | CH(c-Pr) | $CH_2$ |
| II.1-59 | i-Pr | H | CH(c-Pr) | $CH_2$ |
| II.1-60 | Ph | H | CH(c-Pr) | $CH_2$ |
| II.1-61 | $CH_3$ | H | $CF_2$ | $CH_2$ |
| II.1-62 | i-Pr | H | $CF_2$ | $CH_2$ |
| II.1-63 | Ph | H | $CF_2$ | $CH_2$ |
| II.1-64 | $CH_3$ | H | $CH_2$ | CHF |
| II.1-65 | i-Pr | H | $CH_2$ | CHF |
| II.1-66 | Ph | H | $CH_2$ | CHF |
| II.1-67 | $CH_3$ | H | $CH_2$ | CH($CH_3$) |
| II.1-68 | i-Pr | H | $CH_2$ | CH($CH_3$) |
| II.1-69 | Ph | H | $CH_2$ | CH($CH_3$) |
| II.1-70 | $CH_3$ | H | $CH_2$ | CH(i-Pr) |

TABLE 5-continued (II)

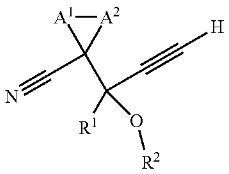

| No. | $R^1$ | $R^2$ | $A^1$ | $A^2$ |
|---|---|---|---|---|
| II.1-71 | i-Pr | H | $CH_2$ | CH(i-Pr) |
| II.1-72 | Ph | H | $CH_2$ | CH(i-Pr) |
| II.1-73 | $CH_3$ | H | $CH_2$ | CH(c-Pr) |
| II.1-74 | i-Pr | H | $CH_2$ | CH(c-Pr) |
| II.1-75 | Ph | H | $CH_2$ | CH(c-Pr) |
| II.1-76 | $CH_3$ | H | $CH_2$ | $CF_2$ |
| II.1-77 | i-Pr | H | $CH_2$ | $CF_2$ |
| II.1-78 | Ph | H | $CH_2$ | $CF_2$ |
| II.1-79 | 2,4-$Cl_2$—Ph | H | $CH_2$ | $CH_2$ |
| II.1-80 | c-Bu | H | $CH_2$ | $CH_2$ |
| II.1-81 | c-Pent | H | $CH_2$ | $CH_2$ |
| II.1-82 | c-Hex | H | $CH_2$ | $CH_2$ |
| II.1-83 | Adamantyl | H | $CH_2$ | $CH_2$ |
| II.1-84 | 1-Ethyl-propyl | H | $CH_2$ | $CH_2$ |
| II.1-85 | t-Bu | H | $CH_2$ | $CH_2$ |
| II.1-86 | o—F—Ph | H | $CH_2$ | $CH_2$ |

TABLE 6

(II)

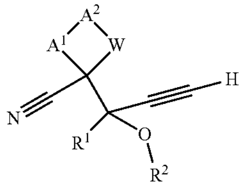

| No. | $R^1$ | $R^2$ | $A^1$ | $A^2$ | W |
|---|---|---|---|---|---|
| II.2-1 | $CH_3$ | H | $CH_2$ | $CH_2$ | $CH_2$ |
| II.2-2 | i-Pr | H | $CH_2$ | $CH_2$ | $CH_2$ |
| II.2-3 | Ph | H | $CH_2$ | $CH_2$ | $CH_2$ |
| II.2-4 | n-Pr | H | $CH_2$ | $CH_2$ | $CH_2$ |
| II.2-5 | c-Pr | H | $CH_2$ | $CH_2$ | $CH_2$ |
| II.2-6 | $CH_3$ | $CH_3$ | $CH_2$ | $CH_2$ | $CH_2$ |
| II.2-7 | i-Pr | $CH_3$ | $CH_2$ | $CH_2$ | $CH_2$ |
| II.2-8 | Ph | $CH_3$ | $CH_2$ | $CH_2$ | $CH_2$ |
| II.2-9 | n-Pr | $CH_3$ | $CH_2$ | $CH_2$ | $CH_2$ |
| II.2-10 | c-Pr | $CH_3$ | $CH_2$ | $CH_2$ | $CH_2$ |
| II.2-11 | $CH_3$ | C(═O)$CH_3$ | $CH_2$ | $CH_2$ | $CH_2$ |
| II.2-12 | i-Pr | C(═O)$CH_3$ | $CH_2$ | $CH_2$ | $CH_2$ |
| II.2-13 | Ph | C(═O)$CH_3$ | $CH_2$ | $CH_2$ | $CH_2$ |
| II.2-14 | n-Pr | C(═O)$CH_3$ | $CH_2$ | $CH_2$ | $CH_2$ |
| II.2-15 | c-Pr | C(═O)$CH_3$ | $CH_2$ | $CH_2$ | $CH_2$ |
| II.2-16 | $CH_3$ | $SiEt_3$ | $CH_2$ | $CH_2$ | $CH_2$ |
| II.2-17 | i-Pr | $SiEt_3$ | $CH_2$ | $CH_2$ | $CH_2$ |
| II.2-18 | Ph | $SiEt_3$ | $CH_2$ | $CH_2$ | $CH_2$ |
| II.2-19 | n-Pr | $SiEt_3$ | $CH_2$ | $CH_2$ | $CH_2$ |
| II.2-20 | c-Pr | $SiEt_3$ | $CH_2$ | $CH_2$ | $CH_2$ |
| II.2-21 | $CH_3$ | H | $CH_2$ | O | $CH_2$ |
| II.2-22 | i-Pr | H | $CH_2$ | O | $CH_2$ |
| II.2-23 | Ph | H | $CH_2$ | O | $CH_2$ |
| II.2-24 | n-Pr | H | $CH_2$ | O | $CH_2$ |
| II.2-25 | c-Pr | H | $CH_2$ | O | $CH_2$ |
| II.2-26 | $CH_3$ | $CH_3$ | $CH_2$ | O | $CH_2$ |
| II.2-27 | i-Pr | $CH_3$ | $CH_2$ | O | $CH_2$ |
| II.2-28 | Ph | $CH_3$ | $CH_2$ | O | $CH_2$ |
| II.2-29 | n-Pr | $CH_3$ | $CH_2$ | O | $CH_2$ |
| II.2-30 | c-Pr | $CH_3$ | $CH_2$ | O | $CH_2$ |
| II.2-31 | $CH_3$ | C(═O)$CH_3$ | $CH_2$ | O | $CH_2$ |
| II.2-32 | i-Pr | C(═O)$CH_3$ | $CH_2$ | O | $CH_2$ |
| II.2-33 | Ph | C(═O)$CH_3$ | $CH_2$ | O | $CH_2$ |
| II.2-34 | n-Pr | C(═O)$CH_3$ | $CH_2$ | O | $CH_2$ |

TABLE 6-continued (II)

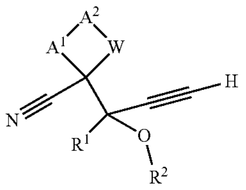

| No. | $R^1$ | $R^2$ | $A^1$ | $A^2$ | W |
|---|---|---|---|---|---|
| II.2-35 | c-Pr | C(═O)$CH_3$ | $CH_2$ | O | $CH_2$ |
| II.2-36 | $CH_3$ | $SiEt_3$ | $CH_2$ | O | $CH_2$ |
| II.2-37 | i-Pr | $SiEt_3$ | $CH_2$ | O | $CH_2$ |
| II.2-38 | Ph | $SiEt_3$ | $CH_2$ | O | $CH_2$ |
| II.2-39 | n-Pr | $SiEt_3$ | $CH_2$ | O | $CH_2$ |
| II.2-40 | c-Pr | $SiEt_3$ | $CH_2$ | O | $CH_2$ |
| II.2-41 | c-Bu | H | $CH_2$ | $CH_2$ | $CH_2$ |
| II.2-42 | c-Pentyl | H | $CH_2$ | $CH_2$ | $CH_2$ |
| II.2-43 | c-Hexyl | H | $CH_2$ | $CH_2$ | $CH_2$ |
| II.2-44 | p—F—Ph | H | $CH_2$ | $CH_2$ | $CH_2$ |
| II.2-45 | p—Me—Ph | H | $CH_2$ | $CH_2$ | $CH_2$ |
| II.2-46 | p—Cl—Ph | H | $CH_2$ | $CH_2$ | $CH_2$ |
| II.2-47 | m—F—Ph | H | $CH_2$ | $CH_2$ | $CH_2$ |
| II.2-48 | m—Me—Ph | H | $CH_2$ | $CH_2$ | $CH_2$ |
| II.2-49 | m—Cl—Ph | H | $CH_2$ | $CH_2$ | $CH_2$ |
| II.2-50 | Adamantyl | H | $CH_2$ | $CH_2$ | $CH_2$ |
| II.2-51 | t-Bu | H | $CH_2$ | $CH_2$ | $CH_2$ |
| II.2-52 | 1-Ethyl-propyl | H | $CH_2$ | $CH_2$ | $CH_2$ |

TABLE 7

(III)

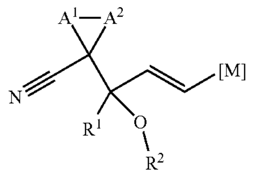

| No. | $R^1$ | $R^2$ | $A^1$ | $A^2$ | [M] |
|---|---|---|---|---|---|
| III.1-1 | $CH_3$ | H | $CH_2$ | $CH_2$ | $Sn(n-Bu)_3$ |
| III.1-2 | i-Pr | H | $CH_2$ | $CH_2$ | $Sn(n-Bu)_3$ |
| III.1-3 | Ph | H | $CH_2$ | $CH_2$ | $Sn(n-Bu)_3$ |
| III.1-4 | Et | H | $CH_2$ | $CH_2$ | $Sn(n-Bu)_3$ |
| III.1-5 | c-Pr | H | $CH_2$ | $CH_2$ | $Sn(n-Bu)_3$ |
| III.1-6 | n-Pr | H | $CH_2$ | $CH_2$ | $Sn(n-Bu)_3$ |
| III.1-7 | $CH_3$ | $SiEt_3$ | $CH_2$ | $CH_2$ | $Sn(n-Bu)_3$ |
| III.1-8 | i-Pr | $SiEt_3$ | $CH_2$ | $CH_2$ | $Sn(n-Bu)_3$ |
| III.1-9 | Ph | $SiEt_3$ | $CH_2$ | $CH_2$ | $Sn(n-Bu)_3$ |
| III.1-10 | c-Pr | $SiEt_3$ | $CH_2$ | $CH_2$ | $Sn(n-Bu)_3$ |
| III.1-11 | $CH_3$ | H | $CH_2$ | $CH_2$ | $Sn(n-Pr)_3$ |
| III.1-12 | i-Pr | H | $CH_2$ | $CH_2$ | $Sn(n-Pr)_3$ |
| III.1-13 | Ph | H | $CH_2$ | $CH_2$ | $Sn(n-Pr)_3$ |
| III.1-14 | $CH_3$ | $SiEt_3$ | $CH_2$ | $CH_2$ | $Sn(n-Pr)_3$ |
| III.1-15 | i-Pr | $SiEt_3$ | $CH_2$ | $CH_2$ | $Sn(n-Pr)_3$ |
| III.1-16 | Ph | $SiEt_3$ | $CH_2$ | $CH_2$ | $Sn(n-Pr)_3$ |
| III.1-17 | $CH_3$ | H | $CH_2$ | $CH_2$ | $Sn(c-Hex)_3$ |
| III.1-18 | i-Pr | H | $CH_2$ | $CH_2$ | $Sn(c-Hex)_3$ |
| III.1-19 | Ph | H | $CH_2$ | $CH_2$ | $Sn(c-Hex)_3$ |
| III.1-20 | $CH_3$ | $SiEt_3$ | $CH_2$ | $CH_2$ | $Sn(c-Hex)_3$ |
| III.1-21 | i-Pr | $SiEt_3$ | $CH_2$ | $CH_2$ | $Sn(c-Hex)_3$ |
| III.1-22 | Ph | $SiEt_3$ | $CH_2$ | $CH_2$ | $Sn(c-Hex)_3$ |
| III.1-23 | $CH_3$ | H | $CH_2$ | $CH_2$ | $GeEt_3$ |
| III.1-24 | i-Pr | H | $CH_2$ | $CH_2$ | $GeEt_3$ |
| III.1-25 | Ph | H | $CH_2$ | $CH_2$ | $GeEt_3$ |
| III.1-26 | $CH_3$ | $SiEt_3$ | $CH_2$ | $CH_2$ | $GeEt_3$ |
| III.1-27 | i-Pr | $SiEt_3$ | $CH_2$ | $CH_2$ | $GeEt_3$ |
| III.1-28 | Ph | $SiEt_3$ | $CH_2$ | $CH_2$ | $GeEt_3$ |
| III.1-29 | $CH_3$ | H | $CH_2$ | $CH_2$ | $Zr(C_5H_5)_2$ |
| III.1-30 | i-Pr | H | $CH_2$ | $CH_2$ | $Zr(C_5H_5)_2$ |
| III.1-31 | Ph | H | $CH_2$ | $CH_2$ | $Zr(C_5H_5)_2$ |
| III.1-32 | $CH_3$ | $SiEt_3$ | $CH_2$ | $CH_2$ | $Zr(C_5H_5)_2$ |

TABLE 7-continued (III)

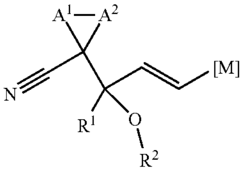

| No. | $R^1$ | $R^2$ | $A^1$ | $A^2$ | [M] |
|---|---|---|---|---|---|
| III.1-33 | i-Pr | $SiEt_3$ | $CH_2$ | $CH_2$ | $Zr(C_5H_5)_2$ |
| III.1-34 | Ph | $SiEt_3$ | $CH_2$ | $CH_2$ | $Zr(C_5H_5)_2$ |
| III.1-35 | $CH_3$ | H | $CH_2$ | $CH_2$ | $Hf(C_5H_5)_2$ |
| III.1-36 | i-Pr | H | $CH_2$ | $CH_2$ | $Hf(C_5H_5)_2$ |
| III.1-37 | Ph | H | $CH_2$ | $CH_2$ | $Hf(C_5H_5)_2$ |
| III.1-38 | $CH_3$ | $SiEt_3$ | $CH_2$ | $CH_2$ | $Hf(C_5H_5)_2$ |
| III.1-39 | i-Pr | $SiEt_3$ | $CH_2$ | $CH_2$ | $Hf(C_5H_5)_2$ |
| III.1-40 | Ph | $SiEt_3$ | $CH_2$ | $CH_2$ | $Hf(C_5H_5)_2$ |
| III.1-41 | $CH_3$ | H | $CH_2$ | $CH_2$ | $B(OH)_2$ |
| III.1-42 | i-Pr | H | $CH_2$ | $CH_2$ | $B(OH)_2$ |
| III.1-43 | Ph | H | $CH_2$ | $CH_2$ | $B(OH)_2$ |
| III.1-44 | $CH_3$ | $SiEt_3$ | $CH_2$ | $CH_2$ | $B(OH)_2$ |
| III.1-45 | i-Pr | $SiEt_3$ | $CH_2$ | $CH_2$ | $B(OH)_2$ |
| III.1-46 | Ph | $SiEt_3$ | $CH_2$ | $CH_2$ | $B(OH)_2$ |
| III.1-47 | $CH_3$ | H | $CH_2$ | $CH_2$ | $B(OMe)_2$ |
| III.1-48 | i-Pr | H | $CH_2$ | $CH_2$ | $B(OMe)_2$ |
| III.1-49 | Ph | H | $CH_2$ | $CH_2$ | $B(OMe)_2$ |
| III.1-50 | $CH_3$ | $SiEt_3$ | $CH_2$ | $CH_2$ | $B(OMe)_2$ |
| III.1-51 | i-Pr | $SiEt_3$ | $CH_2$ | $CH_2$ | $B(OMe)_2$ |
| III.1-52 | Ph | $SiEt_3$ | $CH_2$ | $CH_2$ | $B(OMe)_2$ |
| III.1-53 | $CH_3$ | H | $CH_2$ | $CH_2$ | 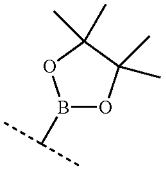 |
| III.1-54 | i-Pr | H | $CH_2$ | $CH_2$ | 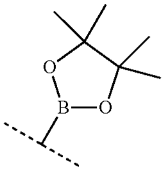 |
| III.1-55 | Ph | H | $CH_2$ | $CH_2$ | 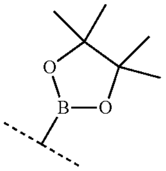 |
| III.1-56 | $CH_3$ | $SiEt_3$ | $CH_2$ | $CH_2$ | 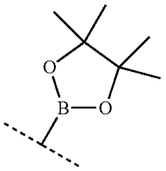 |
| III.1-57 | i-Pr | $SiEt_3$ | $CH_2$ | $CH_2$ | 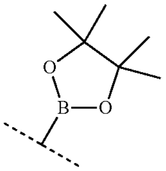 |

TABLE 7-continued (III)

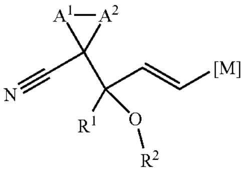

| No. | $R^1$ | $R^2$ | $A^1$ | $A^2$ | [M] |
|---|---|---|---|---|---|
| III.1-58 | Ph | $SiEt_3$ | $CH_2$ | $CH_2$ | 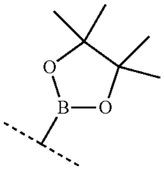 |
| III.1-59 | $CH_3$ | H | $CH_2$ | $CH_2$ | 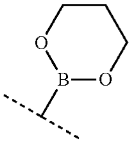 |
| III.1-60 | i-Pr | H | $CH_2$ | $CH_2$ | 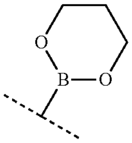 |
| III.1-61 | Ph | H | $CH_2$ | $CH_2$ | 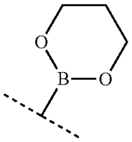 |
| III.1-62 | $CH_3$ | $SiEt_3$ | $CH_2$ | $CH_2$ | 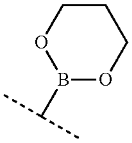 |
| III.1-63 | i-Pr | $SiEt_3$ | $CH_2$ | $CH_2$ | 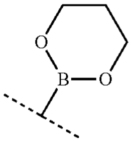 |
| III.1-64 | Ph | $SiEt_3$ | $CH_2$ | $CH_2$ | 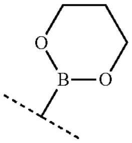 |
| III.1-65 | c-Bu | H | $CH_2$ | $CH_2$ | $Sn(n-Bu)_3$ |
| III.1-66 | c-Hexyl | H | $CH_2$ | $CH_2$ | $Sn(n-Bu)_3$ |
| III.1-67 | 1-Ethylpropyl | H | $CH_2$ | $CH_2$ | $Sn(n-Bu)_3$ |
| III.1-68 | Adamantyl | H | $CH_2$ | $CH_2$ | $Sn(n-Bu)_3$ |
| III.1-69 | p—F—Ph | H | $CH_2$ | $CH_2$ | $Sn(n-Bu)_3$ |
| III.1-70 | m—F—Ph | H | $CH_2$ | $CH_2$ | $Sn(n-Bu)_3$ |
| III.1-71 | p—Cl—Ph | H | $CH_2$ | $CH_2$ | $Sn(n-Bu)_3$ |
| III.1-72 | m—Cl—Ph | H | $CH_2$ | $CH_2$ | $Sn(n-Bu)_3$ |
| III.1-73 | p—$CH_3$—Ph | H | $CH_2$ | $CH_2$ | $Sn(n-Bu)_3$ |
| III.1-74 | m—$CH_3$—Ph | H | $CH_2$ | $CH_2$ | $Sn(n-Bu)_3$ |
| III.1-75 | t-Bu | H | $CH_2$ | $CH_2$ | $Sn(n-Bu)_3$ |
| III.1-76 | c-Pentyl | H | $CH_2$ | $CH_2$ | $Sn(n-Bu)_3$ |

TABLE 8

(III)

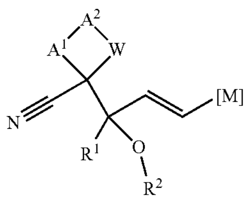

| No. | $R^1$ | $R^2$ | $A^1$ | $A^2$ | W | [M] |
|---|---|---|---|---|---|---|
| III.2-1 | $CH_3$ | H | $CH_2$ | $CH_2$ | $CH_2$ | $Sn(n\text{-}Bu)_3$ |
| III.2-2 | i-Pr | H | $CH_2$ | $CH_2$ | $CH_2$ | $Sn(n\text{-}Bu)_3$ |
| III.2-3 | Ph | H | $CH_2$ | $CH_2$ | $CH_2$ | $Sn(n\text{-}Bu)_3$ |
| III.2-4 | Et | H | $CH_2$ | $CH_2$ | $CH_2$ | $Sn(n\text{-}Bu)_3$ |
| III.2-5 | c-Pr | H | $CH_2$ | $CH_2$ | $CH_2$ | $Sn(n\text{-}Bu)_3$ |
| III.2-6 | n-Pr | H | $CH_2$ | $CH_2$ | $CH_2$ | $Sn(n\text{-}Bu)_3$ |
| III.2-7 | $CH_3$ | $SiEt_3$ | $CH_2$ | $CH_2$ | $CH_2$ | $Sn(n\text{-}Bu)_3$ |
| III.2-8 | i-Pr | $SiEt_3$ | $CH_2$ | $CH_2$ | $CH_2$ | $Sn(n\text{-}Bu)_3$ |
| III.2-9 | Ph | $SiEt_3$ | $CH_2$ | $CH_2$ | $CH_2$ | $Sn(n\text{-}Bu)_3$ |
| III.2-10 | c-Pr | $SiEt_3$ | $CH_2$ | $CH_2$ | $CH_2$ | $Sn(n\text{-}Bu)_3$ |
| III.2-11 | $CH_3$ | H | $CH_2$ | $CH_2$ | $CH_2$ | $Sn(n\text{-}Pr)_3$ |
| III.2-12 | i-Pr | H | $CH_2$ | $CH_2$ | $CH_2$ | $Sn(n\text{-}Pr)_3$ |
| III.2-13 | Ph | H | $CH_2$ | $CH_2$ | $CH_2$ | $Sn(n\text{-}Pr)_3$ |
| III.2-14 | $CH_3$ | $SiEt_3$ | $CH_2$ | $CH_2$ | $CH_2$ | $Sn(n\text{-}Pr)_3$ |
| III.2-15 | i-Pr | $SiEt_3$ | $CH_2$ | $CH_2$ | $CH_2$ | $Sn(n\text{-}Pr)_3$ |
| III.2-16 | Ph | $SiEt_3$ | $CH_2$ | $CH_2$ | $CH_2$ | $Sn(n\text{-}Pr)_3$ |
| III.2-17 | $CH_3$ | H | $CH_2$ | $CH_2$ | $CH_2$ | $Sn(c\text{-}Hex)_3$ |
| III.2-18 | i-Pr | H | $CH_2$ | $CH_2$ | $CH_2$ | $Sn(c\text{-}Hex)_3$ |
| III.2-19 | Ph | H | $CH_2$ | $CH_2$ | $CH_2$ | $Sn(c\text{-}Hex)_3$ |
| III.2-20 | $CH_3$ | $SiEt_3$ | $CH_2$ | $CH_2$ | $CH_2$ | $Sn(c\text{-}Hex)_3$ |
| III.2-21 | i-Pr | $SiEt_3$ | $CH_2$ | $CH_2$ | $CH_2$ | $Sn(c\text{-}Hex)_3$ |
| III.2-22 | Ph | $SiEt_3$ | $CH_2$ | $CH_2$ | $CH_2$ | $Sn(c\text{-}Hex)_3$ |
| III.2-23 | $CH_3$ | H | $CH_2$ | $CH_2$ | $CH_2$ | $GeEt_3$ |
| III.2-24 | i-Pr | H | $CH_2$ | $CH_2$ | $CH_2$ | $GeEt_3$ |
| III.2-25 | Ph | H | $CH_2$ | $CH_2$ | $CH_2$ | $GeEt_3$ |
| III.2-26 | $CH_3$ | $SiEt_3$ | $CH_2$ | $CH_2$ | $CH_2$ | $GeEt_3$ |
| III.2-27 | i-Pr | $SiEt_3$ | $CH_2$ | $CH_2$ | $CH_2$ | $GeEt_3$ |
| III.2-28 | Ph | $SiEt_3$ | $CH_2$ | $CH_2$ | $CH_2$ | $GeEt_3$ |
| III.2-29 | $CH_3$ | H | $CH_2$ | $CH_2$ | $CH_2$ | $Zr(C_5H_5)_2$ |
| III.2-30 | i-Pr | H | $CH_2$ | $CH_2$ | $CH_2$ | $Zr(C_5H_5)_2$ |
| III.2-31 | Ph | H | $CH_2$ | $CH_2$ | $CH_2$ | $Zr(C_5H_5)_2$ |
| III.2-32 | $CH_3$ | $SiEt_3$ | $CH_2$ | $CH_2$ | $CH_2$ | $Zr(C_5H_5)_2$ |
| III.2-33 | i-Pr | $SiEt_3$ | $CH_2$ | $CH_2$ | $CH_2$ | $Zr(C_5H_5)_2$ |
| III.2-34 | Ph | $SiEt_3$ | $CH_2$ | $CH_2$ | $CH_2$ | $Zr(C_5H_5)_2$ |
| III.2-35 | $CH_3$ | H | $CH_2$ | $CH_2$ | $CH_2$ | $Hf(C_5H_5)_2$ |
| III.2-36 | i-Pr | H | $CH_2$ | $CH_2$ | $CH_2$ | $Hf(C_5H_5)_2$ |
| III.2-37 | Ph | H | $CH_2$ | $CH_2$ | $CH_2$ | $Hf(C_5H_5)_2$ |
| III.2-38 | $CH_3$ | $SiEt_3$ | $CH_2$ | $CH_2$ | $CH_2$ | $Hf(C_5H_5)_2$ |
| III.2-39 | i-Pr | $SiEt_3$ | $CH_2$ | $CH_2$ | $CH_2$ | $Hf(C_5H_5)_2$ |
| III.2-40 | Ph | $SiEt_3$ | $CH_2$ | $CH_2$ | $CH_2$ | $Hf(C_5H_5)_2$ |
| III.2-41 | $CH_3$ | H | $CH_2$ | $CH_2$ | $CH_2$ | $B(OH)_2$ |
| III.2-42 | i-Pr | H | $CH_2$ | $CH_2$ | $CH_2$ | $B(OH)_2$ |
| III.2-43 | Ph | H | $CH_2$ | $CH_2$ | $CH_2$ | $B(OH)_2$ |
| III.2-44 | $CH_3$ | $SiEt_3$ | $CH_2$ | $CH_2$ | $CH_2$ | $B(OH)_2$ |
| III.2-45 | i-Pr | $SiEt_3$ | $CH_2$ | $CH_2$ | $CH_2$ | $B(OH)_2$ |
| III.2-46 | Ph | $SiEt_3$ | $CH_2$ | $CH_2$ | $CH_2$ | $B(OH)_2$ |
| III.2-47 | $CH_3$ | H | $CH_2$ | $CH_2$ | $CH_2$ | $B(OMe)_2$ |
| III.2-48 | i-Pr | H | $CH_2$ | $CH_2$ | $CH_2$ | $B(OMe)_2$ |
| III.2-49 | Ph | H | $CH_2$ | $CH_2$ | $CH_2$ | $B(OMe)_2$ |
| III.2-50 | $CH_3$ | $SiEt_3$ | $CH_2$ | $CH_2$ | $CH_2$ | $B(OMe)_2$ |
| III.2-51 | i-Pr | $SiEt_3$ | $CH_2$ | $CH_2$ | $CH_2$ | $B(OMe)_2$ |
| III.2-52 | Ph | $SiEt_3$ | $CH_2$ | $CH_2$ | $CH_2$ | $B(OMe)_2$ |
| III.2-53 | $CH_3$ | H | $CH_2$ | $CH_2$ | $CH_2$ | 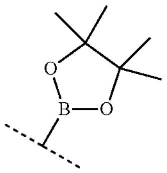 |

TABLE 8-continued (III)

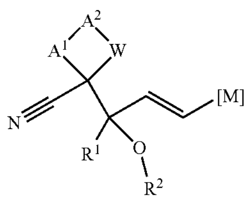

| No. | $R^1$ | $R^2$ | $A^1$ | $A^2$ | W | [M] |
|---|---|---|---|---|---|---|
| III.2-54 | i-Pr | H | $CH_2$ | $CH_2$ | $CH_2$ | 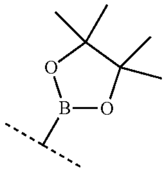 |
| III.2-55 | Ph | H | $CH_2$ | $CH_2$ | $CH_2$ | 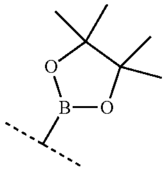 |
| III.2-56 | $CH_3$ | $SiEt_3$ | $CH_2$ | $CH_2$ | $CH_2$ | 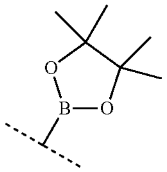 |
| III.2-57 | i-Pr | $SiEt_3$ | $CH_2$ | $CH_2$ | $CH_2$ | 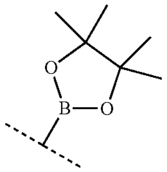 |
| III.2-58 | Ph | $SiEt_3$ | $CH_2$ | $CH_2$ | $CH_2$ | 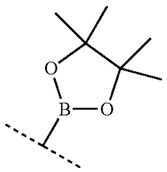 |
| III.2-59 | $CH_3$ | H | $CH_2$ | $CH_2$ | $CH_2$ | 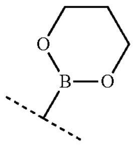 |
| III.2-60 | i-Pr | H | $CH_2$ | $CH_2$ | $CH_2$ | 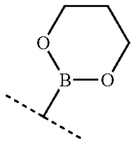 |
| III.2-61 | Ph | H | $CH_2$ | $CH_2$ | $CH_2$ | 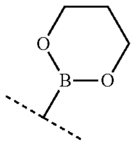 |

TABLE 8-continued (III)

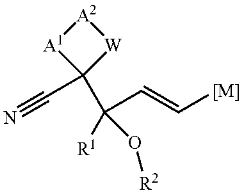

| No. | $R^1$ | $R^2$ | $A^1$ | $A^2$ | W | [M] |
|---|---|---|---|---|---|---|
| III.2-62 | $CH_3$ | $SiEt_3$ | $CH_2$ | $CH_2$ | $CH_2$ | 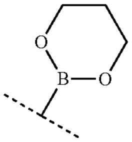 |
| III.2-63 | i-Pr | $SiEt_3$ | $CH_2$ | $CH_2$ | $CH_2$ | 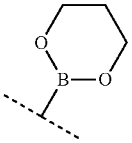 |
| III.2-64 | Ph | $SiEt_3$ | $CH_2$ | $CH_2$ | $CH_2$ | 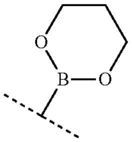 |
| III.2-65 | $CH_3$ | H | $CH_2$ | O | $CH_2$ | $Sn(n\text{-}Bu)_3$ |
| III.2-66 | i-Pr | H | $CH_2$ | O | $CH_2$ | $Sn(n\text{-}Bu)_3$ |
| III.2-67 | Ph | H | $CH_2$ | O | $CH_2$ | $Sn(n\text{-}Bu)_3$ |
| III.2-68 | $CH_3$ | $SiEt_3$ | $CH_2$ | O | $CH_2$ | $Sn(n\text{-}Bu)_3$ |
| III.2-69 | i-Pr | $SiEt_3$ | $CH_2$ | O | $CH_2$ | $Sn(n\text{-}Bu)_3$ |
| III.2-70 | Ph | $SiEt_3$ | $CH_2$ | O | $CH_2$ | $Sn(n\text{-}Bu)_3$ |
| III.2-71 | c-Pr | $SiEt_3$ | $CH_2$ | O | $CH_2$ | $Sn(n\text{-}Bu)_3$ |
| III.2-72 | $CH_3$ | H | $CH_2$ | O | $CH_2$ | $Sn(n\text{-}Pr)_3$ |
| III.2-73 | i-Pr | H | $CH_2$ | O | $CH_2$ | $Sn(n\text{-}Pr)_3$ |
| III.2-74 | Ph | H | $CH_2$ | O | $CH_2$ | $Sn(n\text{-}Pr)_3$ |
| III.2-75 | i-Pr | $SiEt_3$ | $CH_2$ | O | $CH_2$ | $Sn(n\text{-}Pr)_3$ |
| III.2-76 | Ph | $SiEt_3$ | $CH_2$ | O | $CH_2$ | $Sn(n\text{-}Pr)_3$ |
| III.2-77 | $CH_3$ | H | $CH_2$ | O | $CH_2$ | $Sn(c\text{-}Hex)_3$ |
| III.2-78 | i-Pr | H | $CH_2$ | O | $CH_2$ | $Sn(c\text{-}Hex)_3$ |
| III.2-79 | Ph | H | $CH_2$ | O | $CH_2$ | $Sn(c\text{-}Hex)_3$ |
| III.2-80 | $CH_3$ | $SiEt_3$ | $CH_2$ | O | $CH_2$ | $Sn(c\text{-}Hex)_3$ |
| III.2-81 | i-Pr | $SiEt_3$ | $CH_2$ | O | $CH_2$ | $Sn(c\text{-}Hex)_3$ |
| III.2-82 | Ph | $SiEt_3$ | $CH_2$ | O | $CH_2$ | $Sn(c\text{-}Hex)_3$ |
| III.2-83 | $CH_3$ | H | $CH_2$ | O | $CH_2$ | $GeEt_3$ |
| III.2-84 | i-Pr | H | $CH_2$ | O | $CH_2$ | $GeEt_3$ |
| III.2-85 | Ph | H | $CH_2$ | O | $CH_2$ | $GeEt_3$ |
| III.2-86 | $CH_3$ | $SiEt_3$ | $CH_2$ | O | $CH_2$ | $GeEt_3$ |
| III.2-87 | i-Pr | $SiEt_3$ | $CH_2$ | O | $CH_2$ | $GeEt_3$ |
| III.2-88 | Ph | $SiEt_3$ | $CH_2$ | O | $CH_2$ | $GeEt_3$ |
| III.2-89 | $CH_3$ | $SiEt_3$ | $CH_2$ | O | $CH_2$ | $Zr(C_5H_5)_2$ |
| III.2-90 | i-Pr | $SiEt_3$ | $CH_2$ | O | $CH_2$ | $Zr(C_5H_5)_2$ |
| III.2-91 | Ph | $SiEt_3$ | $CH_2$ | O | $CH_2$ | $Zr(C_5H_5)_2$ |
| III.2-92 | $CH_3$ | $SiEt_3$ | $CH_2$ | O | $CH_2$ | $Hf(C_5H_5)_2$ |
| III.2-93 | i-Pr | $SiEt_3$ | $CH_2$ | O | $CH_2$ | $Hf(C_5H_5)_2$ |
| III.2-94 | Ph | $SiEt_3$ | $CH_2$ | O | $CH_2$ | $Hf(C_5H_5)_2$ |
| III.2-95 | $CH_3$ | H | $CH_2$ | O | $CH_2$ | $B(OH)_2$ |
| III.2-96 | i-Pr | H | $CH_2$ | O | $CH_2$ | $B(OH)_2$ |
| III.2-97 | Ph | H | $CH_2$ | O | $CH_2$ | $B(OH)_2$ |
| III.2-98 | $CH_3$ | $SiEt_3$ | $CH_2$ | O | $CH_2$ | $B(OH)_2$ |
| III.2-99 | i-Pr | $SiEt_3$ | $CH_2$ | O | $CH_2$ | $B(OH)_2$ |
| III.2-100 | Ph | $SiEt_3$ | $CH_2$ | O | $CH_2$ | $B(OH)_2$ |
| III.2-101 | $CH_3$ | H | $CH_2$ | O | $CH_2$ | $B(OMe)_2$ |
| III.2-102 | i-Pr | H | $CH_2$ | O | $CH_2$ | $B(OMe)_2$ |
| III.2-103 | Ph | H | $CH_2$ | O | $CH_2$ | $B(OMe)_2$ |
| III.2-104 | $CH_3$ | $SiEt_3$ | $CH_2$ | O | $CH_2$ | $B(OMe)_2$ |
| III.2-105 | i-Pr | $SiEt_3$ | $CH_2$ | O | $CH_2$ | $B(OMe)_2$ |
| III.2-106 | Ph | $SiEt_3$ | $CH_2$ | O | $CH_2$ | $B(OMe)_2$ |

TABLE 8-continued (III)

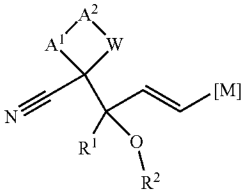

| No. | $R^1$ | $R^2$ | $A^1$ | $A^2$ | W | [M] |
|---|---|---|---|---|---|---|
| III.2-107 | $CH_3$ | H | $CH_2$ | O | $CH_2$ | 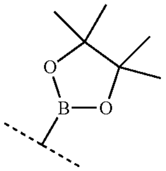 |
| III.2-108 | i-Pr | H | $CH_2$ | O | $CH_2$ | 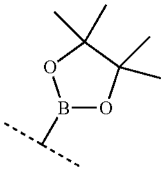 |
| III.2-109 | Ph | H | $CH_2$ | O | $CH_2$ | 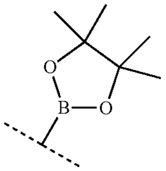 |
| III.2-110 | $CH_3$ | $SiEt_3$ | $CH_2$ | O | $CH_2$ | 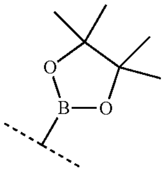 |
| III.2-111 | i-Pr | $SiEt_3$ | $CH_2$ | O | $CH_2$ | 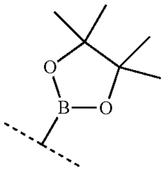 |
| III.2-112 | Ph | $SiEt_3$ | $CH_2$ | O | $CH_2$ | 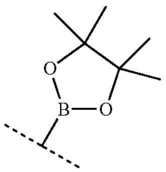 |
| III.2-113 | $CH_3$ | H | $CH_2$ | O | $CH_2$ | 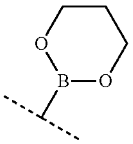 |

TABLE 8-continued

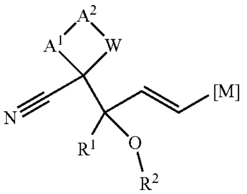

(III)

| No. | $R^1$ | $R^2$ | $A^1$ | $A^2$ | W | [M] |
|---|---|---|---|---|---|---|
| III.2-114 | i-Pr | H | $CH_2$ | O | $CH_2$ | 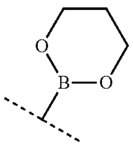 |
| III.2-115 | Ph | H | $CH_2$ | O | $CH_2$ | 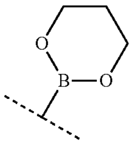 |
| III.2-116 | $CH_3$ | $SiEt_3$ | $CH_2$ | O | $CH_2$ | 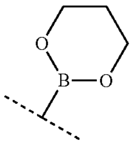 |
| III.2-117 | i-Pr | $SiEt_3$ | $CH_2$ | O | $CH_2$ | 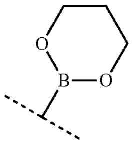 |
| III.2-118 | Ph | $SiEt_3$ | $CH_2$ | O | $CH_2$ | 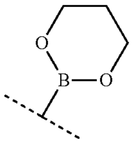 |

Spectroscopic Data of Selected Table Examples

Example No. I.1-36

$^1H$ NMR (400 MHz, $CDCl_3$ δ, ppm) 6.03 (s, 1H), 4.19 (q, 2H), 2.87 (br. s, 1H, OH), 2.02 (s, 3H), 1.80 (s, 3H), 1.44 (m, 1H), 1.34 (m, 1H), 1.28 (t, 3H), 1.23 (m, 2H).

Example No. I.1-102

$^1H$ NMR (400 MHz, $CDCl_3$ δ, ppm) 6.03 (s, 1H), 3.72 (s, 3H), 2.72 (br. s, 1H, OH), 2.47 (sept, 1H), 2.30 (q, 2H), 1.44 (m, 1H), 1.42 (m, 1H), 1.30 (m, 1H), 1.22 (m, 1H), 1.17-1.12 (m, 9H).

Example No. I.1-103

$^1H$ NMR (400 MHz, $CDCl_3$ δ, ppm) 6.03 (s, 1H), 4.19 (q, 2H), 2.68 (br. s, 1H, OH), 2.48 (sept, 1H), 2.29 (q, 2H), 1.45 (m, 1H), 1.43 (m, 1H), 1.32 (m, 1H), 1.29 (t, 3H), 1.22 (m, 1H), 1.16-1.11 (m, 9H).

Example No. I.1-120

$^1H$ NMR (400 MHz, $CDCl_3$ δ, ppm) 6.67 (s, 1H), 3.82 (s, 3H), 2.55 (br. s, 1H, OH), 2.51 (sept, 1H), 1.41 (m, 2H), 1.38 (m, 1H), 1.27 (m, 1H), 1.18 (d, 3H), 1.13 (d, 3H).

Example No. I.1-135

$^1H$ NMR (400 MHz, $CDCl_3$ δ, ppm) 6.03 (s, 1H), 3.72 (s, 3H), 2.66 (br. s, 1H, OH), 2.46 (sept, 1H), 2.03 (s, 3H), 1.44 (m, 1H), 1.42 (m, 1H), 1.33 (m, 1H), 1.21 (m, 1H), 1.13 (d, 3H), 1.11 (d, 3H).

Example No. I.1-136

$^1H$ NMR (400 MHz, $CDCl_3$ δ, ppm) 6.02 (s, 1H), 4.18 (q, 2H), 2.68 (br. s, 1H, OH), 2.48 (sept, 1H), 2.02 (s, 3H), 1.43 (m, 2H), 1.31 (m, 1H), 1.28 (t, 3H), 1.21 (m, 1H), 1.14 (d, 3H), 1.12 (d, 3H).

Example No. I.1-158

$^1H$ NMR (400 MHz, $CDCl_3$ δ, ppm) 5.95 (s, 1H), 5.82 (br. s, 1H, NH), 4.12 (m, 1H), 2.88 (br.s, 1H, OH), 2.46 (sept, 1H), 2.27 (br. q, 2H), 1.42 (m, 1H), 1.33 (m, 1H), 1.26 (m, 2H), 1.18 (d, 6H), 1.14 (d, 3H), 1.13 (t, 3H), 1.11 (d, 3H).

Example No. I.1-202

$^1H$ NMR (400 MHz, $CDCl_3$ δ, ppm) 7.76 (m, 2H), 7.43-7.35 (m, 3H), 6.07 (s, 1H), 3.72 (s, 3H), 3.35 (br. s, 1H, OH), 2.34 (q, 2H), 1.60 (m, 1H), 1.57 (m, 1H), 1.28 (m, 2H), 1.18 (t, 3H).

Example No. I.1-203

$^1H$ NMR (400 MHz, $CDCl_3$ δ, ppm) 7.75 (m, 2H), 7.42-7.34 (m, 3H), 6.07 (s, 1H), 4.20 (q, 2H), 3.55 (br. s, 1H, OH), 2.34 (q, 2H), 1.62 (m, 1H), 1.56 (m, 1H), 1.28 (t, 3H), 1.26 (m, 2H), 1.18 (t, 3H).

Example No. I.1-220

$^1H$ NMR (400 MHz, $CDCl_3$ δ, ppm) 7.73 (m, 2H), 7.44-7.37 (m, 3H), 6.71 (s, 1H), 3.83 (s, 2H), 3.09 (br. s, 1H, OH), 1.61 (m, 1H), 1.50 (m, 1H), 1.32 (m, 2H).

Example No. I.1-502

$^1H$ NMR (400 MHz, $CDCl_3$ δ, ppm) 7.75 (m, 2H), 7.10 (m, 2H), 6.09 (s, 1H), 3.73 (s, 3H), 3.42 (br. s, 1H, OH), 2.35 (q, 2H), 1.58 (m, 1H), 1.56 (m, 1H), 1.29 (m, 2H), 1.17 (t, 3H).

Example No. I.1-520

$^1H$ NMR (400 MHz, $CDCl_3$ δ, ppm) 7.73 (m, 2H), 7.12 (m, 2H), 6.73 (s, 1H), 3.83 (s, 3H), 3.12 (br. s, 1H, OH), 1.60 (m, 1H), 1.49 (m, 1H), 1.33 (m, 1H), 1.31 (m, 1H).

Example No. I.1-557

$^1H$ NMR (400 MHz, $CDCl_3$ δ, ppm) 7.73 (m, 2H), 7.55 (br. m, 1H, NH), 7.11 (m, 2H), 7.03 (s, 1H), 2.94 (m, 1H), 2.49 (q, 2H), 2.28 (br.s, 1H, OH), 1.48 (m, 2H), 1.42 (m, 2H), 1.38 (m, 2H), 1.27 (t, 3H), 1.12 (m, 2H).

Example No. I.1-558

$^1H$ NMR (400 MHz, $CDCl_3$ δ, ppm) 7.73 (m, 2H), 7.11 (m, 2H), 6.23 (s, 1H), 5.53 (br. m, 1H, NH), 4.18 (m, 1H), 2.63 (q, 2H), 2.37 (br.s, 1H, OH), 1.43 (m, 2H), 1.38 (m, 2H), 1.20 (d, 3H), 1.18 (d, 3H), 1.13 (t, 3H).

Example No. I.1-605

$^1$H NMR (400 MHz, $CDCl_3$ δ, ppm) 6.04 (s, 1H), 4.08 (t, 2H), 2.75 (br. s, 1H, OH), 2.47 (sept, 1H), 2.30 (q, 2H), 1.68 (sext, 2H), 1.45 (m, 2H), 1.43 (m, 1H), 1.31 (m, 1H), 1.17-1.11 (m, 9H), 0.95 (t, 3H).

Example No. I.1-608

$^1$H NMR (400 MHz, $CDCl_3$ δ, ppm) 6.68 (s, 1H), 4.17 (t, 2H), 2.52 (br. s, 1H, OH), 2.48 (sept, 1H), 1.71 (sext, 2H), 1.41 (m, 2H), 1.38 (m, 1H), 1.27 (m, 1H), 1.16 (d, 3H), 1.13 (d, 3H), 0.97 (t, 3H).

Example No. I.1-609

$^1$H NMR (400 MHz, $CDCl_3$ δ, ppm) 7.75 (m, 2H), 7.43-7.36 (m, 3H), 6.08 (s, 1H), 4.09 (t, 2H), 3.42 (br. s, 1H, OH), 2.37 (q, 2H), 1.68 (sext, 2H), 1.61 (m, 1H), 1.57 (m, 1H), 1.27 (m, 2H), 1.18 (t, 3H), 0.96 (t, 3H).

Example No. I.1-610

$^1$H NMR (400 MHz, $CDCl_3$ δ, ppm) 7.73 (m, 2H), 7.42-7.36 (m, 3H), 6.06 (s, 1H), 4.58 (br. s, 1H, OH), 4.29 (m, 2H), 3.63 (m, 1H), 3.58 (m, 1H), 3.31 (s, 3H), 2.39 (q, 2H), 1.53 (m, 1H), 1.44 (m, 1H), 1.24 (m, 2H), 1.20 (t, 3H).

Example No. I.1-613

$^1$H NMR (400 MHz, $CDCl_3$ δ, ppm) 7.75 (m, 2H), 7.09 (m, 2H), 6.09 (s, 1H), 4.09 (t, 2H), 3.49 (br. s, 1H, OH), 2.37 (q, 2H), 1.68 (sext, 2H), 1.58 (m, 1H), 1.54 (m, 1H), 1.29 (m, 2H), 1.18 (t, 3H), 0.97 (t, 3H).

Example No. I.1-614

$^1$H NMR (400 MHz, $CDCl_3$ δ, ppm) 7.72 (m, 2H), 7.10 (m, 2H), 6.07 (s, 1H), 4.61 (br. s, 1H, OH), 4.30 (m, 2H), 3.67-3.60 (m, 2H), 3.32 (s, 3H), 2.38 (q, 2H), 1.53 (m, 1H), 1.44 (m, 1H), 1.25 (m, 2H), 1.20 (t, 3H).

Example No. I.1-616

$^1$H NMR (400 MHz, $CDCl_3$ δ, ppm) 7.73 (m, 2H), 7.11 (m, 2H), 6.73 (s, 1H), 4.18 (t, 2H), 3.12 (br. s, 1H, OH), 1.70 (sext, 2H), 1.58 (m, 1H), 1.49 (m, 1H), 1.32 (m, 2H), 0.96 (t, 3H).

Example No. I.1-618

$^1$H NMR (400 MHz, $CDCl_3$ δ, ppm) 6.02 (s, 1H), 3.73 (s, 3H), 2.73 (br. s, 1H, OH), 2.29 (q, 2H), 1.53 (m, 1H), 1.46 (m, 1H), 1.36 (m, 1H), 1.24 (m, 2H), 1.14 (t, 3H), 0.79 (m, 1H), 0.72 (m, 2H), 0.62 (m, 1H).

Example No. I.1-632

$^1$H NMR (400 MHz, $CDCl_3$ δ, ppm) 6.66 (s, 1H), 3.83 (s, 3H), 3.51 (br. s, 1H, OH), 1.58 (m, 1H), 1.46 (m, 1H), 1.33-1.25 (m, 3H), 0.81-0.73 (m, 2H), 0.71-0.63 (m, 2H).

Example No. I.1-648

$^1$H NMR (400 MHz, $CDCl_3$ δ, ppm) 6.05 (s, 1H), 3.73 (s, 3H), 3.07 (m, 1H), 2.78 (br. s, 1H, OH), 2.33 (q, 2H), 2.24 (m, 1H), 2.13-2.05 (m, 3H), 1.93 (m, 1H), 1.78 (m, 1H), 1.42 (m, 1H), 1.34 (m, 1H), 1.21 (m, 5H).

Example No. I.1-662

$^1$H NMR (400 MHz, $CDCl_3$ δ, ppm) 6.69 (s, 1H), 3.83 (s, 3H), 3.10 (m, 1H), 2.53 (br. s, 1H, OH), 2.28 (m, 1H), 2.13-2.06 (m, 3H), 1.95 (m, 1H), 1.41 (m, 1H), 1.30 (m, 1H), 1.24-1.18 (m, 2H).

Example No. I.1-678

$^1$H NMR (400 MHz, $CDCl_3$ δ, ppm) 6.02 (s, 1H), 3.72 (s, 3H), 2.68 (br. s, 1H, OH), 2.31 (q, 2H), 2.11 (m, 2H), 2.02 (m, 1H), 1.82 (m, 2H), 1.72 (m, 1H), 1.45-1.38 (m, 3H), 1.32-1.28 (m, 3H), 1.22-1.16 (m, 4H), 1.14 (t, 3H).

Example No. I.1-692

$^1$H NMR (400 MHz, $CDCl_3$ δ, ppm) 6.66 (s, 1H), 3.82 (s, 3H), 2.54 (br. s, 1H, OH), 2.17 (m, 1H), 2.10 (m, 1H), 2.02 (m, 1H), 1.83 (m, 2H), 1.72 (m, 1H), 1.41-1.34 (m, 6H), 1.32-1.22 (m, 1H), 1.18-1.11 (m, 2H).

Example No. I.1-702

$^1$H NMR (400 MHz, $CDCl_3$ δ, ppm) 6.02 (s, 1H), 4.18 (q, 2H), 2.69 (br. s, 1H, OH), 2.10 (m, 2H), 2.02 (s, 3H), 1.98 (m, 1H), 1.82 (m, 2H), 1.71 (m, 1H), 1.42 (m, 2H), 1.38 (m, 1H), 1.32-1.26 (m, 2H), 1.29 (t, 3H), 1.21-1.14 (m, 4H).

Example No. I.1-711

$^1$H NMR (400 MHz, $CDCl_3$ δ, ppm) 6.02 (s, 1H), 4.31 (m, 2H), 3.67 (m, 2H), 3.58 (br. s, 1H, OH), 3.41 (s, 1H), 2.28 (q, 2H), 1.97 (m, 1H), 1.88 (m, 1H), 1.78 (m, 1H), 1.51-1.42 (m, 3H), 1.38-1.29 (m, 2H), 1.21 (m, 1H), 1.14 (t, 3H), 1.04 (m, 6H).

Example No. I.1-722

$^1$H NMR (400 MHz, $CDCl_3$ δ, ppm) 6.65 (s, 1H), 3.82 (s, 3H), 2.49 (br. s, 1H, OH), 2.03 (m, 1H), 1.88 (m, 1H), 1.78 (m, 1H), 1.51 (m, 1H), 1.45-1.38 (m, 4H), 1.27 (m, 1H), 1.05 (m, 6H).

Example No. I.1-723

$^1$H NMR (400 MHz, $CDCl_3$ δ, ppm) 6.65 (s, 1H), 4.28 (q, 2H), 2.51 (br. s, 1H, OH), 2.03 (m, 1H), 1.87 (m, 1H), 1.76 (m, 1H), 1.51-1.38 (m, 4H), 1.33 (t, 3H), 1.27 (m, 2H), 1.06 (m, 6H).

Example No. I.1-732

$^1$H NMR (400 MHz, $CDCl_3$ δ, ppm) 6.01 (s, 1H), 4.18 (q, 2H), 2.65 (br. s, 1H, OH), 2.03 (s, 3H), 1.99 (m, 1H), 1.87 (m, 1H), 1.78 (m, 1H), 1.53-1.39 (m, 4H), 1.33 (m, 1H), 1.28 (t, 3H), 1.22 (m, 1H), 1.04 (m, 6H).

Example No. I.1-738

$^1$H NMR (400 MHz, $CDCl_3$ δ, ppm) 6.04 (s, 1H), 3.72 (s, 3H), 2.74 (br. s, 1H, OH), 2.34 (q, 2H), 2.08 (m, 4H), 1.97 (m, 4H), 1.94 (m, 1H), 1.72 (m, 6H), 1.55 (m, 1H), 1.38 (m, 1H), 1.29-1.20 (m, 2H), 1.19 (t, 3H).

Example No. I.1-752

$^1H$ NMR (400 MHz, $CDCl_3$ δ, ppm) 6.67 (s, 1H), 3.83 (s, 3H), 2.45 (br. s, 1H, OH), 2.09 (m, 4H), 1.97 (m, 4H), 1.72 (m, 7H), 1.58 (m, 1H), 1.42 (m, 1H), 1.33-1.22 (m, 2H).

Example No. I.1-753

$^1H$ NMR (400 MHz, $CDCl_3$ δ, ppm) 6.67 (s, 1H), 4.29 (q, 2H), 2.50 (br. s, 1H, OH), 2.09 (m, 3H), 1.98 (m, 5H), 1.92 (m, 1H), 1.71 (m, 6H), 1.58 (m, 1H), 1.33 (m, 4H), 1.25-1.20 (m, 2H).

Example No. I.1-762

$^1H$ NMR (400 MHz, $CDCl_3$ δ, ppm) 6.03 (s, 1H), 4.18 (q, 2H), 2.80 (br. s, 1H, OH), 2.07 (m, 4H), 1.98 (m, 4H), 1.71 (m, 6H), 1.68 (m, 1H), 1.55 (m, 1H), 1.38 (m, 1H), 1.27 t, 3H), 1.21 (m, 2H).

Example No. I.1-768

$^1H$ NMR (400 MHz, $CDCl_3$ δ, ppm) 7.56 (m, 1H), 7.48 (m, 1H), 7.39 (m, 1H), 7.07 (m, 1H), 6.09 (s, 1H), 3.73 (s, 3H), 3.58 (br. s, 1H, OH), 2.37 (q, 2H), 1.61-1.55 (m, 2H), 1.31-1.27 (m, 2H), 1.19 (t, 3H).

Example No. I.1-771

$^1H$ NMR (400 MHz, $CDCl_3$ δ, ppm) 7.54 (m, 1H), 7.45-7.37 (m, 2H), 7.06 (m, 1H), 6.07 (s, 1H), 4.71 (br. s, 1H, OH), 4.30 (t, 2H), 3.65-3.58 (m, 2H), 3.33 (s, 3H), 2.39 (q, 2H), 1.54 (m, 1H), 1.47 (m, 1H), 1.28-1.25 (m, 2H), 1.21 (t, 3H).

Example No. I.1-782

$^1H$ NMR (400 MHz, $CDCl_3$ δ, ppm) 7.55 (m, 1H), 7.47-7.39 (m, 2H), 7.11-7.07 (m, 1H), 6.73 (s, 1H), 3.84 (s, 3H), 3.19 (br. s, 1H, OH), 1.60 (m, 1H), 1.52 (m, 1H), 1.36-1.30 (m, 2H).

Example No. I.1-783

$^1H$ NMR (400 MHz, $CDCl_3$ δ, ppm) 7.54 (m, 1H), 7.46-7.39 (m, 2H), 7.10-7.06 (m, 1H), 6.73 (s, 1H), 4.20 (q, 2H), 3.19 (br. s, 1H, OH), 1.60-1.53 (m, 2H), 1.31-1.24 (m, 5H).

Example No. I.1-792

$^1H$ NMR (400 MHz, $CDCl_3$ δ, ppm) 7.56 (m, 1H), 7.46 (m, 1H), 7.39 (m, 1H), 7.09-7.05 (m, 1H), 6.09 (s, 1H), 4.20 (q, 2H), 3.57 (br. s, 1H, OH), 2.07 (s, 3H), 1.59 (m, 2H), 1.30-1.25 (m, 5H).

Example No. I.1-798

$^1H$ NMR (400 MHz, $CDCl_3$ δ, ppm) 7.64 (d, 2H), 7.22 (d, 2H), 6.06 (s, 1H), 3.73 (s, 3H), 3.18 (br. s, 1H, OH), 2.37 (s, 3H), 2.32 (q, 2H), 1.58 (m, 1H), 1.54 (m, 1H), 1.29-1.25 (m, 2H), 1.16 (t, 3H).

Example No. I.1-801

$^1H$ NMR (400 MHz, $CDCl_3$ δ, ppm) 7.61 (d, 2H), 7.22 (d, 2H), 6.05 (s, 1H), 4.48 (br. s, 1H, OH), 4.29 (m, 2H), 3.67-3.57 (m, 2H), 3.32 (s, 3H), 2.40-2.34 (m, 5H), 1.53 (m, 1H), 1.44 (m, 1H), 1.24 (m, 2H), 1.20 (t, 3H).

Example No. I.1-812

$^1H$ NMR (400 MHz, $CDCl_3$ δ, ppm) 7.61 (d, 2H), 7.24 (d, 2H), 6.71 (s, 1H), 3.83 (s, 3H), 2.93 (br. s, 1H, OH), 2.38 (s, 3H), 1.58 (m, 1H), 1.46 (m, 1H), 1.33-1.28 (m, 2H).

Example No. I.1-813

$^1H$ NMR (400 MHz, $CDCl_3$ δ, ppm) 7.61 (d, 2H), 7.22 (d, 2H), 6.70 (s, 1H), 4.29 (q, 2H), 2.99 (br. s, 1H, OH), 2.37 (s, 3H), 1.58 (m, 1H), 1.44 (m, 1H), 1.34-1.27 (m, 5H).

Example No. I.1-822

$^1H$ NMR (400 MHz, $CDCl_3$ δ, ppm) 7.63 (d, 2H), 7.23 (d, 2H), 6.06 (s, 1H), 4.19 (q, 2H), 3.28 (br. s, 1H, OH), 2.37 (s, 3H), 1.57 (m, 1H), 1.54 (m, 1H), 1.29-1.22 (m, 5H).

Example No. I.1-831

$^1H$ NMR (400 MHz, $CDCl_3$ δ, ppm) 6.03 (s, 1H), 4.31 (m, 2H), 3.67 (m, 2H), 3.82 (s, 3H), 3.59 (br. s, 1H, OH), 3.41 (s, 3H), 2.72-2.66 (m, 1H), 2.28 (q, 2H), 1.96-1.89 (m, 2H), 1.72-1.56 (m, 6H), 1.42 (m, 1H), 1.32 (m, 1H), 1.25-1.18 (m, 2H), 1.14 (t, 3H).

Example No. I.1-842

$^1H$ NMR (400 MHz, $CDCl_3$ δ, ppm) 6.66 (s, 1H), 3.82 (s, 3H), 2.73 (m, 1H), 2.50 (br. s, 1H, OH), 1.98-1.91 (m, 2H), 1.73-1.60 (m, 6H), 1.46-1.30 (m, 3H), 1.28-1.24 (m, 1H).

Example No. I.1-851

$^1H$ NMR (400 MHz, $CDCl_3$ δ, ppm) 6.03 (s, 1H), 3.72 (s, 3H), 2.71 (m, 1H), 2.58 (br. s, 1H, OH), 2.02 (s, 3H), 1.97-1.90 (m, 2H), 1.72-1.59 (m, 6H), 1.47-1.41 (m, 2H), 1.28 (m, 1H), 1.21 (m, 1H).

Example No. I.1-858

$^1H$ NMR (400 MHz, $CDCl_3$ δ, ppm) 6.04 (s, 1H), 3.72 (s, 3H), 2.70 (br. s, 1H, OH), 2.33 (q, 2H), 1.59-1.55 (m, 1H), 1.43-1.39 (m, 1H), 1.25 (s, 9H), 1.23 (m, 2H).

Example No. I.1-872

$^1H$ NMR (400 MHz, $CDCl_3$ δ, ppm) 6.67 (s, 1H), 3.83 (s, 3H), 2.47 (br. s, 1H, OH), 1.59-1.56 (m, 1H), 1.41-1.32 (m, 2H), 1.25 (s, 9H), 1.23 (m, 1H).

Example No. I.1-881

$^1H$ NMR (400 MHz, $CDCl_3$ δ, ppm) 6.04 (s, 1H), 3.72 (s, 3H), 2.72 (br. s, 1H, OH), 2.05 (s, 3H), 1.59-1.55 (m, 1H), 1.43-1.40 (m, 1H), 1.25 (s, 9H), 1.23 (m, 2H).

Example No. I.1-887

$^1H$ NMR (400 MHz, $CDCl_3$ δ, ppm) 6.66 (s, 1H), 4.17 (t, 2H), 2.50 (br. s, 1H, OH), 2.03 (m, 1H), 1.85 (m, 1H), 1.78 (m, 1H), 1.72 (sext, 2H), 1.49-1.37 (m, 4H), 1.27 (m, 2H), 1.05 (m, 6H), 0.98 (t, 3H).

Example No. I.1-888

$^1H$ NMR (400 MHz, $CDCl_3$ δ, ppm) 7.62 (d, 2H), 7.22 (d, 2H), 6.71 (s, 1H), 4.17 (t, 2H), 3.07 (br. s, 1H, OH), 2.37 (s, 3H), 1.73-1.67 (m, 2H), 1.59 (m, 1H), 1.47 (m, 1H), 1.32-1.27 (m, 2H), 0.96 (t, 3H).

Example No. I.1-889

$^1$H NMR (400 MHz, $CDCl_3$ δ, ppm) 6.68 (s, 1H), 4.17 (t, 2H), 2.49 (br. s, 1H, OH), 1.73-1.67 (m, 2H), 1.59 (m, 1H), 1.39-1.30 (m, 2H), 1.26 (s, 9H), 1.24 (m, 1H), 0.97 (t, 3H).

Example No. I.1-890

$^1$H NMR (400 MHz, $CDCl_3$ δ, ppm) 6.67 (s, 1H), 4.17 (t, 2H), 2.72 (m, 1H), 2.49 (br. s, 1H, OH), 1.98-1.90 (m, 2H), 1.74-1.60 (m, 8H), 1.46-1.38 (m, 2H), 1.32 (m, 1H), 1.24 (m, 1H), 0.97 (t, 3H).

Example No. I.1-892

$^1$H NMR (400 MHz, $CDCl_3$ δ, ppm) 7.71 (d, 2H), 7.40 (d, 2H), 6.09 (s, 1H), 3.73 (s, 3H), 3.24 (br. s, 1H, OH), 2.36 (q, 2H), 1.59-1.55 (m, 2H), 1.32-1.26 (m, 2H), 1.16 (t, 3H).

Example No. I.1-906

$^1$H NMR (400 MHz, $CDCl_3$ δ, ppm) 7.69 (d, 2H), 7.42 (d, 2H), 6.73 (s, 1H), 3.83 (s, 2H), 2.98 (br. s, 1H, OH), 1.59 (m, 1H), 1.47 (m, 1H), 1.34-1.28 (m, 2H).

Example No. I.1-916

$^1$H NMR (400 MHz, $CDCl_3$ δ, ppm) 7.71 (d, 2H), 7.40 (d, 2H), 6.09 (s, 1H), 4.19 (q, 2H), 3.25 (br. s, 1H, OH), 2.05 (s, 3H), 1.59-1.55 (m, 2H), 1.32-1.24 (m, 5H).

Example No. I.1-921

$^1$H NMR (400 MHz, $CDCl_3$ δ, ppm) 7.69 (d, 2H), 7.41 (d, 2H), 6.73 (s, 1H), 4.17 (t, 2H), 3.05 (br. s, 1H, OH), 1.73-1.66 (m, 2H), 1.59 (m, 1H), 1.49 (m, 1H), 1.34-1.28 (m, 2H), 0.97 (t, 3H).

Example No. I.2-102

$^1$H NMR (400 MHz, $CDCl_3$ δ, ppm) 7.68 (d, 1H), 6.26 (d, 1H), 5.74 (s, 1H), 3.72 (s, 3H), 2.94 (br. s, 1H, OH), 2.41 (q, 2H), 2.37 (sept, 1H), 1.34 (m, 1H), 1.19 (m, 1H), 1.14 (t, 3H), 1.07 (d, 3H), 1.03 (m, 1H), 0.96 (m, 1H), 0.92 (d, 3H).

Example No. I.2-130

$^1$H NMR (400 MHz, $CDCl_3$ δ, ppm) 7.67 (d, 1H), 6.23 (d, 1H), 5.75 (s, 1H), 4.17 (q, 2H), 2.95 (m, 1H), 2.39 (sept, 1H), 1.94 (m, 2H), 1.73 (m, 1H), 1.68 (m, 2H), 1.63 (br. s, 1H, OH), 1.51 (m, 2H), 1.44 (m, 2H), 1.30 (t, 3H), 1.20 (m, 1H), 1.07 (d, 3H), 1.05 (m, 1H), 0.98 (m, 1H), 0.93 (d, 3H).

Example No. I.2-134

$^1$H NMR (400 MHz, $CDCl_3$ δ, ppm) 7.73 (d, 1H), 6.29 (d, 1H), 5.77 (s, 1H), 2.38 (sept, 1H), 2.08 (s, 3H), 1.68 (br. s, 1H, OH), 1.33 (m, 1H), 1.22 (m, 1H), 1.07 (d, 3H), 1.03 (m, 1H), 0.96 (m, 1H), 0.93 (d, 3H).

Example No. I.2-507

$^1$H NMR (400 MHz, $CDCl_3$ δ, ppm) 7.68 (d, 1H), 6.25 (d, 1H), 5.74 (s, 1H), 4.09 (t, 2H), 2.42 (q, 2H), 2.38 (sept, 1H), 1.68 (sext, 2H), 1.58 (br. s, 1H, OH), 1.39 (m, 1H), 1.34 (m, 1H), 1.20 (m, 1H), 1.16 (t, 3H), 1.06 (d, 3H), 1.02 (m, 1H), 0.97 (d, 3H), 0.93 (t, 3H).

Example No. I.2-581

$^1$H NMR (400 MHz, $CDCl_3$ δ, ppm) 7.44 (d, 1H), 6.36 (d, 1H), 6.31 (s, 1H), 3.79 (s, 3H), 2.08-1.99 (m, 2H), 1.88-1.75 (m, 2H), 1.71 (m, 2H), 1.62 (br. s, 1H, OH), 1.39-1.28 (m, 4H), 1.25-1.18 (m, 2H), 1.09 (m, 1H), 1.05-0.92 (m, 2H).

Example No. I.2-582

$^1$H NMR (400 MHz, $CDCl_3$ δ, ppm) 7.45 (d, 1H), 6.34 (d, 1H), 6.30 (s, 1H), 4.15 (t, 2H), 2.09-1.98 (m, 2H), 1.87-1.76 (m, 3H), 1.72 (sext, 2H), 1.64 (br. s, 1H, OH), 1.39-1.28 (m, 3H), 1.25-1.17 (m, 2H), 1.08 (m, 3H), 0.98 (t, 3H), 0.94 (m, 2H).

Example No. I.2-583

$^1$H NMR (400 MHz, $CDCl_3$ δ, ppm) 7.67 (d, 1H), 6.24 (d, 1H), 5.73 (s, 1H), 3.72 (s, 3H), 2.41 (q, 2H), 1.89 (m, 1H), 1.79 (m, 1H), 1.63 (m, 1H), 1.59 (br. s, 1H, OH), 1.41-1.32 (m, 3H), 1.31-1.22 (m, 3H) 1.13 (t, 3H), 1.04 (t, 3H), 0.97 (t, 3H).

Example No. I.2-586

$^1$H NMR (400 MHz, $CDCl_3$ δ, ppm) 7.46 (d, 1H), 6.34 (d, 1H), 6.31 (s, 1H), 4.17 (t, 2H), 1.91 (m, 1H), 1.78 (m, 1H), 1.70 (sext, 2H), 1.61 (m, 1H), 1.59 (br. s, 1H, OH), 1.37 (m, 1H), 1.33-1.22 (m, 4H) 1.12 (m, 1H), 1.03 (t, 3H), 1.00-0.91 (m, 6H).

Example No. I.2-591

$^1$H NMR (400 MHz, $CDCl_3$ δ, ppm) 7.94 (d, 1H), 7.46 (d, 2H), 7.21 (d, 2H), 6.54 (d, 1H), 5.78 (s, 1H), 3.71 (s, 3H), 2.45 (q, 2H), 2.36 (s, 3H), 2.15 (br. s, 1H, OH), 1.42-1.38 (m, 1H), 1.34-1.21 (m, 3H), 1.17 (t, 3H).

Example No. I.2-593

$^1$H NMR (400 MHz, $CDCl_3$ δ, ppm) 7.70 (d, 1H), 7.44 (d, 2H), 7.23 (d, 2H), 6.69 (d, 1H), 6.37 (s, 1H), 3.79 (s, 3H), 2.36 (s, 3H), 2.12 (br. s, 1H, OH), 1.42-1.37 (m, 1H), 1.36-1.26 (m, 2H), 1.23-1.18 (m, 1H).

Example No. I.2-599

$^1$H NMR (400 MHz, $CDCl_3$ δ, ppm) 7.70 (d, 1H), 6.32 (d, 1H), 5.74 (s, 1H), 3.72 (s, 3H), 2.65-2.58 (m, 1H), 2.44-2.38 (q, 2H), 1.92-1.85 (m, 1H), 1.72-1.55 (m, 8H), 1.35-1.28 (m, 2H) 1.14 (t, 3H), 1.02 (m, 2H).

Example No. I.2-601

$^1$H NMR (400 MHz, $CDCl_3$ δ, ppm) 7.47 (d, 1H), 6.42 (d, 1H), 6.32 (s, 1H), 3.80 (s, 3H), 2.70-2.63 (m, 1H), 1.95-1.88 (m, 1H), 1.81-1.73 (m, 1), 1.68-1.58 (m, 4H), 1.52 (br. s, 1H, OH), 1.47-1.38 (m, 2H), 1.29 (m, 1H) 1.18 (m, 1H), 1.10 (m, 1H), 1.02 (m, 2H).

Example No. I.2-603

$^1$H NMR (400 MHz, $CDCl_3$ δ, ppm) 7.69 (d, 1H), 6.64 (d, 1H), 5.76 (s, 1H), 3.71 (s, 3H), 2.46 (q, 2H), 1.61 (br. s, 1H, OH), 1.44-1.39 (m, 1H), 1.31-1.27 (m, 1H), 1.15 (s, 9H), 1.12-1.08 (m, 1H), 0.97-0.93 (m, 1H).

Example No. I.2-605

$^1$H NMR (400 MHz, $CDCl_3$ δ, ppm) 7.48 (d, 1H), 6.72 (d, 1H), 6.33 (s, 1H), 3.80 (s, 3H), 1.67 (m, 1H), 1.62 (br. s, 1H, OH), 1.40-1.26 (m, 2H), 1.16 (s, 9H), 1.12-1.04 (m, 1H).

Example No. I.2-615

$^1$H NMR (400 MHz, $CDCl_3$ δ, ppm) 7.76 (d, 1H), 6.23 (d, 1H), 5.74 (s, 1H), 4.17 (q, 2H), 2.03 (s, 3H), 1.86 (m, 1H), 1.80 (m, 1H), 1.63 (m, 1H), 1.59 (br. s, 1H, OH), 1.41-1.33 (m, 3H), 1.32-1.21 (m, 6H) 1.04 (t, 3H), 0.96 (t, 3H).

Example No. I.2-616

7.75 (d, 1H), 6.24 (d, 1H), 5.73 (s, 1H), 4.17 (q, 2H), 2.04 (s, 3H), 2.03-1.95 (m, 2H), 1.80 (m, 2H), 1.71 (m, 2H), 1.62 (br. s, 1H, OH), 1.42-1.30 (m, 4H), 1.28 (t, 3H), 1.20-1.16 (m, 1H), 1.14-1.08 (m, 1H), 1.04-0.92 (m, 3H).

Example No. I.2-617

$^1$H NMR (400 MHz, $CDCl_3$ δ, ppm) 8.04 (d, 1H), 7.46 (d, 2H), 7.22 (d, 2H), 6.51 (d, 1H), 5.79 (s, 1H), 4.17 (q, 2H), 2.36 (s, 3H), 2.12 (br. s, 1H, OH), 2.07 (s, 3H), 1.41-1.37 (m, 1H), 1.35-1.22 (m, 6H).

Example No. I.2-619

$^1$H NMR (400 MHz, $CDCl_3$ δ, ppm) 7.81 (d, 1H), 6.61 (d, 1H), 5.76 (s, 1H), 4.16 (q, 2H), 2.07 (s, 3H), 1.62 (br. s, 1H, OH), 1.42-1.35 (m, 2H), 1.29 (t, 3H), 1.15 (s, 9H), 1.10 (m, 1H), 0.97-0.92 (m, 1H).

Example No. I.2-620

$^1$H NMR (400 MHz, $CDCl_3$ δ, ppm) 7.48 (d, 1H), 6.71 (d, 1H), 6.33 (s, 1H), 4.26 (q, 2H), 1.63 (br. s, 1H, OH), 1.39-1.24 (m, 5H), 1.15 (s, 9H), 1.12-1.04 (m, 2H).

Example No. I.3-23

$^1$H NMR (400 MHz, $CDCl_3$ δ, ppm) 6.07 (s, 1H), 3.73 (s, 3H), 2.83-2.71 (m, 2H), 2.63 (br. s, 1H, OH), 2.41-2.25 (m, 6H), 1.92 (m, 1H), 1.19 (t, 3H), 1.11 (d, 3H), 1.04 (d, 3H).

Example No. I.3-33

$^1$H NMR (400 MHz, $CDCl_3$ δ, ppm) 6.71 (s, 1H), 4.29 (q, 2H), 2.80-2.68 (m, 2H), 2.44 (br. s, 1H, OH), 2.40 (m, 4H), 2.30 (m, 2H), 1.95 (m, 1H), 1.33 (t, 3H), 1.13 (d, 3H), 1.02 (d, 3H).

Example No. I.3-39

$^1$H NMR (400 MHz, $CDCl_3$ δ, ppm) 6.07 (s, 1H), 4.19 (q, 2H), 2.81-2.72 (m, 2H), 2.77 (br. s, 1H, OH), 2.41-2.25 (m, 4H), 2.08 (s, 3H), 1.92 (m, 1H), 1.28 (t, 3H), 1.10 (d, 3H), 1.03 (d, 3H).

Example No. I.3-53

$^1$H NMR (400 MHz, $CDCl_3$ δ, ppm) 7.73 (m, 2H), 7.42-7.36 (m, 3H), 6.73 (s, 1H), 3.83 (q, 2H), 3.04 (br. s, 1H, OH), 2.87-2.772 (m, 2H), 2.35-2.27 (m, 2H), 2.25-2.17 (m, 1H), 1.97-1.89 (m, 1H).

Example No. I.3-60

$^1$H NMR (400 MHz, $CDCl_3$ δ, ppm) 7.75 (m, 2H), 7.41-7.34 (m, 3H), 6.10 (s, 1H), 4.20 (q, 2H), 3.29 (br. s, 1H, OH), 2.85-2.76 (m, 2H), 2.32-2.25 (m, 2H), 2.23-2.14 (m, 1H), 2.10 (s, 3H), 1.96-1.88 (m, 1H), 1.27 (t, 3H).

Example No. I.3-128

$^1$H NMR (400 MHz, $CDCl_3$ δ, ppm) 6.07 (s, 1H), 4.32 (m, 2H), 3.67 (m, 2H), 3.40 (s, 3H), 3.61 (br. s, 1H, OH), 2.80-2.66 (m, 2H), 2.40-2.24 (m, 6H), 1.90 (m, 1H), 1.20 (t, 3H), 1.08 (d, 3H), 1.02 (d, 3H).

Example No. I.3-132

$^1$H NMR (400 MHz, $CDCl_3$ δ, ppm) 6.72 (s, 1H), 4.18 (t, 2H), 2.81-2.69 (m, 2H), 2.43 (br. s, 1H, OH), 2.42-2.34 (m, 4H), 2.32 (m, 2H), 1.97-1.92 (m, 1H), 1.71 (sext, 2H), 1.12 (d, 3H), 1.02 (d, 3H), 0.97 (t, 3H).

Example No. 1.4-23

$^1$H NMR (400 MHz, $CDCl_3$ δ, ppm) 7.76 (d, 1H), 6.09 (d, 1H), 5.73 (s, 1H), 3.72 (s, 3H), 2.73 (m, 1H), 2.41 (m, 1H), 2.38 (m, 2H), 2.29-2.18 (m, 3H), 2.03 (m, 1H), 1.82 (br. s, 1H, OH), 1.80 (m, 1H), 1.12 (t, 3H), 0.94 (d, 3H), 0.89 (d, 3H).

Example No. 1.4-39

$^1$H NMR (400 MHz, $CDCl_3$ δ, ppm) 7.86 (d, 1H), 6.07 (d, 1H), 5.73 (s, 1H), 4.19 (q, 2H), 2.73 (m, 1H), 2.41 (m, 1H), 2.29-2.18 (m, 3H), 2.02 (s, 3H), 1.83 (br. s, 1H, OH), 1.79 (m, 1H), 1.68 (m, 1H), 1.29 (t, 3H), 0.94 (d, 3H), 0.89 (d, 3H).

Example No. II.1-8

$^1$H NMR (400 MHz, $CDCl_3$ δ, ppm) 7.51 (m, 1H), 7.42-7.38 (m, 2H), 7.11-7.07 (m, 1H), 2.79 (s, 1H), 2.73 (br. s, 1H, OH), 1.52 (m, 1H), 1.45-1.37 (m, 1H), 1.32-1.27 (m, 2H).

Example No. II.1-9

$^1$H NMR (400 MHz, $CDCl_3$ δ, ppm) 7.66 (d, 2H), 7.42 (d, 2H), 2.79 (s, 1H), 2.66 (br. s, 1H, OH), 1.50 (m, 1H), 1.40 (m, 1H), 1.32-1.25 (m, 2H).

Example No. II.1-11

$^1$H NMR (400 MHz, $CDCl_3$ δ, ppm) 7.60 (d, 2H), 7.22 (d, 2H), 2.76 (s, 1H), 2.58 (br. s, 1H, OH), 2.38 (s, 3H), 1.50 (m, 1H), 1.38 (m, 1H), 1.28 (m, 2H).

Example No. II.1-79

$^1$H NMR (400 MHz, $CDCl_3$ δ, ppm) 7.69 (m, 1H), 7.49 (m, 1H), 7.33 (m, 1H), 2.77 (s, 1H), 2.64 (br. s, 1H, OH), 1.48 (m, 1H), 1.35 (m, 1H), 1.28 (m, 2H).

Example No. II.1-80

$^1$H NMR (400 MHz, $CDCl_3$ δ, ppm) 3.04 (m, 1H), 2.77 (s, 1H), 2.21 (m, 1H), 2.09 (br. s, 1H, OH), 2.07 (m, 2H), 1.93 (m, 1H), 1.78 (m, 1H), 1.31 (m, 1H), 1.24-1.15 (m, 4H).

Example No. II.1-82

$^1$H NMR (400 MHz, $CDCl_3$ δ, ppm) 2.48 (m, 1H), 2.18 (br. s, 1H, OH), 2.11-1.94 (m, 3H), 1.86-1.78 (m, 2H), 1.74-1.68 (m, 1H), 1.42-1.23 (m, 5H), 1.21-1.08 (m, 4H).

Example No. II.1-83

$^1$H NMR (400 MHz, $CDCl_3$ δ, ppm) 3.38 (m, 1H), 3.29 (m, 1H), 2.82 (m, 1H), 2.56 (br. s, 1H, OH), 2.11-2.03 (m, 4H), 2.01-1.78 (m, 3H), 1.87 (m, 1H), 1.83 (m, 1H), 1.76-1.65 (m, 4H), 1.48-1.43 (m, 2H), 1.31-1.16 (m, 2H).

Example No. II.1-85

$^1$H NMR (400 MHz, $CDCl_3$ δ, ppm) 2.56 (s, 1H), 2.04 (br. s, 1H, OH), 1.54-1.47 (m, 2H), 1.33-1.25 (m, 2H), 1.24 (s, 9H).

Example No. III.1-3

$^1$H NMR (400 MHz, $CDCl_3$ δ, ppm) 7.71 (m, 2H), 7.57 (m, 1H), 7.39 (m, 2H), 6.57 (d, 1H), 6.18 (d, 1H), 2.08 (br. s, 1H, OH), 1.48 (m, 2H), 1.41-1.36 (m, 12H), 1.31-1.19 (m, 15H), 1.09 (m, 2H).

Example No. III.1-66

$^1$H NMR (400 MHz, $CDCl_3$ δ, ppm) 6.03 (d, 1H), 5.93 (d, 1H), 1.83 (m, 2H), 1.68 (m, 2H), 1.58 (m, 1H), 1.42 (br. s, 1H, OH), 1.41-1.32 (m, 4H), 1.22-1.13 (m, 9H), 1.09 (m, 1H), 1.04-0.99 (m, 2H), 0.95 (m, 1H), 0.88 (m, 2H), 0.82-0.73 (m, 17H), 0.69 (m, 1H).

Example No. III.1-73

$^1$H NMR (400 MHz, $CDCl_3$ δ, ppm) 7.45 (d, 2H), 7.19 (d, 2H), 6.46 (d, 1H), 6.35 (d, 1H), 2.35 (s, 3H), 2.01 (br. s, 1H, OH), 1.52 (m, 2H), 1.37-1.20 (m, 12H), 0.96-0.84 (m, 15H), 0.74 (m, 2H).

Example No. III.1-75

$^1$H NMR (400 MHz, $CDCl_3$ δ, ppm) 6.48 (d, 1H), 6.14 (d, 1H), 1.58 (br. s, 1H, OH), 1.52 (m, 2H), 1.37-1.20 (m, 12H), 1.11 (s, 9H), 0.96-0.84 (m, 15H), 0.74 (m, 2H).

The present invention further provides for the use of at least one inventive compound selected from the group consisting of substituted cyanocycloalkylpenta-2,4-dienes and cyanocycloalkylpent-2-en-4-ynes of the general formula (I), and of any desired mixtures of these inventive substituted cyanocycloalkylpenta-2,4-dienes, cyanocycloalkylpent-2-en-4-ynes, cyanoheterocyclylpenta-2,4-dienes and cyanoheterocyclylpent-2-en-4-ynes of the general formula (I) with further active agrochemical ingredients for enhancing the resistance of plants to abiotic stress factors, preferably drought stress, and for enhancing plant growth and/or for increasing plant yield.

The present invention further provides a spray solution for treatment of plants, comprising an amount, effective for enhancing the resistance of plants to abiotic stress factors, of at least one compound selected from the group consisting of the inventive substituted cyanocycloalkylpenta-2,4-dienes and cyanocycloalkylpent-2-en-4-ynes of the general formula (I). The abiotic stress conditions which can be relativized may include, for example, heat, drought, cold and aridity stress (stress caused by aridity and/or lack of water), osmotic stress, waterlogging, elevated soil salinity, elevated exposure to minerals, ozone conditions, strong light conditions, limited availability of nitrogen nutrients, limited availability of phosphorus nutrients.

In one embodiment, it is possible, for example, that the compounds envisaged in accordance with the invention, i.e. the appropriate inventive substituted cyanocycloalkylpenta-2,4-dienes, cyanocycloalkylpent-2-en-4-ynes, cyanoheterocyclylpenta-2,4-dienes and cyanoheterocyclylpent-2-en-4-ynes of the general formula (I), are applied by spray application to appropriate plants or plant parts to be treated. The compounds of the general formula (I) or salts thereof are used as envisaged in accordance with the invention preferably with a dosage between 0.00005 and 3 kg/ha, more preferably between 0.0001 and 2 kg/ha, especially preferably between 0.0005 and 1 kg/ha, specifically preferably between 0.001 and 0.25 kg/ha. If, in the context of the present invention, abscisic acid is used simultaneously with substituted cyanocycloalkylpenta-2,4-dienes and cyanocycloalkylpent-2-en-4-ynes of the general formula (I), for example in the context of a combined preparation or formulation, the addition of abscisic acid is preferably effected in a dosage between 0.0001 and 3 kg/ha, more preferably between 0.001 and 2 kg/ha, especially preferably between 0.005 and 1 kg/ha, very especially preferably between 0.006 and 0.25 kg/ha.

The term "resistance to abiotic stress" is understood in the context of the present invention to mean various kinds of advantages for plants. Such advantageous properties are manifested, for example, in the improved plant characteristics given below: improved root growth with regard to surface area and depth, increased stolon or tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibres, better fibre quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soil and water, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the inventive use of one or more inventive compounds of the general formula (I) exhibits the advantages described in spray application to plants and plant parts. Combinations of the inventive substituted cyanocycloalkylpenta-2,4-dienes and cyanocycloalkylpent-2-en-4-ynes of the general formula (I) with substances including insecticides, attractants, acaricides, fungicides, nematicides, herbicides, growth regulators, safeners, substances which influence plant maturity, and bactericides can likewise be employed in the control of plant disorders and/or for increasing the plant yield in the context of the present invention. The combined use of inventive substituted cyanocycloalkylpenta-2,4-dienes and cyanocycloalkylpent-2-en-4-ynes of the general formula (I) with genetically modified cultivars with a view to increased tolerance to abiotic stress is additionally likewise possible.

The further various benefits for plants mentioned above can be combined in a known manner in component form, and generally applicable terms can be used to describe them. Such terms are, for example, the following names: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is entirely familiar.

In the context of the present invention, a good effect on resistance to abiotic stress is understood to mean, without limitation,

- at least an emergence improved by generally 3%, especially more than 5%, more preferably more than 10%,
- at least a yield enhanced by generally 3%, especially more than 5%, more preferably more than 10%,
- at least a root development improved by generally 3%, especially more than 5%, more preferably more than 10%,
- at least a shoot size rising by generally 3%, especially more than 5%, more preferably more than 10%,
- at least a leaf area increased by generally 3%, especially more than 5%, more preferably more than 10%,
- at least a photosynthesis performance improved by generally 3%, especially more than 5%, more preferably more than 10%, and/or
- at least a flower development improved by generally 3%, especially more than 5%, more preferably more than 10%, and the effects may occur individually or else in any combination of two or more effects.

The present invention further provides a spray solution for treatment of plants, comprising an amount, effective for enhancing the resistance of plants to abiotic stress factors, of at least one compound selected from the group of the inventive substituted cyanocycloalkylpenta-2,4-dienes, cyanocycloalkylpent-2-en-4-ynes, cyanoheterocyclylpenta-2,4-dienes and cyanoheterocyclylpent-2-en-4-ynes of the general formula (I). The spray solution may comprise other customary constituents, such as solvents, formulation auxiliaries, especially water. Further constituents may include active agrochemical ingredients which are described in more detail below.

The present invention further provides for the use of corresponding spray solutions for increasing the resistance of plants to abiotic stress factors. The remarks which follow apply both to the use according to the invention of one or more inventive compounds of the general formula (I) per se and to the corresponding spray solutions.

In accordance with the invention, it has additionally been found that the application, to plants or in their environment, of one or more inventive compounds of the general formula (I) in combination with at least one fertilizer as defined further below is possible.

Fertilizers which can be used in accordance with the invention together with the inventive compounds of the general formula (I) elucidated in detail above are generally organic and inorganic nitrogen compounds, for example ureas, urea/formaldehyde condensation products, amino acids, ammonium salts and ammonium nitrates, potassium salts (preferably chlorides, sulphates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonium sulphate nitrate (general formula $(NH_4)_2SO_4NH_4NO_3$), ammonium phosphate and ammonium sulphate. These fertilizers are common knowledge to those skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may additionally comprise salts of micronutrients (preferably calcium, sulphur, boron, manganese, magnesium, iron, boron, copper, zinc, molybdenum and cobalt) and of phytohormones (for example vitamin B1 and indole-3-acetic acid) or mixtures of these. Fertilizers used in accordance with the invention may also contain other salts such as monoammonium phosphate (MAP), diammonium phosphate (DAP), potassium sulphate, potassium chloride, magnesium sulphate. Suitable amounts for the secondary nutrients or trace elements are amounts of 0.5% to 5% by weight, based on the overall fertilizer. Further possible constituents are crop protection agents, insecticides or fungicides, growth regulators or mixtures thereof. Further details of these are given further down.

The fertilizers can be used, for example, in the form of powders, granules, prills or compactates. However, the fertilizers can also be used in liquid form, dissolved in an aqueous medium. In this case, dilute aqueous ammonia can also be used as a nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764. The general composition of the fertilizers, which, in the context of the present invention, may take the form of straight and/or compound fertilizers, for example composed of nitrogen, potassium or phosphorus, may vary within a wide range. In general, a content of 1% to 30% by weight of nitrogen (preferably 5% to 20% by weight), of 1% to 20% by weight of potassium (preferably 3% to 15% by weight) and a content of 1% to 20% by weight of phosphorus (preferably 3% to 10% by weight) is advantageous. The microelement content is usually in the ppm range, preferably in the range from 1 to 1000 ppm.

In the context of the present invention, the fertilizer and one or more inventive compounds of the general formula (I) may be administered simultaneously. However, it is also possible first to apply the fertilizer and then one or more inventive compounds of the general formula (I), or first to apply one or more compounds of the general formula (I) and then the fertilizer. In the case of nonsynchronous application of one or more compounds of the general formula (I) and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, one or more compounds of the formula (I) according to the invention and the fertilizer are applied within a time frame of less than 1 hour, preferably less than 30 minutes, more preferably less than 15 minutes.

Preference is given to the use of compounds of the general formula (I) on plants from the group of the useful plants, ornamentals, turfgrass types, commonly used trees which are used as ornamentals in the public and domestic sectors, and forestry trees. Forestry trees include trees for the production of timber, cellulose, paper and products made from parts of the trees. The term useful plants as used here refers to crop plants which are used as plants for obtaining foods, animal feeds, fuels or for industrial purposes.

The useful plants include, for example, the following types of plants: triticale, durum (hard wheat), turf, vines, cereals, for example wheat, barley, rye, oats, rice, maize and millet; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cocoa beans and peanuts; cucurbits, for example pumpkin/squash, cucumbers and melons; fibre plants, for example cotton, flax, hemp and jute; citrus fruits, for example oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, aubergine, sugar cane, tea, pepper, grapevines, hops, bananas, latex plants and ornamentals, for example flowers, shrubs, deciduous trees and coniferous trees. This enumeration does not represent any limitation.

The following plants are considered to be particularly suitable target crops for the application of the method according to the invention: oats, rye, triticale, durum, cotton, aubergine, turf, pome fruit, stone fruit, soft fruit, maize, wheat, barley, cucumber, tobacco, vines, rice, cereals, pears, pepper, beans, soybeans, oilseed rape, tomato, bell pepper, melons, cabbage, potatoes and apples.

Examples of trees which can be improved by the method according to the invention include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention include: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus.*

Particularly preferred trees which can be improved by the method according to the invention include: from the tree species *Pinus: P. radiate, P. ponderosa, P. contorta, P. sylvestre, P. strobes*; from the tree species *Eucalyptus: E. grandis, E. globulus* and *E. camadentis.*

Particularly preferred trees which can be improved by the method according to the invention include: horse chestnut, Platanaceae, linden tree and maple tree.

The present invention can also be applied to any desired turfgrasses, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.); fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and “western wheatgrass” (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog’s-tail (*Cynosurus cristatus* L.).

Examples of warm-season turfgrasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue grama (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.)). Cool-season turfgrasses are generally preferred for the use according to the invention. Particular preference is given to bluegrass, bentgrass and redtop, fescues and ryegrasses. Bentgrass is especially preferred.

Particular preference is given to using the inventive compounds of the general formula (I) to treat plants of the respective commercially available or commonly used plant cultivars. Plant cultivars are understood to mean plants which have new properties (“traits”) and which have been bred by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant cultivars which are protectable or non-protectable by plant breeders’ rights.

The treatment method according to the invention can thus also be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced into the nuclear, chloroplastic or hypochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene that is located in the genome is also called a transgene. A transgene that is defined by its specific presence in the plant genome is called a transformation or transgenic event.

Plants and plant varieties which are preferably treated with the compounds of the general formula (I) according to the invention include all plants which have genetic material which imparts particularly advantageous, useful traits to these plants (whether obtained by breeding and/or biotechnological means or not).

Plants and plant varieties which can likewise be treated with the compounds of the general formula (I) according to the invention are those plants which are resistant to one or more abiotic stress factors. Abiotic stress conditions may include, for example, heat, drought, cold and aridity stress, osmotic stress, waterlogging, increased soil salinity, increased exposure to minerals, ozone conditions, strong light conditions, limited availability of nitrogen nutrients, limited availability of phosphorus nutrients or shade avoidance.

Plants and plant cultivars which can likewise be treated with the compounds of the general formula (I) according to the invention are those plants which are characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including but not limited to early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and oil composition, nutritional value, reduction in antinutritional compounds, improved processability and better storage stability.

Plants that may also be treated with the compounds of the general formula (I) according to the invention are hybrid plants that already express the characteristics of heterosis, or hybrid effect, which results in generally higher yield, higher vigour, better health and better resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (for example in maize) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species (WO 92/005251, WO 95/009910, WO 98/27806, WO2005/002324, WO2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 91/002069).

Plants or plant varieties (obtained by plant biotechnology methods such as genetic engineering) which may also be treated with the compounds of the general formula (I) according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a *petunia* EPSPS (Shah et al., Science (1986), 233, 478-481), a tomato EPSPS (Gasser et al., J. Biol. Chem. (1988), 263, 4280-4289) or an *Eleusine* EPSPS (WO2001/66704). It can also be a mutated EPSPS, as described, for example, in EP-A 0837944, WO 00/066746, WO2000/066747 or WO2002/026995. Glyphosate-tolerant plants can also be obtained by expressing a gene that encodes a glyphosate oxidoreductase enzyme as described in U.S. Pat. Nos. 5,776,760 and 5,463,175. Glyphosate-tolerant plants can also be obtained by expressing a gene that encodes a glyphosate acetyl transferase enzyme as described, for example, in WO2002/036782, WO2003/092360, WO2005/012515 and WO2007/024782. Glyphosate-tolerant plants can also be obtained by selecting plants containing naturally occurring mutations of the abovementioned genes, as described, for example, in WO2001/024615 or WO2003/013226.

Other herbicide-resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition.

One such effective detoxifying enzyme is an enzyme encoding a phosphinothricin acetyltransferase (such as the bar or pat protein from *Streptomyces* species). Plants expressing an exogenous phosphinothricin acetyltransferase are described, for example, in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyse the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated HPPD enzyme according to WO 96/038567, WO 99/024585 and WO 99/024586. Tolerance to HPPD inhibitors can also be obtained by transforming plants with genes encoding certain enzymes enabling the formation of homogentisate despite inhibition of the native HPPD enzyme by the HPPD inhibitor. Such plants and genes are described in WO 99/034008 and WO 2002/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928.

Other herbicide-resistant plants are plants which have been rendered tolerant to acetolactate synthase (ALS) inhibitors. Known ALS inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. Nos. 5,605,011, 5,378,824, 5,141,870 and 5,013,659. The production of sulphonylurea-tolerant plants and imidazolinone-tolerant plants has been described in U.S. Pat. Nos. 5,605,011; 5,013,659; 5,141,870; 5,767,361; 5,731,180; 5,304,732; 4,761,373; 5,331,107; 5,928,937; and 5,378,824; and also in the international publication WO 96/033270. Further imidazolinone-tolerant plants have also been described, for example, in WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants have also been described, for example, in WO 2007/024782.

Further plants tolerant to ALS-inhibitors, in particular to imidazolinones, sulphonylureas and/or sulphamoylcarbonyltriazolinones can be obtained by induced mutagenesis, by selection in cell cultures in the presence of the herbicide or by mutation breeding, as described, for example, for soybeans in U.S. Pat. No. 5,084,082, for rice in WO 97/41218, for sugarbeet in U.S. Pat. No. 5,773,702 and WO 99/057965, for lettuce in U.S. Pat. No. 5,198,599 or for sunflower in WO 2001/065922.

Plants or plant cultivars (obtained by plant biotechnology methods such as genetic engineering) which may also be treated with the compounds of the general formula (I) according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature, (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604; or 5) an insecticidal secreted protein from *Bacillus thuringiensis* or *Bacillus cereus*, or an insecticidal portion thereof, such as the vegetative insecticidal proteins (VIPs) listed under the following link, for example proteins from the VIP3Aa protein class: http://www.lifesci.sussex.ac.uk/Home/Neil_Crickmore/Bt/vip.html; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, the insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of the target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated with the compounds according to the invention of the general formula (I) are tolerant to abiotic stress factors. Such plants can be obtained by genetic transformation, or by selection of plants containing a mutation imparting such stress resistance. Particularly useful stress tolerant plants include:

a. plants which contain a transgene capable of reducing the expression and/or the activity of the poly(ADP-ribose) polymerase (PARP) gene in the plant cells or plants, as described in WO 2000/004173 or EP 04077984.5 or EP 06009836.5;

b. plants which contain a stress tolerance-enhancing transgene capable of reducing the expression and/or the activity of the PARG-encoding genes of the plants or plant cells, as described, for example, in WO 2004/090140;

c. plants which contain a stress tolerance-enhancing transgene encoding a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, for example, in EP 04077624.7 or WO 2006/133827 or PCT/EP07/002433.

Plants or plant varieties (obtained by plant biotechnology methods such as genetic engineering) which may also be treated with the compounds of the general formula (I) according to the invention show altered quantity, quality and/or storage stability of the harvested product and/or altered properties of specific ingredients of the harvested product such as, for example:

1) Transgenic plants which synthesize a modified starch which, in its physicochemical characteristics, in particular the amylose content or the amylose/amylopectin ratio, the degree of branching, the average chain length, the side chain distribution, the viscosity behaviour, the gelling strength, the starch granule size and/or the starch granule morphology, is changed in comparison with the synthesized starch in wild-type plant cells or plants, so that this modified starch is better suited to specific applications. These transgenic plants synthesizing a modified starch are described, for example, in EP 0571427, WO 95/004826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 95/26407, WO 96/34968, WO 98/20145, WO 99/12950, WO 99/66050, WO 99/53072, U.S. Pat. No. 6,734,341, WO 2000/11192, WO 98/22604, WO 98/32326, WO 2001/98509, WO 2001/98509, WO 2005/002359, U.S. Pat. Nos. 5,824,790, 6,013,861, WO 94/004693, WO 94/009144, WO 94/11520, WO 95/35026 and WO 97/20936.

2) Transgenic plants which synthesize non-starch carbohydrate polymers or which synthesize non-starch carbohydrate polymers with altered properties in comparison to wild-type plants without genetic modification. Examples are plants producing polyfructose, especially of the inulin and levan type, as described in EP 0663956, WO 96/001904, WO 96/021023, WO 98/039460 and WO 99/024593, plants producing alpha-1,4-glucans, as described in WO 95/031553, US 2002/031826, U.S. Pat. Nos. 6,284,479, 5,712,107, WO 97/047806, WO 97/047807, WO 97/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.

3) Transgenic plants which produce hyaluronan, as for example described in WO 06/032538, WO 2007/039314, WO 2007/039315, WO 2007/039316, JP 2006/304779 and WO 2005/012529.

Plants or plant cultivars (obtained by plant biotechnology methods such as genetic engineering) which may also be treated with the compounds of the general formula (I) according to the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes, as described in WO 98/000549;

b) plants, such as cotton plants, which contain an altered form of rsw2 or rsw3 homologous nucleic acids, as described in WO 2004/053219;

c) plants, such as cotton plants, with an increased expression of sucrose phosphate synthase, as described in WO 2001/017333;

d) plants, such as cotton plants, with increased expression of sucrose synthase as described in WO 2002/45485;

e) plants, such as cotton plants, wherein the timing of the plasmodesmatal gating at the basis of the fibre cell is altered, for example through downregulation of fibre-selective β-1,3-glucanase as described in WO 2005/017157;

f) plants, such as cotton plants, which have fibres with altered reactivity, for example through expression of the N-acetylglucosamine transferase gene including nodC and chitin synthase genes, as described in WO 2006/136351.

Plants or plant cultivars (obtained by plant biotechnology methods such as genetic engineering) which may also be treated with the compounds of the general formula (I) according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content, as described, for example, in U.S. Pat. No. 5,969,169, 5,840,946 or 6,323,392 or 6,063,947;

b) plants, such as oilseed rape plants, which produce oil having a low linolenic acid content, as described in U.S. Pat. No. 6,270,828, 6,169,190 or 5,965,755;

c) plants, such as oilseed rape plants, which produce oil having a low level of saturated fatty acids, as described, for example, in U.S. Pat. No. 5,434,283.

Particularly useful transgenic plants which may be treated with the compounds of the general formula (I) according to the invention are plants containing transformation events, or a combination of transformation events, and that are listed for example in the databases of various national or regional regulatory agencies.

Particularly useful transgenic plants which may be treated with the compounds of the general formula (I) according to the invention are, for example, plants which comprise one or more genes which encode one or more toxins and are the transgenic plants available under the following trade names: YIELD GARD® (for example maize, cotton, soybeans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosates, for example maize, cotton, soya), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

The compounds of the formula (I) to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers, and also microencapsulations in polymeric substances. In the context of the present invention, it is especially preferred when the compounds of the general formula (I) are used in the form of a spray formulation.

The present invention therefore additionally also relates to a spray formulation for enhancing the resistance of plants to abiotic stress. A spray formulation is described in detail hereinafter:

The formulations for spray application are produced in a known manner, for example by mixing the compounds of the general formula (I) for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are produced either in suitable facilities or else before or during application.

Auxiliaries used may be those substances which are suitable for imparting particular properties to the composition itself or and/or to preparations derived therefrom (for example spray liquors), such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethyl sulphoxide, and also water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Useful wetting agents which may be present in the formulations usable in accordance with the invention include all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the formulations usable in accordance with the invention are all foam-inhibiting substances conventionally used for the formulation of active agrochemical ingredients. Preference is given to using silicone antifoams and magnesium stearate.

Preservatives which may be present in the formulations usable in accordance with the invention are all substances usable for such purposes in agrochemical compositions. Examples include dichlorophene and benzyl alcohol hemiformal.

Secondary thickeners which may be present in the formulations usable in accordance with the invention include all substances usable for such purposes in agrochemical compositions. Preferred examples include cellulose derivatives, acrylic acid derivatives, xanthan, modified clays and finely divided silica.

Stickers which may be present in the formulations usable in accordance with the invention include all customary binders usable in seed-dressing products. Preferred examples include polyvinylpyrrolidone, polyvinyl acetate, polyvinyl alcohol and tylose. Gibberellins which may be present in the formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schadlingsbekampfungsmittel" [Chemistry of the Crop Protection Compositions and Pesticides], vol. 2, Springer Verlag, 1970, p. 401-412).

Further additives may be fragrances, mineral or vegetable, optionally modified oils, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01% and 98% by weight, preferably between 0.5% and 90%, of the compound of the general formula (I).

The inventive compounds of the general formula (I) may be present in commercial formulations, and in the use forms prepared from these formulations, in a mixture with other active ingredients, such as insecticides, attractants, sterilants, bactericides, acaricides, nematicides, fungicides, growth regulators, herbicides, safeners, fertilizers or semiochemicals.

In addition, the described positive effect of the compounds of the formula (I) on the plants' own defences can be supported by an additional treatment with active insecticidal, fungicidal or bactericidal compounds.

Preferred times for the application of compounds of the general formula (I) to be used according to the invention or salts thereof for enhancing resistance to abiotic stress are treatments of the soil, stems and/or leaves with the approved application rates.

The inventive active ingredients of the general formula (I) or salts thereof may generally additionally be present in their commercial formulations, and in the use forms prepared from these formulations, in mixtures with other active ingredients, such as insecticides, attractants, sterilants, acaricides, nematicides, fungicides, bactericides, growth regulators, substances which influence plant maturity, safeners or herbicides.

The invention is to be illustrated by the biological and biochemical examples which follow, but without restricting it thereto.

BIOLOGICAL EXAMPLES

In Vivo Analyses—Part A:

Seeds of monocotyledonous and dicotyledonous crop plants were sown in sandy loam in wood-fibre pots, covered with soil or sand and cultivated in a greenhouse under good growth conditions. The test plants were treated at the early leaf stage (BBCH10-BBCH13). To assure uniform water supply before commencement of stress, the potted plants were supplied with water by dam irrigation prior to substance application.

The inventive compounds, formulated in the form of wettable powders (WP), were sprayed onto the green parts of the plants as an aqueous suspension at an equivalent water application rate of 600 l/ha with addition of 0.2% wetting agent (e.g. agrotin). Substance application was followed immediately by stress treatment of the plants. For this purpose, the pots were transferred in plastic inserts in order to prevent them from subsequently drying out too quickly.

Drought stress was induced by gradual drying out under the following conditions:

"Day": 14 hours with illumination at 26° C.

"Night": 10 hours without illumination at 18° C.

The duration of the respective stress phases was guided mainly by the condition of the stressed control plants. It was ended (by re-irrigating and transfer to a greenhouse with good growth conditions) as soon as irreversible damage was observed on the stressed control plants.

The end of the stress phase was followed by an about 4-7-day recovery phase, during which the plants were once again kept under good growth conditions in a greenhouse.

The duration of the recovery phase was guided mainly by when the trial plants had attained a state which enabled visual scoring of potential effects, and was therefore variable.

Once this juncture was reached, the intensities of damage were scored visually in comparison to untreated, unstressed controls of the same age. The damage intensity was at first assessed in percent. These values were then used to calculate the efficacy of the test compounds by the following formula:

$$EF = \frac{(DI_s - DI_t) \times 100}{DI_s}$$

EF: Efficacy=reduction in damage intensity as a result of treatment with test substance $DI_s$: Damage intensity of the stressed control plants $DI_t$: Damage intensity of the plants treated with test compound In order to rule out any influence on the effects observed by any fungicidal or insecticidal action of the test compounds, it was additionally ensured that the tests proceeded without fungal infection or insect infestation. The values reported in Tables A-1 to A-3 below are averages from at least one trial with at least two repeats.

Effects of Selected Compounds of the General Formula (I) Under Drought Stress:

TABLE A-1

| No. | Substance | Dosage | Unit | EF [%] (BRSNS) |
|---|---|---|---|---|
| 1 | I.1-124 | 250 | g/ha | >5 |
| 2 | I.1-136 | 250 | g/ha | >5 |
| 3 | I.1-236 | 250 | g/ha | >5 |

TABLE A-2

| No. | Substance | Dosage | Unit | EF [%] (ZEAMX) |
|---|---|---|---|---|
| 1 | I.1-136 | 250 | g/ha | >5 |
| 2 | I.1-236 | 25 | g/ha | >5 |

TABLE A-3

| No. | Substance | Dosage | Unit | EF [%] (TRZAS) |
|---|---|---|---|---|
| 1 | I.1-124 | 25 | g/ha | >5 |
| 2 | I.1-136 | 25 | g/ha | >5 |
| 3 | I.1-236 | 25 | g/ha | >5 |

In Vivo Analyses—Part B:

Seeds of monocotyledonous and dicotyledonous crop plants were sown in sandy loam in plastic pots, covered with soil or sand and cultivated in a greenhouse under good growth conditions. The test plants were treated at the early leaf stage (BBCH10-BBCH13). To assure uniform water supply before commencement of stress, the potted plants were supplied with water by dam irrigation prior to substance application.

The inventive compounds, formulated in the form of wettable powders (WP), were sprayed onto the green parts of the plants as an aqueous suspension at an equivalent water application rate of 600 l/ha with addition of 0.2% wetting agent (e.g. agrotin). Substance application was followed immediately by stress treatment of the plants.

Drought stress was induced by gradual drying out under the following conditions:

"Day": 14 hours with illumination at 26-30° C.

"Night": 10 hours without illumination at 18-20° C.

The duration of the respective stress phases was guided mainly by the condition of the stressed control plants. It was ended (by re-irrigating and transfer to a greenhouse with good growth conditions) as soon as irreversible damage was observed on the stressed control plants.

The end of the stress phase was followed by an about 4-7-day recovery phase, during which the plants were once again kept under good growth conditions in a greenhouse.

The duration of the recovery phase was guided mainly by when the trial plants had attained a state which enabled visual scoring of potential effects, and was therefore variable.

Once this juncture had been reached, the appearance of the plants treated with test substances was recorded in comparison to the stressed control plants by the following categories:

| | |
|---|---|
| 0 | no positive effect |
| 10 | slight positive effect |
| 20 | clear positive effect |
| 30 | strong positive effect |

In order to rule out any influence on the effects observed by any fungicidal or insecticidal action of the test compounds, it was additionally ensured that the tests proceeded without fungal infection or insect infestation. For each substance and dosage, 2-3 pots were treated and evaluated. The respective efficacy ranges are reported in Tables B-1 to B-3 below.

TABLE B-1

| No. | Substance | Dosage | Unit | Effect (BRSNS) |
|---|---|---|---|---|
| 1 | I.1-102 | 250 | g/ha | 30 |
| 2 | I.1-103 | 250 | g/ha | 30 |
| 3 | I.1-120 | 250 | g/ha | 20 |
| 4 | I.1-135 | 250 | g/ha | 30 |
| 5 | I.1-202 | 250 | g/ha | 20 |
| 6 | I.1-502 | 250 | g/ha | 20-30 |
| 7 | I.1-503 | 25 | g/ha | 20-30 |
| 8 | I.1-605 | 250 | g/ha | 20 |
| 9 | I.1-606 | 250 | g/ha | 20 |
| 10 | I.1-609 | 250 | g/ha | 10-20 |
| 11 | I.1-614 | 250 | g/ha | 10-20 |
| 12 | I.2-120 | 250 | g/ha | 30 |

TABLE B-2

| No. | Substance | Dosage | Unit | Effect (ZEAMX) |
|---|---|---|---|---|
| 1 | I.1-103 | 25 | g/ha | 10-20 |
| 2 | I.1-202 | 25 | g/ha | 10-20 |
| 3 | I.1-609 | 25 | g/ha | 20 |

TABLE B-3

| No. | Substance | Dosage | Unit | Effect (TRZAS) |
|---|---|---|---|---|
| 1 | I.1-103 | 250 | g/ha | 10-20 |
| 2 | I.1-135 | 250 | g/ha | 30 |
| 3 | I.1-202 | 250 | g/ha | 20 |
| 4 | I.1-605 | 250 | g/ha | 20 |
| 5 | I.1-609 | 250 | g/ha | 10 |

In Vivo Analyses—Part C:

Seeds of monocotyledonous and dicotyledonous crop plants were sown in sandy loam in plastic or wood-fibre pots, covered with soil or sand and cultivated in a greenhouse under good growth conditions. The test plants were treated at the early leaf stage (BBCH10-BBCH13). To assure uniform water supply before commencement of stress, the potted plants were supplied with water by dam irrigation prior to substance application.

The inventive compounds were first formulated as wettable powders (WP) or dissolved in a solvent mixture. The further dilution was effected with water supplemented with 0.2% wetting agent (e.g. agrotin). The finished spray liquor was sprayed onto the green parts of the plant at an equivalent water application rate of 600 l/ha. Substance application was followed immediately by stress treatment of the plants. For this purpose, the wood-fibre pots were transferred in plastic inserts in order to prevent them from subsequently drying out too quickly.

Drought stress was induced by gradual drying out under the following conditions:

"Day": 14 hours with illumination at 26-30° C.

"Night": 10 hours without illumination at 18-20° C.

The duration of the respective stress phases was guided mainly by the condition of the stressed control plants. It was ended (by re-irrigating and transfer to a greenhouse with good growth conditions) as soon as irreversible damage was observed on the stressed control plants.

The end of the stress phase was followed by an about 4-7-day recovery phase, during which the plants were once again kept under good growth conditions in a greenhouse.

The duration of the recovery phase was guided mainly by when the trial plants had attained a state which enabled visual scoring of potential effects, and was therefore variable.

Once this juncture had been reached, the appearance of the plants treated with test substances was recorded in comparison to the stressed control plants by the following categories:

| | |
|---|---|
| 0 | no positive effect |
| 10 | slight positive effect |
| 20 | clear positive effect |
| 30 | strong positive effect |

For each substance and dosage, 3-4 pots were treated and evaluated. The respective efficacy ranges are reported in Tables C-1 and C-2 below.

TABLE C-1

| No. | Substance | Dosage | Unit | Effect (BRSNS) |
|---|---|---|---|---|
| 1 | I.1-618 | 25 | g/ha | 30 |
| 2 | I.1-648 | 25 | g/ha | 30 |
| 3 | I.1-678 | 250 | g/ha | 10-30 |
| 4 | I.1-812 | 250 | g/ha | 10-20 |
| 5 | I.1-887 | 250 | g/ha | 10-20 |
| 6 | I.2-102 | 250 | g/ha | 10-20 |
| 7 | I.2-201 | 250 | g/ha | 10-30 |
| 8 | I.2-507 | 250 | g/ha | 30 |
| 9 | I.2-543 | 25 | g/ha | 30 |
| 10 | I.2-583 | 250 | g/ha | 10-30 |
| 11 | I.2-615 | 250 | g/ha | 30 |
| 12 | I.2-616 | 250 | g/ha | 20-30 |
| 13 | I.3-128 | 250 | g/ha | 10-30 |

TABLE C-2

| No. | Substance | Dosage | Unit | Effect (TRZAS) |
|---|---|---|---|---|
| 1 | I.1-157 | 25 | g/ha | 10 |
| 2 | I.1-648 | 250 | g/ha | 10-20 |
| 3 | I.1-662 | 25 | g/ha | 10-20 |
| 4 | I.1-702 | 250 | g/ha | 10 |
| 5 | I.1-732 | 25 | g/ha | 10 |
| 6 | I.1-738 | 25 | g/ha | 10 |
| 7 | I.1-752 | 25 | g/ha | 10 |
| 8 | I.1-753 | 25 | g/ha | 10 |
| 9 | I.1-762 | 250 | g/ha | 10 |
| 10 | I.2-103 | 250 | g/ha | 30 |
| 11 | I.2-201 | 25 | g/ha | 10 |
| 12 | I.2-586 | 25 | g/ha | 10 |
| 13 | I.2-591 | 25 | g/ha | 10 |
| 14 | I.4-23 | 250 | g/ha | 10-20 |

In the Above Tables:

BRSNS=*Brassica napus*

TRZAS=*Triticum aestivum*

ZEAMX=*Zea mays*

In Vitro Analyses:

Effects of the phytohormone abscisic acid (ABA) on the behaviour of plants under abiotic stress and the mechanism of action of ABA are described in the literature (cf. Abrams et al, WO97/23441, Cutler, Park et al. Science, 2009, 324, 1068; Grill et al. Science, 2009, 324, 1064; Tanokura et al. Biophysics, 2011, 7, 123; Schroeder et al. Plant J. 2010, 61, 290). Therefore, it is possible with the aid of a suitable in vitro test system to derive a correlation between the action of ABA and the stress response of a plant under abiotic stress. Under drought stress, plants form the phytohormone abscisic acid (ABA). This binds, along with a co-regulator (Regulatory Component of ABA-Receptor=RCAR according to Grill et al. Science, 2009, 324, 1064 or PYR/PYL according to Cutler et al. Science, 2009, 324, 1068), to a phosphatase (e.g. ABI1, a type 2C protein phosphatase, also abbreviated to PP2C) and inhibits its activity. As a result, a "downstream" kinase (e.g. SnRK2) is no longer dephosphorylated. This kinase, which is thus active, via phosphorylation of transcription factors (e.g. AREB/ABF, vgl. Yoshida et al., Plant J. 2010, 61, 672), switches on a genetic protection programme to increase drought stress tolerance.

The assay described hereinafter utilizes the inhibition of the phosphatase ABI1 via the co-regulator RCAR11/PYR1 aus *Arabidopsis thaliana.*

For the determination of activity, the dephosphorylation of 4-methylumbelliferyl phosphate (MUP) was measured at 460 nm. The in vitro assay was conducted in Greiner 384-well PS microplates F-well, using two controls: a) dimethyl sulphoxide (DMSO) 0.5% (f.c.) and b) 5 μM (f.c.) abscisic acid (ABA). The assay described here was generally conducted with substance concentrations of the appropriate chemical test substances in a concentration range of 0.1 μM to 100 μM in a solution of DMSO and water. The substance solution thus obtained, if necessary, was stirred with esterase from porcine liver (EC 3.1.1.1) at room temperature for 3 h and centrifuged at 4000 rpm for 30 min. A total volume of 45 μl was introduced into each cavity of the microplate, having the following composition:

1) 5 μl of substance solution, i.e. a) DMSO 5% or b) abscisic acid solution or c) the corresponding example compound of the general formula (I) dissolved in 5% DMSO.
2) 20 μl of enzyme buffer mix, composed of a) 40% by vol. of enzyme buffer (10 ml contain equal proportions by volume of 500 mM Tris-HCl pH8, 500 mM NaCl, 3.33 mM $MnCl_2$, 40 mM dithiothreitol (DTT)), b) 4% by vol. of ABI1 dilution (protein stock solution was diluted so as to give, after addition, a final concentration in the assay of 0.15 μg ABI1/well), c) 4% by vol. of RCAR11 dilution (enzyme stock was diluted so as to give, on addition of the dilution to the enzyme buffer mix, a final concentration in the assay of 0.30 μg enzyme/well), d) 5% by vol. of Tween20 (1%), e) 47% by vol. $H_2O$ bi-dist.
3) 20 μl of substrate mix, composed of a) 10% by vol. of 500 mM Tris-HCl pH8, b) 10% by vol. of 500 mM NaCl, c) 10% by vol. of 3.33 mM $MnCl_2$, d) 5% by vol. of 25 mM MUP, 5% by vol. of Tween20 (1%), 60% by vol. of $H_2O$ bi-dist.

Enzyme buffer mix and substrate mix were made up 5 minutes prior to the addition and warmed to a temperature of 35° C. On completion of pipetting of all the solutions and on completion of mixing, the plate was incubated at 35° C. for 20 minutes. Finally, a relative fluorescence measurement was made at 35° C. with a BMG Labtech "POLARstar Optima" microplate reader using a 340/10 nm excitation filter and a 460 nm emission filter. The efficacy of the compounds of the general formula (I) is reported in the table which follows using abscisic acid (No. 64) as comparative substance according to the following classification: ++++ (inhibition≥90%), +++ (90%>inhibition≥70%), ++ (70%>inhibition≥50%), +(50%>inhibition≥30%).

Effects of selected compounds of the general formula (I) in the above-described in vitro assay at a concentration of 5 mM of the substance of the general formula (I) in question in a solution of DMSO and water:

TABLE B-1

| No. | Substance | ABI1 inhibition |
|---|---|---|
| 1 | I.1-36 | +++ |
| 2 | I.1-102 | ++++ |
| 3 | I.1-103 | ++++ |
| 4 | I.1-120 | +++ |
| 5 | I.1-124 | ++++ |
| 6 | I.1-135 | ++++ |
| 7 | I.1-136 | +++ |
| 8 | I.1-202 | ++++ |
| 9 | I.1-203 | ++++ |
| 10 | I.1-220 | ++++ |
| 11 | I.1.236 | ++++ |
| 12 | I.1-502 | ++++ |
| 13 | I.1-503 | ++++ |
| 14 | I.1-520 | ++++ |
| 15 | I.1-557 | ++ |
| 16 | I.1-558 | ++ |
| 17 | I.1-605 | ++++ |

TABLE B-1-continued

| No. | Substance | ABI1 inhibition |
|---|---|---|
| 18 | I.1-606 | ++++ |
| 19 | I.1-608 | +++ |
| 20 | I.1-609 | ++++ |
| 21 | I.1-610 | ++++ |
| 22 | I.1-613 | ++++ |
| 23 | I.1-614 | ++++ |
| 24 | I.1-616 | ++++ |
| 25 | I.1-618 | ++++ |
| 26 | I.1-632 | ++++ |
| 27 | I.1-648 | ++++ |
| 28 | I.1-662 | ++++ |
| 29 | I.1-678 | ++++ |
| 30 | I.1-692 | +++ |
| 31 | I.1-702 | ++++ |
| 32 | I.1-723 | +++ |
| 33 | I.1-732 | ++++ |
| 34 | I.1-768 | ++++ |
| 35 | I.1-773 | +++ |
| 36 | I.1-782 | +++ |
| 37 | I.1-783 | +++ |
| 38 | I.1-792 | +++ |
| 39 | I.1-798 | ++++ |
| 40 | I.1-801 | ++++ |
| 41 | I.1-812 | +++ |
| 42 | I.1-813 | +++ |
| 43 | I.1-822 | +++ |
| 44 | I.1-887 | +++ |
| 45 | I.1-888 | +++ |
| 46 | I.2-102 | ++++ |
| 47 | I.2-120 | ++++ |
| 48 | I.2-130 | +++ |
| 49 | I.2-134 | ++++ |
| 50 | I.2-201 | ++++ |
| 51 | I.2-507 | ++++ |
| 52 | I.2-579 | ++++ |
| 53 | I.2-581 | ++++ |
| 54 | I.2-582 | ++++ |
| 55 | I.2-583 | ++++ |
| 56 | I.2-585 | ++++ |
| 57 | I.2-586 | ++++ |
| 58 | I.2-591 | ++++ |
| 59 | I.2-593 | +++ |
| 60 | I.2-615 | ++++ |
| 61 | I.2-616 | ++++ |
| 62 | I.2-617 | +++ |
| 63 | I.3-128 | ++ |
| 64 | abscisic acid | ++++ |

Similar results were also achieved with further compounds of the general formula (I), even on application to different plant species.

The invention claimed is:

1. A cyanocycloalkylpenta-2,4-diene, cyanocycloalkylpent-2-en-4-yne, cyanoheterocyclylpenta-2,4-diene or cyanoheterocyclylpent-2-en-4-yne of formula (I) or salts thereof (I)

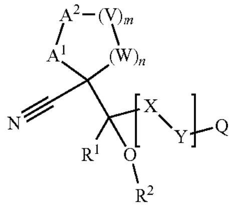

where

[X-Y] represents the moieties

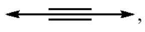

$[X-Y]^1$,

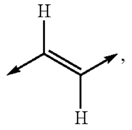

$[X-Y]^2$, or

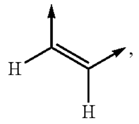

$[X-Y]^3$,

Q represents the moieties

Q-1

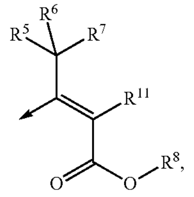

Q-2

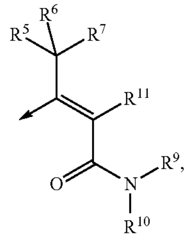

Q-3

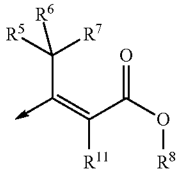

and

Q-4

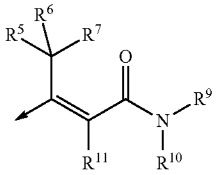

where $R^5$, $R^6$, $R^7$, $R^8$, $R^9$, $R^{10}$ and $R^{11}$ are each as defined below and where the arrow represents a bond to the respective [X-Y] moiety;

$R^1$ is hydrogen, alkyl, aryl, heteroaryl, heterocyclyl, cycloalkyl, alkenyl, alkynyl, alkynylalkyl, alkoxyalkyl, hydroxyalkyl, haloalkyl, haloalkenyl, haloalkoxyalkyl, alkylthioalkyl, arylalkyl, heterocyclylalkyl, halocycloalkyl, cycloalkenyl, alkoxyalkoxyalkyl, cycloalkylalkyl, cycloalkenylalkyl, haloalkynyl, alkylsulphinylalkyl, alkylsulphonylalkyl, halocycloalkylalkyl, cycloalkylsulphinylalkyl, cycloalkylsulphonylalkyl, arylsulphinylalkyl, arylsulphonylalkyl, arylthioalkyl, cycloalkylthioalkyl, alkoxyhaloalkyl, or haloalkoxyhaloalkyl, $R^2$ is hydrogen, alkyl, alkoxyalkyl, alkoxyalkoxyalkyl, alkenyl, alkynyl, alkylcarbonyl, arylcarbonyl, heteroarylcarbonyl, cycloalkylcarbonyl, alkenylcarbonyl, heterocyclylcarbonyl, alkoxycarbonyl, alkenyloxycarbonyl, aryloxyalkyl, arylalkoxycarbonyl, cycloalkoxycarbonyl, cycloalkylalkoxycarbonyl, arylalkoxyalkyl, arylalkyl, alkoxyalkoxyalkyl, alkylthioalkyl, trialkylsilyl, alkyl(bisalkyl)silyl, alkyl(bisaryl)silyl, aryl (bisalkyl)silyl, cycloalkyl(bisalkyl)silyl, halo(bisalkyl) silyl, trialkylsilylalkoxyalkyl, trialkylsilylalkyl, alkynyloxycarbonyl, cycloalkyl, cycloalkylalkyl, aminocarbonyl, alkylaminocarbonyl, bisalkylaminocarbonyl, cycloalkylaminocarbonyl, alkylsulphonyl, haloalkylsulphonyl, arylsulphonyl, heteroarylsulphonyl, or cycloalkylsulphonyl, $A^1$, $A^2$, V, W are each independently a $CR^3R^4$ group, oxygen or sulphur, where not more than 2 oxygen or 2 sulphur atoms are present in the ring formed by the $A^1$, $A^2$, V, W groups and the carbon atom to which they are bonded, and where the oxygen and sulphur atoms are not adjacent to one another, m is 0, 1, or 2, n is 0, 1, or 2, $R^3$ and $R^4$ are each independently hydrogen, alkyl, halogen, cycloalkyl, alkoxy, aryl, heterocyclyl, heteroaryl, arylalkyl, alkylthio, haloalkyl, haloalkyloxy, haloalkylthio, alkoxyalkyl, alkylthioalkyl, heteroarylalkyl, heterocyclylalkyl, cycloalkylalkyl, cycloalkenyl, alkynyl, alkenyl, haloalkenyl, haloalkynyl, alkylsulphinyl, alkylsulphonyl, cycloalkylsulphinyl, cycloalkylsulphonyl, arylsulphinyl, arylsulphonyl, alkoxyhaloalkyl, or haloalkoxyhaloalkyl, or $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, halogen, alkyl, haloalkyl, cycloalkyl, or cycloalkylalkyl, $R^7$ is hydrogen, halogen, alkyl, haloalkyl, haloalkoxy, haloalkoxyalkyl, haloalkoxyhaloalkyl, alkoxyhaloalkyl, alkynyloxyhaloalkyl, alkenyloxyhaloalkyl, alkylthio, haloalkylthio, aryl, arylalkyl, heteroaryl, heteroarylalkyl, heterocyclyl, alkoxy, hydroxyl, alkylcarbonyloxy, arylcarbonyloxy, cycloalkylcarbonyloxy, trisalkylsilyloxy, bisalkyl(alkyl)silyloxy, alkyl(bisaryl) silyloxy, aryl(bisalkyl)silyloxy, cycloalkyl(bisalkyl) silyloxy, halo(bisalkyl)silyloxy, trialkylsilylalkoxyalkyloxy, trialkylsilylalkyloxy, alkylsulphinyl, alkylsulphonyl, cycloalkylsulphinyl, cycloalkylsulphonyl, arylsulphinyl, arylsulphonyl, cycloalkyl, or cycloalkylalkyl, or $R^6$ and $R^7$ together with the atoms to which they are bonded form a fully saturated 3- to 6-membered ring optionally interrupted by heteroatoms and optionally having further substitution, $R^8$ is hydrogen, alkyl, alkoxyalkyl, cycloalkyl, cycloalkylalkyl, aryl, arylalkyl, heteroarylalkyl, bisarylalkyl, trisarylalkyl, alkenyl, cycloalkenylalkyl, alkynylalkyl, trialkylsilylalkoxyalkyl, alkoxyalkoxyalkyl, alkylthioalkyl, haloalkyl, arylsulphonylalkyl, trialkylsilyl, alkyl (bisaryl)silyl, alkyl(bisalkyl)silyl, bisalkylaminoalkyl, heterocyclylalkyl, alkynyl, cyanoalkyl, heterocyclyl, or cycloalkenyl, $R^9$ is hydrogen, alkyl, cycloalkyl, halogen, alkynylalkyl, haloalkyl, alkynyl, alkenyl, cyanoalkyl, cycloalkylalkyl, arylalkyl, heteroarylalkyl, alkylcarbonyl, alkoxycarbonyl, alkenyloxycarbonyl, alkenylalkyloxycarbonyl, arylalkyloxycarbonyl, cycloalkoxycarbonyl, cycloalkylalkoxycarbonyl, alkylsulphonyl, arylsulphonyl, cycloalkylsulphonyl, alkylsulphinyl, arylsulphinyl, cycloalkylsulphinyl, alkoxycarbonylalkyl, hydroxycarbonylalkyl, arylalkoxycarbonylalkyl, cycloalkylalkoxycarbonylalkyl, alkoxycarbonylcycloalkyl, hydroxycarbonylcycloalkyl, arylalkoxycarbonylcycloalkyl, alkenyloxycarbonylcycloalkyl, aminocarbonylcycloalkyl, alkylaminocarbonylcycloalkyl, cycloalkylaminocarbonylcycloalkyl, alkoxycarbonylcycloalkenyl, hydroxycarbonylcycloalkenyl, bisalkylaminoalkyl, hydroxycarbonylheterocyclyl, alkoxycarbonylheterocyclyl, alkenyloxycarbonylheterocyclyl, alkenylalkoxycarbonylheterocyclyl, arylalkoxycarbonylheterocyclyl, cycloalkoxycarbonylheterocyclyl, cycloalkylalkoxycarbonylheterocyclyl, aminocarbonylheterocyclyl, alkylaminocarbonylheterocyclyl, bisalkylaminocarbonylheterocyclyl, cycloalkylaminocarbonylheterocyclyl, arylalkylaminocarbonylheterocyclyl, alkenylaminocarbonylheterocyclyl, hydroxycarbonylheterocyclylalkyl, alkoxycarbonylheterocyclylalkyl, hydroxycarbonylcycloalkylalkyl, alkoxycarbonylcycloalkylalkyl, hydroxyl, alkoxy, heterocyclyl, heterocyclylalkyl, aryl, cycloalkenyl, or cycloalkenylalkyl, $R^{10}$ is hydrogen, alkyl, cycloalkyl, halogen, haloalkyl, alkynyl, alkenyl, cyanoalkyl, arylalkyl, heteroarylalkyl, alkylcarbonyl, alkoxycarbonyl, alkylsulphonyl, arylsulphonyl, cycloalkylsulphonyl, alkylsulphinyl, arylsulphinyl, cycloalkylsulphinyl, or alkoxycarbonylalkyl or $R^9$ and $R^{10}$ with the nitrogen to which they are attached form an optionally halogen-, alkyl-, haloalkyl-, alkoxy-, alkoxycarbonyl-, cycloalkoxycarbonyl-, cycloalkylalkoxycarbonyl-, alkenyloxycarbonyl-, hydroxycarbonyl-, aminocarbonyl-, alkylaminocarbonyl-, cycloalkylaminocarbonyl-, or arylalkylaminocarbonyl-substituted three- to eight-membered ring which is optionally interrupted by O, S or N or $R^9$ and $R^{10}$ together are part of an optionally substituted sulphilimine or amidine group or form an iminophosphorane and $R^{11}$ is hydrogen, alkyl, cycloalkyl, haloalkyl, alkoxyalkyl, or alkylthioalkyl.

2. The cyanocycloalkylpenta-2,4-diene, cyanocycloalkylpent-2-en-4-yne, cyanoheterocyclylpenta-2,4-diene and or cyanoheterocyclylpent-2-en-4-yne according to claim 1, where

[X-Y] represents the moieties $[X\text{-}Y]^1$ or

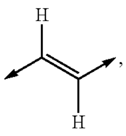, $[X\text{-}Y]^2$

Q represents the moieties

Q-1

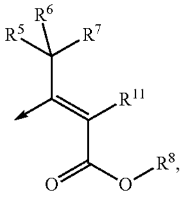

-continued

Q-2

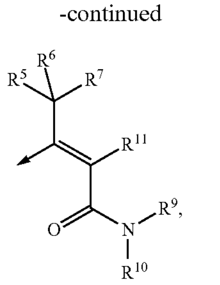

Q-3

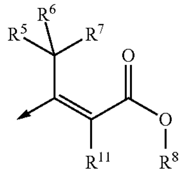

or

Q-4

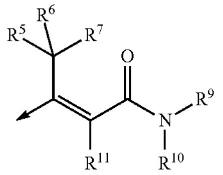

where $R^5$, $R^6$, $R^7$, $R^8$, $R^9$, $R^{10}$ and $R^{11}$ are each as defined below and where the arrow represents a bond to the respective [X-Y] moiety, $R^1$ is hydrogen, ($C_1$-$C_8$)-alkyl, aryl, heteroaryl, heterocyclyl, ($C_3$-$C_{10}$)-cycloalkyl, ($C_2$-$C_8$)-alkenyl, ($C_2$-$C_8$)-alkynyl, ($C_2$-$C_8$)-alkynyl-($C_1$-$C_8$)-alkyl, ($C_1$-$C_8$)-alkoxy-($C_1$-$C_8$)-alkyl, hydroxy-($C_1$-$C_8$)-alkyl, ($C_1$-$C_8$)-haloalkyl, ($C_2$-$C_8$)-haloalkenyl, ($C_1$-$C_8$)-haloalkoxy-($C_1$-$C_8$)-alkyl, ($C_1$-$C_8$)-alkylthio-($C_1$-$C_8$)-alkyl, aryl-($C_1$-$C_8$)-alkyl, heterocyclyl-($C_1$-$C_8$)-alkyl, ($C_3$-$C_8$)-halocycloalkyl, ($C_4$-$C_8$)-cycloalkenyl, ($C_1$-$C_8$)-alkoxy-($C_1$-$C_8$)-alkoxy-($C_1$-$C_8$)-alkyl, ($C_3$-$C_8$)-cycloalkyl-($C_1$-$C_8$)-alkyl, ($C_3$-$C_8$)-cycloalkenyl-($C_1$-$C_8$)-alkyl, ($C_2$-$C_8$)-haloalkynyl, ($C_1$-$C_8$)-alkylsulphinyl-($C_1$-$C_8$)-alkyl, ($C_1$-$C_8$)-alkylsulphonyl-($C_1$-$C_8$)-alkyl, ($C_3$-$C_8$)-halocycloalkyl-($C_1$-$C_8$)-alkyl, ($C_3$-$C_8$)-cycloalkylsulphinyl-($C_1$-$C_8$)-alkyl, ($C_3$-$C_8$)-cycloalkylsulphonyl-($C_1$-$C_8$)-alkyl, arylsulphinyl-($C_1$-$C_8$)-alkyl, arylsulphonyl-($C_1$-$C_8$)-alkyl, arylthio-($C_1$-$C_8$)-alkyl, ($C_3$-$C_8$)-cycloalkylthio-($C_1$-$C_8$)-alkyl, ($C_1$-$C_8$)-alkoxy-($C_1$-$C_8$)-haloalkyl, or ($C_1$-$C_8$)-haloalkoxy-($C_1$-$C_8$)-haloalkyl, $R^2$ is hydrogen, ($C_1$-$C_8$)-alkyl, ($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkyl, ($C_2$-$C_8$)-alkenyl, ($C_2$-$C_8$)-alkynyl, ($C_1$-$C_8$)-alkylcarbonyl, arylcarbonyl, heteroarylcarbonyl, ($C_3$-$C_8$)-cycloalkylcarbonyl, ($C_2$-$C_8$)-alkenylcarbonyl, heterocyclylcarbonyl, ($C_1$-$C_8$)-alkoxycarbonyl, ($C_2$-$C_8$)-alkenyloxycarbonyl, aryloxy-($C_1$-$C_8$)-alkyl, aryl-($C_1$-$C_8$)-alkoxycarbonyl, ($C_3$-$C_8$)-cycloalkoxycarbonyl, ($C_3$-$C_8$)-cycloalkyl-($C_1$-$C_8$)-alkoxycarbonyl, aryl-($C_1$-$C_8$)-alkoxy-($C_1$-$C_8$)-alkyl, aryl-($C_1$-$C_8$)-alkyl, ($C_1$-$C_8$)-alkoxy-($C_1$-$C_8$)-alkoxy-($C_1$-$C_8$)-alkyl, ($C_1$-$C_8$)-alkylthio-($C_1$-$C_8$)-alkyl, tris[($C_1$-$C_8$)-alkyl]silyl, ($C_1$-$C_8$)-alkylbis[($C_1$-$C_8$)-alkyl]silyl, ($C_1$-$C_8$)-alkylbis(aryl)silyl, arylbis[($C_1$-$C_8$)-alkyl]silyl, ($C_3$-$C_8$)-cycloalkylbis[($C_1$-$C_8$)-alkyl]silyl, halobis[($C_1$-$C_8$)-alkyl]silyl, tris[($C_1$-$C_8$)-alkyl]silyl-($C_1$-$C_8$)-alkoxy-($C_1$-$C_8$)-alkyl, tris[($C_1$-$C_8$)-alkyl]silyl-($C_1$-$C_8$)-alkyl, ($C_2$-$C_8$)-alkynyloxycarbonyl, ($C_3$-$C_8$)-cycloalkyl, ($C_3$-$C_8$)-cycloalkyl-($C_1$-$C_8$)-alkyl, aminocarbonyl, ($C_1$-$C_8$)-alkylaminocarbonyl, bis[($C_1$-$C_8$)-alkyl]aminocarbonyl, ($C_3$-$C_8$)-cycloalkylaminocarbonyl, ($C_1$-$C_8$)-alkylsulphonyl, ($C_1$-$C_8$)-haloalkylsulphonyl, arylsulphonyl, heteroarylsulphonyl, or ($C_3$-$C_8$)-cycloalkylsulphonyl, $A^1$, $A^2$, V, W are each independently a $CR^3R^4$ group, oxygen or sulphur, where not more than 2 oxygen or 2 sulphur atoms are present in the ring formed by the $A^1$, $A^2$, V, W groups and the carbon atom to which they are bonded, and where the oxygen and sulphur atoms are not adjacent to one another, m is 0, 1, or 2, n is 0, 1, or 2, $R^3$ and $R^4$ are each independently hydrogen, ($C_1$-$C_8$)-alkyl, halogen, ($C_3$-$C_8$)-cycloalkyl, ($C_1$-$C_8$)-alkoxy, aryl, heterocyclyl, heteroaryl, aryl-($C_1$-$C_8$)-alkyl, ($C_1$-$C_8$)-alkylthio, ($C_1$-$C_8$-haloalkyl, ($C_1$-$C_8$-haloalkyloxy, ($C_1$-$C_8$)-haloalkylthio, ($C_1$-$C_8$)-alkoxy-($C_1$-$C_8$)-alkyl, ($C_1$-$C_8$)-alkylthio-($C_1$-$C_8$)-alkyl, heteroaryl-($C_1$-$C_8$)-alkyl, heterocyclyl-($C_1$-$C_8$)-alkyl, ($C_1$-$C_8$)-alkoxy-($C_1$-$C_8$)-haloalkyl, ($C_1$-$C_8$)-haloalkoxy-($C_1$-$C_8$)-haloalkyl, ($C_2$-$C_8$)-alkynyl, or ($C_2$-$C_8$)-alkenyl, or $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, halogen, ($C_1$-$C_8$)-alkyl, ($C_1$-$C_8$)-haloalkyl, ($C_3$-$C_8$)-cycloalkyl, or ($C_3$-$C_8$)-cycloalkyl-($C_1$-$C_8$)-alkyl, $R^7$ is hydrogen, halogen, ($C_1$-$C_8$)-alkyl, ($C_1$-$C_8$)-haloalkyl, ($C_1$-$C_8$)-haloalkoxy, ($C_1$-$C_8$)-haloalkoxy-($C_1$-$C_8$)-alkyl, ($C_1$-$C_8$)-haloalkoxy-($C_1$-$C_8$)-haloalkyl, ($C_1$-$C_8$)-alkoxy-($C_1$-$C_8$)-haloalkyl, ($C_1$-$C_8$)-alkynyloxy-($C_1$-$C_8$)-haloalkyl, ($C_1$-$C_8$)-alkenyloxy-($C_1$-$C_8$)-haloalkyl, ($C_1$-$C_8$)-alkylthio, ($C_1$-$C_8$)-haloalkylthio, optionally substituted phenyl, aryl-($C_1$-$C_8$)-alkyl, heteroaryl, heteroaryl-($C_1$-$C_8$)-alkyl, heterocyclyl, ($C_1$-$C_8$)-alkoxy, hydroxyl, ($C_1$-$C_8$)-alkylcarbonyloxy, arylcarbonyloxy, ($C_3$-$C_8$)-cycloalkylcarbonyloxy, tris[($C_1$-$C_8$)-alkyl]silyloxy, bis[($C_1$-$C_8$)-alkyl]-[($C_1$-$C_8$)-alkyl]silyloxy, ($C_1$-$C_8$)-alkylbisarylsilyloxy, arylbis[($C_1$-$C_8$)-alkyl]silyloxy, ($C_3$-$C_8$)-cycloalkylbis[($C_1$-$C_8$)-alkyl]silyloxy, halobis[($C_1$-$C_8$)-alkyl]silyloxy, tris[($C_1$-$C_8$)-alkyl]silyl-($C_1$-$C_8$)-alkoxy-($C_1$-$C_8$)-alkyloxy, tris[($C_1$-$C_8$)-alkyl]silyl-($C_1$-$C_8$)-alkyloxy, ($C_3$-$C_8$)-cycloalkyl, or ($C_3$-$C_8$)-cycloalkyl-($C_1$-$C_8$)-alkyl, or $R^6$ and $R^7$ together with the atoms to which they are bonded form a fully saturated 3- to 6-membered ring optionally interrupted by heteroatoms and optionally having further substitution, $R^8$ is hydrogen, ($C_1$-$C_8$)-alkyl, ($C_1$-$C_8$)-alkoxy-($C_1$-$C_8$)-alkyl, ($C_3$-$C_8$)-cycloalkyl, ($C_3$-$C_8$)-cycloalkyl-($C_1$-$C_8$)-alkyl, optionally substituted phenyl, aryl-($C_1$-$C_8$)-alkyl, heteroaryl-($C_1$-$C_8$)-alkyl, bisaryl-($C_1$-$C_8$)-alkyl, trisaryl-($C_1$-$C_8$)-alkyl, ($C_2$-$C_8$)-alkenyl, ($C_4$-$C_8$)-cycloalkenyl-($C_1$-$C_8$)-alkyl, ($C_2$-$C_8$)-alkynyl-($C_1$-$C_8$)-alkyl, tri-($C_1$-$C_8$)-alkylsilyl-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkyl, ($C_1$-$C_8$)-alkylthio-($C_1$-$C_8$)-alkyl, ($C_1$-$C_8$)-haloalkyl, arylsulphonyl-($C_1$-$C_8$)-alkyl, tri-($C_1$-$C_8$)-alkylsilyl, ($C_1$-$C_8$)-alkyl(bisaryl)silyl, ($C_1$-$C_8$)-alkyl(bis-($C_1$-$C_8$)-alkyl)silyl, bis($C_1$-$C_8$)-alkylamino-($C_1$-$C_8$)-alkyl, heterocyclyl-($C_1$-$C_8$)-alkyl, ($C_2$-$C_8$)-alkynyl, cyano-($C_1$-$C_8$)-alkyl, heterocyclyl, or optionally further-substituted phenyl, $R^9$ is hydrogen, ($C_1$-$C_8$)-alkyl, ($C_3$-$C_8$)-cycloalkyl, halogen, ($C_2$-$C_8$)-alkynyl-($C_1$-$C_8$)-alkyl, ($C_1$-$C_8$)-haloalkyl, $(C_2-C_8)$-alkynyl, $(C_2-C_8)$-alkenyl, cyano-$(C_1-C_8)$-alkyl, $(C_3-C_8)$-cycloalkyl-$(C_1-C_8)$-alkyl, aryl-$(C_1-C_8)$-alkyl, heteroaryl-$(C_1-C_8)$-alkyl, $(C_1-C_8)$-alkylcarbonyl, $(C_1-C_8)$-alkoxycarbonyl, $(C_2-C_8)$-alkenyloxycarbonyl, $(C_2-C_8)$-alkenyl-$(C_1-C_8)$-alkyloxycarbonyl, aryl-$(C_1-C_8)$-alkyloxycarbonyl, $(C_3-C_8)$-cycloalkoxycarbonyl, $(C_3-C_8)$-cycloalkyl-$(C_1-C_8)$-alkoxycarbonyl, $(C_1-C_8)$-alkylsulphonyl, arylsulphonyl, $(C_3-C_8)$-cycloalkylsulphonyl, $(C_1-C_8)$-alkylsulphinyl, arylsulphinyl, $(C_3-C_8)$-cycloalkylsulphinyl, $(C_1-C_8)$-alkoxycarbonyl-$(C_1-C_8)$-alkyl, hydroxycarbonyl-$(C_1-C_8)$-alkyl, aryl-$(C_1-C_8)$-alkoxycarbonyl-$(C_1-C_8)$-alkyl, $(C_3-C_8)$-cycloalkyl-$(C_1-C_8)$-alkoxycarbonyl-$(C_1-C_8)$-alkyl, $(C_1-C_8)$-alkoxycarbonyl-$(C_3-C_8)$-cycloalkyl, hydroxycarbonyl-$(C_3-C_8)$-cycloalkyl, aryl-$(C_1-C_8)$-alkoxycarbonyl-$(C_3-C_8)$-cycloalkyl, $(C_2-C_8)$-alkenyloxycarbonyl-$(C_3-C_8)$-cycloalkyl, aminocarbonyl-$(C_3-C_8)$-cycloalkyl, $(C_1-C_8)$-alkylaminocarbonyl-$(C_3-C_8)$-cycloalkyl, $(C_3-C_8)$-cycloalkylaminocarbonyl-$(C_3-C_8)$-cycloalkyl, $(C_1-C_8)$-alkoxycarbonyl-$(C_4-C_8)$-cycloalkenyl, hydroxycarbonyl-$(C_4-C_8)$-cycloalkenyl, bis-$(C_1-C_8)$-alkylamino-$(C_1-C_8)$-alkyl, hydroxycarbonylheterocyclyl, $(C_1-C_8)$-alkoxycarbonylheterocyclyl, $(C_2-C_8)$-alkenyloxycarbonylheterocyclyl, $(C_2-C_8)$-alkenyl-$(C_1-C_8)$-alkoxycarbonylheterocyclyl, aryl-$(C_1-C_8)$-alkoxycarbonylheterocyclyl, $(C_3-C_8)$-cycloalkoxycarbonylheterocyclyl, $(C_3-C_8)$-cycloalkyl-$(C_1-C_8)$-alkoxycarbonylheterocyclyl, aminocarbonylheterocyclyl, $(C_1-C_8)$-alkylaminocarbonylheterocyclyl, bis-$(C_1-C_8)$-alkylaminocarbonylheterocyclyl, $(C_3-C_8)$-cycloalkylaminocarbonylheterocyclyl, aryl-$(C_1-C_8)$-alkylaminocarbonylheterocyclyl, $(C_2-C_8)$-alkenylaminocarbonylheterocyclyl, hydroxycarbonylheterocyclyl-$(C_1-C_8)$-alkyl, $(C_1-C_8)$-alkoxycarbonylheterocyclyl-$(C_1-C_8)$-alkyl, hydroxycarbonyl-$(C_3-C_8)$-cycloalkyl-$(C_1-C_8)$-alkyl, $(C_1-C_8)$-alkoxycarbonyl-$(C_3-C_8)$-cycloalkyl-$(C_1-C_8)$-alkyl, hydroxyl, $(C_1-C_8)$-alkoxy, heterocyclyl, heterocyclyl-$(C_1-C_8)$-alkyl, or optionally substituted phenyl, $R^{10}$ is hydrogen, $(C_1-C_8)$-alkyl, $(C_3-C_8)$-cycloalkyl, halogen, $(C_1-C_8)$-haloalkyl, $(C_2-C_8)$-alkynyl, $(C_2-C_8)$-alkenyl, cyano-$(C_1-C_8)$-alkyl, aryl-$(C_1-C_8)$-alkyl, heteroaryl-$(C_1-C_8)$-alkyl, $(C_1-C_8)$-alkylcarbonyl, $(C_1-C_8)$-alkoxycarbonyl, $(C_1-C_8)$-alkylsulphonyl, arylsulphonyl, $(C_3-C_8)$-cycloalkylsulphonyl, $(C_1-C_8)$-alkylsulphinyl, arylsulphinyl, $(C_3-C_8)$-cycloalkylsulphinyl, or $(C_1-C_8)$-alkoxycarbonyl-$(C_1-C_8)$-alkyl, or $R^9$ and $R^{10}$ together with the nitrogen to which they are bonded form an optionally halogen-, $(C_1-C_8)$-alkyl-, $(C_1-C_8)$-haloalkyl-, $(C_1-C_8)$-alkoxy-, $(C_1-C_8)$-alkoxycarbonyl-, $(C_3-C_8)$-cycloalkoxycarbonyl-, $(C_3-C_8)$-cycloalkyl-$(C_1-C_8)$-alkoxycarbonyl-, $(C_2-C_8)$-alkenyloxycarbonyl-, hydroxycarbonyl-, aminocarbonyl-, $(C_1-C_8)$-alkylaminocarbonyl-, $(C_3-C_8)$-cycloalkylaminocarbonyl-, or aryl-$(C_1-C_8)$-alkylaminocarbonyl-substituted three- to eight-membered ring optionally interrupted by O, S or N, or $R^9$ and $R^{10}$ together form an N-(bis-$(C_1-C_6)$-alkyl)sulphanylidene, N-(aryl-$(C_1-C_6)$-alkyl)sulphanylidene, N-(bis-$(C_3-C_7)$-cycloalkyl)sulphanylidene, N—($(C_1-C_6)$-alkyl-$(C_3-C_7)$-cycloalkyl)sulphanylidene group or an N,N-di-$(C_1-C_6)$-alkylformylidene group and $R^{11}$ is hydrogen, $(C_1-C_8)$-alkyl, $(C_3-C_8)$-cycloalkyl, $(C_1-C_8)$-haloalkyl, $(C_1-C_8)$-alkoxy-$(C_1-C_8)$-alkyl, or $(C_1-C_8)$-alkylthio-$(C_1-C_8)$-alkyl.

3. The cyanocycloalkylpenta-2,4-diene, cyanocycloalkylpent-2-en-4-yne, cyanoheterocyclylpenta-2,4-diene and or cyanoheterocyclylpent-2-en-4-yne according to claim 1, where

[X-Y] represents the moieties

[X-Y]$^1$ or

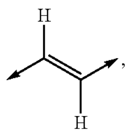

[X-Y]$^2$

Q represents the moieties

Q-1

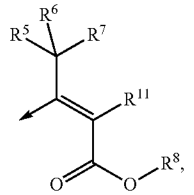

Q-2

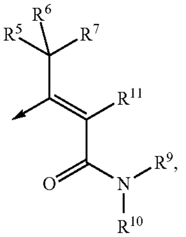

or

Q-3

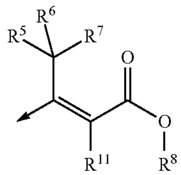

where $R^5$, $R^6$, $R^7$, $R^8$, $R^9$, $R^{10}$ and $R^{11}$ are each as defined below and where the arrow represents a bond to the respective [X-Y] moiety, $R^1$ is hydrogen, $(C_1-C_7)$-alkyl, aryl, heteroaryl, heterocyclyl, $(C_3-C_{10})$-cycloalkyl, $(C_2-C_7)$-alkenyl, $(C_2-C_7)$-alkynyl, $(C_1-C_7)$-alkoxy-$(C_1-C_7)$-alkyl, hydroxy-$(C_1-C_7)$-alkyl, $(C_1-C_7)$-haloalkyl, $(C_2-C_7)$-haloalkenyl, $(C_1-C_7)$-haloalkoxy-$(C_1-C_7)$-alkyl, $(C_1-C_7)$-alkylthio-$(C_1-C_7)$-alkyl, aryl-$(C_1-C_7)$-alkyl, heterocyclyl-$(C_1-C_7)$-alkyl, $(C_3-C_7)$-halocycloalkyl, $(C_4-C_7)$-cycloalkenyl, $(C_1-C_7)$-alkoxy-$(C_1-C_7)$-alkoxy-$(C_1-C_7)$-alkyl, $(C_1-C_7)$-alkoxy-$(C_1-C_7)$-haloalkyl, $(C_1-C_7)$-haloalkoxy-$(C_1-C_7)$-haloalkyl, or $(C_3-C_8)$-cycloalkyl-$(C_1-C_7)$-alkyl, $R^2$ is hydrogen, $(C_1-C_7)$-alkyl, $(C_1-C_7)$-alkoxy-$(C_1-C_7)$-alkyl, $(C_1-C_7)$-alkoxy-$(C_1-C_7)$-alkoxy-$(C_1-C_7)$-alkyl, $(C_2-C_7)$-alkenyl, $(C_2-C_7)$-alkynyl, $(C_1-C_7)$-alkylcarbonyl, arylcarbonyl, heteroarylcarbonyl, $(C_3-C_7)$-cycloalkylcarbonyl, $(C_2-C_7)$-alkenylcarbonyl, heterocyclylcarbonyl, $(C_1-C_7)$-alkoxycarbonyl, $(C_2-C_7)$-alkenyloxycarbonyl, aryloxy-$(C_1-C_7)$-alkyl, aryl-$(C_1-C_7)$-alkoxycarbonyl, $(C_3-C_7)$-cycloalkoxycarbonyl, $(C_3-C_7)$-cycloalkyl-$(C_1-C_7)$-alkoxycarbonyl, aryl-$(C_1-C_7)$-alkoxy-$(C_1-C_7)$-alkyl, aryl-$(C_1-C_7)$-alkyl, $(C_1-C_7)$-alkoxy-$(C_1-C_7)$-alkoxy-$(C_1-C_7)$-alkyl, $(C_1-C_7)$-alkylthio-$(C_1-C_7)$-alkyl, tris[$(C_1-C_7)$-alkyl]silyl, $(C_1-C_7)$-alkylbis[$(C_1-C_7)$-alkyl]silyl, $(C_1-C_7)$-alkylbis(aryl)silyl, arylbis[$(C_1-C_7)$-alkyl]silyl, $(C_3-C_7)$-cycloalkylbis[$(C_1-C_7)$-alkyl]silyl, halobis[$(C_1-C_7)$-alkyl]silyl, tris[$(C_1-C_7)$-alkyl]silyl-$(C_1-C_7)$-alkoxy-$(C_1-C_7)$-alkyl, or tris[$(C_1-C_7)$-alkyl]silyl-$(C_1-C_7)$-alkyl, $A^1$, $A^2$, V, W are each independently a $CR^3R^4$ group, oxygen or sulphur, where not more than 2 oxygen or 2 sulphur atoms are present in the ring formed by the $A^1$, $A^2$, V, W groups and the carbon atom to which they are bonded, and where the oxygen and sulphur atoms are not adjacent to one another, m is 0, 1, or 2, n is 0, 1, or 2, $R^3$ and $R^4$ are each independently hydrogen, $(C_1-C_7)$-alkyl, halogen, $(C_3-C_7)$-cycloalkyl, $(C_1-C_7)$-alkoxy, aryl, heterocyclyl, heteroaryl, aryl-$(C_1-C_7)$-alkyl, $(C_1-C_7)$-alkylthio, $(C_1-C_7)$-haloalkyl, $(C_1-C_7)$-haloalkyloxy, $(C_1-C_7)$-haloalkylthio, $(C_1-C_7)$-alkoxy-$(C_1-C_7)$-alkyl, $(C_1-C_7)$-alkylthio-$(C_1-C_7)$-alkyl, heteroaryl-$(C_1-C_7)$-alkyl, heterocyclyl-$(C_1-C_7)$-alkyl, $(C_1-C_7)$-alkoxy-$(C_1-C_7)$-haloalkyl, $(C_1-C_7)$-haloalkoxy-$(C_1-C_7)$-haloalkyl, $(C_2-C_7)$-alkynyl, or $(C_2-C_7)$-alkenyl, or $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, halogen, $(C_1-C_7)$-alkyl, $(C_1-C_7)$-haloalkyl, $(C_3-C_7)$-cycloalkyl, or $(C_3-C_7)$-cycloalkyl-$(C_1-C_7)$-alkyl, $R^7$ is hydrogen, halogen, $(C_1-C_8)$-alkyl, $(C_1-C_8)$-haloalkyl, $(C_1-C_7)$-haloalkoxy, $(C_1-C_7)$-haloalkoxy-$(C_1-C_7)$-alkyl, $(C_1-C_7)$-haloalkoxy-$(C_1-C_7)$-haloalkyl, $(C_1-C_7)$-alkoxy-$(C_1-C_7)$-haloalkyl, $(C_1-C_7)$-alkynyloxy-$(C_1-C_7)$-haloalkyl, $(C_1-C_7)$-alkenyloxy-$(C_1-C_7)$-haloalkyl, $(C_1-C_7)$-alkylthio, $(C_1-C_7)$-haloalkylthio, optionally substituted phenyl, aryl-$(C_1-C_7)$-alkyl, heteroaryl, heteroaryl-$(C_1-C_7)$-alkyl, heterocyclyl, $(C_1-C_7)$-alkoxy, hydroxyl, $(C_1-C_7)$-alkylcarbonyloxy, arylcarbonyloxy, $(C_3-C_7)$-cycloalkylcarbonyloxy, tris[$(C_1-C_7)$-alkyl]silyloxy, bis[$(C_1-C_7)$-alkyl]-[$(C_1-C_7)$-alkyl]silyloxy, $(C_1-C_7)$-alkylbisarylsilyloxy, arylbis[$(C_1-C_7)$-alkyl]silyloxy, $(C_3-C_7)$-cycloalkylbis[$(C_1-C_7)$-alkyl]silyloxy, halobis[$(C_1-C_7)$-alkyl]silyloxy, tris[$(C_1-C_7)$-alkyl]silyl-$(C_1-C_7)$-alkoxy-$(C_1-C_7)$-alkyloxy, tris[$(C_1-C_7)$-alkyl]silyl-$(C_1-C_7)$-alkyloxy, $(C_3-C_7)$-cycloalkyl, or $(C_3-C_7)$-cycloalkyl-$(C_1-C_7)$-alkyl, or $R^6$ and $R^7$ together with the atoms to which they are bonded form a fully saturated 3- to 6-membered ring optionally interrupted by heteroatoms and optionally having further substitution, $R^8$ is hydrogen, $(C_1-C_7)$-alkyl, $(C_1-C_7)$-alkoxy-$(C_1-C_7)$-alkyl, $(C_3-C_7)$-cycloalkyl, $(C_3-C_7)$-cycloalkyl-$(C_1-C_7)$-alkyl, optionally substituted phenyl, aryl-$(C_1-C_7)$-alkyl, heteroaryl-$(C_1-C_7)$-alkyl, bisaryl-$(C_1-C_7)$-alkyl, trisaryl-$(C_1-C_7)$-alkyl, $(C_2-C_7)$-alkenyl, $(C_4-C_7)$-cycloalkenyl-$(C_1-C_7)$-alkyl, $(C_2-C_7)$-alkynyl-$(C_1-C_7)$-alkyl, tri-$(C_1-C_7)$-alkylsilyl-$(C_1-C_7)$-alkoxy-$(C_1-C_7)$-alkyl, $(C_1-C_7)$-alkoxy-$(C_1-C_7)$-alkoxy-$(C_1-C_7)$-alkyl, $(C_1-C_7)$-alkylthio-$(C_1-C_7)$-alkyl, $(C_1-C_7)$-haloalkyl, arylsulphonyl-$(C_1-C_7)$-alkyl, tri-$(C_1-C_7)$-alkylsilyl, $(C_1-C_7)$-alkyl(bisaryl)silyl, $(C_1-C_7)$-alkyl(bis-$(C_1-C_7)$-alkyl)silyl, bis$(C_1-C_7)$-alkylamino-$(C_1-C_7)$-alkyl, heterocyclyl-$(C_1-C_7)$-alkyl, $(C_2-C_7)$-alkynyl, cyano-$(C_1-C_7)$-alkyl, heterocyclyl, or optionally further-substituted phenyl, $R^9$ is hydrogen, $(C_1-C_7)$-alkyl, $(C_3-C_7)$-cycloalkyl, halogen, $(C_2-C_7)$-alkynyl-$(C_1-C_7)$-alkyl, $(C_1-C_7)$-haloalkyl, $(C_2-C_7)$-alkynyl, $(C_2-C_7)$-alkenyl, cyano-$(C_1-C_7)$-alkyl, $(C_3-C_7)$-cycloalkyl-$(C_1-C_7)$-alkyl, aryl-$(C_1-C_7)$-alkyl, heteroaryl-$(C_1-C_7)$-alkyl, $(C_1-C_7)$-alkylcarbonyl, $(C_1-C_7)$-alkoxycarbonyl, $(C_2-C_7)$-alkenyloxycarbonyl, $(C_2-C_7)$-alkenyl-$(C_1-C_7)$-alkyloxycarbonyl, aryl-$(C_1-C_7)$-alkyloxycarbonyl, $(C_3-C_7)$-cycloalkoxycarbonyl, $(C_3-C_7)$-cycloalkyl-$(C_1-C_7)$-alkoxycarbonyl, $(C_1-C_7)$-alkylsulphonyl, arylsulphonyl, $(C_3-C_7)$-cycloalkylsulphonyl, $(C_1-C_7)$-alkylsulphinyl, arylsulphinyl, $(C_3-C_7)$-cycloalkylsulphinyl, $(C_1-C_7)$-alkoxycarbonyl-$(C_1-C_7)$-alkyl, hydroxycarbonyl-$(C_1-C_7)$-alkyl, aryl-$(C_1-C_7)$-alkoxycarbonyl-$(C_1-C_7)$-alkyl, $(C_3-C_7)$-cycloalkyl-$(C_1-C_7)$-alkoxycarbonyl-$(C_1-C_7)$-alkyl, $(C_1-C_7)$-alkoxycarbonyl-$(C_3-C_7)$-cycloalkyl, hydroxycarbonyl-$(C_3-C_7)$-cycloalkyl, aryl-$(C_1-C_7)$-alkoxycarbonyl-$(C_3-C_7)$-cycloalkyl, $(C_2-C_7)$-alkenyloxycarbonyl-$(C_3-C_7)$-cycloalkyl, aminocarbonyl-$(C_3-C_7)$-cycloalkyl, $(C_1-C_7)$-alkylaminocarbonyl-$(C_3-C_7)$-cycloalkyl, $(C_3-C_7)$-cycloalkylaminocarbonyl-$(C_3-C_7)$-cycloalkyl, $(C_1-C_7)$-alkoxycarbonyl-$(C_4-C_7)$-cycloalkenyl, hydroxycarbonyl-$(C_4-C_7)$-cycloalkenyl, bis-$(C_1-C_7)$-alkylamino-$(C_1-C_7)$-alkyl, hydroxycarbonylheterocyclyl, $(C_1-C_7)$-alkoxycarbonylheterocyclyl, $(C_2-C_7)$-alkenyloxycarbonylheterocyclyl, $(C_2-C_7)$-alkenyl-$(C_1-C_7)$-alkoxycarbonylheterocyclyl, aryl-$(C_1-C_7)$-alkoxycarbonylheterocyclyl, $(C_3-C_7)$-cycloalkoxycarbonylheterocyclyl, $(C_3-C_7)$-cycloalkyl-$(C_1-C_7)$-alkoxycarbonylheterocyclyl, aminocarbonylheterocyclyl, $(C_1-C_7)$-alkylaminocarbonylheterocyclyl, bis-$(C_1-C_7)$-alkylaminocarbonylheterocyclyl, $(C_3-C_7)$-cycloalkylaminocarbonylheterocyclyl, aryl-$(C_1-C_7)$-alkylaminocarbonylheterocyclyl, $(C_2-C_7)$-alkenylaminocarbonylheterocyclyl, hydroxycarbonylheterocyclyl-$(C_1-C_7)$-alkyl, $(C_1-C_7)$-alkoxycarbonylheterocyclyl-$(C_1-C_7)$-alkyl, hydroxycarbonyl-$(C_3-C_7)$-cycloalkyl-$(C_1-C_7)$-alkyl, $(C_1-C_7)$-alkoxycarbonyl-$(C_3-C_7)$-cycloalkyl-$(C_1-C_7)$-alkyl, hydroxyl, $(C_1-C_7)$-alkoxy, heterocyclyl, heterocyclyl-$(C_1-C_7)$-alkyl, or optionally substituted phenyl, $R^{10}$ is hydrogen, $(C_1-C_7)$-alkyl, $(C_3-C_7)$-cycloalkyl, halogen, $(C_1-C_7)$-haloalkyl, $(C_2-C_7)$-alkynyl, $(C_2-C_7)$-alkenyl, cyano-$(C_1-C_7)$-alkyl, aryl-$(C_1-C_7)$-alkyl, heteroaryl-$(C_1-C_7)$-alkyl, $(C_1-C_7)$-alkylcarbonyl, $(C_1-C_7)$-alkoxycarbonyl, $(C_1-C_7)$-alkylsulphonyl, arylsulphonyl, $(C_3-C_7)$-cycloalkylsulphonyl, $(C_1-C_7)$-alkylsulphinyl, arylsulphinyl, $(C_3-C_7)$-cycloalkylsulphinyl, or $(C_1-C_7)$-alkoxycarbonyl-$(C_1-C_7)$-alkyl, or $R^9$ and $R^{10}$ together with the nitrogen to which they are bonded form an optionally halogen-, $(C_1-C_7)$-alkyl-, $(C_1-C_7)$-haloalkyl-, $(C_1-C_7)$-alkoxy-, $(C_1-C_7)$-alkoxycarbonyl-, $(C_3-C_7)$-cycloalkoxycarbonyl-, $(C_3-C_7)$-cycloalkyl-$(C_1-C_7)$-alkoxycarbonyl-, $(C_2-C_7)$-alkenyloxycarbonyl-, hydroxycarbonyl-, aminocarbonyl-, $(C_1-C_7)$-alkylaminocarbonyl-, $(C_3-C_7)$-cycloalkylaminocarbonyl-, or aryl-$(C_1-C_7)$-alkylaminocarbonyl-substituted three- to eight-membered ring optionally interrupted by 0, S or N, or $R^9$ and $R^{10}$ together form an N-(bis-$(C_1-C_6)$-alkyl)sulphanylidene, N-(aryl-$(C_1-C_6)$-alkyl)sulphanylidene, N-(bis-$(C_3-C_7)$-cycloalkyl)sulphanylidene, N—(($C_1$-

$C_6$)-alkyl-($C_3$-$C_7$)-cycloalkyl)sulphanylidene group or an N,N-di-($C_1$-$C_6$)-alkylformylidene group and $R^{11}$ is hydrogen, ($C_1$-$C_7$)-alkyl, ($C_3$-$C_7$)-cycloalkyl, ($C_1$-$C_7$)-haloalkyl, ($C_1$-$C_7$)-alkoxy-($C_1$-$C_7$)-alkyl, or ($C_1$-$C_7$)-alkylthio-($C_1$-$C_7$)-alkyl.

4. A compound according to claim 1, wherein

[X-Y] represents

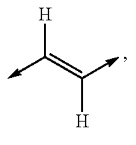

, $[X-Y]^2$

Q represents

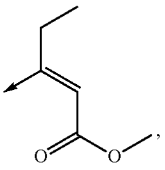

, $A^1$ represents $CH_2$, $A^2$ represents $CH_2$, m is 0, n is 0, $R^1$ represents i-Pr, and $R^2$ represents hydrogen.

5. The cyanocycloalkylpenta-2,4-diene, cyanocycloalkylpent-2-en-4-yne, cyanoheterocyclylpenta-2,4-diene or cyanoheterocyclylpent-2-en-4-yne according to claim 1, where

[X-Y] represents the moieties $[X-Y]^1$ or

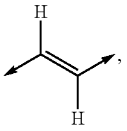

, $[X-Y]^2$

Q represents the moieties

Q-1

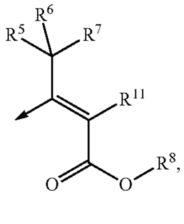

,

-continued

Q-2

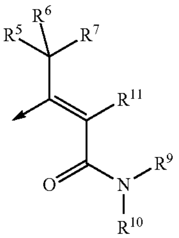

or

Q-3

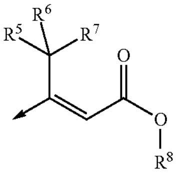

where $R^5$, $R^6$, $R^7$, $R^8$, $R^9$, $R^{10}$ and $R^{11}$ are each as defined below and where the arrow represents a bond to the respective [X-Y] moiety, $R^1$ is hydrogen, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-allylcyclopropyl, 1-vinylcyclobutyl, 1-vinylcyclopropyl, 1-ethylcyclopropyl, 1-methylcyclohexyl, 2-methylcyclohexyl, 3-methylcyclohexyl, 1-methoxycyclohexyl, 2-methoxycyclohexyl, 3-methoxycyclohexyl, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, hydroxymethyl, hydroxyethyl, hydroxypropyl, hydroxybutyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, difluoromethyl, 2,2-difluoroethyl, 2,2,2-trifluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, methylthiomethyl, methylthioethyl, ethylthioethyl, methylthio-n-propyl, ethylthio-n-propyl, aryl-($C_1$-$C_6$)-alkyl, heterocyclyl-($C_1$-$C_6$)-alkyl, ($C_3$-$C_6$)-halocycloalkyl, 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, methoxymethoxymethyl, methoxyethoxymethyl, methoxyethoxyethyl, methoxymethoxyethyl, ethoxy-n-propoxymethyl, ethoxy-n-propoxyethyl, ethoxyethoxymethyl, or ethoxyethoxyethyl, $R^2$ is hydrogen, tert-butyldimethylsilyl, trimethylsilyl, triethylsilyl, tri-(isopropyl)silyl, tri-(n-propyl)silyl, dimethyl(phenyl)silyl, tert-butyldiphenylsilyl, diethylisopropylsilyl, Isopropyldimethylsilyl, tert-hexyldimethylsilyl, 2-(trimethylsilyl)ethoxymethyl, 2-(trimethylsilyl)ethyl, methyl, ethyl, n-propyl, isopropyl, n-butyl, isobutyl, n-pentyl, iso-pentyl, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, methoxymethoxymethyl, methoxyethoxymethyl, methoxyethoxyethyl, methoxymethoxyethyl, ethoxy-n-propoxymethyl, ethoxy-n-propoxyethyl, ethoxyethoxymethyl, ethoxyethoxyethyl, allyl, methylcarbonyl, ethylcarbonyl, n-propylcarbonyl, isopropylcarbonyl, n-butylcarbonyl, n-pentylcarbonyl, tert-butylcarbonyl, isobutylcarbonyl, iso-pentylcarbonyl, neo-pentylcarbonyl, n-hexylcarbonyl, arylcarbonyl, heteroarylcarbonyl, cyclopropylcarbonyl, cyclobutylcarbonyl, cyclopentylcarbonyl, cyclohexylcarbonyl, ($C_2$-$C_6$)-alkenylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, phenyloxycarbonyl, p-Cl-phenyloxycarbonyl, benzyloxycarbonyl, p-Cl-benzyloxycarbonyl, p-methoxybenzyloxycarbonyl, p-methylbenzyloxycarbonyl, cyclopropyloxycarbonyl, cyclobutyloxycarbonyl, cyclopentyloxycarbonyl, cyclohexyloxycarbonyl, benzyl, p-Cl-benzyl, p-F-benzyl, p-methoxybenzyl, p-methylbenzyl, methylthiomethyl, methylthioethyl, ethylthioethyl, methylthio-n-propyl, or ethylthio-n-propyl, $A^1$, $A^2$, V, W are each independently a $CR^3R^4$ group, oxygen or sulphur, where not more than 2 oxygen or 2 sulphur atoms are present in each ring formed by the $A^1$, $A^2$, V, W groups and the carbon atom to which they are bonded, and where the oxygen and sulphur atoms are not adjacent to one another, m is 0 or 1, n is 0 or 1, $R^3$ and $R^4$ are each independently hydrogen, methyl, ethyl, n-propyl, isopropyl, n-butyl, isobutyl, tert-butyl, n-hexyl, fluorine, chlorine, bromine, iodine, cyclopropyl, cyclobutyl, cyclopentyl, cyclohexyl, cyclopropylcyclopropyl, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl, methoxy, ethoxy, n-propoxy, isopropoxy, n-butyloxy, tert-butyloxy, isobutyloxy, n-pentyloxy, aryl, heterocyclyl, heteroaryl, benzyl, p-Cl-benzyl, p-F-benzyl, p-methoxybenzyl, p-methylbenzyl, methylthio, ethylthio, n-propylthio, n-butylthio, n-pentylthio, isopropylthio, isobutylthio, tert-butylthio, n-pentylthio, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluororethyl, 2-chloro-2,2-difluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, vinyl, prop-1-en-1-yl, but-1-en-1-yl, allyl, 1-methylprop-2-en-1-yl, 2-methylprop-2-en-1-yl, but-2-en-1-yl, 1-methyl-but-3-en-1-yl and 1-methyl-but-2-en-1-yl, 2-methylprop-1-en-1-yl, but-3-en-1-yl, pentenyl, 2-methylpentenyl, hexenyl, ethynyl, propargyl, 1-methylprop-2-yn-1-yl, 2-butynyl, 2-pentynyl, 2-hexynyl, but-2-yn-1-yl, but-3-yn-1-yl, 1-methyl-but- 3-yn-1-yl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, methylthiomethyl, heteroaryl-($C_1$-$C_6$)-alkyl, or heterocyclyl-($C_1$-$C_6$)-alkyl, or $R^3$ and $R^4$ together with the atom to which they are bonded form a fully saturated 3- to 6-membered ring optionally interrupted by heteroatoms and optionally having further substitution, $R^5$ and $R^6$ are each independently hydrogen, fluorine, chlorine, bromine, iodine, methyl, ethyl, n-propyl, n-butyl, isobutyl, isopropyl, n-pentyl, n-hexyl, isopentyl, trifluoromethyl, pentafluoroethyl, heptafluoropropyl, nonafluorobutyl, chlorodifluoromethyl, bromodifluoromethyl, dichlorofluoromethyl, bromofluoromethyl, 1-fluoroethyl, 2-fluoroethyl, fluoromethyl, difluoromethyl, 2,2-difluoroethyl, 2,2,2-trifluoroethyl, 2,2-dichloro-2-fluoroethyl, 2-chloro-2,2-difluoroethyl, difluoro-tert-butyl, cyclopropyl, cyclobutyl, or cyclopentyl, $R^7$ is hydrogen, fluorine, chlorine, bromine, iodine, ($C_1$-$C_8$)-alkyl, ($C_1$-$C_8$)-haloalkyl, ($C_1$-$C_6$)-haloalkoxy, ($C_1$-$C_6$)-haloalkoxy-($C_1$-$C_6$)-alkyl, ($C_1$-$C_6$)-haloalkoxy-($C_1$-$C_6$)-haloalkyl, ($C_1$-$C_6$)-alkoxy-($C_1$-$C_6$)-haloalkyl, ($C_1$-$C_6$)-alkynyloxy-($C_1$-$C_6$)-haloalkyl, ($C_1$-$C_6$)-alkenyloxy-($C_1$-$C_6$)-haloalkyl, ($C_1$-$C_6$)-alkylthio, ($C_1$-$C_6$)-haloalkylthio, optionally substituted phenyl, aryl-($C_1$-$C_6$)-alkyl, heteroaryl, heteroaryl-($C_1$-$C_6$)-alkyl, heterocyclyl, ($C_1$-$C_6$)-alkoxy, hydroxyl, ($C_1$-$C_6$)-alkylcarbonyloxy, arylcarbonyloxy, ($C_3$-$C_6$)-cycloalkylcarbonyloxy, tris[($C_1$-$C_6$)-alkyl]silyloxy, bis[($C_1$-$C_6$)-alkyl]-[($C_1$-$C_6$)-alkyl]silyloxy, ($C_1$-$C_6$)-alkylbisarylsilyloxy, arylbis[($C_1$-$C_6$)-alkyl]silyloxy, ($C_3$-$C_6$)-cycloalkylbis[($C_1$-$C_6$)-alkyl]silyloxy, halobis[($C_1$-$C_6$)-alkyl]silyloxy, tris[($C_1$-$C_6$)-alkyl]silyl-($C_1$-$C_6$)-alkoxy-($C_1$-$C_6$)-alkyloxy, tris[($C_1$-$C_6$)-alkyl]silyl-($C_1$-$C_6$)-alkyloxy, ($C_3$-$C_7$)-cycloalkyl, or ($C_3$-$C_7$)-cycloalkyl-($C_1$-$C_6$)-alkyl, or $R^6$ and $R^7$ together with the atoms to which they are bonded form a fully saturated 3- to 6-membered ring optionally interrupted by heteroatoms and optionally having further substitution, $R^8$ is hydrogen, ($C_1$-$C_6$)-alkyl, ($C_1$-$C_6$)-alkoxy-($C_1$-$C_6$)-alkyl, ($C_3$-$C_6$)-cycloalkyl, ($C_3$-$C_6$)-cycloalkyl-($C_1$-$C_6$)-alkyl, optionally substituted phenyl, aryl-($C_1$-$C_6$)-alkyl, heteroaryl-($C_1$-$C_6$)-alkyl, bisaryl-($C_1$-$C_6$)-alkyl, trisaryl-($C_1$-$C_6$)-alkyl, ($C_2$-$C_6$)-alkenyl, ($C_4$-$C_6$)-cycloalkenyl-($C_1$-$C_6$)-alkyl, ($C_2$-$C_6$)-alkynyl-($C_1$-$C_6$)-alkyl, tri-($C_1$-$C_6$)-alkylsilyl-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkylthio-($C_1$-$C_6$)-alkyl, ($C_1$-$C_6$)-haloalkyl, arylsulphonyl-($C_1$-$C_6$)-alkyl, tri-($C_1$-$C_6$)-alkylsilyl, ($C_1$-$C_6$)-alkyl(bisaryl)silyl, ($C_1$-$C_6$)-alkyl(bis-($C_1$-$C_6$)-alkyl)silyl, bis($C_1$-$C_6$)-alkylamino-($C_1$-$C_6$)-alkyl, heterocyclyl-($C_1$-$C_6$)-alkyl, ($C_2$-$C_6$)-alkynyl, cyano-($C_1$-$C_6$)-alkyl, heterocyclyl, or optionally further-substituted phenyl, $R^9$ is hydrogen, ($C_1$-$C_6$)-alkyl, ($C_3$-$C_6$)-cycloalkyl, halogen, ($C_2$-$C_6$)-alkynyl-($C_1$-$C_6$)-alkyl, ($C_1$-$C_6$)-haloalkyl, ($C_2$-$C_6$)-alkynyl, ($C_2$-$C_6$)-alkenyl, cyano-($C_1$-$C_6$)-alkyl, ($C_3$-$C_6$)-cycloalkyl-($C_1$-$C_6$)-alkyl, aryl-($C_1$-$C_6$)-alkyl, heteroaryl-($C_1$-$C_6$)-alkyl, ($C_1$-$C_6$)-alkylcarbonyl, ($C_1$-$C_6$)-alkoxycarbonyl, ($C_2$-$C_6$)-alkenyloxycarbonyl, ($C_2$-$C_6$)-alkenyl-($C_1$-$C_6$)-alkyloxycarbonyl, aryl-($C_1$-$C_6$)-alkyloxycarbonyl, ($C_3$-$C_6$)-cycloalkoxycarbonyl, ($C_3$-$C_6$)-cycloalkyl-($C_1$-$C_6$)-alkoxycarbonyl, ($C_1$-$C_6$)-alkylsulphonyl, arylsulphonyl, ($C_3$-$C_6$)-cycloalkylsulphonyl, ($C_1$-$C_6$)-alkylsulphinyl, arylsulphinyl, ($C_3$-$C_6$)-cycloalkylsulphinyl, ($C_1$-$C_6$)-alkoxycarbonyl-($C_1$-$C_6$)-alkyl, hydroxycarbonyl-($C_1$-$C_6$)-alkyl, aryl-($C_1$-$C_6$)-alkoxycarbonyl-($C_1$-$C_6$)-alkyl, ($C_3$-$C_6$)-cycloalkyl-($C_1$-$C_6$)-alkoxycarbonyl-($C_1$-$C_6$)-alkyl, ($C_1$-$C_6$)-alkoxycarbonyl-($C_3$-$C_6$)-cycloalkyl, hydroxycarbonyl-($C_3$-$C_6$)-cycloalkyl, aryl-($C_1$-$C_6$)-alkoxycarbonyl-($C_3$-$C_6$)-cycloalkyl, ($C_2$-$C_6$)-alkenyloxycarbonyl-($C_3$-$C_6$)-cycloalkyl, aminocarbonyl-($C_3$-$C_6$)-cycloalkyl, ($C_1$-$C_6$)-alkylaminocarbonyl-($C_3$-$C_6$)-cycloalkyl, ($C_3$-$C_6$)-cycloalkylaminocarbonyl-($C_3$-$C_6$)-cycloalkyl, ($C_1$-$C_6$)-alkoxycarbonyl-($C_4$-$C_6$)-cycloalkenyl, hydroxycarbonyl-($C_4$-$C_6$)-cycloalkenyl, bis-($C_1$-$C_6$)-alkylamino-($C_1$-$C_6$)-alkyl, hydroxycarbonylheterocyclyl, ($C_1$-$C_6$)-alkoxycarbonylheterocyclyl, ($C_2$-$C_6$)-alkenyloxycarbonylheterocyclyl, ($C_2$-$C_6$)-alkenyl-($C_1$-$C_6$)-alkoxycarbonylheterocyclyl, aryl-($C_1$-$C_6$)-alkoxycarbonylheterocyclyl, ($C_3$-$C_6$)-cycloalkoxycarbonylheterocyclyl, ($C_3$-$C_6$)-cycloalkyl-($C_1$-$C_6$)-alkoxycarbonylheterocyclyl, aminocarbonylheterocyclyl, ($C_1$-$C_6$)-alkylaminocarbonylheterocyclyl, bis-($C_1$-$C_6$)-alkylaminocarbonylheterocyclyl, ($C_3$-$C_6$)-cycloalkylaminocarbonylheterocyclyl, aryl-($C_1$-$C_6$)-alkylaminocarbonylheterocyclyl, ($C_2$-$C_6$)-alkenylaminocarbonylheterocyclyl, hydroxycarbonylheterocyclyl-($C_1$-$C_6$)-alkyl, ($C_1$-$C_6$)-alkoxycarbonylheterocyclyl-($C_1$-$C_6$)-alkyl, hydroxycarbonyl-($C_3$-$C_6$)-cycloalkyl-($C_1$-$C_6$)-alkyl, ($C_1$-$C_6$)-alkoxycarbonyl-($C_3$-$C_6$)-cycloalkyl-($C_1$-$C_6$)-alkyl, hydroxyl, ($C_1$-$C_6$)-alkoxy, heterocyclyl, heterocyclyl-($C_1$-$C_6$)-alkyl, or optionally substituted phenyl, $R^{10}$ is hydrogen, ($C_1$-$C_6$)-alkyl, ($C_3$-$C_6$)-cycloalkyl, halogen, ($C_1$-$C_6$)-haloalkyl, ($C_2$-$C_6$)-alkynyl, ($C_2$-$C_6$)-alkenyl, cyano-($C_1$-$C_6$)-alkyl, aryl-($C_1$-$C_6$)-alkyl, heteroaryl-($C_1$-$C_6$)-alkyl, ($C_1$-$C_6$)-alkylcarbonyl, ($C_1$-$C_6$)-alkoxycarbonyl, ($C_1$-$C_6$)-alkylsulphonyl, arylsulphonyl, ($C_3$-$C_6$)-cycloalkylsulphonyl, ($C_1$-$C_6$)-alkylsulphinyl, arylsulphinyl, ($C_3$-$C_6$)-cycloalkylsulphinyl, or ($C_1$-$C_6$)-alkoxycarbonyl-($C_1$-$C_6$)-alkyl, or $R^9$ and $R^{10}$ together with the nitrogen to which they are bonded form an optionally fluorine-, chlorine-, bromine-, iodine-, ($C_1$-$C_6$)-alkyl-, ($C_1$-$C_6$)-haloalkyl-, ($C_1$-$C_6$)-alkoxy-, ($C_1$-$C_6$)-alkoxycarbonyl-, ($C_3$-$C_7$)-cycloalkoxycarbonyl-, ($C_3$-$C_6$)-cycloalkyl-($C_1$-$C_6$)-alkoxycarbonyl-, ($C_2$-$C_6$)-alkenyloxycarbonyl-, hydroxycarbonyl-, aminocarbonyl-, ($C_1$-$C_6$)-alkylaminocarbonyl-, ($C_3$-$C_7$)-cycloalkylaminocarbonyl-, aryl-($C_1$-$C_6$)— or alkylaminocarbonyl-substituted three- to seven-membered ring optionally interrupted by O, S or N, or $R^9$ and $R^{10}$ together are N-(di-n-butylsulphanylidene), N-(diisopropylsulphanylidene), N-(di-n-propyl sulphanylidene), N-(di-n-pentyl sulphanylidene), N-(diisobutylsulphanylidene), N-(cyclobutylisopropylsulphanylidene), N-(n-propylisopropylsulphanylidene), N-(cyclopropylisopropylsulphanylidene), N-(isobutylisopropylsulphanylidene), or N,N-dimethylformylidene, and $R^{11}$ is hydrogen, ($C_1$-$C_6$)-alkyl, ($C_3$-$C_6$)-cycloalkyl, ($C_1$-$C_6$)-haloalkyl, ($C_1$-$C_6$)-alkoxy-($C_1$-$C_6$)-alkyl, or ($C_1$-$C_6$)-alkylthio-($C_1$-$C_6$)-alkyl.

6. The cyanocycloalkylpenta-2,4-diene, cyanocycloalkylpent-2-en-4-yne, cyanoheterocyclylpenta-2,4-diene or cyanoheterocyclylpent-2-en-4-yne according to claim 1, where

[X-Y] represents the moieties

[X-Y][1]

or

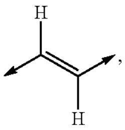,

[X-Y][2]

$R^1$ is methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylprop, 2-dimethylpropyl, 2.2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1, 2-trimethylpropyl, 1,2,2-trimethylpropyl, 1-ethyl-1-methylpropyl, 1-ethyl-2-methylpropyl, cyclopropylmethyl, cyclobutylmethyl, cyclopentylmethyl, cyclohexylmethyl, optionally substituted phenyl, heteroaryl, heterocyclyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl, adamantan-2-yl, 1-methylcyclopropyl, 2-methylcyclopropyl, 2.2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanopropyl, 2-cyanopropyl, 1-methylcyclobutyl, 2-methylcyclobutyl, 3-methylcyclobutyl, 1-cyanocyclobutyl, 2-cyanocyclobutyl, 3-cyanocyclobutyl, 1-methylcyclohexyl, 2-methylcyclohexyl, 3-methylcyclohexyl, 1-methoxycyclohexyl, 2-methoxycyclohexyl, 3-methoxycyclohexyl, aryl-($C_1$-$C_5$)-alkyl, or heterocyclyl-($C_1$-$C_5$)-alkyl, $R^2$ is hydrogen, tert-butyldimethylsilyl, trimethylsilyl, triethylsilyl, tri(isopropyl)silyl, tri(n-propyl)silyl, dimethyl(phenyl)silyl, tert-butyldiphenylsilyl, diethylisopropylsilyl, isopropyldimethylsilyl, tert-hexyldimethylsilyl, 2-(trimethylsilyl)ethoxymethyl, 2-(trimethylsilyl)ethyl, methyl, ethyl, allyl, methylcarbonyl, ethylcarbonyl, n-propylcarbonyl, isopropylcarbonyl, n-butylcarbonyl, tert-butylcarbonyl, isobutylcarbonyl, isopentylcarbonyl, neopentylcarbonyl, arylcarbonyl, heteroarylcarbonyl, cyclopropylcarbonyl, cyclobutylcarbonyl, cyclopentylcarbonyl, cyclohexylcarbonyl, heterocyclylcarbonyl, methoxycarbonyl, ethoxycarbonyl, n-propoxycarbonyl, n-butyloxycarbonyl, isopropoxycarbonyl, isobutyloxycarbonyl, tert-butyloxycarbonyl, allyloxycarbonyl, benzyl, p-Cl-benzyl p-F-benzyl, p-methoxybenzyl, p-methylbenzyl, methylthiomethyl, methylthioethyl, ethylthioethyl, methylthio-n-propyl, or ethylthio-n-propyl, $A^1$, V, W are each independently a $CR^3R^4$ group, $A^2$ is a $CR^3R^4$ group or oxygen, m is 0, n is 0 or 1, $R^3$ and $R^4$ are each independently hydrogen, methyl, ethyl, n-propyl, isopropyl, n-butyl, isobutyl, tert-butyl, fluorine, chlorine, bromine, iodine, cyclopropyl, cyclobutyl, cyclopentyl, cyclohexyl, methoxy, optionally substituted phenyl, heterocyclyl, heteroaryl, methylthio, trifluoromethyl, difluoromethyl, vinyl, prop-1-en-1-yl, but-1-en-1-yl, allyl, trifluoromethoxy, difluoromethoxy, 2,2-difluoroethoxy, 2,2,2-trifluoroethoxy, trifluoromethylthio, methoxymethyl, ethoxymethyl, ethoxyethyl, methoxyethyl, or methylthiomethyl or $R^3$ and $R^4$ together with the atom to which they are bonded form a fully saturated 3- to 6-membered ring optionally interrupted by heteroatoms and optionally having further substitution.

7. A spray solution for treatment of plants, comprising an amount, effective for enhancing the resistance of plants to one or more abiotic stress factors, of one or more compounds of formula (I) according to claim 1 or salts thereof.

8. A method of treating one or more plants comprising applying a nontoxic amount, effective for enhancing the resistance of plants to one or more abiotic stress factors, of one or more of the compounds of formula (I) or salts thereof according to claim 1 to the one or more plants or plant parts.

9. The method according to claim 8, wherein the one or more abiotic stress conditions correspond to one or more conditions selected from the group consisting of heat, drought, cold and drought stress, osmotic stress, waterlogging, elevated soil salinity, elevated exposure to minerals, ozone conditions, strong light conditions, limited availability of nitrogen nutrients, and limited availability of phosphorus nutrients.

10. The method according to claim 8, wherein the one or more compounds of formula (I) or salts thereof are applied in spray application to the one or more plants and plant parts in combinations with one or more active ingredients selected from the group of insecticides, attractants, acaricides, fungicides, nematicides, herbicides, growth regulators, safeners, substances which influence plant maturity and bactericides.

11. The method according to claim 8, wherein one or more of the compounds of formula (I) or salts thereof are applied in spray application to the one or more plants and plant parts in combinations with fertilizers.

12. The method according to claim 8, wherein one or more of the compounds of formula (I) or salts thereof are applied to genetically modified cultivars, the seed thereof, or to cultivated areas in which these cultivars grow.

13. The method according to claim 8, wherein application of one or more of the compounds of formula (I) or salts thereof enhances plant growth and/or increases plant yield.

14. The method according to claim 8, wherein a sufficient, nontoxic amount of one or more compounds of formula (I) or salts thereof is applied to one or more plants selected from the group consisting of useful plants, ornamental plants, turfgrass types, and trees, the seed thereof or to the area in which the plants grow, and wherein the application of one or more compounds of formula (I) or salts thereof increases stress tolerance in the one or more plants.

15. The method according to claim 14, wherein the resistance of the treated plants to abiotic stress is increased by at least 3% compared to untreated plants.

16. The method according to claim 8, wherein the one or more abiotic stress conditions correspond to drought.

* * * * *